US010131904B2

(12) United States Patent
Pavco et al.

(10) Patent No.: US 10,131,904 B2
(45) Date of Patent: *Nov. 20, 2018

(54) MODIFIED RNAI POLYNUCLEOTIDES AND USES THEREOF

(75) Inventors: Pamela A. Pavco, Longmont, CO (US); Joanne Kamens, Newton, MA (US); Tod M. Woolf, Sudbury, MA (US); William Salomon, Worcester, MA (US); Anastasia Khvorova, Northborough, MA (US)

(73) Assignee: RXi Pharmaceuticals Corporation, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/867,181

(22) PCT Filed: Feb. 11, 2009

(86) PCT No.: PCT/US2009/000852
§ 371 (c)(1),
(2), (4) Date: Nov. 1, 2010

(87) PCT Pub. No.: WO2009/102427
PCT Pub. Date: Aug. 20, 2009

(65) Prior Publication Data
US 2011/0039914 A1   Feb. 17, 2011

Related U.S. Application Data

(60) Provisional application No. 61/065,335, filed on Feb. 11, 2008.

(51) Int. Cl.
*C12N 15/113* (2010.01)
*C12N 15/11* (2006.01)

(52) U.S. Cl.
CPC .......... *C12N 15/111* (2013.01); *C12N 15/113* (2013.01); *C12N 15/1136* (2013.01); *C12N 15/1137* (2013.01); *C12N 2310/14* (2013.01); *C12N 2310/315* (2013.01); *C12N 2310/321* (2013.01); *C12N 2310/322* (2013.01); *C12N 2310/341* (2013.01); *C12N 2320/51* (2013.01); *C12N 2320/53* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,201,860 A | 5/1980 | Naito et al. |
| 4,235,871 A | 11/1980 | Papahadjopoulos et al. |
| 4,415,732 A | 11/1983 | Caruthers et al. |
| 4,426,330 A | 1/1984 | Sears |
| 4,501,728 A | 2/1985 | Geho et al. |
| 4,737,323 A | 4/1988 | Martin et al. |
| 4,837,028 A | 6/1989 | Allen |
| 4,897,355 A | 1/1990 | Eppstein et al. |
| 4,904,582 A | 2/1990 | Tullis |
| 4,958,013 A | 9/1990 | Letsinger |
| 5,023,243 A | 6/1991 | Tullis |
| 5,112,963 A | 5/1992 | Pieles et al. |
| 5,151,510 A | 9/1992 | Stec et al. |
| 5,188,897 A | 2/1993 | Suhadolnik et al. |
| 5,264,423 A | 11/1993 | Cohen et al. |
| 5,264,562 A | 11/1993 | Matteucci |
| 5,405,939 A | 4/1995 | Suhadolnik et al. |
| 5,416,203 A | 5/1995 | Letsinger |
| 5,417,978 A | 5/1995 | Tari et al. |
| 5,432,272 A | 7/1995 | Benner |
| 5,453,496 A | 9/1995 | Caruthers et al. |
| 5,459,255 A | 10/1995 | Cook et al. |
| 5,466,786 A | 11/1995 | Buhr et al. |
| 5,470,967 A | 11/1995 | Huie et al. |
| 5,486,603 A | 1/1996 | Buhr |
| 5,489,677 A | 2/1996 | Sanghvi et al. |
| 5,495,009 A | 2/1996 | Matteucci et al. |
| 5,514,786 A | 5/1996 | Cook et al. |
| 5,532,130 A | 7/1996 | Alul |
| 5,534,259 A | 7/1996 | Zalipsky et al. |
| 5,556,948 A | 9/1996 | Tagawa et al. |
| 5,561,225 A | 10/1996 | Maddry et al. |
| 5,578,718 A | 11/1996 | Cook et al. |
| 5,580,731 A | 12/1996 | Chang et al. |
| 5,580,972 A | 12/1996 | Tu et al. |
| 5,587,469 A | 12/1996 | Cook et al. |
| 5,591,721 A | 1/1997 | Agrawal et al. |

(Continued)

FOREIGN PATENT DOCUMENTS

| | | |
|---|---|---|
| AU | 2004206255 B2 | 8/2004 |
| CN | 1 568 373 A | 1/2005 |

(Continued)

OTHER PUBLICATIONS

Leuschner, et al. (2006) Cleavage of the siRNA Passenger Strand During RISC Assembly in Human Cells, EMBO Reports, v.7(3):314-20.*

(Continued)

*Primary Examiner* — Jennifer Pitrak McDonald
(74) *Attorney, Agent, or Firm* — Wolf, Greenfield & Sacks, P.C.

(57) ABSTRACT

The invention relates to improved RNAi constructs and uses thereof. The construct has a double stranded region of 19-49 nucleotides, preferably 25, 26, or 27 nucleotides, and preferably blunt-ended. The construct has selective minimal modifications to confer an optimal balance of biological activity, toxicity, stability, and target gene specificity. For example, the sense strand may be modified (e.g., one or both ends of the sense strand is/are modified by four 2'-O-methyl groups), such that the construct is not cleaved by Dicer or other RNAse III, and the entire length of the antisense strand is loaded into RISC. In addition, the antisense strand may also be modified by 2'-O-methyl group at the 2nd 5'-end nucleotide to greatly reduce off-target silencing. The constructs of the invention largely avoids the interferon response and sequence-independent apoptosis in mammalian cells, exhibits better serum stability, and enhanced target specificity.

8 Claims, 32 Drawing Sheets

Specification includes a Sequence Listing.

(56) References Cited

U.S. PATENT DOCUMENTS

| | | |
|---|---|---|
| 5,591,722 A | 1/1997 | Montgomery et al. |
| 5,591,843 A | 1/1997 | Eaton |
| 5,594,121 A | 1/1997 | Froehler et al. |
| 5,596,086 A | 1/1997 | Matteucci et al. |
| 5,596,091 A | 1/1997 | Switzer |
| 5,599,797 A | 2/1997 | Cook et al. |
| 5,602,240 A | 2/1997 | De Mesmaeker et al. |
| 5,607,923 A | 3/1997 | Cook et al. |
| 5,614,617 A | 3/1997 | Cook et al. |
| 5,614,621 A | 3/1997 | Ravikumar et al. |
| 5,623,070 A | 4/1997 | Cook et al. |
| 5,625,050 A | 4/1997 | Beaton et al. |
| 5,633,360 A | 5/1997 | Bischofberger et al. |
| 5,643,889 A | 7/1997 | Suhadolnik et al. |
| 5,646,126 A | 7/1997 | Cheng et al. |
| 5,646,265 A | 7/1997 | McGee |
| 5,658,731 A | 8/1997 | Sproat et al. |
| 5,661,134 A | 8/1997 | Cook et al. |
| 5,663,312 A | 9/1997 | Chaturvedula |
| 5,670,633 A | 9/1997 | Cook et al. |
| 5,681,940 A | 10/1997 | Wang et al. |
| 5,681,941 A | 10/1997 | Cook et al. |
| 5,684,143 A | 11/1997 | Gryaznov et al. |
| 5,700,920 A | 12/1997 | Altmann et al. |
| 5,466,786 B1 | 4/1998 | Buhr et al. |
| 5,736,392 A | 4/1998 | Hawley-Nelson et al. |
| 5,750,666 A | 5/1998 | Caruthers et al. |
| 5,767,099 A | 6/1998 | Harris et al. |
| 5,770,713 A | 6/1998 | Imbach et al. |
| 5,777,153 A | 7/1998 | Lin et al. |
| 5,780,053 A | 7/1998 | Ashley et al. |
| 5,789,416 A | 8/1998 | Lum et al. |
| 5,792,847 A | 8/1998 | Buhr et al. |
| 5,808,023 A | 9/1998 | Sanghvi et al. |
| 5,817,781 A | 10/1998 | Swaminathan et al. |
| 5,830,430 A | 11/1998 | Unger et al. |
| 5,830,653 A | 11/1998 | Froehler et al. |
| 5,851,548 A | 12/1998 | Dattagupta et al. |
| 5,855,910 A | 1/1999 | Ashley et al. |
| 5,856,455 A | 1/1999 | Cook |
| 5,914,396 A | 6/1999 | Cook et al. |
| 5,945,521 A | 8/1999 | Just et al. |
| 5,948,767 A | 9/1999 | Scheule et al. |
| 5,969,116 A | 10/1999 | Martin |
| 5,976,567 A | 11/1999 | Wheeler et al. |
| 5,981,501 A | 11/1999 | Wheeler et al. |
| 5,986,083 A | 11/1999 | Dwyer et al. |
| 6,001,841 A | 12/1999 | Cook et al. |
| 6,005,096 A | 12/1999 | Matteucci et al. |
| 6,015,886 A | 1/2000 | Dale et al. |
| 6,020,475 A | 2/2000 | Capaldi et al. |
| 6,020,483 A | 2/2000 | Beckvermit et al. |
| 6,028,183 A | 2/2000 | Lin et al. |
| 6,033,910 A | 3/2000 | Monia et al. |
| 6,043,352 A | 3/2000 | Manoharan et al. |
| 6,051,699 A | 4/2000 | Ravikumar |
| 6,107,094 A | 8/2000 | Crooke |
| 6,111,085 A | 8/2000 | Cook et al. |
| 6,121,437 A | 9/2000 | Guzaev et al. |
| 6,153,737 A | 11/2000 | Manoharan et al. |
| 6,207,819 B1 | 3/2001 | Manoharan et al. |
| 6,248,878 B1 | 6/2001 | Matulic-Adamic et al. |
| 6,271,358 B1 | 8/2001 | Manoharan et al. |
| 6,326,358 B1 | 12/2001 | Manoharan |
| 6,328,765 B1 | 12/2001 | Hardwick et al. |
| 6,331,617 B1 | 12/2001 | Weeks et al. |
| 6,335,434 B1 | 1/2002 | Guzaev et al. |
| 6,355,787 B1 | 3/2002 | Beckvermit et al. |
| 6,358,931 B1 | 3/2002 | Cook et al. |
| 6,395,492 B1 | 5/2002 | Manoharan et al. |
| 6,399,754 B1 | 6/2002 | Cook |
| 6,410,702 B1 | 6/2002 | Swaminathan et al. |
| 6,420,549 B1 | 7/2002 | Cook et al. |
| 6,432,963 B1 | 8/2002 | Hisamichi et al. |
| 6,440,943 B1 | 8/2002 | Cook et al. |
| 6,444,806 B1 | 9/2002 | Veerapanani et al. |
| 6,455,586 B1 | 9/2002 | Kaplan et al. |
| 6,465,628 B1 | 10/2002 | Ravikumar et al. |
| 6,476,205 B1 | 11/2002 | Buhr et al. |
| 6,506,559 B1 | 1/2003 | Fire et al. |
| 6,528,631 B1 | 3/2003 | Cook et al. |
| 6,531,584 B1 | 3/2003 | Cook et al. |
| 6,673,611 B2 | 1/2004 | Thompson et al. |
| 6,683,167 B2 | 1/2004 | Metelev et al. |
| 6,815,432 B2 | 11/2004 | Wheeler et al. |
| 6,849,726 B2 | 2/2005 | Usman et al. |
| 6,858,225 B2 | 2/2005 | Semple et al. |
| 7,041,824 B2 | 5/2006 | Bordon-Pallier et al. |
| 7,056,704 B2 | 6/2006 | Tuschl et al. |
| 7,078,196 B2 | 7/2006 | Tuschl et al. |
| 7,132,530 B2 | 11/2006 | Bennett et al. |
| 7,205,297 B2 | 4/2007 | Beauchamp et al. |
| 7,432,250 B2 | 10/2008 | Crooke |
| 7,534,774 B2 | 5/2009 | Sosnowski et al. |
| 7,538,095 B2 | 5/2009 | Fire et al. |
| 7,560,438 B2 | 7/2009 | Fire et al. |
| 7,595,387 B2 | 9/2009 | Leake et al. |
| 7,605,251 B2 | 10/2009 | Tan et al. |
| 7,622,455 B2 | 11/2009 | Bennett et al. |
| 7,622,633 B2 | 11/2009 | Fire et al. |
| 7,629,321 B2 | 12/2009 | Crooke |
| 7,695,902 B2 | 4/2010 | Crooke |
| 7,745,608 B2 | 6/2010 | Manoharan et al. |
| 7,750,144 B2 * | 7/2010 | Zamore et al. ............ 536/25.3 |
| 7,786,290 B2 | 8/2010 | Woppmann et al. |
| 7,829,693 B2 | 11/2010 | Kreutzer et al. |
| 7,902,163 B2 | 3/2011 | Bennett et al. |
| 8,084,437 B2 | 12/2011 | Freier et al. |
| 8,110,674 B2 | 2/2012 | Manoharan et al. |
| 8,263,569 B2 | 9/2012 | Baulcombe et al. |
| 8,383,600 B2 | 2/2013 | Czech et al. |
| 8,664,189 B2 | 3/2014 | Khvorova et al. |
| 8,796,443 B2 | 8/2014 | Khvorova et al. |
| 8,815,818 B2 | 8/2014 | Samarsky et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,222,092 B2 | 12/2015 | Giese et al. |
| 9,303,259 B2 | 4/2016 | Khvorova et al. |
| 9,340,786 B2 | 5/2016 | Khvorova et al. |
| 9,493,774 B2 | 11/2016 | Kamens |
| 9,745,574 B2 | 8/2017 | Woolf et al. |
| 9,938,530 B2 | 4/2018 | Khvorova et al. |
| 2002/0132788 A1 | 9/2002 | Lewis et al. |
| 2002/0147332 A1 | 10/2002 | Kaneko et al. |
| 2002/0160393 A1 | 10/2002 | Symonds et al. |
| 2002/0162126 A1 | 10/2002 | Beach et al. |
| 2003/0004325 A1 | 1/2003 | Cook et al. |
| 2003/0077829 A1 | 4/2003 | MacLachlan |
| 2003/0108923 A1 | 6/2003 | Tuschl et al. |
| 2003/0139585 A1 | 7/2003 | Uhlmann et al. |
| 2003/0143732 A1 * | 7/2003 | Fosnaugh et al. ............ 435/325 |
| 2003/0157030 A1 | 8/2003 | Davis et al. |
| 2003/0158403 A1 | 8/2003 | Manoharan et al. |
| 2003/0166282 A1 | 9/2003 | Brown et al. |
| 2004/0009938 A1 | 1/2004 | Manoharan et al. |
| 2004/0014956 A1 | 1/2004 | Woolf et al. |
| 2004/0014957 A1 | 1/2004 | Eldrup et al. |
| 2004/0018999 A1 | 1/2004 | Beach et al. |
| 2004/0054155 A1 | 3/2004 | Woolf et al. |
| 2004/0087526 A1 | 5/2004 | Lin et al. |
| 2004/0137471 A1 | 7/2004 | Vickers et al. |
| 2004/0167090 A1 | 8/2004 | Monahan et al. |
| 2004/0171033 A1 | 9/2004 | Baker et al. |
| 2004/0180351 A1 | 9/2004 | Giese et al. |
| 2004/0192629 A1 | 9/2004 | Xu et al. |
| 2004/0204377 A1 | 10/2004 | Rana |
| 2004/0229266 A1 | 11/2004 | Tuschl et al. |
| 2004/0241845 A1 | 12/2004 | Desgroseillers et al. |
| 2004/0248839 A1 | 12/2004 | Kowalik |
| 2004/0259247 A1 | 12/2004 | Tuschl et al. |
| 2005/0020521 A1 | 1/2005 | Rana |
| 2005/0032733 A1 | 2/2005 | McSwiggen et al. |

(56) References Cited

U.S. PATENT DOCUMENTS

| | | |
|---|---|---|
| 2005/0080246 A1 | 4/2005 | Allerson et al. |
| 2005/0107325 A1 | 5/2005 | Manoharan et al. |
| 2005/0142535 A1 | 6/2005 | Damha et al. |
| 2005/0181382 A1 | 8/2005 | Zamore et al. |
| 2005/0239731 A1 | 10/2005 | McSwiggen et al. |
| 2005/0246794 A1 | 11/2005 | Khvorova et al. |
| 2005/0255487 A1 | 11/2005 | Khvorova et al. |
| 2006/0009409 A1* | 1/2006 | Woolf ............................ 514/44 |
| 2006/0035344 A1 | 2/2006 | Pachuk et al. |
| 2006/0127891 A1 | 6/2006 | McSwiggen et al. |
| 2006/0160133 A1 | 7/2006 | Czech et al. |
| 2006/0178324 A1 | 8/2006 | Hadwiger et al. |
| 2006/0178327 A1 | 8/2006 | Yeung |
| 2006/0211766 A1 | 9/2006 | Kaplan et al. |
| 2006/0229268 A1 | 10/2006 | Benjamin et al. |
| 2007/0032441 A1 | 2/2007 | McSwiggen et al. |
| 2007/0166734 A1 | 7/2007 | Bhat et al. |
| 2007/0173473 A1* | 7/2007 | McSwiggen et al. .......... 514/44 |
| 2007/0173476 A1 | 7/2007 | Leake et al. |
| 2007/0231392 A1 | 10/2007 | Wagner et al. |
| 2007/0269889 A1 | 11/2007 | Leake et al. |
| 2008/0008697 A1 | 1/2008 | Mintier et al. |
| 2008/0071068 A1 | 3/2008 | Oba et al. |
| 2008/0085869 A1 | 4/2008 | Yamada et al. |
| 2008/0108583 A1 | 5/2008 | Feinstein et al. |
| 2008/0125386 A1 | 5/2008 | Rana et al. |
| 2008/0306015 A1 | 12/2008 | Khvorova et al. |
| 2008/0311040 A1 | 12/2008 | Berry et al. |
| 2009/0023216 A1 | 1/2009 | Woolf |
| 2009/0131360 A1 | 5/2009 | Woolf et al. |
| 2009/0306005 A1 | 12/2009 | Bhanot et al. |
| 2010/0069620 A1 | 3/2010 | Zon |
| 2010/0081705 A1 | 4/2010 | Bennett et al. |
| 2010/0136695 A1 | 6/2010 | Woolf |
| 2011/0237522 A1 | 9/2011 | Khvorova et al. |
| 2011/0237648 A1 | 9/2011 | Khvorova et al. |
| 2011/0251258 A1 | 10/2011 | Samarsky et al. |
| 2011/0263680 A1 | 10/2011 | Khvorova et al. |
| 2011/0268761 A1 | 11/2011 | Levis et al. |
| 2012/0016005 A1 | 1/2012 | Samarsky et al. |
| 2012/0040459 A1 | 2/2012 | Khvorova et al. |
| 2012/0059046 A1 | 3/2012 | Woolf et al. |
| 2012/0065243 A1 | 3/2012 | Woolf et al. |
| 2013/0131141 A1 | 5/2013 | Khvorova et al. |
| 2013/0131142 A1 | 5/2013 | Libertine et al. |
| 2013/0197055 A1 | 8/2013 | Kamens et al. |
| 2014/0072613 A1 | 3/2014 | Lander et al. |
| 2014/0113950 A1 | 4/2014 | Khvorova et al. |
| 2014/0315974 A1 | 10/2014 | Khvorova et al. |
| 2014/0364482 A1 | 12/2014 | Khvorova et al. |
| 2015/0057362 A1 | 2/2015 | Levis et al. |
| 2016/0115482 A1 | 4/2016 | Libertine et al. |
| 2016/0115484 A1 | 4/2016 | Woolf et al. |
| 2016/0130578 A1 | 5/2016 | Khvorova et al. |
| 2016/0244765 A1 | 8/2016 | Khvorova et al. |
| 2016/0304873 A1 | 10/2016 | Wolfson et al. |
| 2016/0304875 A1 | 10/2016 | Cauwenbergh et al. |
| 2016/0319278 A1 | 11/2016 | Khvorova et al. |
| 2016/0355808 A1 | 12/2016 | Khvorova et al. |
| 2016/0355826 A1 | 12/2016 | Khvorova et al. |
| 2017/0009239 A1 | 1/2017 | Khvorova et al. |
| 2017/0051288 A1 | 2/2017 | Byrne et al. |
| 2017/0051290 A1 | 2/2017 | Byrne et al. |
| 2017/0067056 A1 | 3/2017 | Khvorova et al. |
| 2017/0137823 A1 | 5/2017 | Kamens et al. |
| 2018/0030451 A1 | 2/2018 | Cauwenbergh |

FOREIGN PATENT DOCUMENTS

| | | |
|---|---|---|
| EP | 0 552 766 A2 | 7/1993 |
| EP | 1 214 945 A2 | 6/2002 |
| EP | 1 144 623 B9 | 3/2003 |
| EP | 1 352 061 B1 | 10/2003 |
| EP | 0 928 290 B9 | 3/2005 |
| EP | 1 407 044 B1 | 9/2007 |
| EP | 1 605 978 B1 | 1/2010 |
| JP | 4 095 895 B2 | 9/2004 |
| JP | 2009-519033 | 5/2009 |
| WO | WO 90/14074 A1 | 11/1990 |
| WO | WO 91/16024 A1 | 10/1991 |
| WO | WO 91/17424 A1 | 11/1991 |
| WO | WO 92/03464 A1 | 3/1992 |
| WO | WO 94/23028 A2 | 10/1994 |
| WO | WO 95/11910 A1 | 5/1995 |
| WO | WO 95/23162 A1 | 8/1995 |
| WO | WO 96/40964 A2 | 12/1996 |
| WO | WO 03/012052 A2 | 2/2003 |
| WO | WO 2003/064626 | 8/2003 |
| WO | WO 2004/042027 A2 | 5/2004 |
| WO | WO 2004/065600 A2 | 8/2004 |
| WO | WO 2004/065601 A2 | 8/2004 |
| WO | WO 2004/090105 A2 | 10/2004 |
| WO | WO 2005/019430 A2 | 3/2005 |
| WO | WO 2005/079533 A2 | 9/2005 |
| WO | WO 2005/097992 A2 | 10/2005 |
| WO | WO 2006/019430 A2 | 2/2006 |
| WO | WO 2006/039656 A2 | 4/2006 |
| WO | WO 2006/060246 A2 | 6/2006 |
| WO | WO 2006/065601 A2 | 6/2006 |
| WO | WO 2006/128141 A2 | 11/2006 |
| WO | WO 2007/030167 A1 | 3/2007 |
| WO | WO 2007/044362 A2 | 4/2007 |
| WO | WO 2007/069068 A2 | 6/2007 |
| WO | WO 2007/089607 A2 | 8/2007 |
| WO | WO 2008/036825 A2 | 3/2008 |
| WO | WO 2008/109353 A1 | 9/2008 |
| WO | WO 2009/044392 A2 | 4/2009 |
| WO | WO 2009/114475 A2 | 9/2009 |
| WO | WO 2009/134487 A2 | 11/2009 |
| WO | WO 2010/006237 A2 | 1/2010 |
| WO | WO 2010/011346 A2 | 1/2010 |
| WO | WO 2010/027830 A2 | 3/2010 |
| WO | WO 2010/042281 A2 | 4/2010 |
| WO | WO 2011/109698 A1 | 9/2011 |
| WO | WO 2014/191493 A1 | 12/2014 |
| WO | WO 2015/031392 A1 | 3/2015 |

OTHER PUBLICATIONS

Kraynack, et al. (2006) Small Interfering RNAs Containing Full 2'-O-Methylribonucleotide-modified Sense Strands Display Argonaute2/eIF2C2-Dependent Activity, RNA, v.12:163-76.*

Choung et al. Chemical modification of siRNAs to improve serum stability without loss of efficacy. Biochem Biophys Res Commun. Apr. 14, 2006;342(3):919-27.

Jackson et al., Position-specific chemical modification of siRNAs reduces "off-target" transcript silencing. RNA. Jul. 2006;12(7):1197-1205. Epub May 8, 2006.

Kubo et al., Modified 27-nt dsRNAs with dramatically enhanced stability in serum and long-term RNAi activity. Oligonucleotides. 2007 Winter;17(4):445-64.

Meade et al., Role of hypoxia-inducible transcription factors 1alpha and 2alpha in the regulation of plasminogen activator inhibitor-1 expression in a human trophoblast cell line. Placenta. Oct. 2007;28(10):1012-9. Epub Jun. 13, 2007.

[No Author Listed] RedChip Small-Cap Investor Conference. RXI Pharmaceuticals (Nasdaq RXII). Jun. 16, 2009 Presentation. 5 pages.

Abifadel et al., Mutations in PCSK9 cause autosomal dominant hypercholesterolemia. Nat Genet. Jun. 2003;34(2):154-6.

Aleckovic et al., RNAi at Oxford. J RNAi Gene Silencing. May 27, 2008;4(1):266-8.

Aouadi et al., Orally delivered siRNA targeting macrophage Map4k4 suppresses systemic inflammation. Nature. Apr. 30, 2009;458(7242):1180-4. doi: 10.1038/nature07774.

Baigude et al., Design and creation of new nanomaterials for therapeutic RNAi. ACS Chem Biol. Apr. 24, 2007;2(4):237-41.

Bartzatt, Cotransfection of nucleic acid segments by Sendai virus envelopes. Biotechnol Appl Biochem. Feb. 1989;11(1):133-5.

Benjannet et al., NARC-1/PCSK9 and its natural mutants: zymogen

(56) References Cited

OTHER PUBLICATIONS cleavage and effects on the low density lipoprotein (LDL) receptor and LDL cholesterol. J Biol Chem. Nov. 19, 2004;279(47):48865-75. Epub Sep. 9, 2004.
Bergan et al., Electroporation enhances c-myc antisense oligodeoxynucleotide efficacy. Nucleic Acids Res. Jul. 25, 1993;21(15):3567-73.
Bergeron et al., Subtilase-like pro-protein convertases: from molecular specificity to therapeutic applications. J Mol Endocrinol. Feb. 2000;24(1):1-22.
Bjergarde et al., Solid phase synthesis of oligodeoxyribonucleoside phosphorodithioates from thiophosphoramidites. Nucleic Acids Res. Nov. 11, 1991;19(21):5843-50.
Boutorin et al., Synthesis of alkylating oligonucleotide derivatives containing cholesterol or phenazinium residues at their 3'-terminus and their interaction with DNA within mammalian cells. Febs Lett. Aug. 28, 1989;254(1-2):129-32.
Braasch et al., RNA Interference in Mammalian Cells by Chemically-Modified RNA. Biochem. 2003;42(26):7967-75.
Brown et al., Light at the end of the tunnel. J RNAi Gene Silencing. Jul. 28, 2006;2(2):175-7.
Chiu et al., siRNA function in RNAi: a chemical modification analysis. RNA. Sep. 2003;9(9):1034-48.
Cohen et al., Low LDL cholesterol in individuals of African descent resulting from frequent nonsense mutations in PCSK9. Nat Genet. Feb. 2005;37(2):161-5. Epub Jan. 16, 2005.
Cohen et al., Molecular mechanisms of autosomal recessive hypercholesterolemia. Curr Opin Lipidol. Apr. 2003;14(2):121-7.
Cohen et al., Sequence variations in PCSK9, low LDL, and protection against coronary heart disease. N Engl J Med. Mar. 23, 2006;354(12):1264-72.
Collins et al., A small interfering RNA screen for modulators of tumor cell motility identifies MAP4K4 as a promigratory kinase. Proc Natl Acad Sci U S A. Mar. 7, 2006; 103(10): 3775-3780.
Constantinides et al., Formulation and intestinal absorption enhancement evaluation of water-in-oil microemulsions incorporating medium-chain glycerides. Pharm Res. Oct. 1994;11(10):1385-90.
Czauderna et al., Structural variations and stabilising modifications of synthetic siRNAs in mammalian cells. Nucleic Acids Res. Jun. 1, 2003;31(11):2705-16.
De Smidt et al., Association of antisense oligonucleotides with lipoproteins prolongs the plasma half-life and modifies the tissue distribution. Nucleic Acids Res. Sep. 11, 1991;19(17):4695-700.
Debart et al., Chemical modifications to improve the cellular uptake of oligonucleotides. Curr Top Med Chem. 2007;7(7):727-37.
Dubuc et al., Statins upregulate PCSK9, the gene encoding the proprotein convertase neural apoptosis-regulated convertase-1 implicated in familial hypercholesterolemia. Arterioscler Thromb Vasc Biol. Aug. 2004;24(8):1454-9. Epub Jun. 3, 2004.
Dykxhoorn et al., The silent treatment: siRNAs as small molecule drugs. Gene Ther. Mar. 2006;13(6):541-52.
Elbashir et al., Functional anatomy of siRNAs for mediating efficient RNAi in *Drosophila melanogaster* embryo lysate. EMBO J. Dec. 3, 2001;20(23):6877-88.
Fedorov et al., Off-target effects by siRNA can induce toxic phenotype. RNA. Jul. 2006;12(7):1188-96. Epub May 8, 2006.
Ferentz et al., Disulfide-crosslinked oligonucleotides. Journal of the American Chemical Society. 1991;113 (10): 4000-4002.
Frank-Kamenetsky et al., Therapeutic RNAi targeting PCSK9 acutely lowers plasma cholesterol in rodents and LDL cholesterol in non-human primates. Proc Natl Acad Sci U S A. Aug. 19, 2008;105(33):11915-20. Epub Aug. 11, 2008.
Genbank Submission; NCBI, Accession No. NM_004834; Bouzakri et al.; Oct. 24, 2008.
Gensberg et al., Subtilisin-related serine proteases in the mammalian constitutive secretory pathway. Semin Cell Dev Biol. Feb. 1998;9(1):11-7.
Ho et al., Preparation of microemulsions using polyglycerol fatty acid esters as surfactant for the delivery of protein drugs. J Pharm Sci. Feb. 1996;85(2):138-43.

Huang et al., Lipitoids—novel cationic lipids for cellular delivery of plasmid DNA in vitro. Chem Biol. Jun. 1998;5(6):345-54.
Kamata et al., Amphiphilic peptides enhance the efficiency of liposome-mediated DNA transfection. Nucleic Acids Res. Feb. 11, 1994;22(3):536-7.
Kim et al., Synthetic dsRNA Dicer substrates enhance RNAi potency and efficacy. Nat Biotechnol. Feb. 2005;23(2):222-6. Epub Dec. 26, 2004.
Kim et al., Systemic and specific delivery of small interfering RNAs to the liver mediated by apolipoprotein A-I. Mol Ther. Jun. 2007;15(6):1145-52. Epub Apr. 17, 2007.
Layzer et al., In vivo activity of nuclease-resistant siRNAs. RNA. May 2004;10(5):766-71.
Lemaitre et al., Specific antiviral activity of a poly(L-lysine)-conjugated oligodeoxyribonucleotide sequence complementary to vesicular stomatitis virus N protein mRNA initiation site. Proc Natl Acad Sci U S A. Feb. 1987;84(3):648-52.
Leren, Mutations in the PCSK9 gene in Norwegian subjects with autosomal dominant hypercholesterolemia. Clin Genet. May 2004;65(5):419-22.
Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Li et al., Surface-modified LPD nanoparticles for tumor targeting. Ann N Y Acad Sci. Oct. 2006;1082:1-8.
Macrae et al., Structure of Dicer and mechanistic implications for RNAi. Cold Spring Harb Symp Quant Biol. 2006;71:73-80.
Manoharan et al., Chemical modifications to improve uptake and bioavailability of antisense oligonucleotides. Ann N Y Acad Sci. Oct. 28, 1992;660:306-9.
Manoharan, Oligonucleotide conjugates as potential antisense drugs with improved uptake, biodistribution, targeted delivery, and mechanism of action. Antisense Nucleic Acid Drug Dev. Apr. 2002;12(2):103-28.
Martins et al., Sterol side chain length and structure affect the clearance of chylomicron-like lipid emulsions in rats and mice. J Lipid Res. Feb. 1998;39(2):302-12.
Mathews et al., Incorporating chemical modification constraints into a dynamic programming algorithm for prediction of RNA secondary structure. Proc Natl Acad Sci U S A. May 11, 2004;101(19):7287-92. Epub May 3, 2004.
Maxwell et al., Novel putative SREBP and LXR target genes identified by microarray analysis in liver of cholesterol-fed mice. J Lipid Res. Nov. 2003;44(11):2109-19. Epub Aug. 1, 2003.
Maxwell et al., Adenoviral-mediated expression of Pcsk9 in mice results in a low-density lipoprotein receptor knockout phenotype. Proc Natl Acad Sci U S A. May 4, 2004;101(18):7100-5. Epub Apr. 26, 2004.
Mescalchin et al., Cellular uptake and intracellular release are major obstacles to the therapeutic application of siRNA: novel options by phosphorothioate-stimulated delivery. Expert Opin Biol Ther. Oct. 2007;7(10):1531-8. Review.
Murchison et al., Characterization of Dicer-deficient murine embryonic stem cells. Proc Natl Acad Sci U S A. Aug. 23, 2005;102(34):12135-40. Epub Aug. 12, 2005.
Murphy et al., A combinatorial approach to the discovery of efficient cationic peptoid reagents for gene delivery. Proc Natl Acad Sci U S A. Feb. 17, 1998;95(4):1517-22.
Niessen et al., Keratinocyte-derived growth factors play a role in the formation of hypertrophic scars. J Pathol. Jun. 2001;194(2):207-16.
Oberhauser et al., Effective incorporation of 2'-O-methyl-oligoribonucleotides into liposomes and enhanced cell association through modification with thiocholesterol. Nucleic Acids Res. Feb. 11, 1992;20(3):533-8.
Overhoff et al., Phosphorothioate-stimulated uptake of short interfering RNA by human cells. EMBO Rep. Dec. 2005;6(12):1176-81.

(56) References Cited

OTHER PUBLICATIONS

Park et al., Post-transcriptional regulation of low density lipoprotein receptor protein by proprotein convertase subtilisin/kexin type 9a in mouse liver. J Biol Chem. Nov. 26, 2004;279(48):50630-8. Epub Sep. 22, 2004.
Parrish et al., Functional anatomy of a dsRNA trigger: differential requirement for the two trigger strands in RNA interference. Mol Cell. Nov. 2000;6(5):1077-87.
Rader et al., Monogenic hypercholesterolemia: new insights in pathogenesis and treatment. J Clin Invest. Jun. 2003;111(12):1795-803.
Rajeev et al., 2'-modified-2-thiothymidine oligonucleotides. Org Lett. Aug. 21, 2003;5(17):3005-8.
Rashid et al., Decreased plasma cholesterol and hypersensitivity to statins in mice lacking Pcsk9. Proc Natl Acad Sci U S A. Apr. 12, 2005;102(15):5374-9. Epub Apr. 1, 2005.
Reichhart et al., Splice-activated UAS hairpin vector gives complete RNAi knockout of single or double target transcripts in *Drosophila melanogaster*. Genesis. Sep.-Oct. 2002;34(1-2):160-4.
Rump et al., Preparation of conjugates of oligodeoxynucleotides and lipid structures and their interaction with low-density lipoprotein. Bioconjug Chem. May-Jun. 1998;9(3):341-9.
Sato et al., Tumor targeting and imaging of intraperitoneal tumors by use of antisense oligo-DNA complexed with dendrimers and/or avidin in mice. Clin Cancer Res. Nov. 2001;7(11):3606-12.
Schaniel et al., Delivery of short hairpin RNAs—triggers of gene silencing—into mouse embryonic stem cells. Nat Methods. May 2006;3(5):397-400.
Schell et al., Stimulation of the uptake of polynucleotides by poly(L-lysine). Biochim Biophys Acta. Mar. 27, 1974;340(3):323-33.
Seela et al., Oligodeoxyribonucleotides containing 1,3-propanediol as nucleoside substitute. Nucleic Acids Res. Apr. 10, 1987;15(7):3113-29.
Seidah et al., Proprotein and prohormone convertases: a family of subtilases generating diverse bioactive polypeptides. Brain Res. Nov. 27, 1999;848(1-2):45-62.
Shi, Mammalian RNAi for the masses. Trends Genet. Jan. 2003;19(1):9-12.
Shioji et al., Genetic variants in PCSK9 affect the cholesterol level in Japanese. J Hum Genet. 2004;49(2):109-14. Epub Jan. 15, 2004.
Soutschek et al., Therapeutic silencing of an endogenous gene by systemic administration of modified siRNAs. Nature. Nov. 11, 2004;432(7014):173-8.
Sui et al., A DNA vector-based RNAi technology to suppress gene expression in mammalian cells. Proc Natl Acad Sci U S A. Apr. 16, 2002;99(8):5515-20.
Tang et al., An RNA interference-based screen identifies MAP4K4/NIK as a negative regulator of PPARgamma, adipogenesis, and insulin-responsive hexose transport. Proc Natl Acad Sci U S A. Feb. 14, 2006;103(7):2087-92. Epub Feb. 3, 2006.
Taylor et al., Curbing activation: proprotein convertases in homeostasis and pathology. FASEB J. Jul. 2003;17(10):1215-27.
Timms et al., A mutation in PCSK9 causing autosomal-dominant hypercholesterolemia in a Utah pedigree. Hum Genet. Mar. 2004;114(4):349-53. Epub Jan. 15, 2004.
Uhlmann et al., Antisense oligonucleotides: a new therapeutic principle. Chem Rev. 1990;90(4):543-84.
Vlassov et al., Transport of oligonucleotides across natural and model membranes. Biochim Biophys Acta. Jun. 29, 1994;1197(2):95-108.
Wagner et al., Transferrin-polycation-DNA complexes: the effect of polycations on the structure of the complex and DNA delivery to cells. Proc Natl Acad Sci U S A. May 15, 1991;88(10):4255-9.
Wolfrum et al., Mechanisms and optimization of in vivo delivery of lipophilic siRNAs. Nat Biotechnol. Oct. 2007;25(10):1149-57. Epub Sep. 16, 2007.
Xue et al., Mesodermal patterning defect in mice lacking the Ste20 NCK interacting kinase (NIK). Development. May 2001;128(9):1559-72.

Yamada et al., Synthesis and properties of oligonucleotides having a chemically stable 2-(trimethylsilyl)benzoyl group. Nucleic Acids Symp Ser (Oxf). 2008;(52):301-2. doi: 10.1093/nass/nrn152.
Yu et al., RNA interference by expression of short-interfering RNAs and hairpin RNAs in mammalian cells. Proc Natl Acad Sci U S A. Apr. 30, 2002;99(9):6047-52. Epub Apr. 23, 2002.
Zhou et al., Proteolytic processing in the secretory pathway. J Biol Chem. Jul. 23, 1999;274(30):20745-8.
Zuckermann et al., Design, construction and application of a fully automated equimolar peptide mixture synthesizer. Int J Pept Protein Res. Dec. 1992;40(6):497-506.
Zuckermann et al., Efficient method for the preparation of peptoids [oligo(N-substituted glycines)] by submonomer solid-phase synthesis. Journal of the American Chemical Society. 1992;114 (26):10646-10647.
U.S. Appl. No. 14/728,764, filed Jun. 2, 2015, Woolf et al.
U.S. Appl. No. 14/729,006, filed Jun. 2, 2015, Khvorova et al.
U.S. Appl. No. 14/728,653, filed Jun. 2, 2015, Libertine et al.
Behlke, Progress towards in vivo use of siRNAs. Mol Ther. Apr. 2006;13(4):644-70. Epub Feb. 14, 2006.
Alahari et al., Inhibition of expression of the multidrug resistance-associated P-glycoprotein of by phosphorothioate and 5' cholesterol-conjugated phosphorothioate antisense oligonucleotides. Mol Pharmacol. Oct. 1996;50(4):808-19.
Salomon et al., Modified dsRNAs that are not processed by Dicer maintain potency and are incorporated into the RISC. Nucleic Acids Res. Jun. 2010;38(11):3771-9. doi: 10.1093/nar/gkq055. Epub Feb. 18, 2010.
Vermeulen et al., The contributions of dsRNA structure to Dicer specificity and efficiency. RNA. May 2005;11(5):674-82. Epub Apr. 5, 2005.
U.S. Appl. No. 15/508,768, filed Mar. 3, 2017, Cauwenbergh et al.
Fisher et al., Intracellular disposition and metabolism of fluorescently-labeled unmodified and modified oligonucleotides microinjected into mammalian cells. Nucleic Acids Res. Aug. 11, 1993;21(16):3857-65.
Holmes et al., Syntheses and oligonucleotide incorporation of nucleoside analogues containing pendant imidazolyl or amino functionalities—the search for sequence-specific artificial ribonucleases. Eur J Org Chem. Apr. 13, 2005;5171-83. DOI; 10.1002/ejoc.20050413.
Rozners et al., Expanding functionality of RNA: synthesis and properties of RNA containing imidazole modified tandem G-U wobble base pairs. Chem Commun (Camb). Dec. 14, 2005;(46):5778-80.
[No Author Listed] RXi Pharmaceuticals Corporation. Ex 99.1. OTC: RXII. Mar. 2013. 38 pages.
Shoeman et al., Fluorescence microscopic comparison of the binding of phosphodiester and phosphorothioate (antisense) oligodeoxyribonucleotides to subcellular structures, including intermediate filaments, the endoplasmic reticulum, and the nuclear interior. Antisense Nucleic Acid Drug Dev. Aug. 1997;7(4):291-308.
Snead et al., RNA interference trigger variants: getting the most out of RNA for RNA interference-based therapeutics. Nucleic Acid Ther. Jun. 2012;22(3):139-46. doi: 10.1089/nat.2012.0361. Review.
Stein et al., A specificity comparison of four antisense types: morpholino, 2'-O-methyl RNA, DNA, and phosphorothioate DNA. Antisense Nucleic Acid Drug Dev. Jun. 1997;7(3):151-7.
Summerton et al., Morpholino and phosphorothioate antisense oligomers compared in cell-free and in-cell systems. Antisense Nucleic Acid Drug Dev. Apr. 1997;7(2):63-70.
U.S. Appl. No. 15/532,804, filed Jun. 2, 2017, Cauwenbergh et al.
U.S. Appl. No. 15/638,586, filed Jun. 30, 2017, Woolf et al.
U.S. Appl. No. 15/742,093, filed Jan. 5, 2018, Cardia et al.
U.S. Appl. No. 15/742,117, filed Jan. 5, 2018, Byrne et al.
U.S. Appl. No. 15/758,576, filed Mar. 8, 2018, Cauwenbergh et al.
U.S. Appl. No. 15/769,555, filed Apr. 19, 2018, Cardia et al.
U.S. Appl. No. 15/905,118, filed Feb. 26, 2018, Khvorova et al.
U.S. Appl. No. 15/918,605, filed Mar. 12, 2018, Khvorova et al.

* cited by examiner

Figure 1

| Full Sequence Name | ID Numb | Polarity | Sequence (5'->3') |
|---|---|---|---|
| Sequence Designed and Tested | | | |
| SD01-436-21-10033 (R1 var) | 10033 | Sense | P.C*G*A*U.G.U.C.U.A.U.U.G.A.A.G*A*U*U*C |
| | | Antisense | P.A*U*C.U.U.C.A.A.U.A.G.A.C.A.I.C.A*U*C*G*C |
| SD01-395-21-10034 (R2) | 10034 | Sense | P.G*G*A*G.A.I.C.U.U.G.G.G.C.A.A.U.G.U*G*A*U*U |
| | | Antisense | P.U.U.C.A.I.C.A.I.U.G.C.C.C.A.A.G.I.U.C.I.U*C*U*U |
| SD01-436-21-10036 (R1 unmod) | 10036 | Sense | P.C.G.A.U.G.U.C.U.A.U.U.G.A.A.G.A.U.U.C |
| | | Antisense | P.A.U.C.U.U.C.A.A.U.A.G.A.C.A.C.A.U.C.G.C |
| SD01-395-21-10037 (R2 unmod) | 10037 | Sense | P.G.G.A.G.A.C.U.U.G.G.G.C.A.A.U.G.U.G.A.U.U |
| | | Antisense | P.U.C.A.C.A.U.U.G.C.C.C.A.A.G.U.C.U.C.C.U.U |
| SD01-436-21-10104 (R1 var with 2'Ome) | 10104 | Sense | P.C*G*A*mU.G.mU.G.U.C.U.A.U.U.G.A.A.G*A.mU*mU*C |
| | | Antisense | P.A.mU.mC.mU.U.C.A.A.U.A.G.A.C.A.mC.A*mU*mC*G*G*C |
| SD01-436-21-10105 (R1) | 10105 | Sense | P.C*G*A*U.G.U.G.U.C.U.A.U.U.G.A.A.G*A*U*U*C |
| | | Antisense | P.A*U*C.U.U.C.A.A.U.A.G.A.C.A.C.A*U*C*G*G*C |
| Additional Sequence Designed | | | |
| (R1 unmod no Overhangs) | 10881 | Sense | P.C.G.A.U.G.U.C.U.A.U.U.G.A.A.G.A.U |
| | | Antisense | P.A.U.C.U.U.C.A.A.U.A.G.A.C.A.C.A.U.C.G |
| (R1 unmod no Overhangs or 5'P) | 10882 | Sense | C.G.A.U.G.U.C.U.A.U.U.G.A.A.G.A.U |
| | | Antisense | A.U.C.U.U.C.A.A.U.A.G.A.C.A.C.A.U.C.G |
| (R1 unmod no 5'P) | 10883 | Sense | C.G.A.U.G.U.C.U.A.U.U.G.A.A.G.A.U.U.C |
| | | Antisense | A.U.C.U.U.C.A.A.U.A.G.A.C.A.C.A.U.C.G.G.C |
| (R1 with 2'Ome replacing 2'F) | 10884 | Sense | P.C*G*A*mU.G.mU.G.U.C.U.A.U.U.G.A.A.G*A*mU*mU*C |
| | | Antisense | P.A.mU.mC.mU.U.C.A.A.U.A.G.A.C.A.mC.A*mU*mC*G*G*C |
| (R1 with 2'Ome replacing 2'F, no Overhangs) | 10885 | Sense | C*G*A*mU.G.mU.G.U.C.U.A.U.U.G.A*A*G*A.mU |
| | | Antisense | A.mU.mC.mU.U.C.A.A.U.A.G.A.C.A*mC*A*mU*mC*G |
| R1 w/ 001-011 Chem, blunt | 10886 | Sense | mC.mG.mA.mU.G.mU.G.C.U.A.U.U.G.A.mA.mG.mA.mU |
| | | Antisense | A.U.C.U.U.C.A.A.U.A.G.A.C.A.C.A.U.C.G |
| R1 w/ 001-042 Chem, blunt | 10887 | Sense | mC.mG.mA.mU.G.mU.G.C.U.A.U.U.G.A.mA.mG.mA.mU |
| | | Antisense | A.mU.C.U.U.C.A.A.U.A.G.A.C.A.C.A.mU.mG.mA.mU |
| R1 w/ MW001-011 Chem, blunt | 10888 | Sense | mC.mG.mA.mU.G.mU.G.C.U.A.U.U.G.A.mA.mG.mA.mU |
| | | Antisense | A.mU.C.U.U.C.A.A.U.A.G.A.C.A.C.A.U.C.G |
| R1 w/ Extensive 2'Ome Sense, blunt | 10889 | Sense | mC.mG.mA.mU.mG.mU.G.mC.U.A.U.mU.G.mA.mA.mG.mA.mU |
| | | Antisense | A.U.C.U.U.C.A.A.U.A.G.A.C.A.C.A.U.C.G |
| R1 original chemistry, blunt | 10891 | Sense | P.C*G*A*U.G.U.G.U.C.U.A.U.U.G.A.A.G*A*U |
| | | Antisense | P.A*U*C.U.U.C.A.A.U.A.G.A.C.A.C.A*U*C*G |
| R1 w/ 011-013 chem | 10892 | Sense | mC.mG.mA.mU.G.U.G.C.U.A.U.U.G.A.mA.mG.mA.mU |
| | | Antisense | A.U.C.U.U.C.A.A.U.A.G.A.C.A.C.mA*mU*mC*mG |
| Conversion of R1 into Alternate RNAi Compounds (Longer Length) | | | |
| SD01-430-25-10174 (Tested) | 10174 | Sense | 5'-P.mU.mG.mU.mG.C.G.A.U.G.U.C.U.A.U.U.G.A.mA.mG.mA.mU |
| | | Antisense | A.U.C.U.U.C.A.A.U.A.G.A.C.A.U.C.G.G.C.C.A.C.A |
| SD01-429-26-10175 (Tested) | 10175 | Sense | 5'-P.mG.mG.mU.mG.C.C.G.A.U.G.C.A.C.A.U.C.G.G.C.A.mA.mG.mA.mU |
| | | Antisense | A.U.C.U.U.C.A.A.U.A.G.A.C.A.C.A.U.C.G.A*U*U*C*G |
| SD01-428-27-10890 (Designed) | 10890 | Sense | 5'-P.mA.mG.mU.mG.U.G.G.C.C.G.A.U.G.U.G.C.U.A.U.U.G.A.mA.mG.mA.mU |
| | | Antisense | A.U.C.U.U.C.A.A.U.A.G.A.C.A.C.A.U.C.G.G.C.C.A.C.A.C.C |

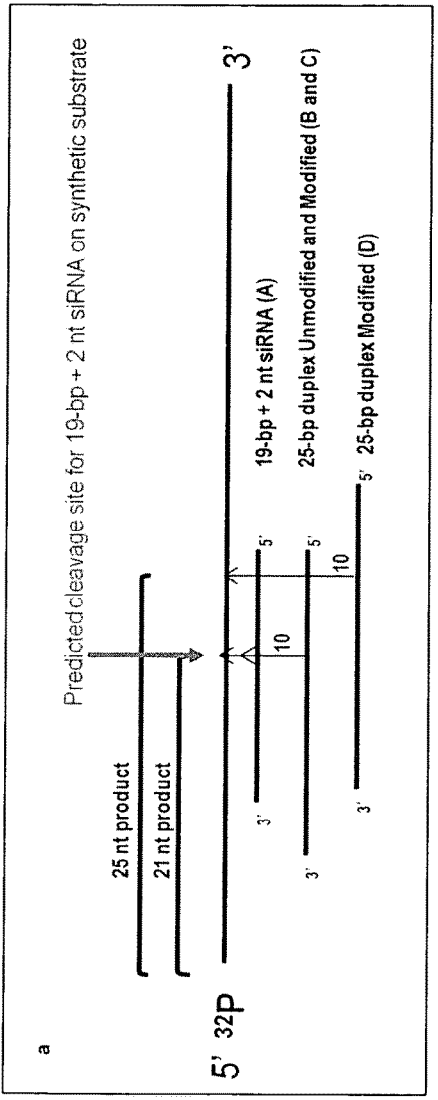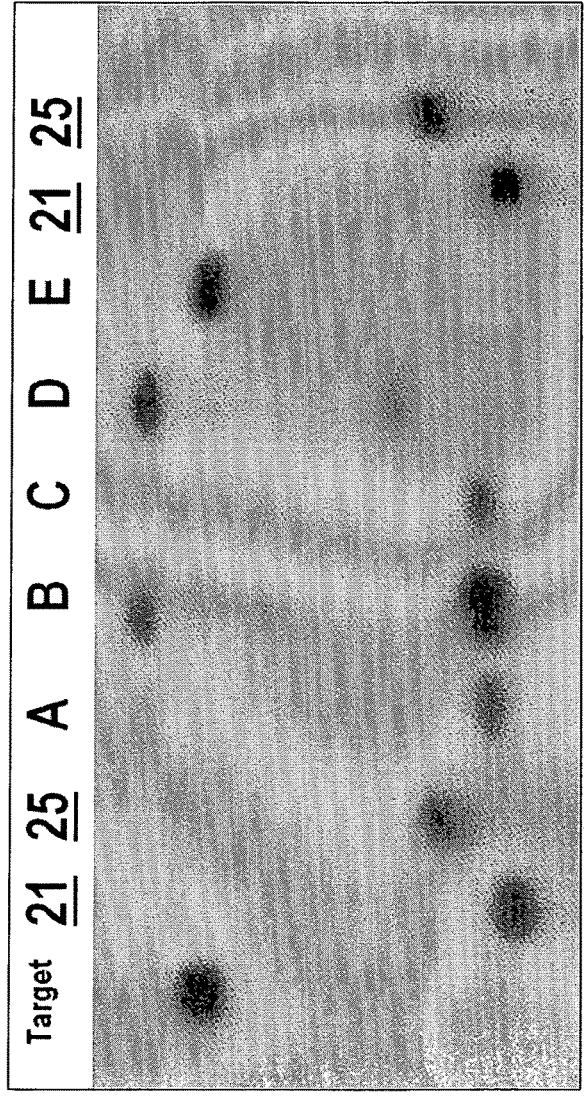
Figure 9A
Figure 9B

Figure 10A

| ID Number | Polarity | Sequence (5'->3') |
|---|---|---|
| 10015 | Sense | P.G.G.C.A.A.G.G.U.G.G.A.A.U.G.A.A.G.A.A.A.G.U.A |
|  | Antisense | U.A.C.U.U.U.C.U.U.C.A.U.U.C.C.A.C.C.U.U.G.C.C |
| 10023 | Sense | P.G.C.C.G.A.U.C.U.U.G.U.C.U.A.U.G.A.A.G.A.U.C.U.G |
|  | Antisense | C.A.G.A.A.U.C.U.U.C.A.U.A.G.A.C.A.A.G.A.U.C.G.G.C |

Figure 10B

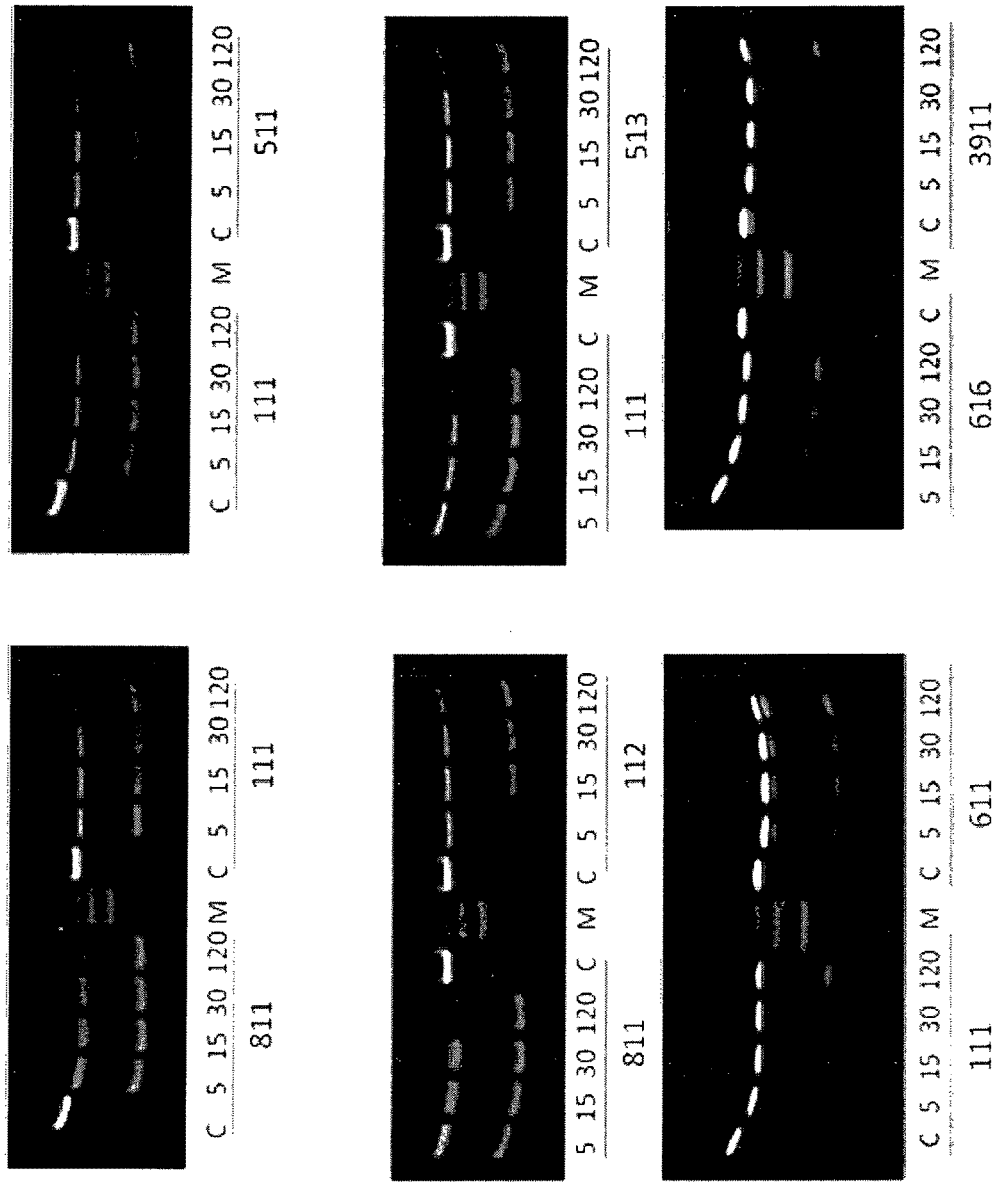
Figure 14A  A  Based on sequence 10023

B  Based on sequence 10015

Figure 15B

| Sequence Name | Polarity | Sequence (5'->3') |
|---|---|---|
| 19-bp + 2 nt duplex (11892) | Sense | U.A.C.U.U.U.C.U.U.C.A.U.U.C.C.A.C.C.U.U |
| | Antisense | G.G.U.G.G.A.A.A.U.G.A.A.G.A.A.A.G.U.A.U.U |
| (11893) | Sense | G.G.C.A.A.A.G.G.U.G.G.A.A.A.U.G.A.A.G.A.A.A.G.U.A |
| | Antisense | U.A.C.U.U.U.C.U.U.C.A.U.U.U.C.C.A.C.C.U.U.U.G.C.C |
| (11897) | Sense | mG.mG.mC.mA.A.A.G.G.U.G.G.A.A.A.U.G.A.A.G.A.A.A.mA.mG.mU.mA |
| | Antisense | U.A.C.U.U.U.C.U.U.C.A.U.U.U.C.C.A.C.C.U.U.U.G.C.C |

Figure 16B

| Sequence Name | Polarity | Sequence (5'->3') |
|---|---|---|
| 19-bp + 2 nt unmodified (10167) | Sense | G.G.A.A.A.G.A.C.U.G.U.U.C.C.A.A.A.A.A.U.U |
| | Antisense | U.U.U.U.G.G.A.A.C.A.G.U.C.U.U.U.C.C.U.U |
| 25-bp unmodified (11388) | Sense | C.U.C.U.U.C.G.G.A.A.A.G.A.C.U.G.U.U.C.C.A.A.A.A.A |
| | Antisense | U.U.U.U.U.G.G.A.A.C.A.G.U.C.U.U.U.C.C.G.A.A.G.A.G |
| 25-bp w/ 2'OMe (10460) | Sense | mC.mU.mC.mU.U.C.G.G.A.A.A.G.A.C.U.G.U.U.C.C.A.mA.mA.mA.mA |
| | Antisense | U.U.U.U.U.G.G.A.A.C.A.G.U.C.U.U.U.C.C.G.A.A.G.A.G |
| 27-bp w/ 2'OMe (10462) | Sense | mG.mU.mC.mU.U.C.G.G.A.A.C.A.G.U.C.U.U.U.C.C.A.mA.mA.mA.mA.m A.mA |
| | Antisense | U.U.U.U.U.G.G.A.A.C.A.G.U.C.U.U.U.C.C.G.A.A.G.A.G.A.C |

MODIFIED RNAI POLYNUCLEOTIDES AND USES THEREOF

RELATED APPLICATIONS

This application is a national stage filing under 35 U.S.C. § 371 of international application PCT/US2009/000852, filed Feb. 11, 2009, which was published under PCT Article 21(2) in English, and claims the benefit under 35 U.S.C. § 119(e) of U.S. Provisional Application Ser. No. 61/065,335, entitled "MODIFIED RNAI POLYNUCLEOTIDES AND USES THEREOF" filed on Feb. 11, 2008, the disclosures of which are incorporated by reference in their entireties.

BACKGROUND OF THE INVENTION

Complementary oligonucleotide sequences are promising therapeutic agents and useful research tools in elucidating gene functions. However, prior art oligonucleotide molecules suffer from several problems that may impede their clinical development, and frequently make it difficult to achieve intended efficient inhibition of gene expression (including protein synthesis) using such compositions.

For example, classic siRNAs have limitations and drawbacks that may result in those agents being only moderately useful as human therapeutics. Specifically, classic siRNA is double-stranded. For each molecule, two strands need to be synthesized and paired up. Classic siRNA is made from naturally occurring ribonucleotides and is vulnerable to nucleases and spontaneous hydrolysis. The strands of classic siRNA are paired to each other except for an overhang of one strand at each end, and are about 19 to 23 nucleotides long. This configuration limits the variety and activity of the compound. For example, longer oligonucleotides can have higher binding activity to target RNA, which often correlates with higher activity. The overhangs of classic siRNA cause instability (because single strands are more nuclease resistant than double strands in most cases) and degradation, and may be the cause of the molecules "sticking" to each other or other nucleotides.

In addition, it is widely believed that double stranded RNAs longer than 21-mer are cleaved by Dicer or Dicer-like RNAse III in mammalian cells, resulting in classic siRNA products. One strand of the Dicer-cleavage products is then loaded onto the RISC complex, and guides the loaded RISC complex to effect RNA interference (RNAi). However, since Dicer is not sequence specific, the Dicer-cleavage products of unmodified long dsRNA is a heterogeneous mixture of 21-mers, each may have different biological activity and/or pharmacological property. In addition, each 21-mer may have a distinct off-target effect (e.g., inhibiting the function of an unintended target due to, for example, spurious sequence homology between the Dicer cleavage product and target mRNAs). In other words, the active drug (e.g., the 21-mers) may be multiple species with relatively unpredictable target specificities, biological activities and/or pharmacological properties. Also, Dicer product is shorter than the parent, which leads to a lower affinity guide strand.

Other problems include the susceptibility of the siRNAs to non-specific nuclease degradation when applied to biological systems. Therefore, it would be of great benefit to improve upon the prior art oligonucleotides by designing improved oligonucleotides that either are free of or have reduced degree of the above-mentioned problems.

SUMMARY OF THE INVENTION

One aspect of the invention relates to a double-stranded RNA (dsRNA) construct of 12-49 (preferably 19-49) nucleotides in length, for inhibiting expression of a target gene, said dsRNA comprising: (1) a sense strand having a 5'-end and a 3'-end, wherein one or more nucleotides at each of said 5'- and 3'-ends of said sense strand have 2'-modified ribose sugars, and, (2) an antisense strand having a 5'-end and a 3'-end, which hybridizes to said sense strand and to mRNA of said target gene, wherein said antisense strand includes a 2'-modified ribose sugar at the 2nd nucleotide from the 5'-end of the antisense strand, wherein (a) said dsRNA is resistant to cleavage by Dicer, (b) the antisense strand associates with RISC, and (c) the dsRNA inhibits expression of the target gene in a sequence-dependent manner.

Another aspect of the invention provides a double-stranded RNA (dsRNA) construct of 12-49 (preferably 19-49) nucleotides in length, for inhibiting expression of a target gene, said dsRNA comprising: (1) a sense strand having a 5'-end and a 3'-end, wherein one or more nucleotides at each of said 5'- and 3'-ends of said sense strand have 2'-modified ribose sugars, and, (2) an antisense strand having a 5'-end and a 3'-end, which hybridizes to said sense strand and to mRNA of said target gene, wherein said antisense strand comprises, at the 3'-end of the antisense strand, (i) at least four consecutive 2'-modified ribose sugars with non-hydrolyzable internucleotide linkages, (ii) 1, 2, 3, 4, 5, 6, 7, 8, 9, 10, 11, or 12 2'-modified ribose sugars, preferably 2'-O-methyl modified ribose sugars, or, (iii) a protective group, wherein (a) said dsRNA is resistant to cleavage by Dicer, (b) the antisense strand associates with RISC, and (c) the dsRNA inhibits expression of the target gene in a sequence-dependent manner.

Another aspect of the invention provides a double-stranded RNA (dsRNA) construct of 12-49 (preferably 19-49) nucleotides in length, for inhibiting expression of a target gene, the dsRNA comprising: (1) a sense strand having a 5'-end and a 3'-end, wherein one or more nucleotides at each of said 5'- and 3'-ends of said sense strand have 2'-modified ribose sugars, and said sense strand comprises a mismatch nucleotide at the 2nd nucleotide from the 3'-end of the sense strand, and, (2) an antisense strand having a 5'-end and a 3'-end, which hybridizes to said sense strand and to mRNA of said target gene, wherein (a) said dsRNA is resistant to cleavage by Dicer, (b) the antisense strand associates with RISC, and (c) the dsRNA inhibits expression of the target gene in a sequence-dependent manner.

Another aspect of the invention provides a double-stranded RNA (dsRNA) construct of 12-49 (preferably 19-49) nucleotides in length, for inhibiting expression of a target gene, the dsRNA comprising: (1) a sense strand having a 5'-end and a 3'-end, wherein four consecutive 2'-O-methyl nucleotides are present at each of said 5'- and 3'-ends of said sense strand, and, (2) an antisense strand having a 5'-end and a 3'-end, which hybridizes to said sense strand and to mRNA of said target gene, wherein said antisense strand: (a) comprises four consecutive 2'-O-methyl modified 3'-end nucleotides with phosphothioate linkages; or, (b) comprises a 2'-O-methyl modified nucleotide at the 2nd nucleotide on the 5'-end and no other modified nucleotides, wherein (a) said dsRNA is resistant to cleavage by Dicer, (b) the antisense strand associates with RISC, and (c) the dsRNA inhibits expression of the target gene in a sequence-dependent manner.

Another aspect of the invention provides a double-stranded RNA (dsRNA) construct of 12-49 (preferably 19-49) nucleotides in length, for inhibiting expression of a target gene, the dsRNA comprising: (1) a sense strand having a 5'-end and a 3'-end, wherein the sense strand comprises 12 and 10 consecutive 2'-O-methyl nucleotides at the 5'-end and the 3'-end, respectively, and, (2) an antisense strand having a 5'-end and a 3'-end, which hybridizes to said sense strand and to mRNA of said target gene, wherein said antisense strand: (a) is unmodified; (b) comprises four consecutive 2'-O-methyl modified 3'-end nucleotides with phosphothioate linkages; or, (c) comprises a 2'-O-methyl modified nucleotide at the 2nd nucleotide on the 5'-end and no other modified nucleotides, wherein (a) said dsRNA is resistant to cleavage by Dicer, (b) the antisense strand associates with RISC, and (c) the dsRNA inhibits expression of the target gene in a sequence-dependent manner.

In certain embodiments, the antisense strand directs the uniform cleavage of the target gene mRNA at a single site between the 10th and 11th nucleotides from the 5'-end of the antisense strand.

In certain embodiments, the sense strand of the dsRNA is cleavable by RISC at a single site between the 10th and the 11th nucleotides from the 3'-end of the sense strand.

In certain embodiments, the dsRNA construct is blunt-ended.

In certain embodiments, the 5'-end 12 nucleotides and the 3'-end 10 nucleotides of the sense strand are 2'-modified ribose sugars.

In certain embodiments, each end of the sense strand comprises a continuous stretch of 2'-modified ribose sugars.

In certain embodiments, each end of the sense strand comprises a continuous stretch of four 2'-modified ribose sugars.

In certain embodiments, the antisense strand comprises discontinuous 2'-modified ribose sugars, wherein the 10th and 11th antisense nucleotides are not modified.

In certain embodiments, the antisense strand comprises 2'-modified ribose sugars for each 2, 3, 4, 5, 6, 7, 8, or 9 nucleotides.

In certain embodiments, the most 5'-end 2'-modified ribose sugar on the antisense strand is the 2nd nucleotide.

In certain embodiments, the dsRNA construct is: 12-35 nucleotides in length; 25-30 nucleotides in length; 25, 26, 27, 28, 29, or 30 nucleotides in length; >22 nucleotides in length; >25 nucleotides in length; or 31-49 nucleotides in length.

In certain embodiments, each end of the sense strand comprises, independently, 4-16 2'-modified ribose sugars and/or non-hydrolyzable internucleotide linkages.

In certain embodiments, each end of the sense strand comprises a symmetrical or an asymmetrical number of 2'-modified ribose sugars.

In certain embodiments, the 2'-modified ribose sugars are 2'-O-alkyl nucleotides, 2'-deoxy-2'-fluoro nucleotides, 2'-deoxy nucleotides, 2'-H (deoxyribonucleotides), or combination thereof.

In certain embodiments, the 2'-O-alkyl nucleotides are 2'-O-methyl nucleotides.

In certain embodiments, the 2'-O-alkyl nucleotides are 2'-O-allyl nucleotides.

In certain embodiments, the antisense strand comprises a 2'-O-methyl modified nucleotide at the 2nd nucleotide on the 5'-end of the antisense strand and no other modified nucleotides.

In certain embodiments, the dsRNA has enhanced target specificity or reduced off-target silencing compared to a similar construct without the 2'-modification at said position(s).

In certain embodiments, the antisense strand comprises at least four consecutive 2'-O-methyl modified 3'-end nucleotides with phosphothioate linkages.

In certain embodiments, the sense strand of the dsRNA comprises a mismatch nucleotide at the 2nd nucleotide from the 3'-end of the sense strand.

In certain embodiments, the dsRNA has improved stability in serum and/or cerebral spinal fluid compared to an unmodified dsRNA having the same sequence.

In certain embodiments, the last 2nd-8th nucleotides at the 3'-end of the sense strand mismatch their corresponding antisense strand nucleotides.

In certain embodiments, the dsRNA does not induce interferon response in primary cells.

In certain embodiments, either end of the sense strand and/or the 3'-end of the antisense strand is blocked by a protective group.

In certain embodiments, the protective group is an inverted nucleotide, an inverted abasic moiety, or an amino-end modified nucleotide.

In certain embodiments, the inverted nucleotide comprises an inverted deoxynucleotide.

In certain embodiments, the inverted abasic moiety comprises an inverted deoxyabasic moiety.

In certain embodiments, the inverted deoxyabasic moiety is a 3',3'-linked or 5',5'-linked deoxyabasic moiety.

In certain embodiments, alternating nucleotides on the ends of the sense and/or antisense strands comprise 2'-modified ribose sugars, and wherein each of the 2'-modified ribose sugars faces an unmodified nucleotide on the opposite strand.

In certain embodiments, the first 2'-modified antisense nucleotide is the most 5'-end antisense nucleotide or the 2nd nucleotide from the 5'-end of the antisense strand.

In certain embodiments, the target gene is SOD1, PPIB, RIP140, PCSK9, TNFα, AP2 (adipocyte lipid-binding protein), or MAP4K4.

In certain embodiments, the sense strand nucleotides between the 2'-modified ribose nucleotides are 2'-F modified.

In certain embodiments, the sense strand nucleotides between the 2'-modified ribose nucleotides are purine nucleotides, optionally having 2'-F modification and/or phosphorothioate linkage.

In certain embodiments, the sense strand nucleotides between the 2'-modified ribose nucleotides form one or more bulges of 1-5 nucleotides each.

In certain embodiments, each continuous stretch of 2'-modified ribose nucleotides independently starts from the terminal nucleotide, the second nucleotide from the terminal nucleotide, or the third nucleotide from the terminal nucleotide.

In certain embodiments, between 50-100% of the pyrimidine nucleotides of the antisense strand are, independently, 2'-F modified or 2'-O-methyl-modified.

In certain embodiments, the 5'-end of the antisense strand is phosphorylated.

In a related aspect, the invention also provides a construct for inhibiting expression of a target gene, wherein the construct is identical to any of the subject dsRNA, except for a single nick on the sense strand. For example, the nick may occupy the opposite position of the nucleotide about 10 bases from the 5' end of the antisense strand. The nick may also occupy the opposite position of a nucleotide about 5-15 bases from the 5' end of the antisense strand. In certain embodiments, the ΔG of each duplex region is less than about −13 kcal/mole.

Another aspect of the invention provides a vector expressing at least one strand of the subject dsRNA (e.g., unmodified sense strand, etc.).

Another aspect of the invention provides a cell comprising the subject vector, or the subject dsRNA.

In certain embodiments, the cell is a mammalian cell in culture.

In certain embodiments, the cell is a human cell.

Another aspect of the invention provides a composition comprising the dsRNA of any of claims 1-5, and a pharmaceutically acceptable carrier or diluent.

Another aspect of the invention provides a method for inhibiting the expression of a target gene in a mammalian cell, comprising contacting the mammalian cell with the subject dsRNA construct.

In certain embodiments, the mammalian cell is in culture.

In certain embodiments, the mammalian cell is a human cell.

In certain embodiments, the mammalian cell is contacted in the presence of a delivery reagent.

In certain embodiments, the delivery reagent is a lipid.

In certain embodiments, the lipid is a cationic lipid.

In certain embodiments, the delivery reagent is a liposome.

Another aspect of the invention provides a method for inhibiting the expression of a target gene in a mammalian cell, comprising contacting the mammalian cell with a vector expressing at least one strand of the subject dsRNA construct.

Another aspect of the invention provides a method for improving the gene silencing effect of a small interference RNA (siRNA), comprising modifying the sense and/or antisense nucleotides of the siRNA to become the subject dsRNA construct.

Another aspect of the invention provides a method for evaluating in vivo delivery of an siRNA construct to a target site, comprising co-delivering the siRNA construct with any of the subject dsRNA construct that targets PPIB, and assaying the inhibition of PPIB function at the target site, wherein successful inhibition of the PPIB function at the target site is indicative of successful in vivo delivery of the siRNA construct to the target site.

Another aspect of the invention relates to any of the dsRNA constructs disclosed herein, such as those disclosed in the tables and/or those against SOD1 or other specific target genes.

It is further contemplated that, any embodiments recited herein and elsewhere in the specification can be combined with any other embodiments where applicable.

BRIEF DESCRIPTION OF THE DRAWINGS

FIG. 1 shows certain modified RNAi constructs of the invention (Alternate RNAi Compounds for simplicity). The sequences listed (in descending order in the table) correspond to the following SEQ ID NOs: 43, 44, 125-130, 171, 172, 171, 172 and 781-808.

FIGS. 9A and 9B indicate the uniform cleavage point at 10 nt from the 5'-end of the antisense strand for non-Dicer processed duplexes longer that 21 nt. A synthetic substrate was chemically synthesized to correspond to a 50 nt region of the SOD1 gene containing the target sequence for the RNA duplexes tested. FIG. 9A is a schematic drawing of the synthetic substrate and predicted cleavage position and products. In FIG. 9B, RNA duplexes targeting SOD1 were transfected into 293 cells expressing c-myc Ago2 as described in methods. The cells were harvested, lysed, c-myc Ago2 was immunoprecipitated, and reconstituted in buffer. The immunoprecipitates were incubated with a 50 nt $^{32}$-P-labeled synthetic substrate for 2 h at 30° C. as described in methods. After 2 h incubations, samples were loaded onto a denaturing, polyacrylamide gel along with size markers (shown underlined). Sample letters correspond to the following duplexes shown in the schematic in panel A. A=unmodified 19-bp+2 nt siRNA, B=unmodified 25-bp duplex, C=25-bp duplex with 4/4 2'OMe, D=25-bp duplex with 4/4 2'OMe, E=Luciferase Ctrl duplex.

FIG. 10A indicates two exemplary sequences, ID Nos. 10015 and 10023, that were used for extensive chemical modification analysis. 10015 Sense corresponds to SEQ ID NO:809; 10015 Antisense corresponds to SEQ ID NO:810; 10023 Sense corresponds to SEQ ID NO:811 and 10023 Antisense corresponds to SEQ ID NO:812.

FIG. 10B lists each modification chemistry ID for sense strand (001, 002, 003, etc.) and antisense strand (011, 012, 013, etc.), indicating for each ID a detailed overview of modifications on each nucleotide position for all 25-mers designed and/or tested.

FIGS. 14A and 14B demonstrate the improvement of duplex stability in serum and/cerebral spinal fluid as a result of modifications on each duplex as indicated.

FIG. 15B shows the sequences used in this study. The sequences listed (in descending order in the table) correspond to SEQ ID NOs:814-819.

FIG. 17 shows that 2'-O-Me modifications inhibit and prevent Dicer enzyme processing of >21 nt RNA duplexes into siRNA.

Figure 2:
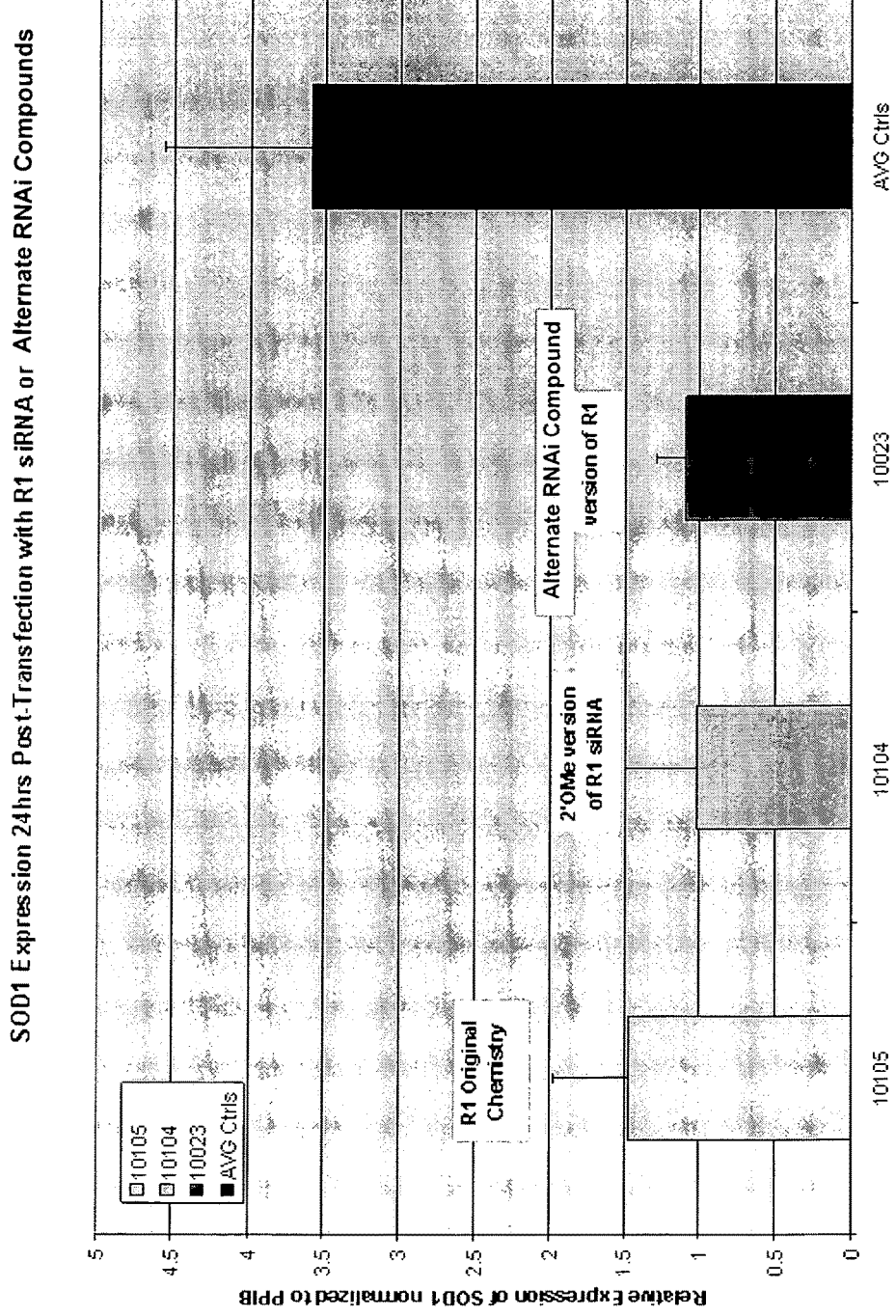
FIG. 2 illustrates SOD1 expression 24 hours post-transfection with R1 siRNA or Alternate RNAi Compounds.

Table 1 provides Alternative RNAi Compound sequences to SOD1 and PPIB. Full Sequence Name is represented by gene name-start site-length-Alternate RNAi Compound ID Number. "P" represents 5' phosphate, while "m" represents 2'O-methyl base modification. "F" represents 2'Fluoro base modification. "*" denotes phosphothioate backbone linkage while "." represents a normal RNA backbone linkage.

Table 2 provides additional Alternative RNAi Compound sequences to SOD1. The notations used in Table 1 applies to Table 2.

Table 3 is a list of RNA duplexes. Single stranded RNA or duplexed RNA was chemically synthesized and annealed as described in methods. "G"=Guanine, "U"=Uracil, "C"=Cytosine, "A"=Adenine, "m"=2'OMethyl base modified, "."=normal RNA backbone linkage. Polarity is shown as PS=Passenger or Sense strand and GS=Guide or antisense strand. Numbers in parentheses correspond to internal sequence database number for duplex tracking.

Table 4 is a list of RNA duplexes in certain figures above. Single stranded RNA or duplexed RNA was chemically synthesized and annealed as described in methods. "G"=Guanine, "U"=Uracil, "C"=Cytosine, "A"=Adenine, "m"=2'OMethyl base modified, "."=normal RNA backbone linkage. Polarity is shown as PS=Passenger or Sense strand and GS=Guide or antisense strand. Numbers in parentheses correspond to internal sequence database number for duplex tracking.

Table 5 is a list of RNA size markers and synthetic substrates used in cleavage assays.

DETAILED DESCRIPTION OF THE INVENTION

I. Overview

The invention is partly based on the surprising discoveries that certain longer dsRNAs (e.g., those with a double-stranded region of more than 21 base pairs) are not cleaved by Dicer or other Dicer-like RNAse III when the sense strands are modified (e.g., at both ends of the sense strand by, for example, 2'-O-methyl groups), and that the antisense strands of such dsRNAs can be loaded into the RISC complex, with the 5'-ends of the antisense strands aligning with the 5'-end of a 21-mer (i.e., the Dicer cleavage product). While the art taught that RNAi compound activity was increased (compared to siRNA) if the compound formed a substrate for Dicer, Applicants have in fact found extremely active RNAi compounds that are not Dicer substrates. The invention is also partly based on the discovery that a RISC complex loaded with such a longer antisense (guide) strand will cleave the target mRNA at a single position corresponding to the position between the 10th and 11th nucleotides from the 5'-end of the antisense (guide) sequence.

A direct implication of Applicants' discoveries is that the antisense strand of such a longer dsRNA becomes the single species of active RNAi reagent, thus facilitating the development of RNAi reagents or therapeutics with higher target specificity, and better-defined biological activity and/or pharmacological property.

Furthermore, with the knowledge that longer dsRNA can be engineered to resist Dicer cleavage, and the knowledge that the Dicer-resistant antisense strand can be loaded onto the RISC complex at defined location to create a single species of active RNAi reagent, one can engineer additional features or modifications into the sense and/or antisense strands to improve the property of the RNAi reagent or therapeutics. In particular, the positioning of modifications in the guide strand relative to the 5' end can now be defined, and this positioning is critical to defining the specificity and activity of such modified RNAi compounds.

Using an exemplary target gene superoxide dismutase 1 (SOD1), Applicants have designed and tested numerous sense and antisense modifications and combinations thereof, and have identified multiple specific modifications that render the long dsRNA Dicer-resistant, yet providing effective target gene silencing and/or a host of other associated benefits.

Thus in one aspect, the invention provides a double-stranded RNA (dsRNA) construct of 12-49 (preferably 19-49) nucleotides in length, for inhibiting expression of a target gene, said dsRNA comprising: (1) a sense strand having a 5'-end and a 3'-end, wherein one or more nucleotides at each of said 5'- and 3'-ends of said sense strand have 2'-modified ribose sugars, and, (2) an antisense strand having a 5'-end and a 3'-end, which hybridizes to said sense strand and to mRNA of said target gene, wherein (a) said dsRNA is resistant to cleavage by Dicer, (b) the antisense strand associates with RISC, and (c) the dsRNA inhibits expression of the target gene in a sequence-dependent manner.

In certain embodiments, the antisense strand is unmodified. In other embodiments, the antisense strand includes a 2'-modified ribose sugar at the 2nd nucleotide from the 5'-end of the antisense strand.

As used herein, "2'-modified ribose sugar" includes those ribose sugars that do not have a 2'-OH group. For example, the 2'-modified ribose sugar may be 2'-O-alkyl nucleotides, 2'-deoxy-2'-fluoro nucleotides, 2'-deoxy nucleotides, 2'-H (deoxyribonucleotides), or combination thereof.

In certain embodiments, the dsRNA of the invention with the above-referenced antisense modification exhibits significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified antisense modification, thus greatly improving the overall specificity of the RNAi reagent or therapeutics.

As used herein, "off-target" gene silencing refers to unintended gene silencing due to, for example, spurious sequence homology between the antisense (guide) sequence and the unintended target mRNA sequence.

In another aspect, the invention provides a double-stranded RNA (dsRNA) construct of 12-49 (preferably 19-49) nucleotides in length, for inhibiting expression of a target gene, said dsRNA comprising: (1) a sense strand having a 5'-end and a 3'-end, wherein one or more nucleotides at each of said 5'- and 3'-ends of said sense strand have 2'-modified ribose sugars, and, (2) an antisense strand having a 5'-end and a 3'-end, which hybridizes to said sense strand and to mRNA of said target gene, wherein said antisense strand comprises, at the 3'-end of the antisense strand, (i) at least four consecutive 2'-modified ribose sugars with non-hydrolyzable internucleotide linkages, (ii) 1, 2, 3, 4, 5, 6, 7, 8, 9, 10, 11, or 12 2'-modified ribose sugars, preferably 2'-O-methyl modified ribose sugars, or, (iii) a protective group, wherein (a) said dsRNA is resistant to cleavage by Dicer, (b) the antisense strand associates with RISC, and (c) the dsRNA inhibits expression of the target gene in a sequence-dependent manner.

According to this aspect of the invention, certain antisense modifications further increase nuclease stability, and/or lower interferon induction, without significantly decrease RNAi activity (or no decrease in RNAi activity at all).

In another aspect, the invention provides a double-stranded RNA (dsRNA) construct of 19-49 nucleotides in length, for inhibiting expression of a target gene, the dsRNA comprising: (1) a sense strand having a 5'-end and a 3'-end, wherein one or more nucleotides at each of said 5'- and 3'-ends of said sense strand have 2'-modified ribose sugars, and said sense strand comprises a mismatch nucleotide at the 2nd nucleotide from the 3'-end of the sense strand, and, (2) an antisense strand having a 5'-end and a 3'-end, which hybridizes to said sense strand and to mRNA of said target gene, wherein (a) said dsRNA is resistant to cleavage by Dicer, (b) the antisense strand associates with RISC, and (c) the dsRNA inhibits expression of the target gene in a sequence-dependent manner.

According to this aspect of the invention, certain mismatches at the 3'-end of the sense strand allow more efficient loading of the antisense strand into the RISC complex, thus leading to more potent RNAi activity. Preferred such sense strand mismatches include: a mismatch at the second to the last nucleotide of the sense strand (which base pairs with the second nucleotide of the Dicer-resistant antisense strand in the RISC complex); and mismatches at the most 3'-end 9 nucleotides, except for the most 3'-end nucleotide, of the sense strand.

It is contemplated that different features of the invention, such as the different sense and/or antisense strand modifications, may be combined except when indicated otherwise, in order to create RNAi constructs with multiple advantages or features over the conventional siRNA constructs.

For example, for all applicable aspects of the invention, the antisense strand may comprise a 2'-modified ribose sugar, such as 2'-O-methyl modified nucleotide, at the $2^{nd}$ nucleotide on the 5'-end of the antisense strand and, preferably no other modified nucleotides. The dsRNA having such modification may have enhanced target specificity or reduced off-target silencing compared to a similar construct without the 2'-O-methyl modification at said position.

For all applicable aspects of the invention, the antisense strand may comprise at least four consecutive 2'-modified ribose sugars, such as 2'-O-methyl modified, 3'-end nucleotides with non-hydrolyzable internucleotide linkages, such as phosphothioate linkages.

For all applicable aspects of the invention, the dsRNA may be cleaved by RISC at a single site between the $10^{th}$ and $11^{th}$ nucleotides of the 3'-end of the sense strand.

For all applicable aspects of the invention, the 5'-end 12 nucleotides and the 3'-end 10 nucleotides of a 25-mer may be 2'-modified ribose sugars. The number of the modified bases may be adjusted depending on the overall length of the construct. For example, for a 27-mer, the 5'-end 12-14 nucleotides and the 3'-end 10-12 nucleotides may be 2'-modified nucleotides, etc.

For all applicable aspects of the invention, the dsRNA may comprise a mismatch nucleotide at the $2^{nd}$ nucleotide from the 3'-end of the sense strand.

Certain combinations of specific antisense and sense strand modifications may even result in unexpected advantages, as partly manifested by enhanced ability to inhibit target gene expression, enhanced serum stability, and/or increased target specificity, etc.

Thus, in another aspect, the invention provides double-stranded RNA (dsRNA) construct of 12-49 (preferably 19-49) nucleotides in length, for inhibiting expression of a target gene, the dsRNA comprising: (1) a sense strand having a 5'-end and a 3'-end, wherein four consecutive 2'-O-methyl nucleotides are present at each of said 5'- and 3'-ends of said sense strand, and, (2) an antisense strand having a 5'-end and a 3'-end, which hybridizes to said sense strand and to mRNA of said target gene, wherein said antisense strand: (a) comprises four consecutive 2'-O-methyl modified 3'-end nucleotides with phosphothioate linkages; or, (b) comprises a 2'-O-methyl modified nucleotide at the 2nd nucleotide on the 5'-end and no other modified nucleotides, wherein (a) said dsRNA is resistant to cleavage by Dicer, (b) the antisense strand associates with RISC, and (c) the dsRNA inhibits expression of the target gene in a sequence-dependent manner.

In another aspect, the invention provides a double-stranded RNA (dsRNA) construct of 12-49 (preferably 19-49) nucleotides in length, for inhibiting expression of a target gene, the dsRNA comprising: (1) a sense strand having a 5'-end and a 3'-end, wherein the sense strand comprises 12 and 10 consecutive 2'-O-methyl nucleotides at the 5'-end and the 3'-end, respectively, and, (2) an antisense strand having a 5'-end and a 3'-end, which hybridizes to said sense strand and to mRNA of said target gene, wherein said antisense strand: (a) is unmodified; (b) comprises four consecutive 2'-O-methyl modified 3'-end nucleotides with phosphothioate linkages; or, (c) comprises a 2'-O-methyl modified nucleotide at the 2nd nucleotide on the 5'-end and no other modified nucleotides, wherein (a) said dsRNA is resistant to cleavage by Dicer, (b) the antisense strand associates with RISC, and (c) the dsRNA inhibits expression of the target gene in a sequence-dependent manner.

In certain embodiments, the antisense strand of the subject dsRNA directs the uniform cleavage of the target gene transcript at a single site between the $10^{th}$ and $11^{th}$ nucleotides from the 5'-end of the antisense strand.

In certain embodiments, the sense strand of the dsRNA is cleavable by RISC at a single site between the 10th and the 11th nucleotides from the 3'-end of the sense strand.

According to this embodiment of the invention, certain sense strand sequences may be cleaved by the RISC complex loaded with the Dicer-resistant guide sequence, at the position where an equivalent mRNA is cleaved. While not wishing to be bound by any particular theory, this is partly because the sense strand share the same or similar sequence as the target mRNA. Therefore, the subject dsRNA constructs include those with a sense strand that can be cleaved between the 10th and 11th 3'-end nucleotides.

The constructs of the invention may have different lengths. In certain embodiments, the preferred lengths of the construct are 12-35, or 12-49, preferably 19-49 nucleotides in length. In certain embodiments, the length of the construct is greater than or equal to 22 nucleotides in length. In certain embodiments, the length of the construct is greater than or equal to 25 nucleotides in length. In certain embodiments, the length of the construct is 26, 27, 28, 29, 30, or 31-49 nucleotides in length. Other lengths are also possible, so long as the lower length limit is the minimal length for a Dicer substrate, and the upper limit is a length that generally will not trigger PKR response in a target cell. In certain embodiments, modifications may alter that upper limit such that longer lengths (such as 50, 60, 70, 80, 90, 100 bp) are tolerable.

In certain embodiments, the dsRNA construct is blunt-ended. In other embodiments, 5'- and/or 3'-end overhangs of 1-4 nucleotides may be present on one or both strands.

For a 25-mer construct, each end of the sense strand may comprise, independently, 4-16 2'-modified nucleotides and/or non-hydrolyzable linkages (e.g., phosphothioate linkages). The number of the modified bases may be adjusted depending on the overall length of the construct. For example, for a 27-mer, each end of the sense strand may comprise, independently, 4-18 2'-modified nucleotides and/or phosphothioate linkages, etc.

In certain embodiments, the 5'-end 12 nucleotides and the 3'-end 10 nucleotides of the sense strand are 2'-modified ribose sugars.

In certain embodiments, each end of the sense strand comprises a continuous stretch of 2'-modified ribose sugars, although each end may have the same number or different numbers of 2'-modified ribose sugars.

In certain embodiments, each end of the sense strand comprises a continuous stretch of four 2'-modified ribose sugars.

In certain embodiments, the antisense strand comprises discontinuous 2'-modified ribose sugars, wherein the 10th and 11th antisense nucleotides are not modified. For example, the antisense strand may comprises 2'-modified ribose sugars for each 2, 3, 4, 5, 6, 7, 8, or 9 nucleotides. The most 5'-end 2'-modified ribose sugar on the antisense strand may be the 2nd nucleotide, or the first nucleotide.

In certain embodiments, the 2'-modified nucleotides are 2'-O-alkyl nucleotides, 2'-deoxy-2'-fluoro nucleotides, 2'-deoxy nucleotides, 2'-H (deoxyribonucleotide), or combination thereof.

In certain embodiments, the 2'-modified nucleotides are pyrimidine nucleotides (e.g., C/U).

For example, the 2'-O-alkyl nucleotides may be 2'-O-methyl nucleotides, or 2'-O-allyl nucleotides.

In certain embodiments, the antisense strand comprises a 2'-O-methyl modified nucleotide at the $2^{nd}$ nucleotide on the 5'-end of the antisense strand and no other modified nucleotides.

In certain embodiments, the modified dsRNA may have improved stability in serum and/or cerebral spinal fluid compared to an unmodified dsRNA having the same sequence.

In certain embodiments, the dsRNA has enhanced target specificity or reduced off-target silencing compared to a similar construct without the 2'-modification at said position(s).

In certain embodiments, the antisense strand comprises at least four consecutive 2'-O-methyl modified 3'-end nucleotides with phosphothioate linkages.

In certain embodiments, the sense strand of the dsRNA comprises a mismatch nucleotide at the $2^{nd}$ nucleotide from the 3'-end of the sense strand.

In certain embodiments, the last $2^{nd}$-$8^{th}$ nucleotides at the 3'-end of the sense strand mismatch their corresponding antisense strand nucleotides.

In certain embodiments, the dsRNA does not induce interferon response in primary cells, such as mammalian primary cells, including primary cells from human, mouse and other rodents, and other non-human mammals.

In certain embodiments, the dsRNA may also be used to inhibit expression of a target gene in an invertebrate organism.

In certain embodiments, the 10th and 11th antisense nucleotides from the 5'-end are not modified.

To further increase the stability of the subject constructs in vivo, either end of the sense strand and/or the 3'-end of the antisense strand may be blocked by protective group(s). For example, protective groups such as inverted nucleotides, inverted abasic moieties, or amino-end modified nucleotides may be used. Inverted nucleotides may comprise an inverted deoxynucleotide. Inverted abasic moieties may comprise an inverted deoxyabasic moiety, such as a 3',3'-linked or 5',5'-linked deoxyabasic moiety.

In certain embodiments, alternating nucleotides on the ends of the sense and antisense strands are modified by 2'-O-alkyl modification, and wherein each of the 2'-O-modified nucleotides faces an unmodified nucleotide on the opposite strand. In a preferred embodiment, the first 2'-O-modified antisense nucleotide (with this pattern of modification) is the most 5'-end antisense nucleotide.

In certain embodiments, alternating nucleotides on the ends of the sense and/or antisense strands comprise 2'-modified ribose sugars, and wherein each of the 2'-modified ribose sugars faces an unmodified nucleotide on the opposite strand. In certain embodiment, the first 2'-modified antisense nucleotide is the most 5'-end antisense nucleotide or the 2nd nucleotide from the 5'-end of the antisense strand.

In certain embodiments, RNAi constructs having the same or similar structures of any of the Alternate RNAi Compounds described herein, but differing by not being resistant to Dicer cleavage, are also desirable, so long as they show high activity against their respective intended target (e.g., mRNA).

In certain embodiments, the subject double-stranded RNA may be chemically cross-linked at one or more points, or linked by a nucleotide loop structure at one or both ends (e.g., a single-stranded hairpin structure or a circular structure). In one embodiment, the chemical cross-link or the loop of the hairpin structure is at the 3'-end of the antisense strand (e.g., linking the 3'-end of the antisense strand to the 5'-end of the sense strand). In another embodiment, the chemical cross-link or the loop of the hairpin structure is at the 5'-end of the antisense strand (e.g., linking the 3'-end of the sense strand to the 5'-end of the antisense strand. In these embodiments, other structural features of the cross-linked or looped constructs, such as 5'-end and 3'-end modifications on the sense strand and/or the other modifications on the antisense strand, are essentially the same as those for the dsRNA described herein.

Double-stranded and/or duplex oligonucleotide constructs of the invention are capable of inhibiting the synthesis of any target protein encoded by target gene(s). The invention includes methods to inhibit expression of a target gene either in a cell in vitro, or in vivo. The target gene can be endogenous or exogenous (e.g., introduced into a cell by a virus or using recombinant DNA technology) to a cell. Such methods may include introduction of RNA into a cell in an amount sufficient to inhibit expression of the target gene, where the RNA is a double-stranded duplex. By way of example, such an RNA molecule may have a first strand having a ribonucleotide sequence that corresponds to a nucleotide sequence of the target gene, and a second strand having a ribonucleotide sequence that is complementary to the nucleotide sequence of the target gene, in which the first and the second strands are separate complementary strands, and they hybridize to each other to form said double-stranded molecule, such that the duplex composition inhibits expression of the target gene. Exemplary (but non-limiting) target genes that are used extensively in this application to illustrate the general principles of the invention include SOD1, PPIB, RIP140, PCSK9, TNFα, AP2 (adipocyte lipid-binding protein), or MAP4K4, just to name a few.

While not wishing to be bound by any particular theory, the presence of 2'-O-methyl block regions on the "sense" strand of the RNAi entity (such as the regions at the ends of the sense strand) may result in significant increase in stability, specificity and minimization of immune response, compared to constructs without such modifications. In some cases, it may be even more beneficial to further increase RNAi duplex stability by applying modifications to the antisense strand. In particular, some of preferred chemical modification patterns might comprise antisense strand containing majority of C and Us modified by 2'-O-methyl, or C and Us modified by 2'F. In some cases, the antisense strand might be modified with the mixture of several chemical modifications.

In certain embodiments, heavily modified antisense strand might not be good substrates for kinases. Thus chemical phosphorylation of the antisense strand might be used to alleviate this problem. In addition, some preferred sequences might contain only purine nucleotides (i.e., A and Gs) in the unmodified region of the sense strand or/and 2'-F or phosphorothiate (PS) modifications. In some cases, additional introduction of PS modifications in combination with 2'-O-methyl and 2'F might be preferred.

In some cases, modification of both the sense and antisense strands is preferred to achieve maximal stabilization of the constructs. Since heavily modified duplexes sometimes are poor substrates for RISC assembly, in some preferred embodiments, presence of single or multiple bulges (e.g., about 1-5 nucleotides in size) might be necessary or at least helpful to enhance RISC entry and efficacy.

In some other embodiments, heavily modified duplexes may contain a single nick in the sense strand. The preferred nick position may be 10 bp on the opposing strand from the 5' end of the antisense strand. In some embodiments, the nick can be placed within 5 bases from the above-referenced preferred position (i.e., 10 bp on the opposing strand from the 5' end of the antisense strand). In some embodiments, additional chemical modifications providing duplex stabilization might be applied to the subject constructs. In some embodiments, the sequences may be selected to have certain thermodynamic characteristics, e.g., ΔG of each duplex region being <−13 kcal/mol.

Therefore, in certain embodiments, the constructs of the invention may contain certain modifications on either the sense/passenger strand or the antisense/guide strand, or both, and confer certain advantages to the construct.

For example, in certain embodiments, the sense strand nucleotides between the 2'-modified ribose nucleotides (e.g., the middle portion or stretch of the sense strand) are 2'-F modified. Alternatively or in addition, the same portion might contain purine nucleotides only, and optionally having 2'-F modification and/or phosphorothioate linkages for some or all of the nucleotides. Alternatively or in addition, the same part of the sense strand may form one or more bulges, such as bulges of about 1-5 nucleotides each.

As used herein, the continuous stretch of 2'-modified ribose nucleotides does not need to start from the 5'-end or 3'-end nucleotides, although such stretches preferably start from the end nucleotides. Thus, in certain embodiments, the continuous stretch of 2'-modified ribose nucleotides independently starts from the terminal nucleotide, the second nucleotide from the terminal nucleotide, or the third nucleotide from the terminal nucleotide, etc.

In certain embodiments, between about 50-100% of the pyrimidine nucleotides of the antisense strand are, independently, 2'-F modified or 2'-O-methyl-modified.

In certain embodiments, the 5'-end of the antisense strand may be phosphorylated.

In certain related embodiments, the invention also provides an RNA construct for inhibiting expression of a target gene, wherein the construct is identical to any of the dsRNA described above, except for a single nick on the sense strand. Thus in those embodiments, the RNA construct in fact contains three polynucleotides forming, via hybridization, a double-stranded structure. The antisense strand is a single-stranded polynucleotide, while the two other polynucleotides both hybridize to the antisense polynucleotide, and forms a "sense strand" that corresponds to any of the other dsRNA constructs described herein.

The location of the nick may vary in this embodiments. For example, the nick may occupy the opposite position of the nucleotide about 10 bases from the 5' end of the antisense strand. Alternatively, the nick may be within 5 nucleotides from this position (e.g., the nick occupies the opposite position of a nucleotide about 5-15 bases from the 5' end of the antisense strand. The sequences of the double-stranded regions in this type of construct may also be selected such that the ΔG of each duplex region is less than about −13 kcal/mole.

The invention also relates to vectors expressing at least one strand of the subject dsRNA constructs, and cells comprising such vectors or the subject dsRNA constructs. The cell may be a mammalian cell in culture, such as a human cell.

The invention further relates to compositions comprising the subject dsRNA constructs, and a pharmaceutically acceptable carrier or diluent.

Another aspect of the invention provides a method for inhibiting the expression of a target gene in a mammalian cell, comprising contacting the mammalian cell with the any of the subject dsRNA constructs.

The method may be carried out in vitro or in vivo, in, for example, mammalian cells in culture, such as a human cell in culture.

The target cells (e.g., mammalian cell) may be contacted in the presence of a delivery reagent, such as a lipid (e.g., a cationic lipid) or a liposome.

Another aspect of the invention provides a method for inhibiting the expression of a target gene in a mammalian cell, comprising contacting the mammalian cell with a vector expressing at least one strand of any of the subject dsRNA constructs.

Another aspect of the invention provides a method for improving the gene silencing effect of a small interference RNA (siRNA), comprising modifying the sense and/or antisense nucleotides of the siRNA to become any of the subject dsRNA constructs.

Another aspect of the invention provides a method for evaluating in vivo delivery of an siRNA construct to a target site, comprising co-delivering the siRNA construct with any of the subject dsRNA constructs designed to target PPIB, a ubiquitous gene universally expressed in almost all tissues, and assaying the inhibition of PPIB function at the target site, wherein successful inhibition of the PPIB function at the target site is indicative of successful in vivo delivery of the siRNA construct to the target site.

More detailed aspects of the invention are described in the sections below.

II. Duplex Structure

Duplex Characteristics

Double-stranded oligonucleotides of the invention may be formed by two separate complementary nucleic acid strands. Duplex formation can occur either inside or outside the cell containing the target gene.

As used herein, the term "double-stranded" includes one or more nucleic acid molecules comprising a region of the molecule in which at least a portion of the nucleomonomers are complementary and hydrogen bond to form a duplex.

As used herein, the term "duplex" includes the region of the double-stranded nucleic acid molecule(s) that is (are) hydrogen bonded to a complementary sequence. Double-stranded oligonucleotides of the invention may comprise a nucleotide sequence that is sense to a target gene and a complementary sequence that is antisense to the target gene. The sense and antisense nucleotide sequences correspond to the target gene sequence, e.g., are identical or are sufficiently identical to effect target gene inhibition (e.g., are about at least about 98% identical, 96% identical, 94%, 90% identical, 85% identical, or 80% identical) to the target gene sequence.

In certain embodiments, the double-stranded oligonucleotide of the invention is double-stranded over its entire length, i.e., with no overhanging single-stranded sequence at either end of the molecule, i.e., is blunt-ended. In other embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). Likewise, when a single nucleic acid molecule is used a portion of the molecule at either end can remain single-stranded.

In one embodiment, a double-stranded oligonucleotide of the invention contains mismatches and/or loops or bulges, but is double-stranded over at least about 70% of the length of the oligonucleotide. In another embodiment, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In another embodiment, a double-stranded oligonucleotide of the invention is double-stranded over at least about 96%-98% of the length of the oligonucleotide. In certain embodiments, the double-stranded oligonucleotide of the invention contains at least or up to 1, 2, 3, 4, 5, 6, 7, 8, 9, 10, 11, 12, 13, 14, or 15 mismatches.

Modifications

The nucleotides of the invention may be modified at various locations, including the sugar moiety, the phosphodiester linkage, and/or the base.

Sugar moieties include natural, unmodified sugars, e.g., monosaccharide (such as pentose, e.g., ribose, deoxyribose), modified sugars and sugar analogs. In general, possible modifications of nucleomonomers, particularly of a sugar moiety, include, for example, replacement of one or more of the hydroxyl groups with a halogen, a heteroatom, an aliphatic group, or the functionalization of the hydroxyl group as an ether, an amine, a thiol, or the like.

One particularly useful group of modified nucleomonomers are 2'-O-methyl nucleotides. Such 2'-O-methyl nucleotides may be referred to as "methylated," and the corresponding nucleotides may be made from unmethylated nucleotides followed by alkylation or directly from methylated nucleotide reagents. Modified nucleomonomers may be used in combination with unmodified nucleomonomers. For example, an oligonucleotide of the invention may contain both methylated and unmethylated nucleomonomers.

Some exemplary modified nucleomonomers include sugar- or backbone-modified ribonucleotides. Modified ribonucleotides may contain a non-naturally occurring base (instead of a naturally occurring base), such as uradines or cytidines modified at the 5'-position, e.g., 5'-(2-amino)propyl uradine and 5'-bromo uradine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides may have the 2'-OH group replaced by a H, alxoxy (or OR), R or alkyl, halogen, SH, SR, amino (such as $NH_2$, NHR, $NR_2$), or CN group, wherein R is lower alkyl, alkenyl, or alkynyl.

Modified ribonucleotides may also have the phosphoester group connecting to adjacent ribonucleotides replaced by a modified group, e.g., of phosphothioate group. More generally, the various nucleotide modifications may be combined.

In one embodiment, sense oligomers may have 2'-modifications on the ends (e.g., 2 on each end, 3 on each end, and 4 on each end, etc.; as well as 1 on one end, 2 on one end, 3 on one end, and 4 on one end, etc.; and even unbalanced combinations such as 12 on one end and 10 on the other end, etc.). Likewise, the antisense strand may have 2'-modifications on the ends (1 on each end, 2 on each end, 3 on each end, and 4 on each end, and so on; as well as 1 on one end, 2 on one end, 3 on one end, and 4 on one end, and so on; and even unbalanced combinations such as 1 on one end and 2 on the other end, and so on). In preferred aspects, the 2'-modifications are 2'-O-methyl modifications in the sense RNA strand and/or the antisense strand.

According to the instant invention, the sense strand can tolerate many 2'-modifications (such as 2'-O-methyl modifications), so long as the central linkages are unmodified. As used herein, "central" is not limited to mean the geometric mid-point of the sense strand. Rather, it can include any location between the 5'-end portion and the 3'-end portion of the sense strand. The 5'-end portion and the 3'-end portion of the sense strand need not be symmetrical.

Thus, in certain embodiments, the sense strand is not completely modified (i.e., at least one or more sense strand nucleotide(s) are unmodified). In certain embodiments, the unmodified sense strand nucleotides are in the central portion of the sense strand, or between the stretch of modified sense strand nucleotides on the 5'-end and the stretch of modified sense strand nucleotides on the 3'-end.

Also according to the instant invention, the sense strand tolerance for 2'-modification is not necessarily symmetrical. Rather, asymmetrical configurations may be desirable when using, for example, a sense strand of 25 or 26 nucleotides. 2'-mofications add nuclease stability, and reduce interferon induction, and are easier to synthesize. Thus it may be desirable to include more such 2'-modified ribose sugars (especially 2'-O-methyl modified) on the sense strand, so long as the teachings of the instant invention is followed to preserve RNAi activity.

In some embodiments of the present invention, the subject highly modified sense strands may be combined with either unmodified or lightly modified antisense strands to allow maximum guide strand activity.

To further maximize endo- and exo-nuclease resistance, in addition to the use of 2'-modified nucleomonomers in the ends, inter-nucleomonomer linkages other than phosphodiesters may be used. For example, such end blocks may be used alone or in conjunction with phosphothioate linkages between the 2'-O-methly linkages. Preferred 2'-modified nucleomonomers are 2'-modified end nucleotides.

Although the antisense strand may be substantially identical to at least a portion of the target gene (or genes), at least with respect to the base pairing properties, the sequence need not be perfectly identical to be useful, e.g., to inhibit expression of a target gene's phenotype. Generally, higher homology can be used to compensate for the use of a shorter antisense gene. In some cases, the antisense strand generally will be substantially identical (although in antisense orientation) to the target gene.

One particular example of a composition of the invention has end-blocks on both ends of a sense oligonucleotide and only the 3'-end of an antisense oligonucleotide. Without wishing to be bound by theory, a 2'-O-modified sense strand may work less well than its unmodified version, possibly because it is not efficiently unwound. Thus, in certain embodiments, mismatches may be introduced into specific positions of the sense strand (modified 2'-O-methyl sense strand, or even unmodified sense strand) to facilitate easier loading into the RISC complex.

In some embodiments, the length of the sense strand can be 30, 29, 28, 27, 26, 25, 24, 23, 22, 21, 20, 19, or 18 nucleotides. Similarly, the length of the antisense strand can be 30, 29, 28, 27, 26, 25, 24, 23, 22, 21, 20, 19, or 18 nucleotides. Further, when a double-stranded nucleic acid molecule is formed from such sense and antisense molecules, the resulting duplex may have blunt ends or overhangs of 0, 1, 2, 3, 4, 5, 6, 7, 8, 9, 10, 11, 12, 13, or 14 nucleotides on one end or independently on each end. Further, double stranded nucleic acid molecules of the invention may be composed of a sense strand and an antisense strand wherein these strands are of lengths described above, and are of the same or different lengths, but share only 10, 11, 12, 13, 14, 15, 16, 17, 18, 19, or 20 nucleotides of sequence complementarity. By way of illustration, in a situation where the sense strand is 20 nucleotides in length and the antisense is 25 nucleotides in length and the two strands share only 15 nucleotides of sequence complementarity, a double stranded nucleic acid molecules may be formed with a 10 nucleotide overhang on one end and a 5 nucleotide overhang on the other end.

The use of 2'-O-methyl RNA may also be beneficially in circumstances in which it is desirable to minimize cellular stress responses. RNA having 2'-O-methyl nucleomonomers may not be recognized by cellular machinery that is thought to recognize unmodified RNA. The use of 2'-O-methylated or partially 2'-O-methylated RNA may avoid the interferon response to double-stranded nucleic acids, while maintaining target RNA inhibition. This may be useful, for example, for avoiding the interferon or other cellular stress responses, both in short RNAi (e.g., siRNA) sequences that induce the interferon response, and in longer RNAi sequences that may induce the interferon response.

Overall, modified sugars may include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy (—OCH$_2$CH═CH$_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.* 18:4711 (1992)). Exemplary nucleomonomers can be found, e.g., in U.S. Pat. No. 5,849,902, incorporated by reference herein.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, unless otherwise specified, the term alkynyl includes both "unsubstituted alkynyls" and "substituted alkynyls," the latter of which refers to alkynyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with independently selected groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O⁻ (with an appropriate counterion).

The term "halogen" includes fluorine, bromine, chlorine, iodine, etc. The term "perhalogenated" generally refers to a moiety wherein all hydrogens are replaced by halogen atoms.

The term "substituted" includes independently selected substituents which can be placed on the moiety and which allow the molecule to perform its intended function. Examples of substituents include alkyl, alkenyl, alkynyl, aryl, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$, $(CR'R'')_{0-3}O(CR'R'')_{0-3}H$, $(CR'R'')_{0-3}COR'$, $(CR'R'')_{0-3}CO_2R'$, or $(CR'R'')_{0-3}OR'$ groups; wherein each R' and R" are each independently hydrogen, a $C_1$-$C_5$ alkyl, $C_2$-$C_5$ alkenyl, $C_2$-$C_5$ alkynyl, or aryl group, or R' and R" taken together are a benzylidene group or a —$(CH_2)_2O(CH_2)_2$— group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl," which refers to an alkyl, alkenyl, or alkynyl group covalently bonded to an oxygen atom which is covalently bonded to another alkyl group.

The term "base" includes the known purine and pyrimidine heterocyclic bases, deazapurines, and analogs (including heterocyclic substituted analogs, e.g., aminoethoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-$N^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

In a preferred embodiment, the nucleomonomers of an oligonucleotide of the invention are RNA nucleotides. In another preferred embodiment, the nucleomonomers of an oligonucleotide of the invention are modified RNA nucleotides. Thus, the oligunucleotides contain modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", 2"Ed., Wiley-Interscience, New York, 1999).

The term "nucleotide" includes nucleosides which further comprise a phosphate group or a phosphate analog.

As used herein, the term "linkage" includes a naturally occurring, unmodified phosphodiester moiety (—O—($PO^2$)—O—) that covalently couples adjacent nucleomonomers. As used herein, the term "substitute linkage" includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47). In certain embodiments, non-hydrolizable linkages are preferred, such as phosphorothiate linkages.

In certain embodiments, oligonucleotides of the invention comprise 3' and 5' termini (except for circular oligonucleotides). In one embodiment, the 3' and 5' termini of an oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (—O—$CH_2$—$CH_2$—O—) phosphate ($PO_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. Antisense Res. Dev. 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3' linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

In one embodiment, the sense strand of an oligonucleotide comprises a 5' group that allows for RNAi activity but which renders the sense strand inactive in terms of gene targeting. Preferably, such a 5' modifying group is a phosphate group or a group larger than a phosphate group. Oligonucleotides of this type often exhibit increased specificity for a target gene in a cell that corresponds to the nucleotide sequence of the antisense strand. This is because the sense strand in such an oligonucleotide is often rendered incapable of mediating cleavage of any nucleotide sequence it might bind to non-specifically and thus will not inactivate any other genes in the cell. Thus, observed decrease in the expression of a gene within a cell transfected with such an oligonucleotide will often be attributed to the direct or indirect effect of the antisense strand. The term "specificity for a target gene," as used herein means the extent to which an effect of an oligonucleotide on a cell can be attributed directly or indirectly to the inhibition of expression of a target gene by an antisense nucleotide sequence present in said oligonucleotide.

Thus, according to another embodiment, the invention provides a method of increasing the specificity of an oligonucleotide for a target gene in a cell, wherein said oligonucleotide comprises a sense strand and an antisense strand, wherein both the sense strand and the antisense strand are capable of binding to corresponding nucleotide sequences if present in said cell, said method comprising the step of modifying the 5' terminal hydroxy moiety of said sense strand with a phosphate group or a group larger than a phosphate group prior to contacting said oligonucleotide with said cell so as to render said sense strand incapable of mediating cleavage of any nucleotide sequence it might bind to non-specifically and thus will not inactivate any other genes in the cell.

Another way to increase target gene specificity, or to reduce off-target silencing effect, is to introduce a 2'-modification (such as the 2'-O methyl modification) at a position corresponding to the second 5'-end nucleotide of the Dicer-cleaved 21-mer. Applicants' discovery allows the positioning of this 2'-modification in the Dicer-resistant dsRNA, thus enabling one to design better siRNA constructs with less or no off-target silencing.

In one embodiment, a double-stranded oligonucleotide of the invention can comprise (i.e., be a duplex of) one nucleic acid molecule which is DNA and one nucleic acid molecule which is RNA. Antisense sequences of the invention can be "chimeric oligonucleotides" which comprise an RNA-like and a DNA-like region.

The language "RNase H activating region" includes a region of an oligonucleotide, e.g., a chimeric oligonucleotide, that is capable of recruiting RNase H to cleave the target RNA strand to which the oligonucleotide binds. Typically, the RNase activating region contains a minimal core (of at least about 3-5, typically between about 3-12, more typically, between about 5-12, and more preferably between about 5-10 contiguous nucleomonomers) of DNA or DNA-like nucleomonomers. (See, e.g., U.S. Pat. No. 5,849,902). Preferably, the RNase H activating region comprises about nine contiguous deoxyribose containing nucleomonomers.

The language "non-activating region" includes a region of an antisense sequence, e.g., a chimeric oligonucleotide, that does not recruit or activate RNase H. Preferably, a non-activating region does not comprise phosphorothioate DNA. The oligonucleotides of the invention comprise at least one non-activating region. In one embodiment, the non-activating region can be stabilized against nucleases or can provide specificity for the target by being complementary to the target and forming hydrogen bonds with the target nucleic acid molecule, which is to be bound by the oligonucleotide.

In one embodiment, at least a portion of the contiguous polynucleotides are linked by a substitute linkage, e.g., a phosphorothioate linkage.

In certain embodiments, most or all of the sense strand nucleotides (2'-modified or not) are linked by phosphorothioate linkages. Such constructs tend to have improved pharmacokinetics due to their higher affinity for serum proteins. The phosphothioate linkages in the sense strand generally do not interfere with guide strand activity, once the latter is loaded into RISC.

Antisense sequences of the present invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by, e.g., non-ionic phosphorodiamidate inter-subunit linkages. Morpholino oligonucleotides have many advantages including: complete resistance to nucleases (Antisense & Nucl. Acid Drug Dev. 1996. 6:267); predictable targeting (Biochemica Biophysica Acta. 1999. 1489:141); reliable activity in cells (Antisense & Nucl. Acid Drug Dev. 1997. 7:63); excellent sequence specificity (Antisense & Nucl. Acid Drug Dev. 1997. 7:151); minimal non-antisense activity (Biochemica Biophysica Acta. 1999. 1489:141); and simple osmotic or scrape delivery (Antisense & Nucl. Acid Drug Dev. 1997. 7:291). Morpholino oligonucleotides are also preferred because of their non-toxicity at high doses. A discussion of the preparation of morpholino oligonucleotides can be found in Antisense & Nucl. Acid Drug Dev. 1997. 7:187.

III. Synthesis

Oligonucleotides of the invention can be synthesized by any method known in the art, e.g., using enzymatic synthesis and/or chemical synthesis. The oligonucleotides can be synthesized in vitro (e.g., using enzymatic synthesis and chemical synthesis) or in vivo (using recombinant DNA technology well known in the art).

In a preferred embodiment, chemical synthesis is used for modified polynucleotides. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. *J. Am. Chem. Soc.* 106:6077; Stec et al. 1985. *J. Org. Chem.* 50:3908; Stec et al. *J. Chromatog.* 1985. 326:263; LaPlanche et al. 1986. *Nucl. Acid. Res.* 1986. 14:9081; Fasman G. D., 1989. Practical Handbook of Biochemistry and Molecular Biology. 1989. CRC Press, Boca Raton, Fla.; Lamone. 1993. *Biochem. Soc. Trans.* 21:1; U.S. Pat. No. 5,013,830; U.S. Pat. No. 5,214,135; U.S. Pat. No. 5,525,719; Kawasaki et al. 1993. *J. Med. Chem.* 36:831; WO 92/03568; U.S. Pat. No. 5,276,019; and U.S. Pat. No. 5,264,423.

The synthesis method selected can depend on the length of the desired oligonucleotide and such choice is within the skill of the ordinary artisan. For example, the phosphoramidite and phosphite triester method can produce oligonucleotides having 175 or more nucleotides, while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, *Chemical Reviews* 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. *Methods in Molecular Biology* 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence, including some sequences with modified nucleotides, are readily available from several commercial sources.

The oligonucleotides may be purified by polyacrylamide gel electrophoresis, or by any of a number of chromatographic methods, including gel chromatography and high pressure liquid chromatography. To confirm a nucleotide sequence, especially unmodified nucleotide sequences, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC(SAX-HPLC) using, e.g., the method of Bergot and Egan. 1992. *J. Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (DN Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

In certain embodiments, the subject RNAi constructs or at least portions thereof are transcribed from expression vectors encoding the subject constructs. Any art recognized vectors may be use for this purpose. The transcribed RNAi constructs may be isolated and purified, before desired modifications (such as replacing an unmodified sense strand with a modified one, etc.) are carried out.

IV. Delivery/Carrier

Uptake of Oligonucleotides by Cells

Oligonucleotides and oligonucleotide compositions are contacted with (i.e., brought into contact with, also referred to herein as administered or delivered to) and taken up by one or more cells or a cell lysate. The term "cells" includes prokaryotic and eukaryotic cells, preferably vertebrate cells, and, more preferably, mammalian cells. In a preferred embodiment, the oligonucleotide compositions of the invention are contacted with human cells.

Oligonucleotide compositions of the invention can be contacted with cells in vitro, e.g., in a test tube or culture dish, (and may or may not be introduced into a subject) or in vivo, e.g., in a subject such as a mammalian subject. Oligonucleotides are taken up by cells at a slow rate by endocytosis, but endocytosed oligonucleotides are generally sequestered and not available, e.g., for hybridization to a target nucleic acid molecule. In one embodiment, cellular uptake can be facilitated by electroporation or calcium phosphate precipitation. However, these procedures are only useful for in vitro or ex vivo embodiments, are not convenient and, in some cases, are associated with cell toxicity.

In another embodiment, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see e.g., WO 90/14074; WO 91/16024; WO 91/17424; U.S. Pat. No. 4,897,355; Bergan et al. 1993. *Nucleic Acids Research.* 21:3567). Enhanced delivery of oligonucleotides can also be mediated by the use of vectors (See e.g., Shi, Y. 2003. Trends Genet. 2003 Jan. 19:9; Reichhart J M et al. Genesis. 2002. 34(1-2):1604, Yu et al. 2002. Proc. Natl. Acad. Sci. USA 99:6047; Sui et al. 2002. Proc. Natl. Acad. Sci. USA 99:5515) viruses, polyamine or polycation conjugates using compounds such as polylysine, protamine, or Ni, N12-bis(ethyl) spermine (see, e.g., Bartzatt, R. et al. 1989. *Biotechnol. Appl. Biochem.* 11:133; Wagner E. et al. 1992. *Proc. Natl. Acad. Sci.* 88:4255).

The optimal protocol for uptake of oligonucleotides will depend upon a number of factors, the most crucial being the type of cells that are being used. Other factors that are important in uptake include, but are not limited to, the nature and concentration of the oligonucleotide, the confluence of the cells, the type of culture the cells are in (e.g., a suspension culture or plated) and the type of media in which the cells are grown.

Conjugating Agents

Conjugating agents bind to the oligonucleotide in a covalent manner. In one embodiment, oligonucleotides can be derivatized or chemically modified by binding to a conjugating agent to facilitate cellular uptake. For example, covalent linkage of a cholesterol moiety to an oligonucleotide can improve cellular uptake by 5- to 10-fold which in turn improves DNA binding by about 10-fold (Boutorin et al., 1989, *FEBS Letters* 254:129-132). Conjugation of octyl, dodecyl, and octadecyl residues enhances cellular uptake by 3-, 4-, and 10-fold as compared to unmodified oligonucleotides (Vlassov et al., 1994, Biochimica et Biophysica Acta 1197:95-108). Similarly, derivatization of oligonucleotides with poly-L-lysine can aid oligonucleotide uptake by cells (Schell, 1974, *Biochem. Biophys. Acta* 340:323, and Lemaitre et al., 1987, *Proc. Natl. Acad. Sci. USA* 84:648).

Certain protein carriers can also facilitate cellular uptake of oligonucleotides, including, for example, serum albumin, nuclear proteins possessing signals for transport to the nucleus, and viral or bacterial proteins capable of cell membrane penetration. Therefore, protein carriers are useful when associated with or linked to the oligonucleotides. Accordingly, the present invention provides for derivatization of oligonucleotides with groups capable of facilitating cellular uptake, including hydrocarbons and non-polar groups, cholesterol, long chain alcohols (i.e., hexanol), poly-L-lysine and proteins, as well as other aryl or steroid groups and polycations having analogous beneficial effects, such as phenyl or naphthyl groups, quinoline, anthracene or phenanthracene groups, fatty acids, fatty alcohols and sesquiterpenes, diterpenes, and steroids. A major advantage of using conjugating agents is to increase the initial membrane interaction that leads to a greater cellular accumulation of oligonucleotides.

Other conjugating agents include various vitamins, such as fat soluble vitamins, which may be used as a conjugate to deliver RNAi constructs specifically into adipose tissue—the primary location where these vitamins are stored. These vitamin-based conjugating agents may be especially useful for targeting certain metabolic disease targets, such as diabetes/obesity. Of the fat soluble vitamins, such as vitamins A, D, E, K, etc., vitamin K may be preferred in some embodiments, as there is no known upper intake level (although large doses could lead to breakdown of red blood cells and possibly to liver disease). In comparison, vitamins A and D have more defined toxicity and established upper intake levels.

In certain embodiments, gamma carboxyglutamic acid residues may be conjugated to the subject RNAi constructs to increased their membrane stickiness, and/or to slow clearance and improve general uptake (infra).

Certain conjugating agents that may be used with the instant constructs include those described in WO04048545A2 and US20040204377A1 (all incorporated herein by their entireties), such as a Tat peptide, a sequence substantially similar to the sequence of SEQ ID NO: 12 of WO04048545A2 and US20040204377A1, a homeobox (hox) peptide, a MTS, VP22, MPG, at least one dendrimer (such as PAMAM), etc.

Other conjugating agents that may be used with the instant constructs include those described in WO07089607A2 (incorporated herein), which describes various nanotransporters and delivery complexes for use in delivery of nucleic acid molecules (such as the subject dsRNA constructs) and/or other pharmaceutical agents in vivo and in vitro. Using such delivery complexes, the subject dsRNA can be delivered while conjugated or associated with a nanotransporter comprising a core conjugated with at least one functional surface group. The core may be a nanoparticle, such as a dendrimer (e.g., a polylysine dendrimer). The core may also be a nanotube, such as a single walled nanotube or a multi-walled nanotube. The functional surface group is at least one of a lipid, a cell type specific targeting moiety, a fluorescent molecule, and a charge controlling molecule. For example, the targeting moiety may be a tissue-selective peptide. The lipid may be an oleoyl lipid or derivative thereof. Exemplary nanotransporter include NOP-7 or HBOLD.

Encapsulating Agents

Encapsulating agents entrap oligonucleotides within vesicles. In another embodiment of the invention, an oligonucleotide may be associated with a carrier or vehicle, e.g., liposomes or micelles, although other carriers could be used, as would be appreciated by one skilled in the art. Liposomes are vesicles made of a lipid bilayer having a structure similar to biological membranes. Such carriers are used to facilitate the cellular uptake or targeting of the oligonucleotide, or improve the oligonucleotide's pharmacokinetic or toxicologic properties.

For example, the oligonucleotides of the present invention may also be administered encapsulated in liposomes, pharmaceutical compositions wherein the active ingredient is contained either dispersed or variously present in corpuscles consisting of aqueous concentric layers adherent to lipidic layers. The oligonucleotides, depending upon solubility, may be present both in the aqueous layer and in the lipidic layer, or in what is generally termed a liposomic suspension. The hydrophobic layer, generally but not exclusively, comprises phopholipids such as lecithin and sphingomyelin, steroids such as cholesterol, more or less ionic surfactants such as diacetylphosphate, stearylamine, or phosphatidic acid, or other materials of a hydrophobic nature. The diameters of the liposomes generally range from about 15 nm to about 5 microns.

The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acids remain biologically active. For example, a lipid delivery vehicle originally designed as a research tool, such as Lipofectin or LIPOFECTAMINE™ 2000, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

Complexing Agents

Complexing agents bind to the oligonucleotides of the invention by a strong but non-covalent attraction (e.g., an electrostatic, van der Waals, pi-stacking, etc. interaction). In one embodiment, oligonucleotides of the invention can be complexed with a complexing agent to increase cellular uptake of oligonucleotides. An example of a complexing agent includes cationic lipids. Cationic lipids can be used to deliver oligonucleotides to cells.

The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In general cationic lipids include saturated and unsaturated alkyl and alicyclic ethers and esters of amines, amides, or derivatives thereof. Straight-chain and branched alkyl and alkenyl groups of cationic lipids can contain, e.g., from 1 to about 25 carbon atoms. Preferred straight chain or branched alkyl or alkene groups have six or more carbon atoms. Alicyclic groups include cholesterol and other steroid groups. Cationic lipids can be prepared with a variety of counterions (anions) including, e.g., $Cl^-$, $Br^-$, $I^-$, $F^-$, acetate, trifluoroacetate, sulfate, nitrite, and nitrate.

Examples of cationic lipids include polyethylenimine, polyamidoamine (PAMAM) starburst dendrimers, Lipofectin (a combination of DOTMA and DOPE), Lipofectase, LIPOFECTAMINE™ (e.g., LIPOFECTAMINE™ 2000), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N-(N',N'-dimethylaminoethane)carbamoyl]cholesterol (DC-Chol), 2,3,-dioleyloxy-N-[2(sperminecarboxamido)ethyl]-N,N-dimethyl-1-propan-aminium trifluoroacetate (DOSPA), 1,2-dimyristyloxypropyl-3-dimethyl-hydroxyethyl ammonium bromide; and dimethyldioctadecylammonium bromide (DDAB). The cationic lipid N-(1-(2,3-dioleyloxy)propyl)-N,N,N-trimethylammonium chloride (DOTMA), for example, was found to increase 1000-fold the antisense effect of a phosphothioate oligonucleotide. (Vlassov et al., 1994, Biochimica et Biophysica Acta 1197:95-108). Oligonucleotides can also be complexed with, e.g., poly (L-lysine) or avidin and lipids may, or may not, be included in this mixture, e.g., steryl-poly (L-lysine).

Cationic lipids have been used in the art to deliver oligonucleotides to cells (see, e.g., U.S. Pat. Nos. 5,855,910; 5,851,548; 5,830,430; 5,780,053; 5,767,099; Lewis et al. 1996. *Proc. Natl. Acad. Sci. USA* 93:3176; Hope et al. 1998. *Molecular Membrane Biology* 15:1). Other lipid compositions which can be used to facilitate uptake of the instant oligonucleotides can be used in connection with the claimed methods. In addition to those listed supra, other lipid compositions are also known in the art and include, e.g., those taught in U.S. Pat. No. 4,235,871; U.S. Pat. Nos. 4,501,728; 4,837,028; 4,737,323.

In one embodiment lipid compositions can further comprise agents, e.g., viral proteins to enhance lipid-mediated transfections of oligonucleotides (Kamata, et al., 1994. *Nucl. Acids. Res.* 22:536). In another embodiment, oligonucleotides are contacted with cells as part of a composition comprising an oligonucleotide, a peptide, and a lipid as taught, e.g., in U.S. Pat. No. 5,736,392. Improved lipids have also been described which are serum resistant (Lewis, et al., 1996. *Proc. Natl. Acad. Sci.* 93:3176). Cationic lipids and other complexing agents act to increase the number of oligonucleotides carried into the cell through endocytosis.

In another embodiment N-substituted glycine oligonucleotides (peptoids) can be used to optimize uptake of oligonucleotides. Peptoids have been used to create cationic lipid-like compounds for transfection (Murphy, et al., 1998.

*Proc. Natl. Acad. Sci.* 95:1517). Peptoids can be synthesized using standard methods (e.g., Zuckemmann, R. N., et al. 1992. *J. Am. Chem. Soc.* 114:10646; Zuckermann, R. N., et al. 1992. *Int. J. Peptide Protein Res.* 40:497). Combinations of cationic lipids and peptoids, liptoids, can also be used to optimize uptake of the subject oligonucleotides (Hunag, et al., 1998. *Chemistry and Biology.* 5:345). Liptoids can be synthesized by elaborating peptoid oligonucleotides and coupling the amino terminal submonomer to a lipid via its amino group (Hunag, et al., 1998. *Chemistry and Biology.* 5:345).

It is known in the art that positively charged amino acids can be used for creating highly active cationic lipids (Lewis et al. 1996. *Proc. Natl. Acad. Sci. U.S.A.* 93:3176). In one embodiment, a composition for delivering oligonucleotides of the invention comprises a number of arginine, lysine, histidine or ornithine residues linked to a lipophilic moiety (see e.g., U.S. Pat. No. 5,777,153).

In another embodiment, a composition for delivering oligonucleotides of the invention comprises a peptide having from between about one to about four basic residues. These basic residues can be located, e.g., on the amino terminal, C-terminal, or internal region of the peptide. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine (can also be considered non-polar), asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Apart from the basic amino acids, a majority or all of the other residues of the peptide can be selected from the non-basic amino acids, e.g., amino acids other than lysine, arginine, or histidine. Preferably a preponderance of neutral amino acids with long neutral side chains are used.

In one embodiment, a composition for delivering oligonucleotides of the invention comprises a natural or synthetic polypeptide having one or more gamma carboxyglutamic acid residues, or γ-Gla residues. These gamma carboxyglutamic acid residues may enable the polypeptide to bind to each other and to membrane surfaces. In other words, a polypeptide having a series of γ-Gla may be used as a general delivery modality that helps an RNAi construct to stick to whatever membrane to which it comes in contact. This may at least slow RNAi constructs from being cleared from the blood stream and enhance their chance of homing to the target.

The gamma carboxyglutamic acid residues may exist in natural proteins (for example, prothrombin has 10 γ-Gla residues). Alternatively, they can be introduced into the purified, recombinantly produced, or chemically synthesized polypeptides by carboxylation using, for example, a vitamin K-dependent carboxylase. The gamma carboxyglutamic acid residues may be consecutive or non-consecutive, and the total number and location of such gamma carboxyglutamic acid residues in the polypeptide can be regulated/fine tuned to achieve different levels of "stickiness" of the polypeptide.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

For example, in one embodiment, an oligonucleotide composition can be contacted with cells in the presence of a lipid such as cytofectin CS or GSV (available from Glen Research; Sterling, Va.), GS3815, GS2888 for prolonged incubation periods as described herein.

In one embodiment, the incubation of the cells with the mixture comprising a lipid and an oligonucleotide composition does not reduce the viability of the cells. Preferably, after the transfection period the cells are substantially viable. In one embodiment, after transfection, the cells are between at least about 70% and at least about 100% viable. In another embodiment, the cells are between at least about 80% and at least about 95% viable. In yet another embodiment, the cells are between at least about 85% and at least about 90% viable.

In one embodiment, oligonucleotides are modified by attaching a peptide sequence that transports the oligonucleotide into a cell, referred to herein as a "transporting peptide." In one embodiment, the composition includes an oligonucleotide which is complementary to a target nucleic acid molecule encoding the protein, and a covalently attached transporting peptide.

The language "transporting peptide" includes an amino acid sequence that facilitates the transport of an oligonucleotide into a cell. Exemplary peptides which facilitate the transport of the moieties to which they are linked into cells are known in the art, and include, e.g., HIV TAT transcription factor, lactoferrin, Herpes VP22 protein, and fibroblast growth factor 2 (Pooga et al. 1998. *Nature Biotechnology.* 16:857; and Derossi et al. 1998. *Trends in Cell Biology.* 8:84; Elliott and O'Hare. 1997. Cell 88:223).

Oligonucleotides can be attached to the transporting peptide using known techniques, e.g., (Prochiantz, A. 1996. *Curr. Opin. Neurobiol.* 6:629; Derossi et al. 1998. *Trends Cell Biol.* 8:84; Troy et al. 1996. *J. Neurosci.* 16:253), Vives et al. 1997. *J. Biol. Chem.* 272:16010). For example, in one embodiment, oligonucleotides bearing an activated thiol group are linked via that thiol group to a cysteine present in a transport peptide (e.g., to the cysteine present in the β turn between the second and the third helix of the antennapedia homeodomain as taught, e.g., in Derossi et al. 1998. *Trends Cell Biol.* 8:84; Prochiantz. 1996. *Current Opinion in Neurobiol.* 6:629; Allinquant et al. 1995. J. Cell Biol. 128:919). In another embodiment, a Boc-Cys-(Npys)OH group can be coupled to the transport peptide as the last (N-terminal) amino acid and an oligonucleotide bearing an SH group can be coupled to the peptide (Troy et al. 1996. *J. Neurosci.* 16:253).

In one embodiment, a linking group can be attached to a nucleomonomer and the transporting peptide can be covalently attached to the linker. In one embodiment, a linker can function as both an attachment site for a transporting peptide and can provide stability against nucleases. Examples of suitable linkers include substituted or unsubstituted $C_1$-$C_{20}$ alkyl chains, $C_2$-$C_{20}$ alkenyl chains, $C_2$-$C_{20}$ alkynyl chains, peptides, and heteroatoms (e.g., S, O, NH, etc.).

Other exemplary linkers include bifunctional crosslinking agents such as sulfosuccinimidyl-4-(maleimidophenyl)-butyrate (SMPB) (see, e.g., Smith et al. Biochem J 1991.276: 417-2).

In one embodiment, oligonucleotides of the invention are synthesized as molecular conjugates which utilize receptor-mediated endocytotic mechanisms for delivering genes into cells (see, e.g., Bunnell et al. 1992. *Somatic Cell and Molecular Genetics*. 18:559, and the references cited therein).

Targeting Agents

The delivery of oligonucleotides can also be improved by targeting the oligonucleotides to a cellular receptor. The targeting moieties can be conjugated to the oligonucleotides or attached to a carrier group (i.e., poly(L-lysine) or liposomes) linked to the oligonucleotides. This method is well suited to cells that display specific receptor-mediated endocytosis.

For instance, oligonucleotide conjugates to 6-phosphomannosylated proteins are internalized 20-fold more efficiently by cells expressing mannose 6-phosphate specific receptors than free oligonucleotides. The oligonucleotides may also be coupled to a ligand for a cellular receptor using a biodegradable linker. In another example, the delivery construct is mannosylated streptavidin which forms a tight complex with biotinylated oligonucleotides. Mannosylated streptavidin was found to increase 20-fold the internalization of biotinylated oligonucleotides. (Vlassov et al. 1994. *Biochimica et Biophysica Acta* 1197:95-108).

In addition specific ligands can be conjugated to the polylysine component of polylysine-based delivery systems. For example, transferrin-polylysine, adenovirus-polylysine, and influenza virus hemagglutinin HA-2 N-terminal fusogenic peptides-polylysine conjugates greatly enhance receptor-mediated DNA delivery in eucaryotic cells. Mannosylated glycoprotein conjugated to poly(L-lysine) in aveolar macrophages has been employed to enhance the cellular uptake of oligonucleotides. Liang et al. 1999. *Pharmazie* 54:559-566.

Because malignant cells have an increased need for essential nutrients such as folic acid and transferrin, these nutrients can be used to target oligonucleotides to cancerous cells. For example, when folic acid is linked to poly(L-lysine) enhanced oligonucleotide uptake is seen in promyelocytic leukaemia (HL-60) cells and human melanoma (M-14) cells. Ginobbi et al. 1997. *Anticancer Res*. 17:29. In another example, liposomes coated with maleylated bovine serum albumin, folic acid, or ferric protoporphyrin IX, show enhanced cellular uptake of oligonucleotides in murine macrophages, KB cells, and 2.2.15 human hepatoma cells. Liang et al. 1999. *Pharmazie* 54:559-566.

Liposomes naturally accumulate in the liver, spleen, and reticuloendothelial system (so-called, passive targeting). By coupling liposomes to various ligands such as antibodies are protein A, they can be actively targeted to specific cell populations. For example, protein A-bearing liposomes may be pretreated with H-2K specific antibodies which are targeted to the mouse major histocompatibility complex-encoded H-2K protein expressed on L cells. (Vlassov et al. 1994. *Biochimica et Biophysica Acta* 1197:95-108).

V. Administration

The optimal course of administration or delivery of the oligonucleotides may vary depending upon the desired result and/or on the subject to be treated. As used herein "administration" refers to contacting cells with oligonucleotides and can be performed in vitro or in vivo. The dosage of oligonucleotides may be adjusted to optimally reduce expression of a protein translated from a target nucleic acid molecule, e.g., as measured by a readout of RNA stability or by a therapeutic response, without undue experimentation.

For example, expression of the protein encoded by the nucleic acid target can be measured to determine whether or not the dosage regimen needs to be adjusted accordingly. In addition, an increase or decrease in RNA or protein levels in a cell or produced by a cell can be measured using any art recognized technique. By determining whether transcription has been decreased, the effectiveness of the oligonucleotide in inducing the cleavage of a target RNA can be determined.

Any of the above-described oligonucleotide compositions can be used alone or in conjunction with a pharmaceutically acceptable carrier. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

Oligonucleotides may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types.

Moreover, the present invention provides for administering the subject oligonucleotides with an osmotic pump providing continuous infusion of such oligonucleotides, for example, as described in Rataiczak et al. (1992 *Proc. Natl. Acad. Sci. USA* 89:11823-11827). Such osmotic pumps are commercially available, e.g., from Alzet Inc. (Palo Alto, Calif.). Topical administration and parenteral administration in a cationic lipid carrier are preferred:

With respect to in vivo applications, the formulations of the present invention can be administered to a patient in a variety of forms adapted to the chosen route of administration, e.g., parenterally, orally, or intraperitoneally. Parenteral administration, which is preferred, includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, or dextran, optionally, the suspension may also contain stabilizers. The oligonucleotides of the invention can be formulated in liquid solutions, preferably in physiologically compatible buffers such as Hank's solution or Ringer's solution. In addition, the oligonucleotides may be formulated in solid form and redissolved or suspended immediately prior to use. Lyophilized forms are also included in the invention.

Pharmaceutical preparations for topical administration include transdermal patches, ointments, lotions, creams, gels, drops, sprays, suppositories, liquids and powders. In addition, conventional pharmaceutical carriers, aqueous, powder or oily bases, or thickeners may be used in pharmaceutical preparations for topical administration.

Pharmaceutical preparations for oral administration include powders or granules, suspensions or solutions in water or non-aqueous media, capsules, sachets or tablets. In addition, thickeners, flavoring agents, diluents, emulsifiers, dispersing aids, or binders may be used in pharmaceutical preparations for oral administration.

For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligonucleotides are formulated into conventional oral administration forms such as capsules, tablets, and tonics. For topical administration, the oligonucleotides of the invention are formulated into ointments, salves, gels, or creams as known in the art.

Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The described oligonucleotides may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. Each of these administration routes delivers the oligonucleotide to accessible diseased cells. Following subcutaneous administration, the therapeutic agent drains into local lymph nodes and proceeds through the lymphatic network into the circulation. The rate of entry into the circulation has been shown to be a function of molecular weight or size. The use of a liposome or other drug carrier localizes the oligonucleotide at the lymph node. The oligonucleotide can be modified to diffuse into the cell, or the liposome can directly participate in the delivery of either the unmodified or modified oligonucleotide into the cell.

The chosen method of delivery will result in entry into cells. Preferred delivery methods include liposomes (10-400 nm), hydrogels, controlled-release polymers, and other pharmaceutically applicable vehicles, and microinjection or electroporation (for ex vivo treatments).

The pharmaceutical preparations of the present invention may be prepared and formulated as emulsions. Emulsions are usually heterogeneous systems of one liquid dispersed in another in the form of droplets usually exceeding 0.1 µm in diameter. The emulsions of the present invention may contain excipients such as emulsifiers, stabilizers, dyes, fats, oils, waxes, fatty acids, fatty alcohols, fatty esters, humectants, hydrophilic colloids, preservatives, and antioxidants may also be present in emulsions as needed. These excipients may be present as a solution in either the aqueous phase, oily phase or itself as a separate phase.

Examples of naturally occurring emulsifiers that may be used in emulsion formulations of the present invention include lanolin, beeswax, phosphatides, lecithin and acacia. Finely divided solids have also been used as good emulsifiers especially in combination with surfactants and in viscous preparations. Examples of finely divided solids that may be used as emulsifiers include polar inorganic solids, such as heavy metal hydroxides, nonswelling clays such as bentonite, attapulgite, hectorite, kaolin, montrnorillonite, colloidal aluminum silicate and colloidal magnesium aluminum silicate, pigments and nonpolar solids such as carbon or glyceryl tristearate.

Examples of preservatives that may be included in the emulsion formulations include methyl paraben, propyl paraben, quaternary ammonium salts, benzalkonium chloride, esters of p-hydroxybenzoic acid, and boric acid. Examples of antioxidants that may be included in the emulsion formulations include free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In one embodiment, the compositions of oligonucleotides are formulated as microemulsions. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both oil/water and water/oil) have been proposed to enhance the oral bioavailability of drugs.

Microemulsions offer improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11:1385; Ho et al., J. Pharm. Sci., 1996, 85:138-143). Microemulsions have also been effective in the transdermal delivery of active components in both cosmetic and pharmaceutical applications. It is expected that the microemulsion compositions and formulations of the present invention will facilitate the increased systemic absorption of oligonucleotides from the gastrointestinal tract, as well as improve the local cellular uptake of oligonucleotides within the gastrointestinal tract, vagina, buccal cavity and other areas of administration.

In an embodiment, the present invention employs various penetration enhancers to affect the efficient delivery of nucleic acids, particularly oligonucleotides, to the skin of animals. Even non-lipophilic drugs may cross cell membranes if the membrane to be crossed is treated with a penetration enhancer. In addition to increasing the diffusion of non-lipophilic drugs across cell membranes, penetration enhancers also act to enhance the permeability of lipophilic drugs.

Five categories of penetration enhancers that may be used in the present invention include: surfactants, fatty acids, bile salts, chelating agents, and non-chelating non-surfactants. Other agents may be utilized to enhance the penetration of the administered oligonucleotides include: glycols such as ethylene glycol and propylene glycol, pyrrols such as 2-15 pyrrol, azones, and terpenes such as limonene, and menthone.

The oligonucleotides, especially in lipid formulations, can also be administered by coating a medical device, for example, a catheter, such as an angioplasty balloon catheter, with a cationic lipid formulation. Coating may be achieved, for example, by dipping the medical device into a lipid formulation or a mixture of a lipid formulation and a suitable solvent, for example, an aqueous-based buffer, an aqueous solvent, ethanol, methylene chloride, chloroform and the like. An amount of the formulation will naturally adhere to the surface of the device which is subsequently administered to a patient, as appropriate. Alternatively, a lyophilized mixture of a lipid formulation may be specifically bound to the surface of the device. Such binding techniques are described, for example, in K. Ishihara et al., Journal of Biomedical Materials Research, Vol. 27, pp. 1309-1314 (1993), the disclosures of which are incorporated herein by reference in their entirety.

The useful dosage to be administered and the particular mode of administration will vary depending upon such factors as the cell type, or for in vivo use, the age, weight and the particular animal and region thereof to be treated, the particular oligonucleotide and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. When lipids are used to deliver the oligonucleotides, the amount of lipid compound that is administered can vary and generally depends upon the amount of oligonucleotide agent being administered. For example, the weight ratio of lipid compound to oligonucleotide agent is preferably from about 1:1 to about 15:1, with a weight ratio of about 5:1 to about 10:1 being more preferred. Generally, the amount of cationic lipid compound which is administered will vary from between about 0.1 milligram (mg) to about 1 gram (g). By way of general guidance, typically between about 0.1 mg and about 10 mg of the particular oligonucleotide agent, and about 1 mg to about 100 mg of the lipid compositions, each per kilogram of patient body weight, is administered, although higher and lower amounts can be used.

The agents of the invention are administered to subjects or contacted with cells in a biologically compatible form suitable for pharmaceutical administration. By "biologically compatible form suitable for administration" is meant that the oligonucleotide is administered in a form in which any toxic effects are outweighed by the therapeutic effects of the oligonucleotide. In one embodiment, oligonucleotides can be administered to subjects. Examples of subjects include mammals, e.g., humans and other primates; cows, pigs, horses, and farming (agricultural) animals; dogs, cats, and other domesticated pets; mice, rats, and transgenic non-human animals.

Administration of an active amount of an oligonucleotide of the present invention is defined as an amount effective, at dosages and for periods of time necessary to achieve the desired result. For example, an active amount of an oligonucleotide may vary according to factors such as the type of cell, the oligonucleotide used, and for in vivo uses the disease state, age, sex, and weight of the individual, and the ability of the oligonucleotide to elicit a desired response in the individual. Establishment of therapeutic levels of oligonucleotides within the cell is dependent upon the rates of uptake and efflux or degradation. Decreasing the degree of degradation prolongs the intracellular half-life of the oligonucleotide. Thus, chemically-modified oligonucleotides, e.g., with modification of the phosphate backbone, may require different dosing.

The exact dosage of an oligonucleotide and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms. Dosage regima may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

VI. Assays of Oligonucleotide Stability

Preferably, the double-stranded oligonucleotides of the invention are stabilized, i.e., substantially resistant to endonuclease and exonuclease degradation. An oligonucleotide is defined as being substantially resistant to nucleases when it is at least about 3-fold more resistant to attack by an endogenous cellular nuclease, and is highly nuclease resistant when it is at least about 6-fold more resistant than a corresponding, single-stranded oligonucleotide. This can be demonstrated by showing that the oligonucleotides of the invention are substantially resistant to nucleases using techniques which are known in the art.

One way in which substantial stability can be demonstrated is by showing that the oligonucleotides of the invention function when delivered to a cell, e.g., that they reduce transcription or translation of target nucleic acid molecules, e.g., by measuring protein levels or by measuring cleavage of mRNA. Assays which measure the stability of target RNA can be performed at about 24 hours post-transfection (e.g., using Northern blot techniques, RNase Protection Assays, or QC-PCR assays as known in the art). Alternatively, levels of the target protein can be measured. Preferably, in addition to testing the RNA or protein levels of interest, the RNA or protein levels of a control, non-targeted gene will be measured (e.g., actin, or preferably a control with sequence similarity to the target) as a specificity control. RNA or protein measurements can be made using any art-recognized technique. Preferably, measurements will be made beginning at about 16-24 hours post transfection. (M. Y. Chiang, et al. 1991. J Biol. Chem. 266:18162-71; T. Fisher, et al. 1993. Nucleic Acids Research. 21 3857).

The ability of an oligonucleotide composition of the invention to inhibit protein synthesis can be measured using techniques which are known in the art, for example, by detecting an inhibition in gene transcription or protein synthesis. For example, Nuclease S1 mapping can be performed. In another example, Northern blot analysis can be used to measure the presence of RNA encoding a particular protein. For example, total RNA can be prepared over a cesium chloride cushion (see, e.g., Ausebel et al., 1987. Current Protocols in Molecular Biology (Greene & Wiley, New York)). Northern blots can then be made using the RNA and probed (see, e.g., Id.). In another example, the level of the specific mRNA produced by the target protein can be measured, e.g., using PCR. In yet another example, Western blots can be used to measure the amount of target protein present. In still another embodiment, a phenotype influenced by the amount of the protein can be detected. Techniques for performing Western blots are well known in the art, see, e.g., Chen et al. J. Biol. Chem. 271:28259.

In another example, the promoter sequence of a target gene can be linked to a reporter gene and reporter gene transcription (e.g., as described in more detail below) can be monitored. Alternatively, oligonucleotide compositions that do not target a promoter can be identified by fusing a portion of the target nucleic acid molecule with a reporter gene so that the reporter gene is transcribed. By monitoring a change in the expression of the reporter gene in the presence of the oligonucleotide composition, it is possible to determine the effectiveness of the oligonucleotide composition in inhibiting the expression of the reporter gene. For example, in one embodiment, an effective oligonucleotide composition will reduce the expression of the reporter gene.

A "reporter gene" is a nucleic acid that expresses a detectable gene product, which may be RNA or protein. Detection of mRNA expression may be accomplished by Northern blotting and detection of protein may be accomplished by staining with antibodies specific to the protein. Preferred reporter genes produce a readily detectable product. A reporter gene may be operably linked with a regulatory DNA sequence such that detection of the reporter gene product provides a measure of the transcriptional activity of the regulatory sequence. In preferred embodiments, the gene product of the reporter gene is detected by an intrinsic activity associated with that product. For instance, the reporter gene may encode a gene product that, by enzymatic activity, gives rise to a detectable signal based on color, fluorescence, or luminescence. Examples of reporter genes include, but are not limited to, those coding for chloramphenicol acetyl transferase (CAT), luciferase, beta-galactosidase, and alkaline phosphatase.

One skilled in the art would readily recognize numerous reporter genes suitable for use in the present invention. These include, but are not limited to, chloramphenicol acetyltransferase (CAT), luciferase, human growth hormone (hGH), and beta-galactosidase. Examples of such reporter genes can be found in F. A. Ausubel et al., Eds., Current Protocols in Molecular Biology, John Wiley & Sons, New York, (1989). Any gene that encodes a detectable product, e.g., any product having detectable enzymatic activity or against which a specific antibody can be raised, can be used as a reporter gene in the present methods.

One reporter gene system is the firefly luciferase reporter system. (Gould, S. J., and Subramani, S. 1988. Anal. Biochem., 7:404-408 incorporated herein by reference). The luciferase assay is fast and sensitive. In this assay, a lysate of the test cell is prepared and combined with ATP and the substrate luciferin. The encoded enzyme luciferase catalyzes a rapid, ATP dependent oxidation of the substrate to generate a light-emitting product. The total light output is measured and is proportional to the amount of luciferase present over a wide range of enzyme concentrations.

CAT is another frequently used reporter gene system; a major advantage of this system is that it has been an extensively validated and is widely accepted as a measure of promoter activity. (Gorman C. M., Moffat, L. F., and Howard, B. H.1982. Mol. Cell. Biol., 2:1044-1051). In this system, test cells are transfected with CAT expression vectors and incubated with the candidate substance within 2-3 days of the initial transfection. Thereafter, cell extracts are prepared. The extracts are incubated with acetyl CoA and radioactive chloramphenicol. Following the incubation, acetylated chloramphenicol is separated from nonacetylated form by thin layer chromatography. In this assay, the degree of acetylation reflects the CAT gene activity with the particular promoter.

Another suitable reporter gene system is based on immunologic detection of hGH. This system is also quick and easy to use. (Selden, R., Burke-Howie, K. Rowe, M. E., Goodman, H. M., and Moore, D. D. (1986), Mol. Cell, Biol., 6:3173-3179 incorporated herein by reference). The hGH system is advantageous in that the expressed hGH polypeptide is assayed in the media, rather than in a cell extract. Thus, this system does not require the destruction of the test cells. It will be appreciated that the principle of this reporter gene system is not limited to hGH but rather adapted for use with any polypeptide for which an antibody of acceptable specificity is available or can be prepared.

In one embodiment, nuclease stability of a double-stranded oligonucleotide of the invention is measured and compared to a control, e.g., an RNAi molecule typically used in the art (e.g., a duplex oligonucleotide of less than 25 nucleotides in length and comprising 2 nucleotide base overhangs) or an unmodified RNA duplex with blunt ends.

VII. Therapeutic Use

By inhibiting the expression of a gene, the oligonucleotide compositions of the present invention can be used to treat any disease involving the expression of a protein. Examples of diseases that can be treated by oligonucleotide compositions, just to illustrate, include: cancer, retinopathies, autoimmune diseases, inflammatory diseases (i.e., ICAM-1 related disorders, Psoriasis, Ulcerative Colitis, Crohn's disease), viral diseases (i.e., HIV, Hepatitis C), and cardiovascular diseases.

In one embodiment, in vitro treatment of cells with oligonucleotides can be used for ex vivo therapy of cells removed from a subject (e.g., for treatment of leukemia or viral infection) or for treatment of cells which did not originate in the subject, but are to be administered to the subject (e.g., to eliminate transplantation antigen expression on cells to be transplanted into a subject). In addition, in vitro treatment of cells can be used in non-therapeutic settings, e.g., to evaluate gene function, to study gene regulation and protein synthesis or to evaluate improvements made to oligonucleotides designed to modulate gene expression or protein synthesis. In vivo treatment of cells can be useful in certain clinical settings where it is desirable to inhibit the expression of a protein. There are numerous medical conditions for which antisense therapy is reported to be suitable (see, e.g., U.S. Pat. No. 5,830,653) as well as respiratory syncytial virus infection (WO 95/22,553) influenza virus (WO 94/23,028), and malignancies (WO 94/08, 003). Other examples of clinical uses of antisense sequences are reviewed, e.g., in Glaser. 1996. Genetic Engineering News 16:1. Exemplary targets for cleavage by oligonucleotides include, e.g., protein kinase Ca, ICAM-1, c-raf kinase, p53, c-myb, and the bcr/abl fusion gene found in chronic myelogenous leukemia.

Mututions in SOD1 cause certain forms of familial ALS disease. Inhibition of SOD1 expression by antisense oligonucleotides or RNAi has been shown to slow the progression of ALS-like symtoms in animal model. The highly active, nuclease stable and specific compounds that are the subject of this invention are well suited for therapeutic application to ALS.

The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, *Molecular Cloning A Laboratory Manual*, 2nd Ed., ed. by Sambrook, J. et al. (Cold Spring Harbor Laboratory Press (1989)); *Short Protocols in Molecular Biology*, 3rd Ed., ed. by Ausubel, F. et al. (Wiley, N.Y. (1995)); *DNA Cloning*, Volumes I and II (D. N. Glover ed., 1985); *Oligonucleotide Synthesis* (M. J. Gait ed. (1984)); Mullis et al. U.S. Pat. No. 4,683,195; *Nucleic Acid Hybridization* (B. D. Hames & S. J. Higgins eds. (1984)); the treatise, *Methods In Enzymology* (Academic Press, Inc., N.Y.); *Immunochemical Methods In Cell And Molecular Biology* (Mayer and Walker, eds., Academic Press, London (1987)); *Handbook Of Experimental Immunology*, Volumes I-IV (D. M. Weir and C. C. Blackwell, eds. (1986)); and Miller, J. *Experiments in Molecular Genetics* (Cold Spring Harbor Press, Cold Spring Harbor, N.Y. (1972)).

EXAMPLES

The invention now being generally described, it will be more readily understood by reference to the following examples, which are included merely for purposes of illustration of certain aspects and embodiments of the present invention, and are not intended to limit the invention.

Although most of the examples below use the SOD1 and/or PPIB genes as the target genes, the methods and reagents of the invention are generally applicable to any other genes, and are not so limited. For simplicity, the subject RNAi constructs are sometimes referred-to as "Alternate RNAi Compound" in the examples below.

Example 1 Alternate RNAi Compound is as Effective or Superior Compared to Standard siRNAs In Vitro In order to demonstrate that the subject modified RNAi constructs ("Alternate RNAi Compounds") are at least as effective, if not superior, when compared to standard siRNAs or siRNA with different chemical modification, the following side-by-side comparison experiment was conducted.

Alternate RNAi Compounds (5 nM) targeting SOD1 were reverse transfected into HEK293 cells in suspension, using LIPOFECTAMINE™ RNAiMAX (Invitrogen) as a transfection agent. Cells were lysed at 24 hrs, and SOD1 mRNA levels were quantified using a bDNA assay (Panomics QUANTIGEN®).

The bDNA assay is a sandwich nucleic acid hybridization method that uses bDNA molecules to amplify signal from captured target RNA. According to the manufacturer, bDNA technology forms the basis of the FDA-approved clinical diagnostic VERSANT 3.0 assays for HIV, HCV and HBV viral load, that are offered commercially by Siemens and have been in use for over a decade. Another advantage of bDNA assays is that RNA is measured directly from the sample source, without RNA purification or enzymatic manipulation, thereby avoiding inefficiencies and variability introduced by or errors inherent to these processes.

In this assay, SOD1 mRNA was normalized to Cyclophilin B (PPIB) mRNA. As shown in FIG. 2, "R1 original chemistry" refers to double stranded 21-mer RNAi construct hybridizing to the SOD1 mRNA starting at nucleotide 436 of NCBI RefSeq ID NM_000454. The 5'-end of both the sense and antisense strands are phosphorylated, and the terminal nucleotides for both strands are modified by 2'-fluoro and/or phosphothioate linkage. See the sequence indicated in FIG. 1 as ID No. 10105.

The modified 2'-OMe version of R1 is indicated in FIG. 1 as ID number 10104, in which 2'-F nucleotides of 10105 have been replaced with 2'-O-Me (ID No. 10104).

ID No. 10023 is a 25-mer blunt-ended Alternate RNAi Compound hybridizing to the SOD1 mRNA starting at nucleotide 434 (i.e., adding two nucleotides to each end of the 21-mer R1 sequence). The 4 nucleotides at the most 5'-end and the 4 nucleotides at the most 3'-end are modified by 2'-O-methyl groups (and the antisense strand is not modified).

"MM ctrls" with related chemistries were used for the siRNAs or Alternate RNAi Compounds and shown as an average. As shown in FIG. 2, applying 2'OMe chemistry and/or extending the length of the R1 sequence trends toward an improvement of activity. This can be beneficial, not only because the cost of making 2'OMe modification is generally less than making 2'-F modification, but also because siRNAs with 2'F modifications have resulted in toxicity in animals whereas an Alternate RNAi Compound with 2'OMe does not exhibit a toxicity even at a higher dose.

Thus, Alternate RNAi Compound is at least as effective as or superior compared to prior art 2'-F modified siRNAs in vitro.

Example 2 Activity of Exemplary SOD1 Alternate RNAi Compounds In Vitro

This example demonstrates that some target regions on a target gene (in this case, the SOD1 gene) may be better target sites than other.

Different 25-mer Alternate RNAi Compounds (5 nM) targeting SOD1 were reverse transfected into HEK293 cells in suspension using LIPOFECTAMINE™ RNAiMAX (Invitrogen) as a transfection agent. Cells were lysed at 24 hrs and SOD1 mRNA levels were quantified using a bDNA assay (Panomics QUANTIGENE®). SOD1 mRNA was normalized to Cyclophilin B (PPIB) mRNA. MM-10025 indicates chemistry-matched mismatch control.

Figure 3:
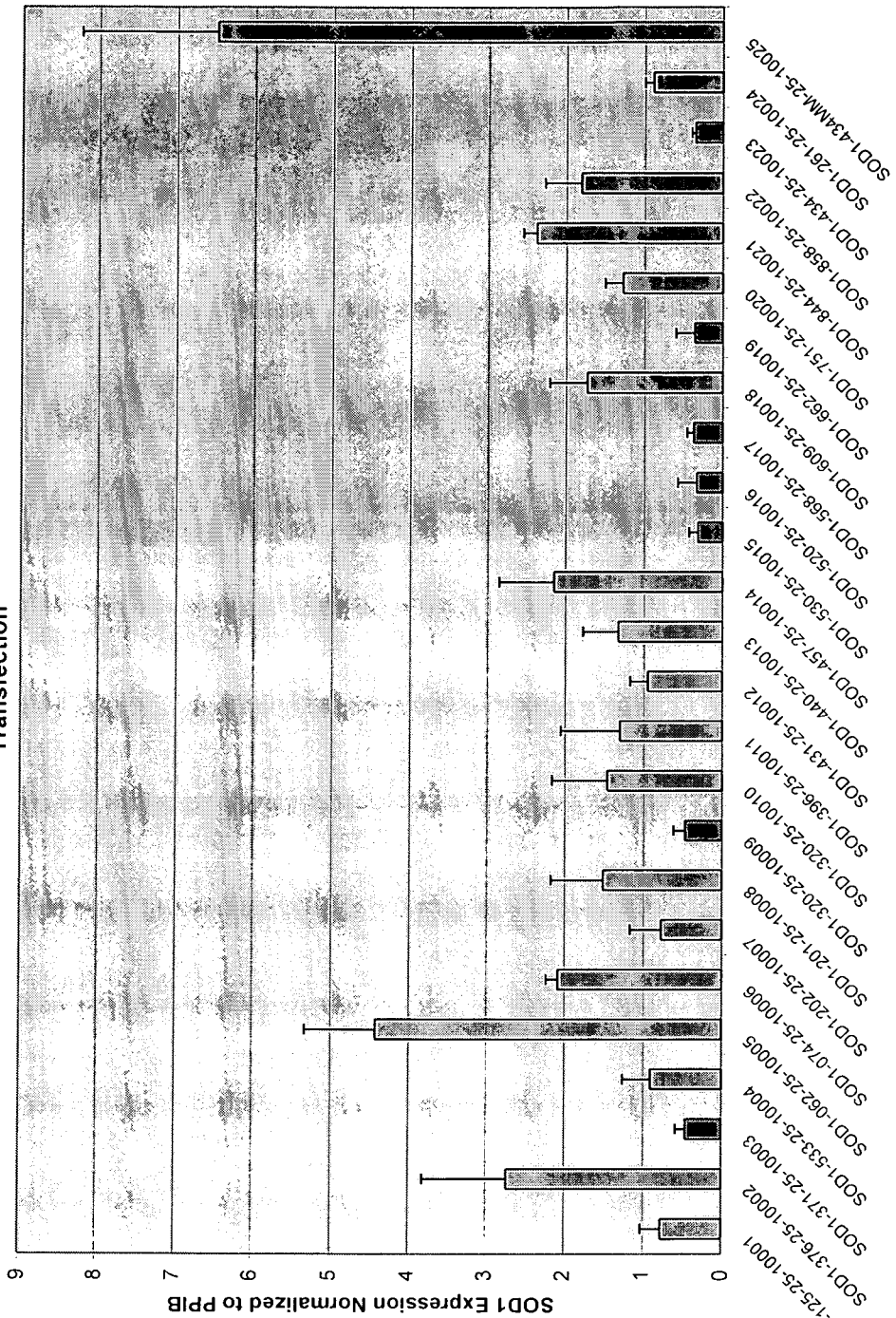
FIG. 3 indicates Alternate RNAi Compounds sequences with activity in reducing SOD1 mRNA levels.

Although all the Alternate RNAi Compounds test here have the same modification chemistry (e.g., sense strand modified at both ends with 2'-O-methyl groups), seven Alternate RNAi Compounds in the primary screen reduced normalized SOD1 levels by ≥90% compared to treatment with a chemistry-matched control, while the majority of the other Alternate RNAi Compounds reduced normalized SOD1 levels by ≥60%. See FIG. 3.

Example 3 Alternate RNAi Compounds Against SOD1

This example demonstrates that certain subject Alternate RNAi Compounds (25-mer with blunt ends, with four 2'OMe on each end of the sense strand) are effective for SOD1 expression knock down.

Eight Alternate RNAi Compounds (5 nM) targeting human SOD1 were reverse transfected into HEK293 cells in suspension using LIPOFECTAMINE™ RNAiMAX (Invitrogen) as a transfection agent. Cells were lysed at 24 hrs and SOD1 mRNA levels were quantified using a bDNA assay (QUANTIGENE®). SOD1 mRNA levels were normalized to Cyclophilin B (PPIB) mRNA and made relative to a chemistry-matched control set at 100. MM-1025 is the chemistry-matched control in Alternate RNAi Compound chemistry. In addition, activity of R1 (modified 21-mer siRNA sequence and chemistry configuration, see Example 1) is given for comparison. MM-10032 is a chemistry-matched control for R1.

Figure 4:
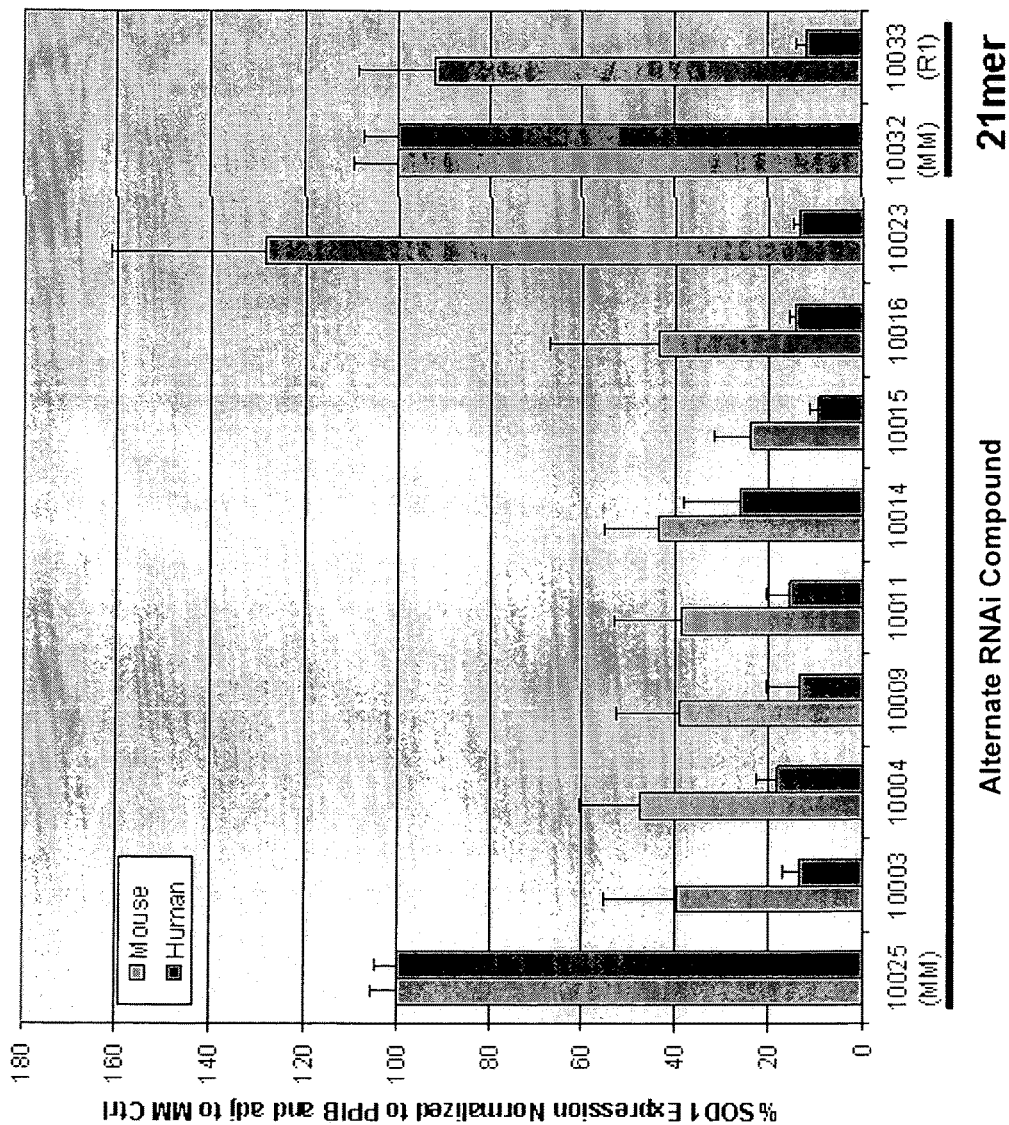
FIG. 4 shows that certain exemplary Alternate RNAi Compounds (e.g., 25-mer with blunt ends, with four 2'OMe on each end of the sense strand) for selected target sites are effective against mouse and human SOD1.

As shown in FIG. 4, the subject Alternate RNAi Compounds had excellent activity against the SOD1 target gene. Activity was improved over the 21-mer modified duplex R1. These sequences also maintained activity against the mouse SOD1 gene.

Example 4 Dose Response Analysis for SOD1 Alternate RNAi Compounds

HEK293 cells were transfected with Alternate RNAi Compounds targeting SOD1 using concentrations from 0.01 nM to 10 nM. In these studies, total duplex concentration at each concentration was maintained at 25 nM by the addition of non-targeting, filler RNA duplex species to the transfection reaction. This method enabled testing of very low concentrations of targeting duplex in a way that maintained transfection of the cells based on recommendations from the manufacturers. Human SOD1 mRNA was measured at 48 hrs post-transfection by QuantiGene bDNA Assay. Alternate RNAi Compound 10014 has been tested multiple times in previous studies, and was included here as a control for comparison. The other duplexes tested in this study were identified as hits in single concentration experiments and were here followed up for $EC_{50}$ determination. Duplexes 10011, 10014 and 10097 are mouse/human homologous and have confirmed activity in mouse and human cell culture. The activity of duplexes 10089 and 10097 has not yet been confirmed in mouse cells, but these duplexes have human/mouse sequence homology.

Figure 5A:
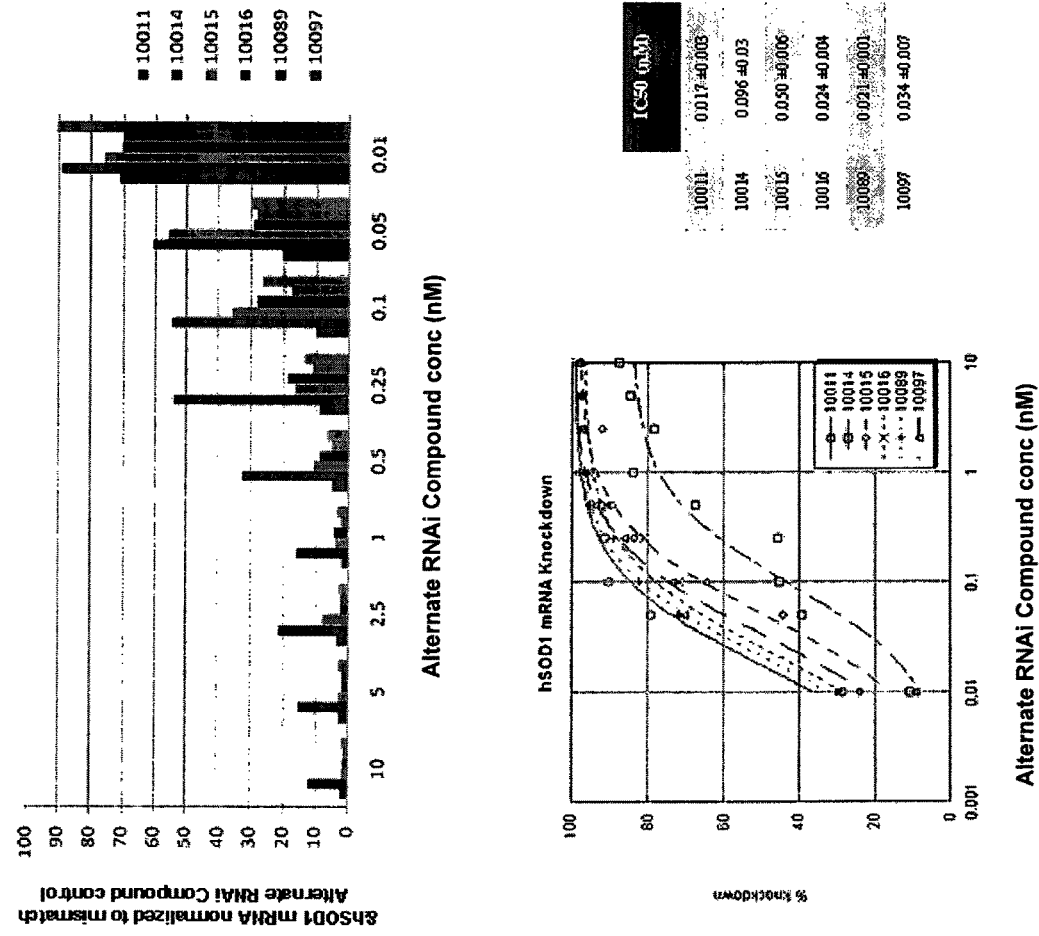
FIG. 5A illustrates a dose response analysis for SOD1 Alternate RNAi Compounds and identification of active duplexes with $EC_{50}$ values of <50 µM.

Dose titration studies using optimized transfection conditions allow direct comparison of duplex potencies. Particularly active duplexes were identified in these studies with $EC_{50}$ values improved over the original hits and with values <50 μM (see FIG. 5A).

Figure 5B:
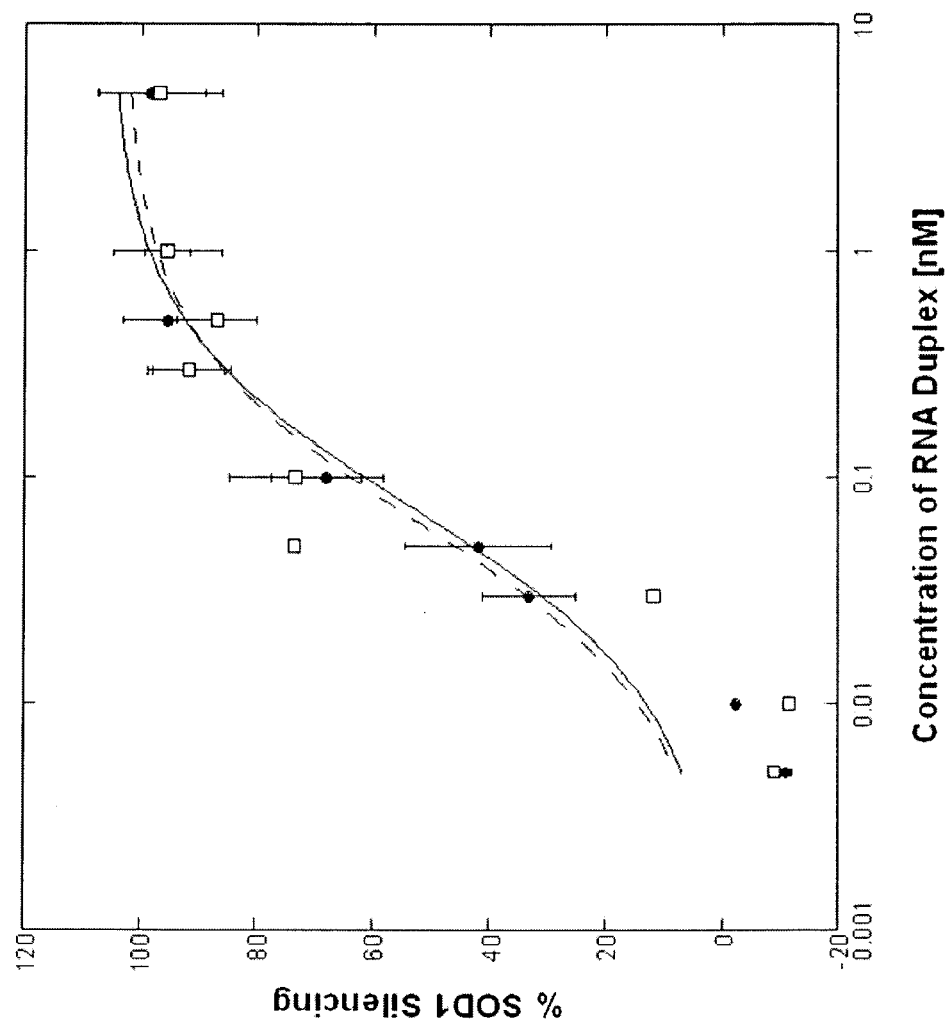
FIG. 5B shows dose response analysis for SOD1 Alternate RNAi Compounds in human HEK293 cells, and identification of active duplexes with $EC_{50}$ values of about 50 µM.

FIG. 5B shows an exemplary dose titration curve comparison between an unmodified, 25-bp, blunt-ended duplex (filled circle) or a subject 25-bp, blunt-ended duplex with "4/4" 2'-O-Me passenger strand modifications (open square). The human HEK293 cells were separately transfected with either construct. Both RNA duplexes target the SOD1 gene and were designed to a region of the gene that is homologous in both human and murine cells. Cells were lysed 48 h after transfection and mRNA levels were measured using a bDNA hybridization assay as described herein. The $EC_{50}$ values for the unmodified 25-bp duplex and "4/4" 2'-O-Me chemistry 25-bp duplex are 0.072 nM±20 nM and 0.062 nM±0.031 nM, respectively.

Figure 5C:
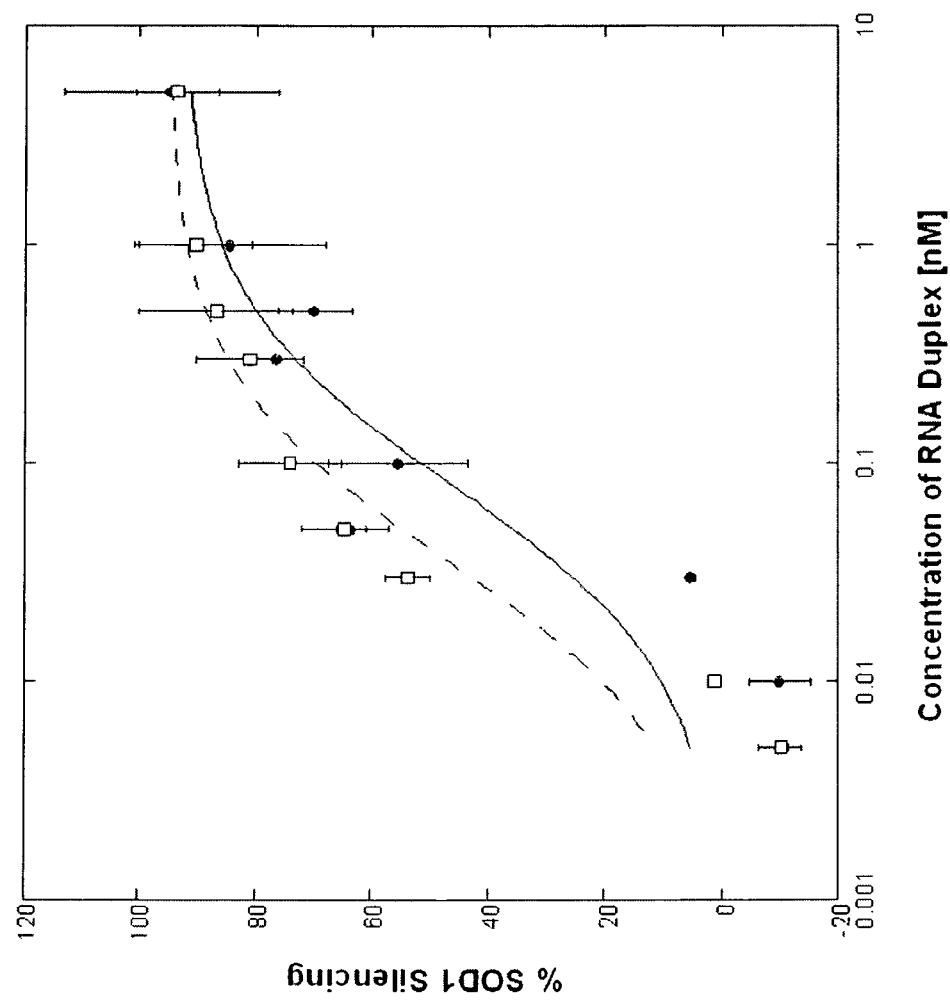
FIG. 5C shows dose response analysis for SOD1 Alternate RNAi Compounds in murine NIH3T3 cells, and identification of active duplexes with $EC_{50}$ values of about 50 µM.

FIG. 5C shows essentially the same experiment conducted in murine NIH3T3 cells. The $EC_{50}$ values for the unmodified 25-bp duplex and "4/4" 2'-O-Me chemistry 25-bp duplex are 0.079 nM±0.042 nM and 0.037 nM±0.013 nM, respectively.

These experiments show that silencing activity of the subject 25-bp modified RNA duplexes is consistently in the picomolar concentration range, and is equivalent to the silencing activity of an unmodified 25-bp duplex of the same sequence.

Example 5 Alternate RNAi Compounds with High Potency Against PPIB

The result in Example 4 is neither site-specific nor gene specific, since potent gene silencing activity is also observed when comparing modified and unmodified duplexes targeting other sites in the SOD1 gene or the cyclophillin B (PPIB) gene, a ubiquitous gene expressed in most (if not all) tissues.

HEK293 cells were transfected with siRNA or Alternate RNAi Compound and incubated for 24 hours. Gene expression was measured using a bDNA assay (Panomics) with probes specific to human PPIB or SOD1. Analysis was performed by normalizing PPIB expression to SOD1 expression (control gene). The percent PPIB knockdown was adjusted using the negative control of Luciferase siRNA or Alternate RNAi Compound.

Figure 6A:
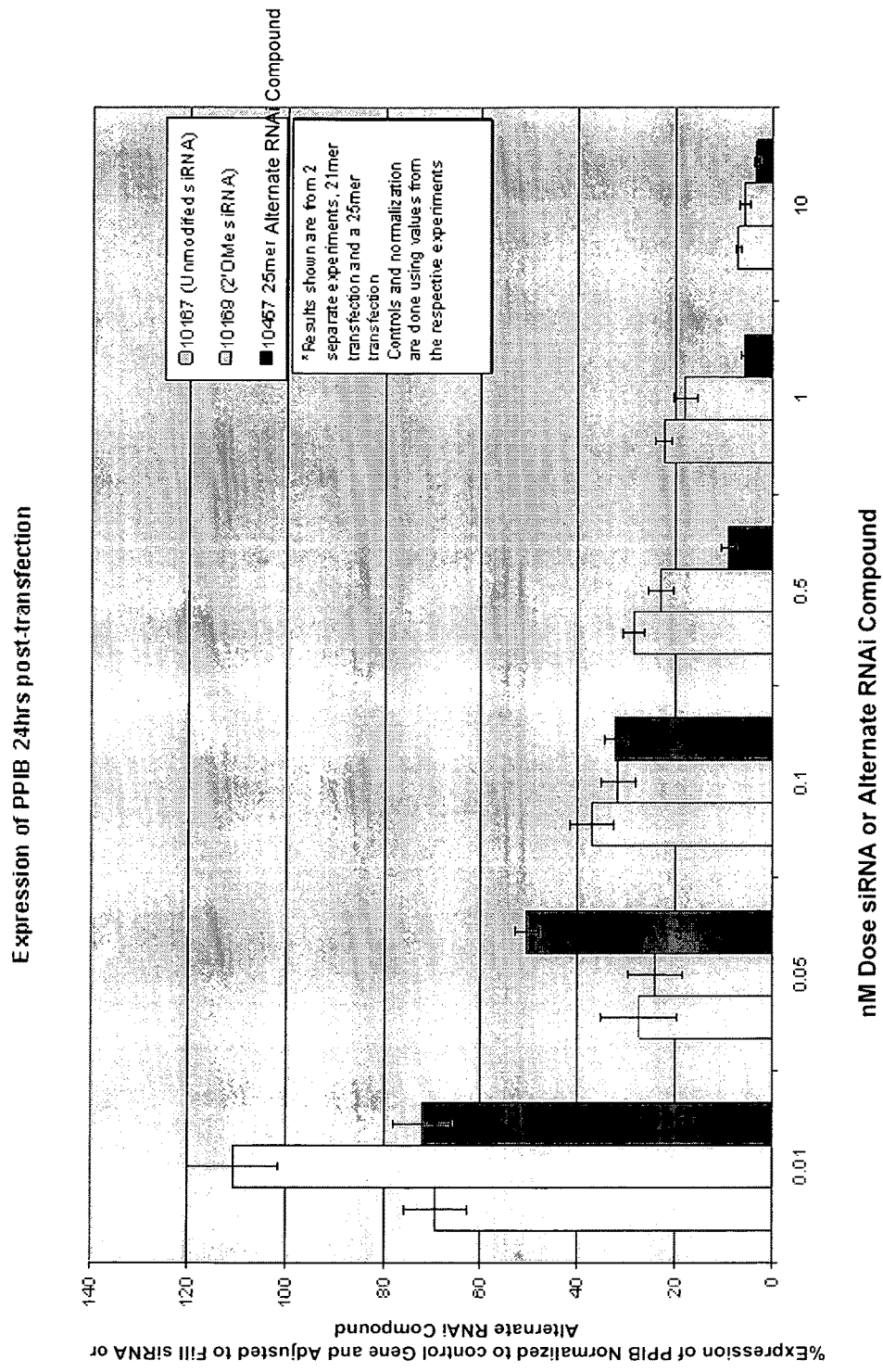
FIG. 6A shows the expression of PPIB (cyclophilin B), a ubiquitous protein, after transfection with siRNA or Alternate RNAi Compound.

FIG. 6A shows that the 25-mer Alternate RNAi Compound ID NO. 10457 (blunt-ended 25-mer with 4 2'OMe at each end of sense strand—"4/4") targeting PPIB maintains or improves upon the high potency demonstrated for an unmodified 21-mer siRNA. Construct 10167 is an unmodified 21-mer siRNA from literature that targets PPIB. Construct 10169 has the same sequence as 10167, but also has 2'-O-Me modification on the first 4 and last 4 nucleotides on its sense strand.

Figure 6B:
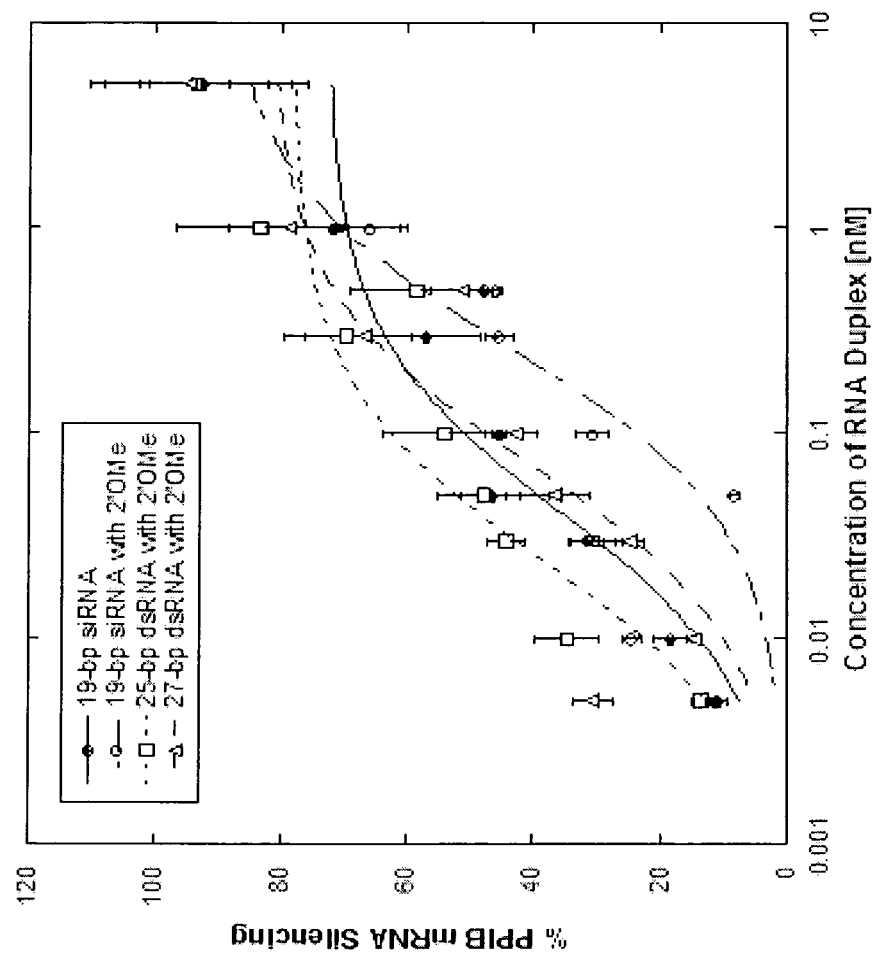
FIG. 6B shows dose response analysis for PPIB Alternate RNAi Compounds in human HEK293 cells, and identification of active duplexes with $EC_{50}$ values of about 25 or 72 µM for 25-mer and 27-mer, respectively.

FIG. 6B shows an exemplary dose titration curve comparison among a 19-bp+2 nt siRNA (FIG. 6B, filled circle); 19-bp+2 nt siRNA with 2'-O-Me on the passenger strand (FIG. 6B, open circle); 25-bp, blunt-ended duplex with 2'-O-Me passenger strand modification (FIG. 6B, open square); or 27-bp, blunt-ended duplex with 2'-O-Me passenger strand modification (FIG. 6B, open triangle). The RNA duplexes target the PPIB gene in a region that is homologous in both human and mouse. Additionally, the duplexes were designed to preserve the same mRNA cleavage site regardless of length. The $EC_{50}$ values are: unmodified 19-bp+2 nt siRNA=0.043 nM±0.019 nM, 19-bp+2 nt siRNA with 2'-O-

Me=0.276 nM 0.144 nM, 25-bp duplex 2'-O-Me=0.025 nM±0.009 nM, 27-bp duplex 2'-O-Me=0.072 nM 0.035 nM.

Figure 6C:
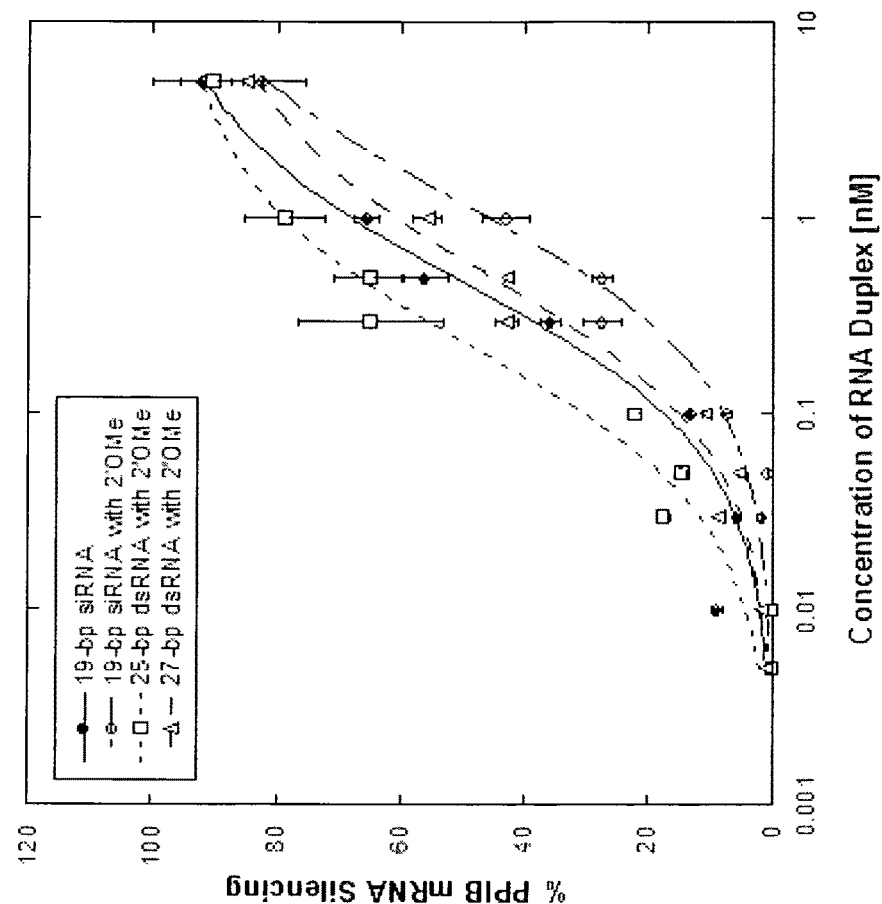
FIG. 6C shows dose response analysis for PPIB Alternate RNAi Compounds in murine NIH3T3 cells, and identification of active duplexes with $EC_{50}$ values of about 200 or about 500 µM for 25-mer and 27-mer, respectively.

The same experiment was also repeated in murine NIH3T3 cells (FIG. 6C). The $EC_{50}$ values are: unmodified 19-bp+2 nt siRNA=0.482 nM±0.076 nM, 19-bp+2 nt siRNA with 2'-O-Me=1.235 nM±0.194 nM, 25-bp duplex 2'-O-Me=0.219 nM±0.044 nM, 27-bp duplex 2'-O-Me=0.518 nM±0.099 nM.

Example 6 Chemical Modifications Prevent Dicer Processing of Alternate RNAi Compound One of the key discoveries made by the Applicants is that certain modified double stranded RNAs are not cleaved by Dicer, despite the prior art teaching that dsRNA longer than 21-mer is cleaved by Dicer to 21-mer products. In addition, Applicants have shown that the antisense strand in the Dicer-resistant dsRNA can be incorporated into the RISC complex and serve as the guide sequence for RNA interference. The 5'-end nucleotide (rather than the 3'-end or other nucleotides) of this Dicer-resistant dsRNA lines up with the 5'-end of the Dicer-cleaved 21-mer in the RISC complex.

Figure 7:
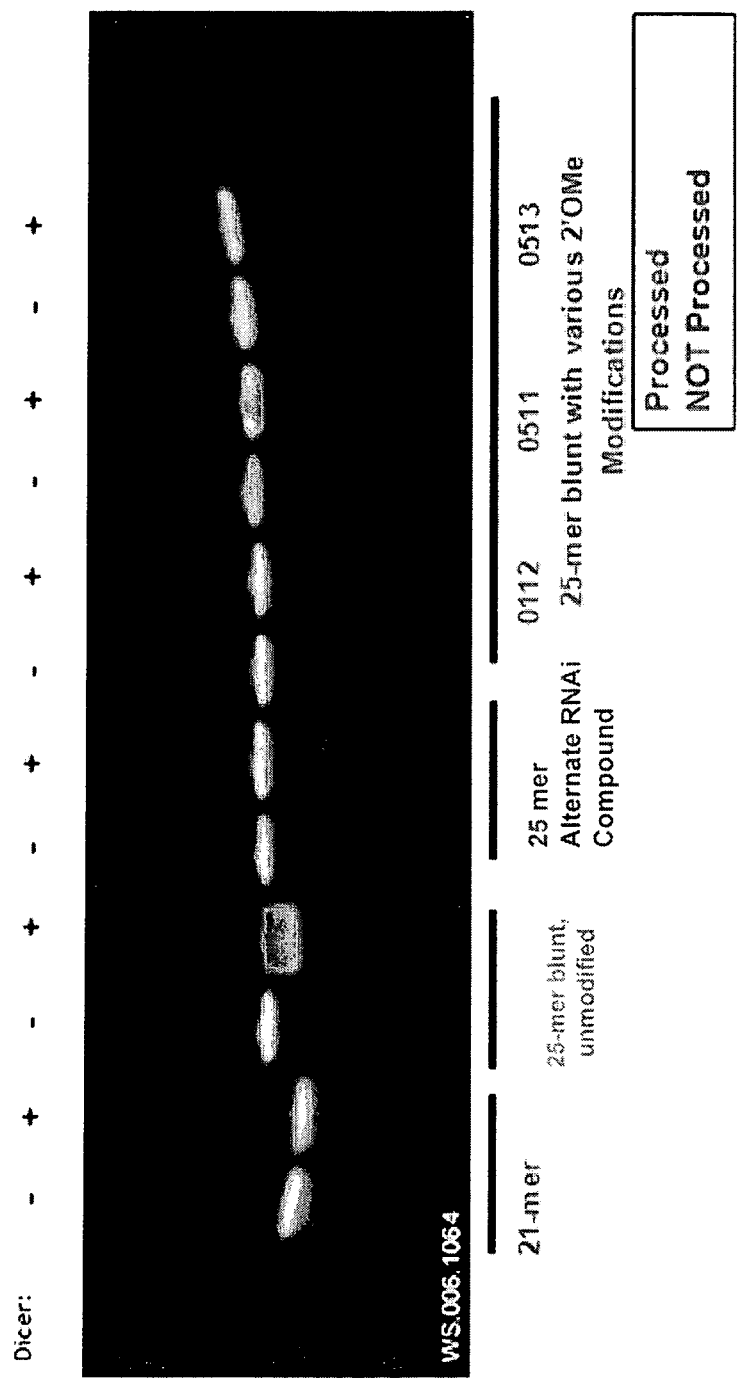
FIG. 7 demonstrate that the Alternate RNAi Compound 25-mers with sense strand modifications are not cleaved by the Dicer enzyme.

In the first experiment, several RNAi duplexes, including several 25-mer Alternate RNAi Compounds with different modification chemistries (see below), were incubated with or without recombinant human Dicer enzyme (0.5 units) (Genlantis, San Diego, Calif.) for 8 hours at 37° C. in 250 mM NaCl, 30 mM HEPES (pH 8.0), 0.05 mM EDTA, 2.5 mM $MgCl_2$ reaction buffer. After incubation, the reaction was stopped by adding loading buffer and snap freezing with liquid nitrogen. An aliquot of each sample (15 pmoles) was run on a native 20% polyacrylamide gel in TBE buffer. Samples were loaded alternating without and with Dicer enzyme as indicated at the top of the gel. As shown in FIG. 7, various 2'-O-Me modifications to blunt-ended 25-mer duplexes resist cleavage by Dicer, in contrast to a 25-mer blunt-ended duplex that has not been modified.

This indicates that Alternate RNAi Compound duplexes would be expected to function in cells as a uniform species and not be cleaved to multiple different 21-mer duplexes or other shorter species to have activity. These findings have important implications for clinical development because the active drug is be a singular species. This is in contrast to current models which suggest that duplexes longer than 21-mer are processed to be that length. Furthermore, data from 27-mer duplexes showing modification on one side of the duplexed RNA shows processing. For example, Kubo et al. (*Oligonucleotides* 17(4): 445-464, 2007) showed that dicer will process long duplexes with modifications on the same side.

Here, Applicants have demonstrated that certain sense and/or antisense strand modification of longer dsRNA, such as blunt, 25-mer duplexes with 4×2' O-methyl modifications on either end of the sequence, are not cleaved by the Dicer enzyme. It is noted that other modification strategies as described herein can also eliminate ability to be cleaved by Dicer. Modifications are generally included on both the 5' and 3' ends of the sense strand.

Example 7 Northern Blot of Immunoprecipitated Ago2 Loaded with Alternate RNAi Compound This example demonstrates that the Dicer-resistant dsRNAs of the invention are loaded onto the RISC complex, and has gene silencing activity.

Figure 8A:
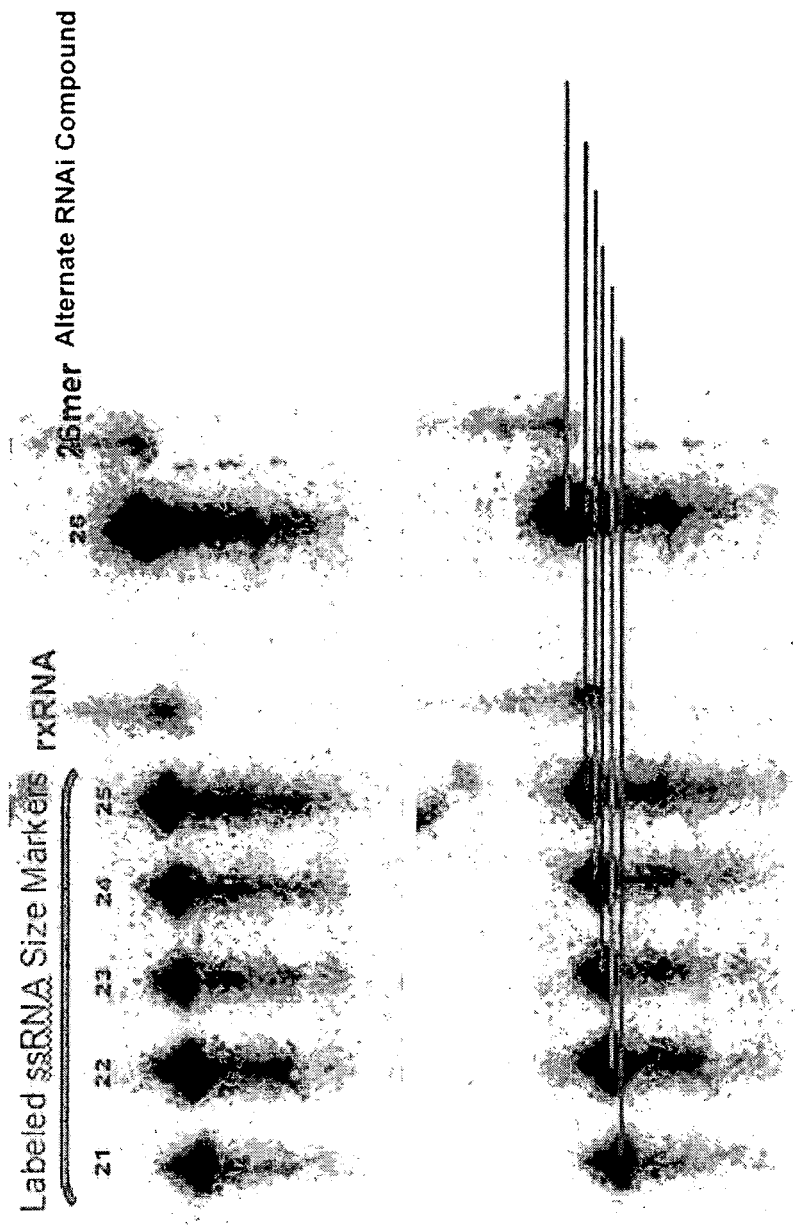
FIG. 8A demonstrates that the 25-mer duplexes are found to be associated with the RNAi silencing Ago2 complex.

293S cells stably expressing myc-Ago2 (courtesy of the Hannon Lab, CSHL) were transfected with either 25-mer (10174 in Table 4) or 26-mer (10175 in Table 4) Alternate RNAi Compound duplexes. After 24 hours, cell lysates were collected and immunoprecipitated using agarose beads conjugated to anti-c-myc antibodies (Sigma) to precipitate myc-Ago2 protein. RNA that was loaded into Ago2 was precipitated and loaded onto a 15% polyacrylamide gel. $^{32}$P end-labeled single stranded RNA markers from 21-26 nt were included on the gel to determine size. RNA from the polyacrylamide gel was transferred to a nylon membrane and UV cross-linked to the membrane. The membrane was incubated overnight with $^{32}$P-labeled LNA probes specific to the Alternate RNAi Compound that was transfected. After washing, the blots were visualized using a phosphor imagining system (Fuji BAS-2500) (FIG. 8A).

This result further supports the conclusion that 25-mer or 26-mer Alternate RNAi Compounds are not cleaved by Dicer as part of the RNAi process. In addition, the 25-mer and 26-mer duplexes were found to be associated with the RNAi silencing Ago2 in the RISC complex. Sequences are shown in Table 4.

In a similar experiment, 293 cells expressing c-myc Ago2 were transfected with various duplexes against SOD1 (e.g., 21-mer with no modification; 25-mer with no modification; and 25-mer with 4/4 2'-O-Me modification). The cells were harvested, lysed, and c-myc Ago2 was immunoprecipitated as described before. After immunoprecipitation, the RNA from the IP fractions was extracted and precipitated. RNA was loaded onto a denaturing polyacrylamide gel, transferred to a nylon membrane, and detected using LNA probes specific to the guide strand of the transfected RNA duplexes as described herein.

Figure 8B:
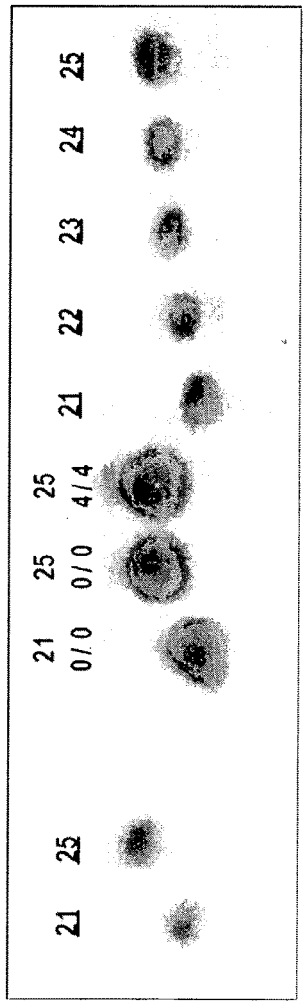
FIG. 8B shows a Northern blot of the guide strand of SOD1 targeting RNA duplexes.

FIG. 8B shows a Northern blot of the guide strand of SOD1 targeting RNA duplexes. Single stranded RNAs were run alongside captured guide strand RNA. The size markers are underlined and correspond to sizes from 21 to 25 nt long. By comparison to single-stranded RNA markers of 21-25 nt, the Ago2:RISC-associated guide strand of the two tested 25-bp duplexes was determined to be 25 nt in length. These data confirm that the modified guide strand is bound by Ago2:RISC in its full length form. Note that in this study, the unmodified 25-bp duplex was not efficiently cleaved to the expected smaller product that would have resulted from efficient Dicer processing in the cell. Since these engineered 293 cell lines dramatically over-express c-myc tagged Ago2 protein, it is possible that the abundance of the Ago2:RISC complex causes the RNA duplex to be loaded before being able to be processed by Dicer.

Figure 8C:
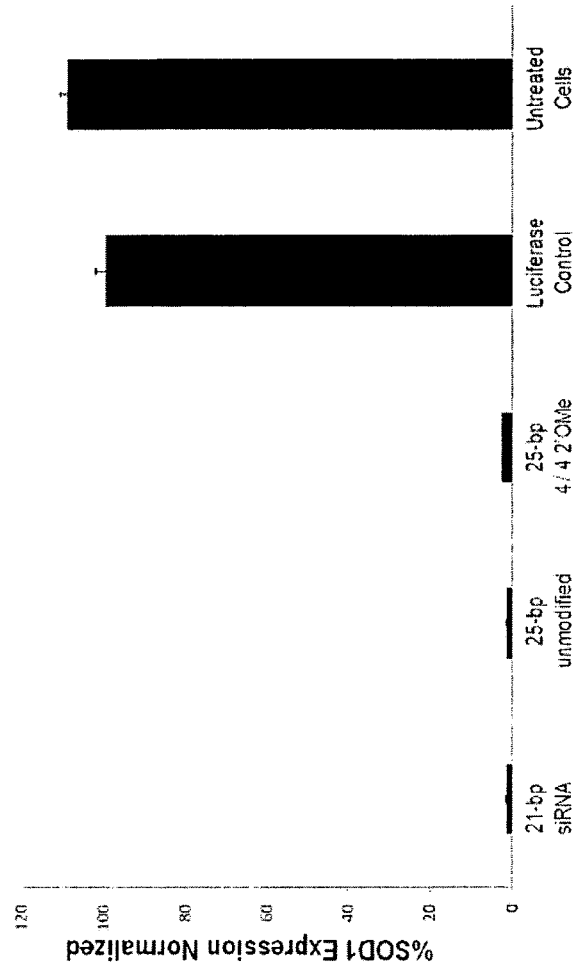
FIG. 8C shows expression of SOD1 after transfection of 293 cells expressing c-myc Ago2.

Potent activity was confirmed in these cells by measuring target mRNA reduction in an aliquot of the cell lysate prior to immunoprecipitation. FIG. 8C shows expression of SOD1 after transfection of 293 cells expressing c-myc Ago2. Before immunoprecipitation of c-myc Ago2, a fraction of the cell lysate was taken for total cell RNA purification. The RNA was purified and gene expression was measured using a bDNA assay as described in the methods. The levels of SOD1 expression are normalized to PPIB and adjusted to a luciferase targeting control duplex. The final concentration of transfected SOD1 targeting RNA duplex was 25 nM.

Example 8 mRNA Cleavage Assay of a Synthetic Substrate Using Purified RISC

This example demonstrates that the 5'-end of the Dicer-resistant antisense strand (guide sequence) in the Alternate RNAi Compound aligns with the 5'-end of the Dicer cleavage product (21-mer), and that the cleavage site (on the target mRNA) is between the 10th and the 11th nucleotides from the 5'-end of the guide sequence.

In one experiment, 293S cells stably expressing myc-Ago2 (courtesy of the Hannon Lab, CSHL) were transfected with several Alternate RNAi Compound duplexes (10023 and 10174), along with the 21-mer modified dsRNA 10036 (R1). After 24 hours, cell lysates were collected and immunoprecipitated using agarose beads conjugated to anti-c-myc antibodies (Sigma). Immunoprecipitation (IP) samples were incubated for 2 hours at 37° C. with a synthetic, radiolabeled 50 nt substrate (Table 5). Samples were then run on a 15% polyacrylamide gel and visualized using a phosphor imager (Fuji BAS-2500).

Note that the 25-mer Alternate RNAi Compound 10023 has 4 extra 5'-end nucleotides compared to R1/10036, and thus its predicted cleavage product would be 4 nucleotides longer than that of the 10036. The 25-mer Alternate RNAi Compound 10174 has 4 extra 3'-end nucleotides compared to R1/10036, but has the same 5'-end, and thus its predicted cleavage product would be the same as that of the 10036.

Cleavage of the target synthetic substrate occurs at a uniform point 10 nt from the 5'-end of the antisense strand for non-Dicer processed duplexes longer than 21 nt (data not shown). There is a single cleavage position which results not in a family of bands, but one product band. This result has implications for the design of active duplexes and enables one to position chemical and sequence modifications on any length duplexes with knowledge of the cleavage position. Key residues are defined by this result.

The result was further confirmed with three other duplexes designed to direct cleavage of a different site on the SOD1 gene (see FIGS. 9A and 9B). Specifically, a synthetic substrate was chemically synthesized to correspond to a 50 nt region of the SOD1 gene containing the target sequence for the RNA duplexes tested. FIG. 9A is a schematic of the synthetic substrate and predicted cleavage position and products. In FIG. 9B, RNA duplexes targeting SOD1 were transfected into 293 cells expressing c-myc. Ago2 as described in methods. The cells were harvested, lysed, c-myc Ago2 was immunoprecipitated, and reconstituted in buffer. The immunoprecipitates were incubated with a 50 nt $^{32}$-P-labeled synthetic substrate for 2 h at 30° C. as described in methods. After 2 hr incubations, samples were loaded onto a denaturing, polyacrylamide gel along with size markers (shown underlined). Sample letters correspond to the following duplexes shown in the schematic in panel a. A=unmodified 19-bp+2 nt siRNA, B=unmodified 25-bp duplex, C=25-bp duplex with 4/4 2'OMe, D=25-bp duplex with 4/4 2'OMe, E=Luciferase Ctrl duplex.

Example 9 Chemical Modifications Prevent Dicer Processing

Figure 17A:
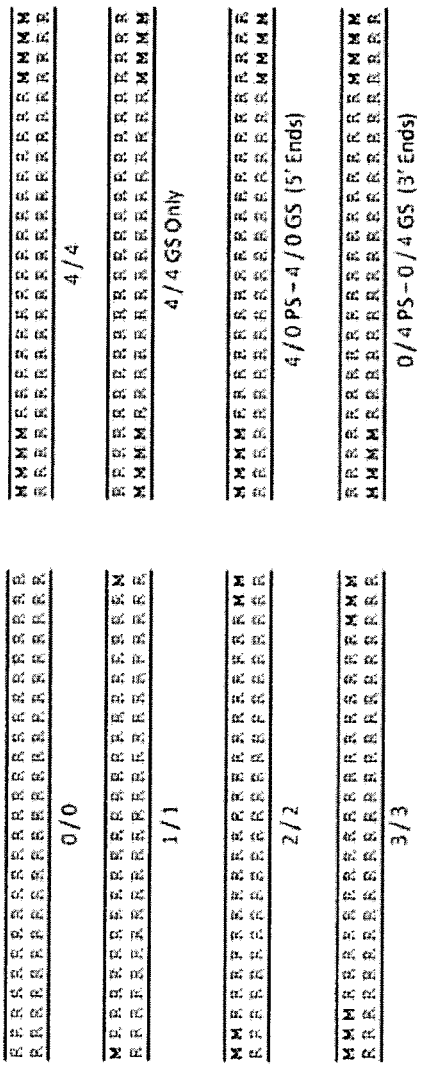
FIG. 17A is a schematic of chemical modifications applied to an RNA duplex that targets SOD1. The R in the duplexes represents a normal or unmodified RNA nucleotide having no 2' position modification. The M represents an O-methyl modification to the 2' position of the RNA nucleotide. Most nucleotide modifications are placed on the passenger strand unless otherwise noted.

The above studies show that the 25-bp RNA duplexes are able to achieve potent gene silencing, load fully into Ago2:RISC, and cleave intended targets across from nucleotide 10 of the guide strand. Previous studies have shown that a methylation modification of nucleic acids can prevent endonuclease activity and it could potentially inhibit Dicer's ability to process duplexes >21-bp. To explore Dicer processing with these chemically modified RNA duplexes, a panel of modification configurations was tested for susceptibility to Dicer cleavage in vitro (FIG. 17A). Since activity and target specificity are defined by the 5' position of the guide strand sequence that is loaded into RISC, an understanding of the cleavage products, if any, would help elucidate the role of Dicer processing in RNAi activity.

Figure 17B:
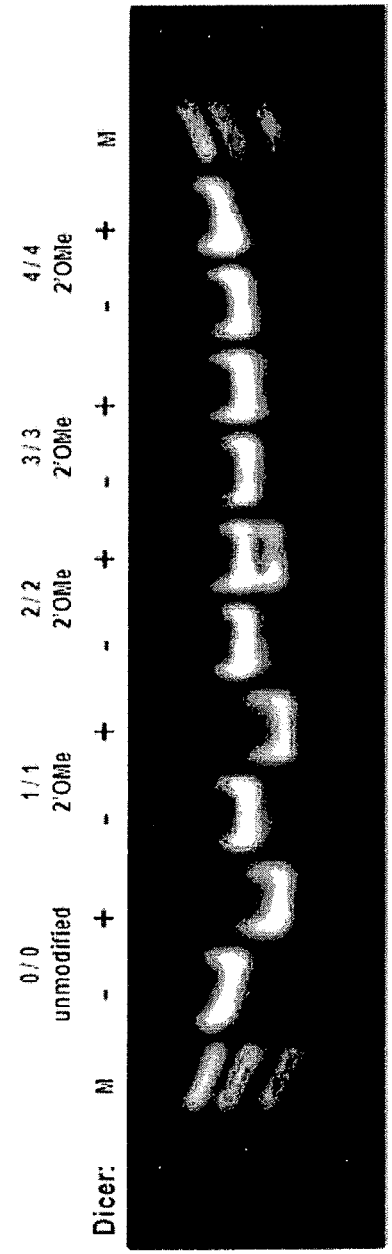
FIG. 17B is a TBE-polyacrylamide gel of RNA duplexes after overnight incubation with recombinant human dicer enzyme as described herein. Lane M designates a siRNA marker, sizes (top to bottom): 25-bp, 21-bp, 17-bp.
Figure 17C:
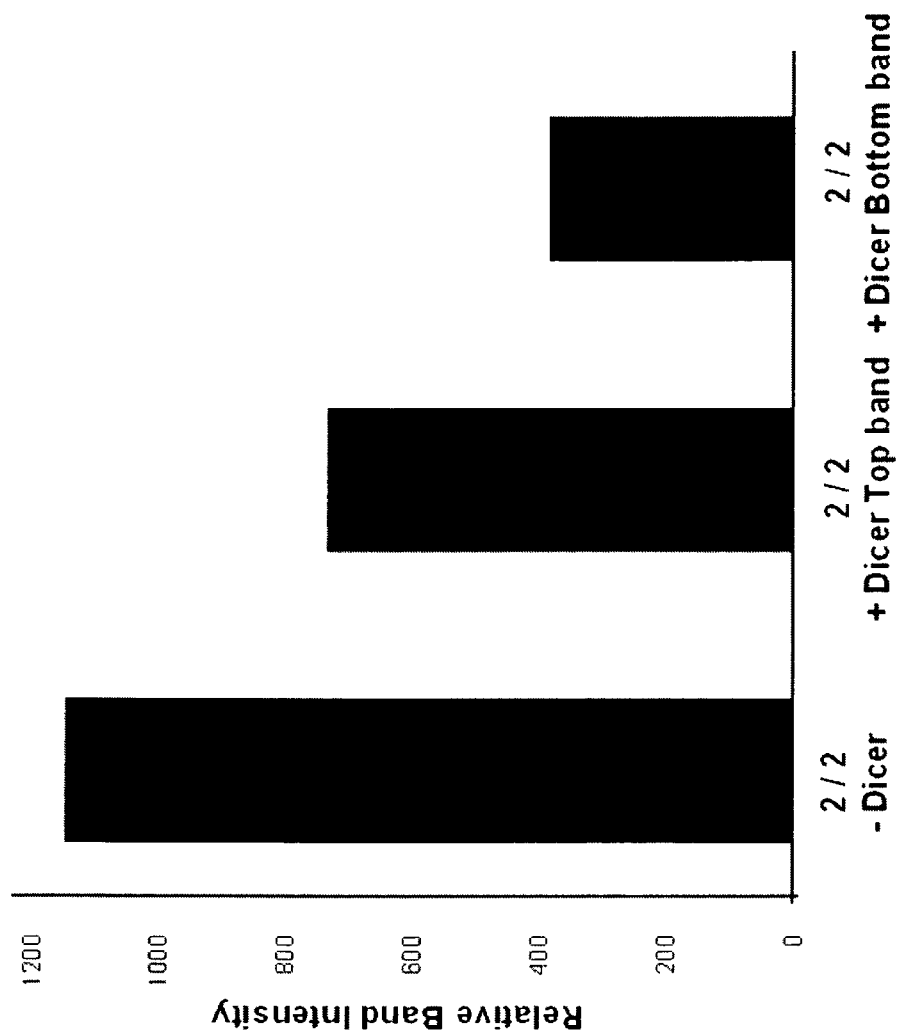
FIG. 17C shows quantification of processing of 25-bp RNA duplex with "2/2" 2'-O-Me chemistry. Density of the partially processed bands was quantified using LabWorks software.

A series of duplexes targeting the SOD1 gene were modified on both ends (5' and 3') of the passenger strand with varying numbers of 2'OMe nucleotides. These duplexes were incubated with recombinant human Dicer enzyme and analyzed for processing (FIG. 17B). The unmodified 25-bp duplex and the duplex with one 2'OMe modification on both ends of the passenger strand (1/1) are completely processed to the 21-bp siRNA product. The duplex with two 2'OMe on both ends of the passenger strand (2/2) showed partial processing under these conditions (16 h incubation) with about 30% of the duplex remaining unprocessed in this study (FIG. 17C). However, the duplex with either three or four 2'OMe modified nucleotides on both ends of the passenger strand (3/3 or 4/4) is not processed by the Dicer enzyme.

Figure 17D:
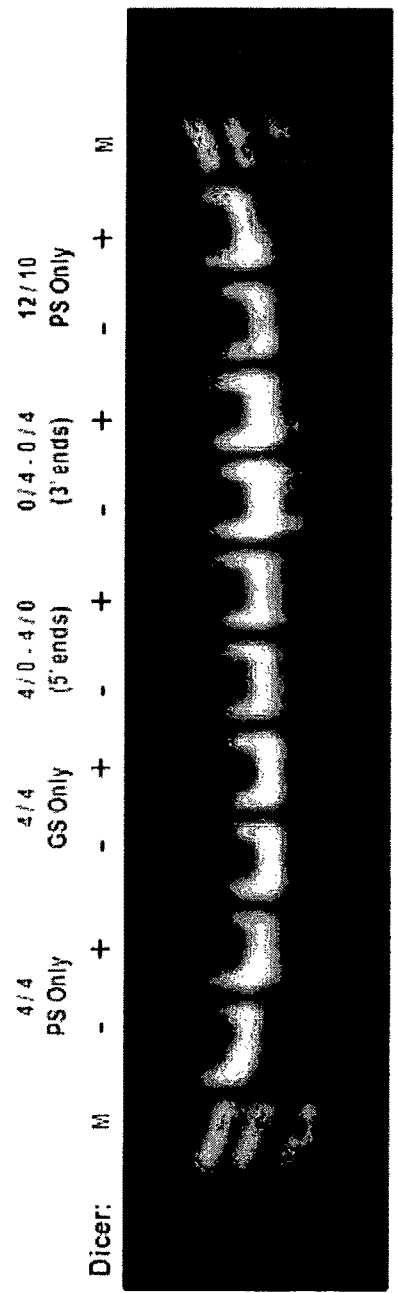
FIG. 17D is a TBE-polyacrylamide gel of RNA duplexes that have different combinations of (4) 2'-O-Me on each end of the duplex after overnight incubation with recombinant human Dicer enzyme as described herein.
Figure 17E:
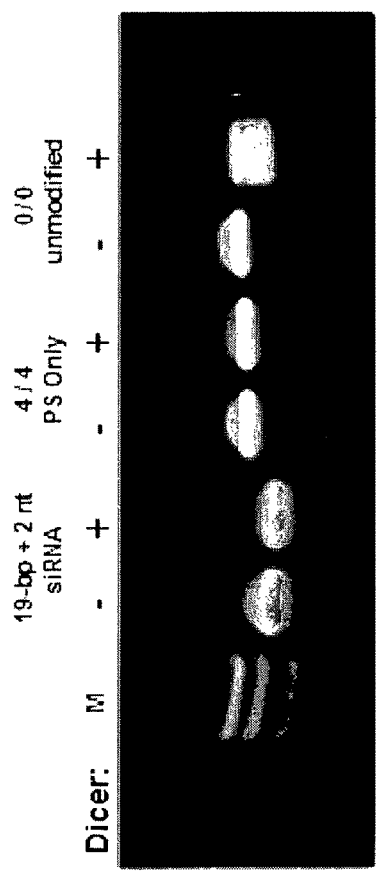
FIG. 17E shows similar results obtained with 2'-O-Me modified 25-bp duplexes targeting a different sequence in the SOD1 gene.

It has been reported that the presence of a blocking group on the 3' ends of both strands of a Dicer substrate can block processing. Dicer processing of this same SOD1 targeting duplex sequence bearing additional modification configurations was explored. Configurations tested included four 2'OMe modifications on both 5' ends, both 3' ends, or both ends (5' and 3') of each individual strand of the duplex (passenger or guide strand). Dicer processing is blocked by all of these modification patterns (FIG. 17D). Similar results are obtained with 2'-O-Me modified 25-bp duplexes targeting a different sequence in the SOD1 gene (FIG. 17E). Specifically, a 25-bp duplex that targets the human SOD1 sequence (see Table 4) was incubated with Dicer enzyme for 16 hr, and loaded onto a TBE-polyacrylamide gel as described herein. The gel was visualized by SYBR green staining and UV transluminator. The sequence shown has a high C and G base content on both ends of the duplex which helps it to be more nuclease resistant. The "M" designates a commercially available siRNA marker described herein.

Example 9 Activity Comparison of 2'OMe-Containing Alternate RNAi Compounds

This example describes the many possible designs for the subject Alternate RNAi Compound constructs, and provides exemplary activity comparison data for the various 2'OMe-containing Alternate RNAi Compounds.

Figure 10B:
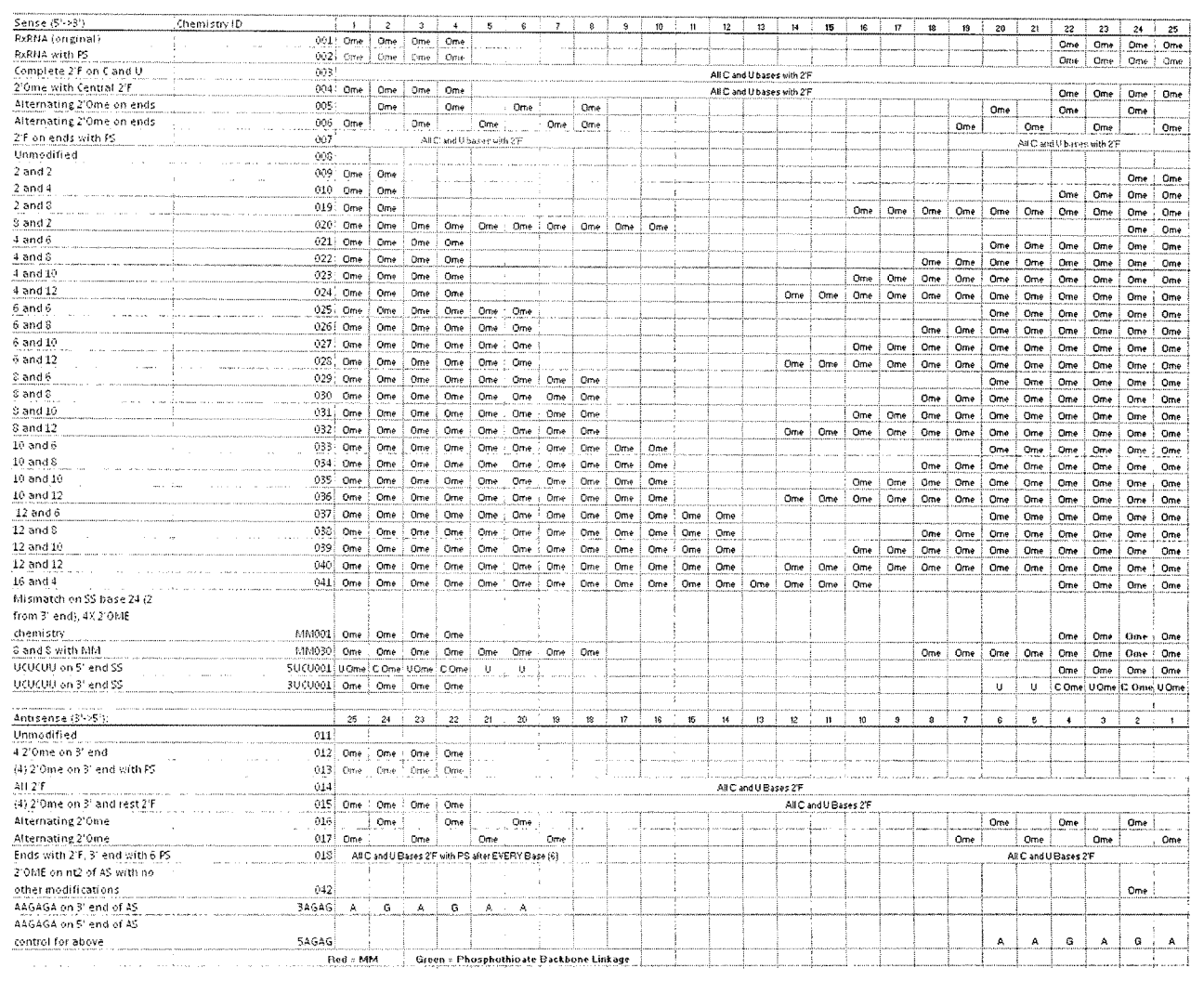
Figure 11:
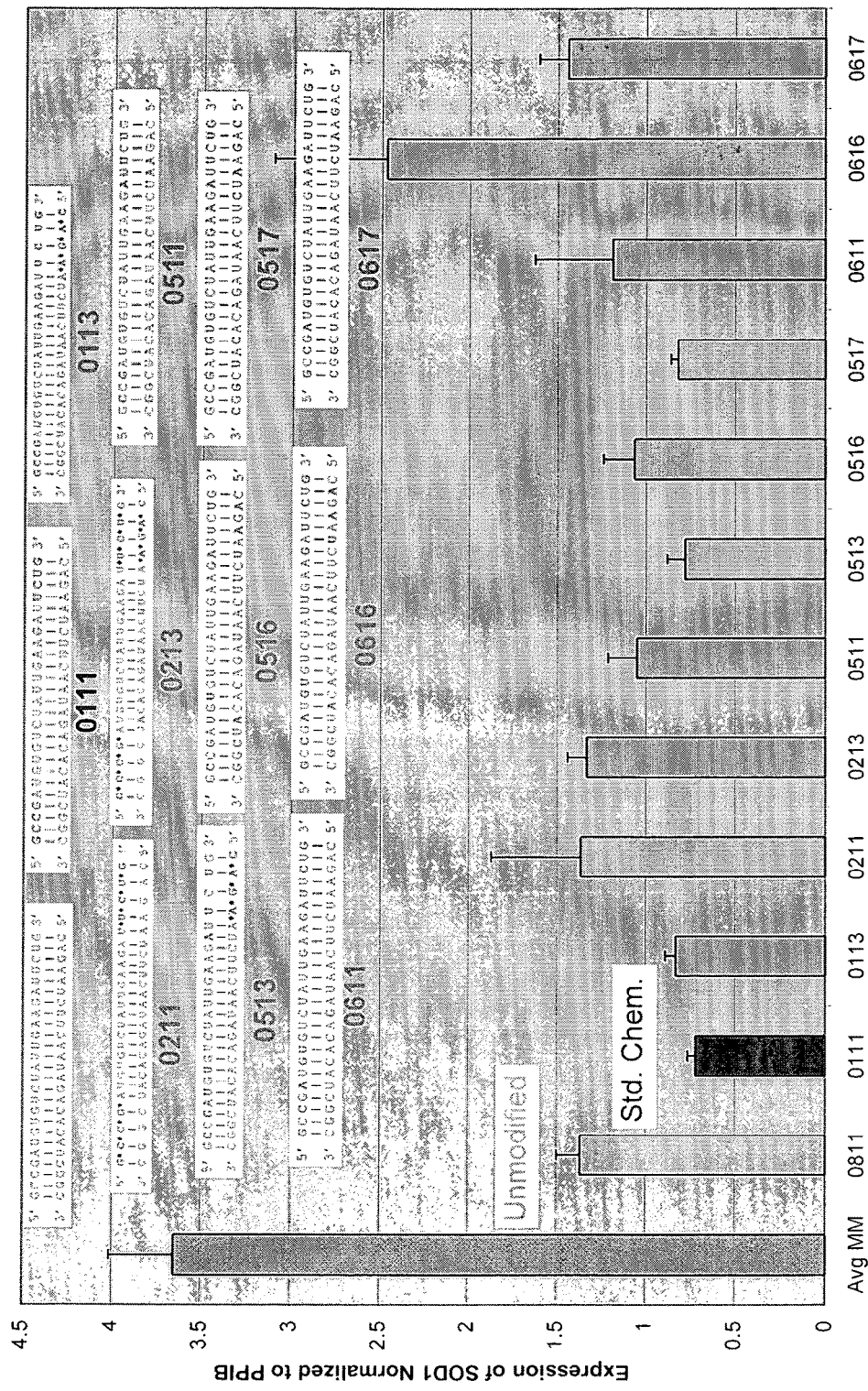
FIG. 11 illustrates the varying degree of SOD1 mRNA level reduction that is dependent on the type of modifications on the sense and antisense strands. The sequences within each duplex correspond to SEQ ID NOs:812 and 813.

A variety of Alternate RNAi Compounds based on either 10015 or 10023 sequence (see FIG. 10A) were compared with chemistry modifications as indicated in FIG. 10B. For example, "0811" refers to 008 chemistry for the sense strand, and 011 chemistry for the antisense strand as indicated in FIG. 10B. For comparison, 0111 i.e., 001-011, is the original Alternate RNAi Compound screening chemistry used in many earlier examples. The results show that some modifications lead to higher activity at reducing SOD1 activity levels (FIG. 11).

Figure 12A:
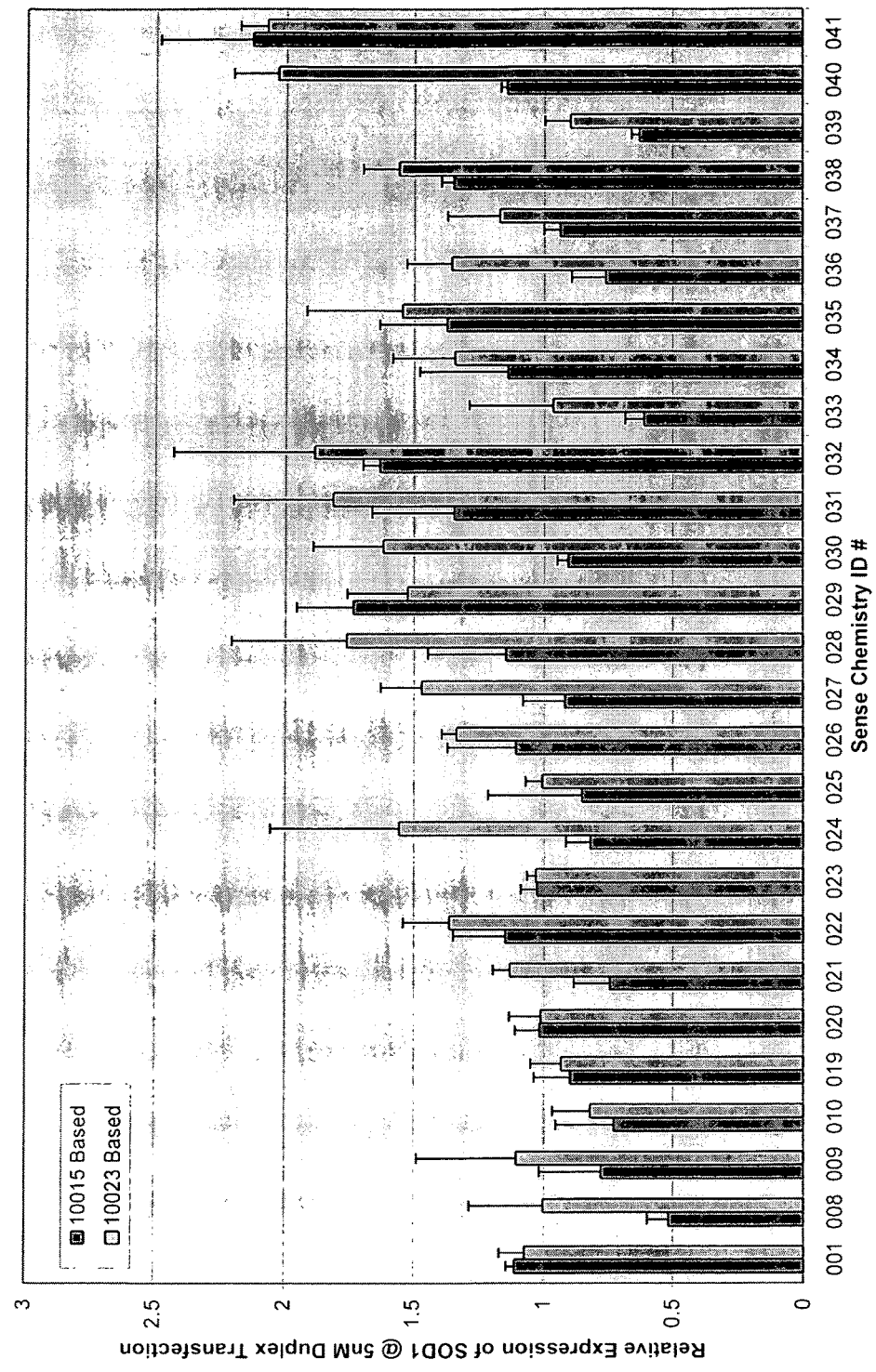
FIGS. 12A-12C show relative activity of duplexes for inhibiting SOD1 expression as a function of varying the 2'OMe positions on only the sense strand. Each duplex is based on the sequence of ID No. 10015 or 10023.
Figure 12C:
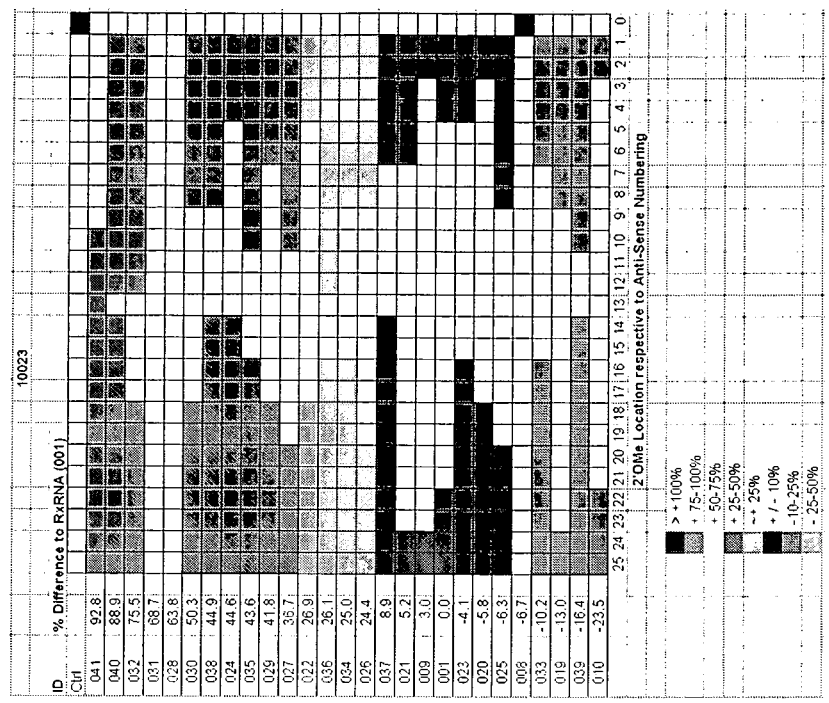
Figure 12B:
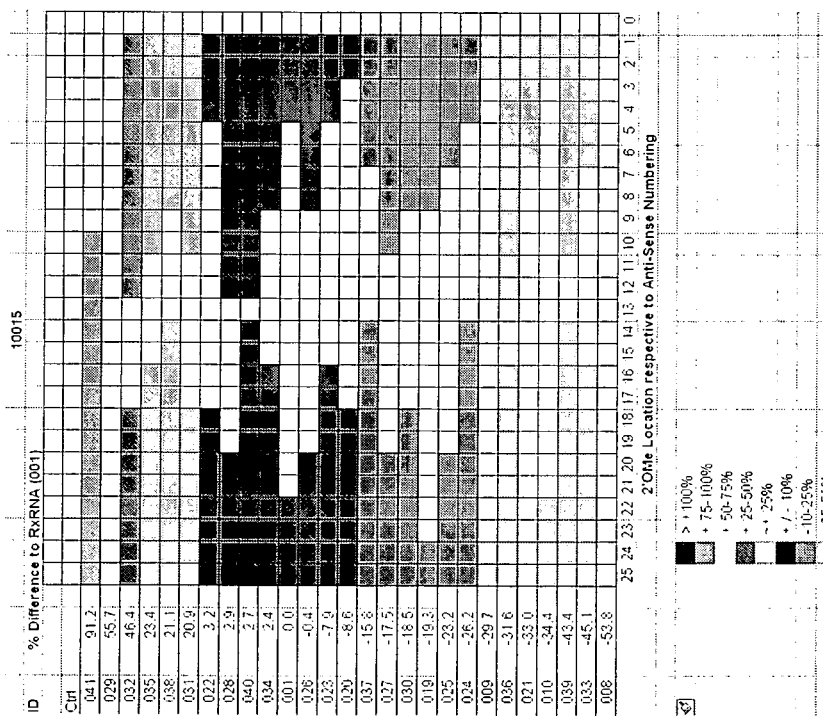

Activity Comparison of Varying amounts of 2'OMe Modifications on Sense strand of Alternate RNAi Compounds. To understand the positional effect that 2'OMe on the sense strand has on the degree of activity of a given duplex, a variety of Alternate RNAi Compounds based on either 10015 or 10023 sequence were compared with varying amounts of 2'OMe modifications to the sense strand (FIGS. 12A, 12B, 12C). All duplexes had unmodified antisense strands (i.e., chemistry 011, see FIG. 10B). FIG. 12A shows relative activity normalized to PPIB (housekeeping gene) of silencing SOD1. FIGS. 12B and 12C are visual maps showing what position (in respect to the antisense strand numbering) a 2'OMe was placed and compared to the original 001 chemistry (see FIG. 10B). The graphs illustrate the activity of each duplex as a relative percentage above or below to the 011 chemistry. IDs for the 10015 sequence (FIG. 12B) corresponding to 025, 024, 009, 036, 021, 010, 039, 033, and 008 showed better activity, and some were selected for further activity analysis. Analogous analysis for the 10023 sequence is also shown in FIG. 12C.

This study was performed by custom annealing different strands together and transfecting HEK293 cells with 5 nM duplex. The activity of the duplex against SOD1 was measured 24 hours post-transfection using bDNA assay and normalizing to PPIB. Mechanism of action studies described above allowed for predictive positioning of other modifications to improve activity and functionality.

Results from two constructs (10015 and 10023) with non-overlapping sequences are remarkably consistent with respect to the specific modification chemistries tested (e.g., 10015 modified by the 019 chemistry has virtually the same result as 10023 modified by the 019 chemistry, etc.). This suggests that the modification chemistry (rather than the targeting sequence) is the main reason for the observed differences in RNAi mediated gene silencing.

Having identified several preferred sense-strand modification schemes, Applicants tested below a few follow-up sense-antisense modification combinations.

Figure 13A:
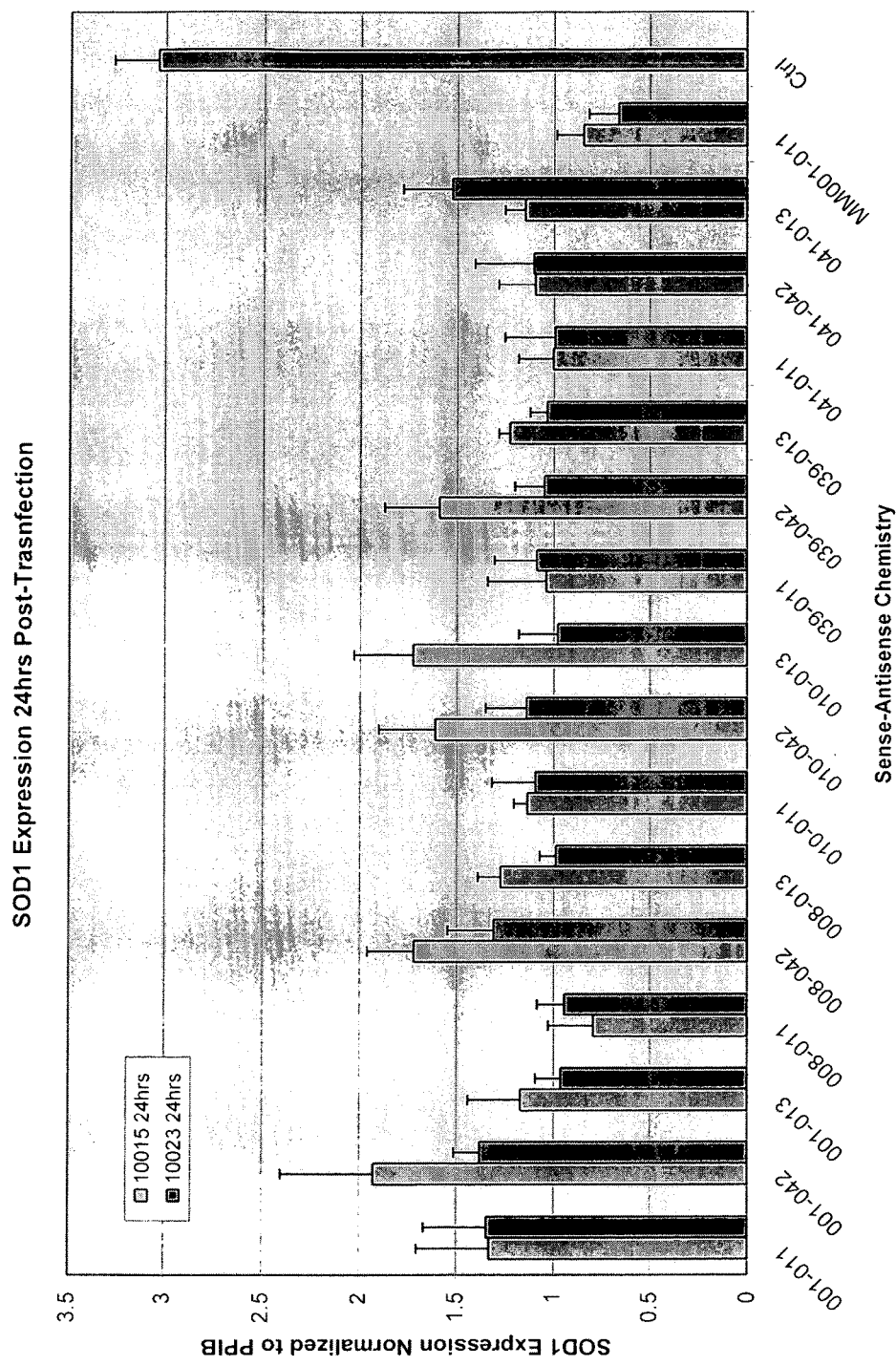
FIG. 13A-13D show relative activity of duplexes for inhibiting SOD1 expression as a function of varying 2'OMe positions on the sense strand in combination with various antisense chemistries indicated (011, 013, 042, etc. See FIG. 11B).
Figure 13B:
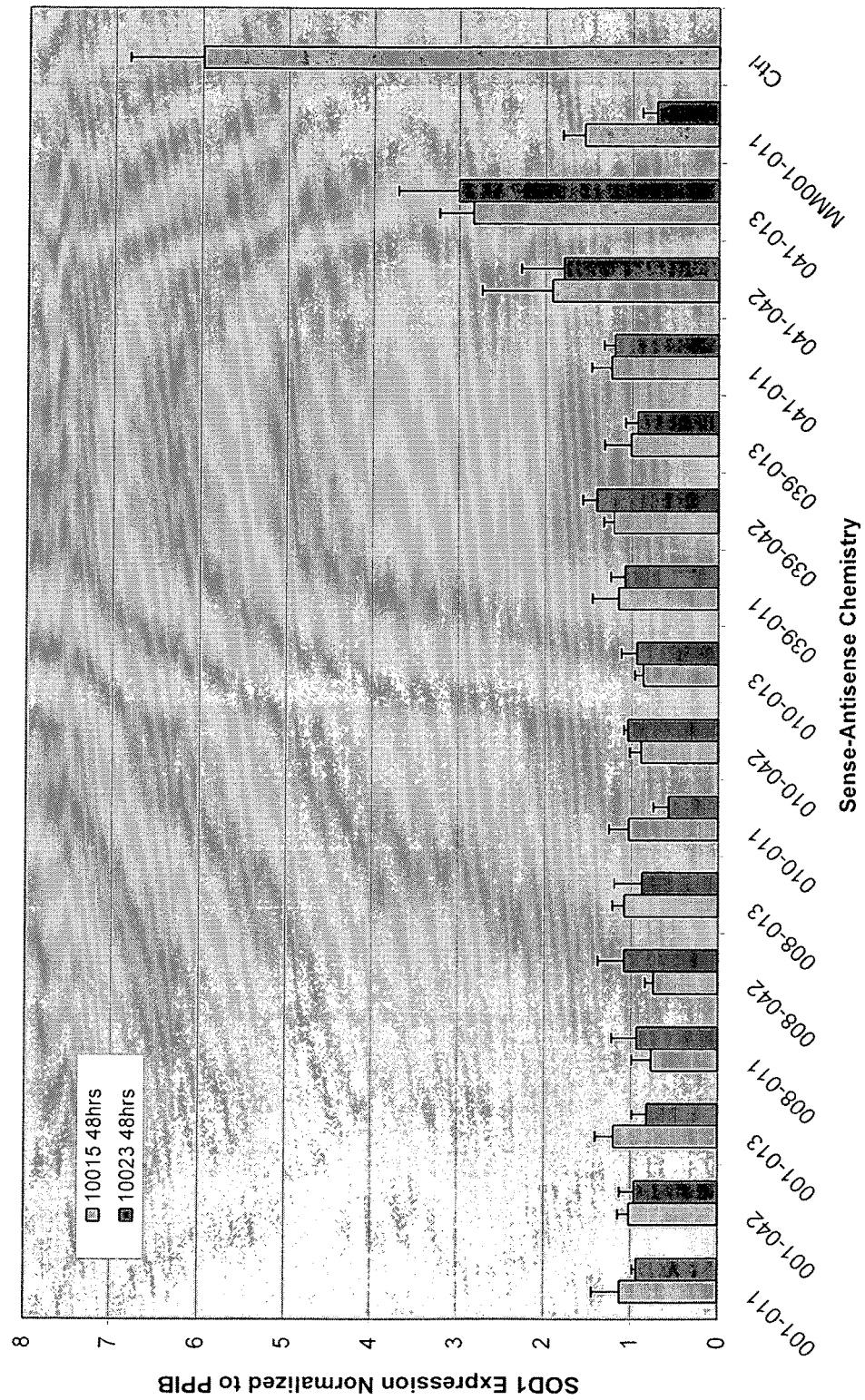
Figure 13C:
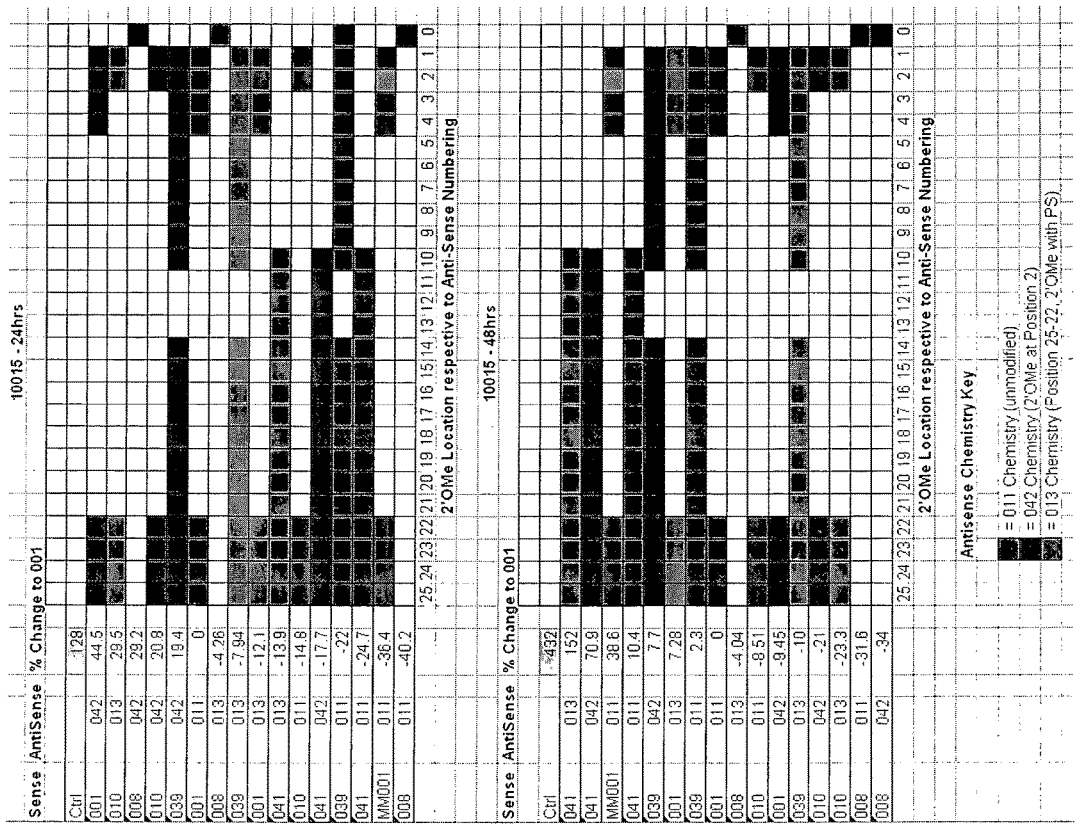
Figure 13D:
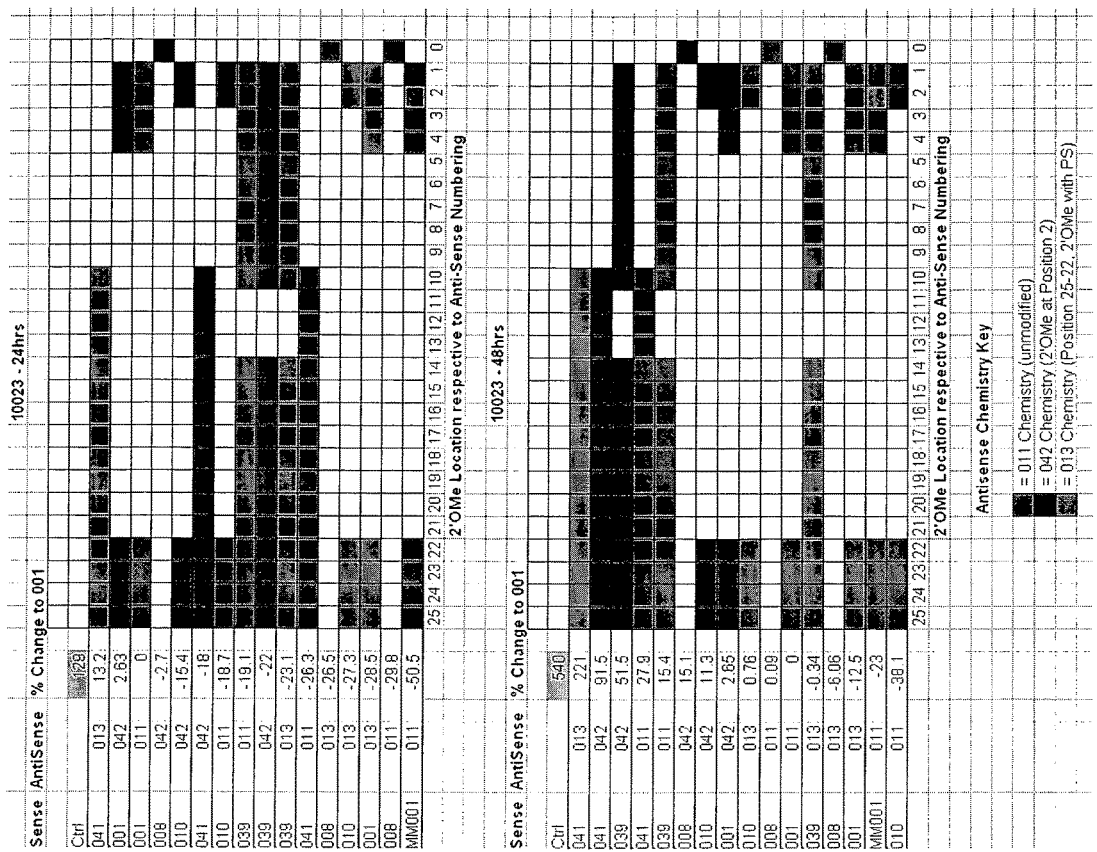
Figure 14B:
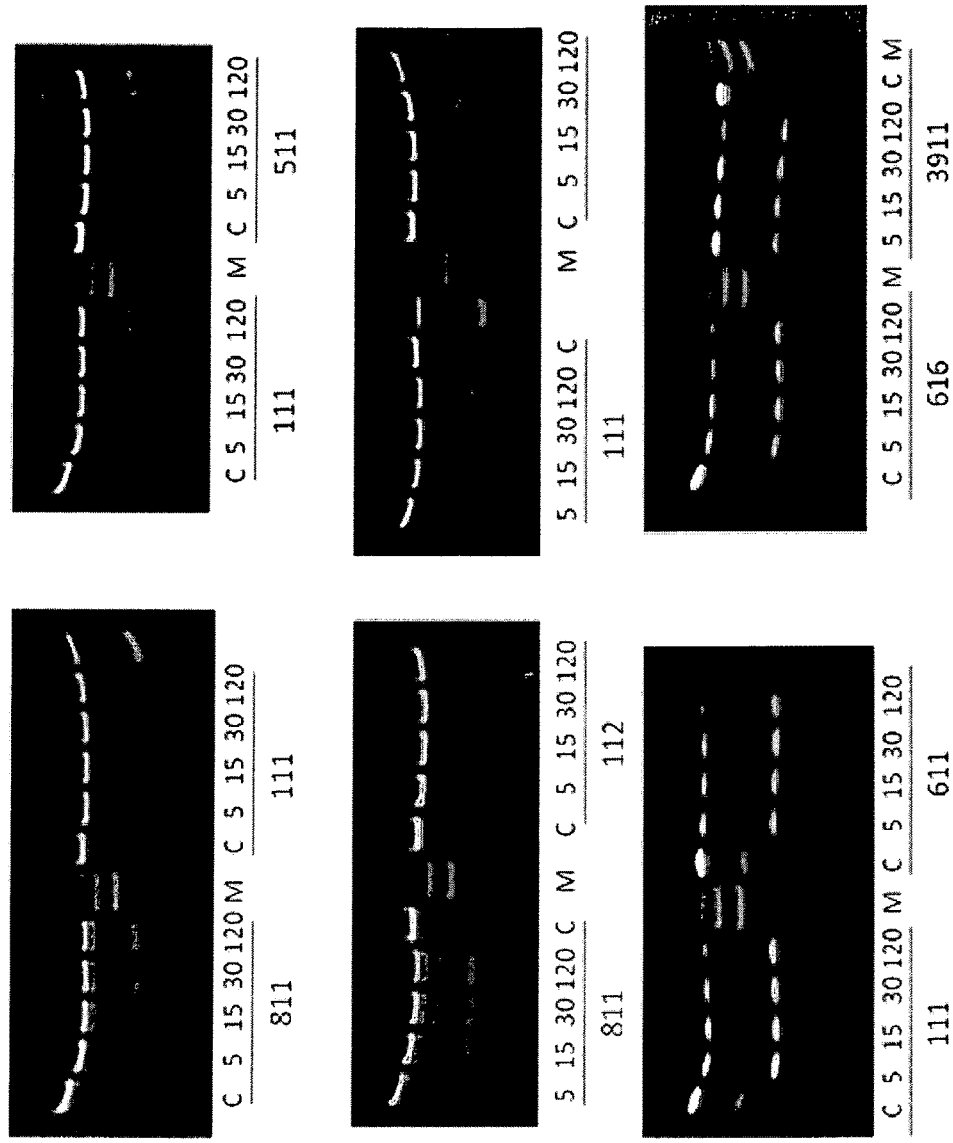

Activity comparison of different 2'OMe modifications patterns. A variety of Alternate RNAi Compounds based on either 10015 or 10023 sequence were tested as a follow-up to the extensive sense-only 2'OMe analysis. FIGS. 13A (24 hours) and 13B (48 hours) show relative activity normalized to PPIB (housekeeping gene) of silencing SOD1. FIGS. 14C and 14D are visual maps showing the relative position of a TOMe (in respect to the antisense strand numbering) and compared to the original chemistry (001). The graphs are colored to represent the type of antisense chemistry present on the duplex. The activity presented in these figures is in relation to 001-011 (original Alternate RNAi Compound). IDs corresponding to the duplexes containing antisense strand with 042 chemistry (2'OMe at position 2) showed better activity in this experiment.

This experiment was performed by custom annealing different strands together and transfecting HEK293 cells with 5 nM duplex. The activity of the duplex against SOD1 was measured 24 or 48 hours post-transfection using bDNA assay and normalizing to PPIB. Mechanism of action studies described above enabled us to position other modifications to improve activity and functionality.

These results confirm that better or equivalent activity is achieved with having increased 2'OMe modification on the sense strand. Further, there are additional designs with beneficial features that improve activity. We have found, surprisingly, that modification of the 25-mer sense strand with 12 2'OMe on the 5' end and 10 2'OMe on the 3' end (i.e., sense chemistry 039) resulted in increased activity. This almost completely modified version has improved activity in more than one duplex and more than one study. The following chemistries found to have increased activities in the studies above are highlighted:

001-011
001-042
001-013
039-011
039-042
039-013
MM001-011

Furthermore, as shown in FIG. 14D, modification on nucleotide 2 of the antisense strand showed increased activity. Modification on nucleotide 2 of the antisense strand has been reported to increase specificity of target cleavage, restricting mRNA reduction more exclusively to the target gene.

In addition, mismatches in the sense strand (chemistry MM001) opposite nucleotides 2-8 of the 5' antisense sequence allow more efficient loading into the RISC complex. We have confirmed that a mismatch at nucleotide 2 on the 3' end of the sense strand leads to more potent mRNA reducing activity. The mechanism of action studies demonstrated above allow for correct positioning of modifications on a duplex longer than 21 nt that is not processed by Dicer.

Example 10 In Vitro Stability Assays

This example shows that, in addition to the benefits described herein above, the subject Alternate RNAi Compound constructs are more stable in serum, and are thus expected to have better in vivo efficacy.

Duplexes based on sequences 10023 (FIG. 14A) or 10015 (FIG. 14B) with various modifications as indicated were incubated in 10% human serum at 37° C. for up to two hours (given in minutes at bottom of panel). Samples were quenched with chloroform and the aqueous phase was run on a 20% TBE gel. Gels were stained with SYBR green. "M" denotes siRNA marker (25mer, 21mer, 17mer duplexes), while "C" indicates duplex without incubation in serum. For the 10015 sequence, all modifications resulted in a more stable duplex as compared to the unmodified 811 duplex (008 sense chemistry, 011 antisense chemistry) under the same conditions. The Alternate RNAi Compound modification 111 i.e., 001 sense, 011 antisense, is one of the most stable tested. Modification with 039 chemistry on the sense strand (3911) also stabilized the duplex and showed increased activity. Modification of the 10023 sequence, however, did not change the stability under the same conditions as compared to the unmodified sequence (811). The 039 modification (3911) displays mild inhibition of degradation (comparing the intensity of the major degradation product to the full length) as compared to other modifications.

Example 11 RNAi with 21-27 bp Duplexes in the Absence of Dicer

This example demonstrates that Dicer is not required to effect RNAi with 21-27 bp duplexes. Here, silencing of target genes in a mouse embryonic stem cell line deficient for the Dicer enzyme (Murchison et al., 2005) was studied to enable a more direct test of the role of Dicer in RNAi with synthetic, chemically modified duplexes. Dicer homozygous null (−/−) or heterozygous (+/−) mutant cells were transfected with RNA duplexes and reduction of the target mRNA was quantified.

Mouse derived embryonic stem cells that are homozygous null or heterozygous for the enzyme Dicer were generated by Murchison and co-workers and cultured as previously described (Murchison et al., 2005). Dose response transfections were carried out by adapting previously described conditions (Schaniel et al., 2006) to a 96-well dose response method described herein. Active RNA duplexes that target the human SOD1 gene that had 100% homology to mouse SOD1 were transfected in concentrations ranging from 0.05 nM to 10 nM in a final RNA concentration of 25 nM. Transfection efficiency was monitored using a DY547 labeled version of the non-targeting control duplex. Cells were incubated for 48 h after transfection and gene silencing activity was measured using the QuantiGene bDNA hybridization assay (Panomics) as described above.

Figure 15A:
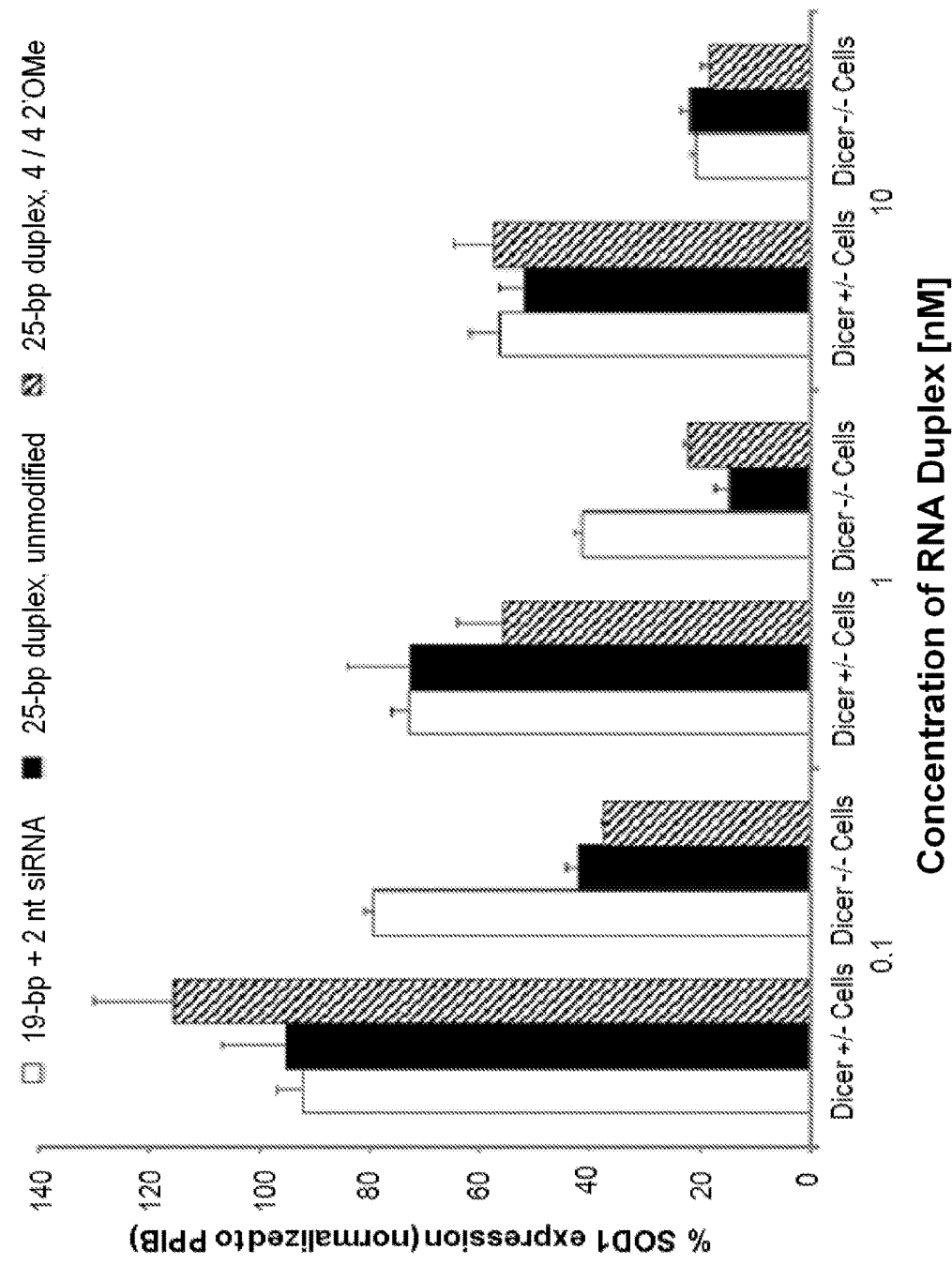
FIG. 15A demonstrates that Dicer is NOT required for RNAi activity with duplexes greater than 21 bp. The bars represent the mRNA levels of SOD1 48 h after transfection as measured by bDNA hybridization assay. SOD1 mRNA reduction data for the three duplexes are shown; 19-bp+2 nt siRNA (solid white bar), unmodified (0/0) 25-bp duplex (solid black bar), and "4/4" 2'OMe 25-bp duplex (striped bar).

The bars in FIG. 15A represent the mRNA levels of SOD1 48 hours post transfection as measured by bDNA hybridization assay. Expression of SOD1 levels are normalized to the PPIB gene and adjusted as a percent of the luciferase control duplex. The three duplexes tested were 19-bp+2 nt siRNA (solid white bar), 25-bp blunt-ended duplex unmodified (black solid bar), and 25-bp blunt-ended duplex with "4/4" 2'-O-Me modification (striped bar). The exact sequences used in this study are shown in FIG. 15B.

Consistent with previously published data, the 19-bp+2 nt siRNA duplexes efficiently silence the target gene in the absence of Dicer (Murchison et al., 2005). Interestingly, 25-bp duplexes (modified and unmodified) silence the target gene in the Dicer null cells with at least the same efficiency (FIG. 15A). In fact, gene silencing activity appeared slightly higher in the Dicer null cells as compared to cells that contained the Dicer protein. This observation might be explained by the fact that Dicer null cells have no endogenous miRNAs to compete for occupancy of Ago2:RISC and thus the transfected duplexes could appear to be more potent. These results confirm that Dicer is not required for efficient silencing with RNA duplexes.

Figure 16A:
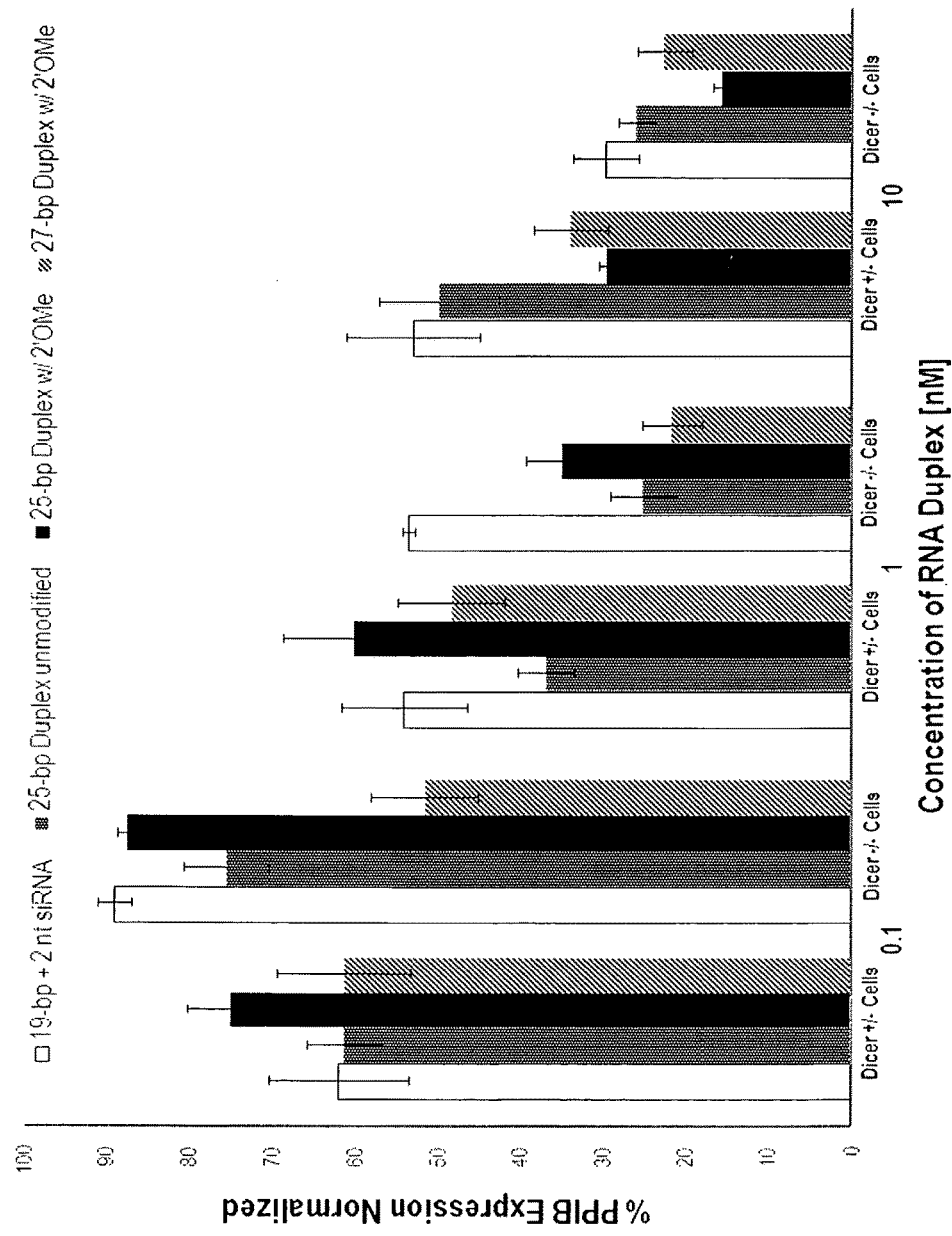
FIG. 16A shows that, similar to the observation of FIG. 15A, Dicer is not required for RNAi activity with duplexes of 27 bp. The bars represent the mRNA levels of PPIB 48 h after transfection as measured by bDNA hybridization assay. The solid white bars are a 19-bp+2 nt siRNA, the dotted bars are an unmodified 25-bp duplex, the solid black bars are a 25-bp duplex with 2'OMe chemistry, and the striped bars are a 27-bp duplex with 2'OMe chemistry. Sequences are shown in FIG. 16B. The sequences listed (in descending order in the table) correspond to SEQ ID NOs:820-827.

This observation was extended to duplexes up to 27-bp in length by testing a sequence to the PPIB gene (FIG. 16A). Here, the solid white bars are a 19-bp+2 nt siRNA, the dotted bars are an unmodified 25-bp duplex, the solid black bars are a 25-bp duplex with 2'-O-Me chemistry, and the striped bars are a 27-bp duplex with 2'-O-Me chemistry. The silencing activity achieved similar results as seen with the SOD1 targeting duplexes in the Dicer null cells. Sequences are shown in FIG. 16B.

Methods

Certain methods lised in the examples herein are provided below for illustration purpose only.

Chemically synthesized RNAs. Single stranded RNA was synthesized by Integrated DNA technologies or Thermo-Fisher Dharmacon products. RNA duplexes were formed by mixing equal molar ratios of single stranded RNA and incubating at 90° C. for 1 min and then incubating at 37° C. for 1 h. All single stranded RNA and RNA duplexes were stored at −20° C. See Table 3 and Table 4 online for RNA sequence information.

Dose response transfections. HEK293 cells (ATCC) were cultured in Dulbecco's Modified Eagle Media (DMEM) with 10% Fetal Bovine Serum and 1% Penicillin-Streptomycin. NIH3T3 Cells (ATCC) was cultured in DMEM with 10% Bovine Calf Serum and 1% Penicillin-Streptomycin. All cells were incubated at 37° C. with 10% $CO_2$ as recommended by ATCC. RNA duplexes were reverse-transfected in a dose dependent manner (0.005 nM to 5 nM) using Lipofectamine RNAiMAX (Invitrogen) reagent as described by the manufacturer and optimized conditions. The RNA duplexes were complexed along with a non-targeting control duplex to make a final concentration of 25 nM RNA duplex transfected. The non-targeting, chemistry, and length matched control duplexes target the luciferase gene. Transfections were performed in 96-well plates with media containing no antibiotics and were incubated for 48 h under normal growth conditions. Gene silencing was measured using the QuantiGene bDNA hybridization assay (Panomics). Cells were lysed and mRNA levels were measured under assay conditions described by the manufacturer. Gene expression was measured for the SOD1 gene and the PPIB gene using species specific probe sets (Panomics). The gene expression values were normalized to the PPIB gene which was used as a housekeeping control since its expression is not affected by SOD1 silencing. The percent silencing and $EC_{50}$ values are based on the normalized SOD1 expression of the non-targeting control duplexes. The values are calculated and graphically displayed using KaleidaGraph (Synergy Software).

Argonaute-2 immunoprecipitation and extraction of complexed RNA from RISC. RNA duplexes were annealed as described and transfected into 293T cells stably expressing c-myc Ago2 (Hannon lab, Cold Spring Harbor Labs). 293 cells were cultured as described above in the presence of 0.5 ug/ml G418 to selectively express c-myc Ago2. Transfection of RNA duplexes was carried out using Lipofectamine RNAiMAX (Invitrogen) in a 10 cm plate as described by the manufacturer. The cells were transfected in media containing no antibiotics and having a final concentration of RNA duplex of 25 nM. Cells were incubated for 48 hours before harvesting and immunoprecipitation (IP) of c-myc Ago2. Cell harvest and IP was performed as previously described. Cells were collected from plates and washed once with 1×PBS and once in 2 ml of Hypotonic Lysis Buffer (HLB) (10 mM Tris pH 7.5, 10 mM KCl, 2 mM $MgCl_2$, 5 mM DTT, and protease inhibitor). Cells were then reconstituted in 0.5 ml of HLB and allowed to swell on ice for 15 min. A fraction of the cell lysate (50 ul) was taken and added to 200 ul Trizol (Invitrogen) for subsequent gene silencing assays using the QuantiGene bDNA hybridization assay (Panomics). The cell lysate was added to a 1 ml dounce homogenizer with tight pestle and cells were homogenized for 30 strokes on ice. Cell lysates were clarified by centrifugation (14,000 rpm, 30 min at 4° C.) and supernatant was transferred to a new tube. The supernatant or cytosolic fraction had 1 ml of buffer (LB650) (0.5% NP40, 150 mM NaCl, 2 mM $MgCl_2$, 2 mM $CaCl_2$, 20 mM Tris pH 7.5, 5 mM DTT, 650 mM KCl, and protease inhibitors) added. Anti-c-myc antibody conjugated to agarose beads (Sigma) were added to each tube and tubes were incubated overnight at 4° C. while rotating. After overnight incubation, IP reactions were spun down for 2 min at 3,000 rpm and then beads were washed three times in LB650 buffer. After washing the beads, 200 ul of Trizol (Invitrogen) was added to disassociate the RNA from the antibody captured Ago2. RNA was precipitated as described by manufacturer instructions forgoing an ethanol wash. RNA was reconstituted in 20 ul of TE buffer.

Northern blot of RNA captured from Ago2 immunoprecipitation. RNA was loaded on to a 15% polyacrylamide, TBE-Urea denaturing gel. Previously labeled $^{32}$P-end size makers ranging from 21 to 25 nt were run alongside IP reactions to determine the size of the captured RNA. The gel was transferred to a nylon membrane and RNA was UV cross-linked. Membrane was pre-hybridized using Ultra-Hyb-Oligo Buffer (Ambion) for 30 min at 42° C. and then previously prepared $^{32}$P-labeled locked nucleic acid probes complimentary to the guide strand were added to the hybridization buffer. After overnight incubation at 42° C., membrane was washed twice for 30 min in wash buffer (1×SSC buffer, 0.1% SDS). The blot was visualized by exposing to BioMAX autoradiograph film (Kodak). Film was developed using automatic film processing unit.

mRNA cleavage position assay. 293 cells expressing c-myc Ago2 were transfected with RNA duplexes as described above. Ago2 was immunoprecipitation was also carried out as described above. After the final wash, the agarose beads containing Ago2 complexes loaded with transfected RNAs were re-constituted in 10 ul buffer (100 mM KCl, 2 mM $MgCl_2$, and 10 mM Tris pH 7.5). A chemically synthesized, synthetic substrate that matched a 50 nt region of the human SOD1 gene to which the transfected 25-bp duplexes or 19-bp+2 nt siRNAs target was $^{32}$P-5' end labeled and gel purified. The synthetic substrate was designed specifically to have base 21 correspond to position 10 of the guide strand of the 19-bp+2 nt siRNA or 25-bp duplex. The labeled RNA was gel purified and precipitated in isopropanol. The cleavage reaction was setup with a final volume of 20 ul. The IP reaction (10 ul) was added to 4 ul of labeled synthetic substrate, 1 ul RNAsin, and 5 ul buffer (100 mM KCl, 2 mM MgCl$_2$, and 10 mM Tris pH 7.5). The reaction was incubated for 2 h at 30° C. After incubation the reactions were run on a 15% polyacrylamide, TBE-urea gel. Gel was exposed to autoradiograph film and developed using methods described above. Size of cleavage product was determined using $^{32}$P-labeled size marker RNAs that were run alongside cleavage assay reactions.

Dicer processing assay. RNA duplexes were incubated with recombinant human Dicer enzyme (Genlantis) according to manufacturer recommendations and previously described conditions. Samples were incubated overnight (~16 h) at 37° C. with and without Dicer enzyme. Reactions were stopped by the addition of TBE gel loading buffer and snap freezing in liquid nitrogen. A fraction (16 pmoles) of the stopped reaction was run on a native, TBE buffered, 20% polyacrylamide gel. A siRNA marker (New England Biolabs) was run alongside samples on the gel. The gel was stained using SYBR green II (Invitrogen) for 20 min and then visualized using a UV transluminator and CCD camera. UV images and relative quantification analysis were carried out using the UVP BioChemi imaging station with LabWorks software (UVP).

Dicer null cell transfections. Dicer null cells were generated and cultured as previously described. Dose response transfections were carried out by adapting previously described conditions to a 96-well dose response method described above. RNA duplexes that targeted the human SOD1 gene that had 100% homology to mouse SOD1 were transfected in concentrations ranging from 0.05 nM to 10 nM. Transfection efficiency was monitored using a DY547 labeled control duplex. Cells were incubated for 48 h after transfection and then gene silencing activity was measured using the QuantiGene bDNA hybridization assay (Panomics). Cells were lysed and assay was carried out as described above and according to manufacturer's recommendations.

TABLE 3

| Sequence Name | Polarity | Sequence (5'→3') | SEQ ID |
|---|---|---|---|
| FIG. 9 | | | |
| A (11892) | PS | G.G.U.G.G.A.A.A.U.G.A.A.G.A.A.A.G.U.A.U.U | 1 |
| | GS | U.A.C.U.U.U.C.U.U.C.A.U.U.U.C.C.A.C.C.U.U | 2 |
| B (11893) | PS | G.C.A.A.A.G.G.U.G.G.A.A.A.U.G.A.A.G.A.A.A.G.U.A | 3 |
| | GS | U.A.C.U.U.U.C.U.U.C.A.U.U.U.C.C.A.C.C.U.U.U.G.C.C | 4 |
| C (11897) | PS | mG.mG.mC.mA.A.A.G.G.U.G.G.A.A.A.U.G.A.A.G.A.A.mA.mG.mU.mA | 5 |
| | GS | U.A.C.U.U.U.C.U.U.C.A.U.U.U.C.C.A.C.C.U.U.U.G.C.C | 6 |
| D (10357) | PS | mA.mG.mG.mU.G.A.A.A.U.G.A.A.G.A.A.A.G.U.A.C.mA.mA.mA.mG | 7 |
| | GS | C.U.U.U.G.U.A.C.U.U.U.C.U.U.C.A.U.U.U.C.C.A.C.C.U | 8 |
| E (10461) | PS | mG.mC.mA.mC.U.C.U.G.A.U.U.G.A.C.A.A.A.U.A.C.G.mA.mU.mU.mU | 9 |
| | GS | A.A.A.U.C.G.U.A.U.U.U.G.U.C.A.A.U.C.A.G.A.G.U.G.C | 10 |
| FIG. 15B | | | |
| 19-bp + 2 nt duplex (11892) | PS | G.G.U.G.G.A.A.A.U.G.A.A.G.A.A.A.G.U.A.U.U | 11 |
| | GS | U.A.C.U.U.U.C.U.U.C.A.U.U.U.C.C.A.C.C.U.U | 12 |
| 0/0 (11893) | PS | G.C.A.A.A.G.G.U.G.G.A.A.A.U.G.A.A.G.A.A.A.G.U.A | 13 |
| | GS | U.A.C.U.U.U.C.U.U.C.A.U.U.U.C.C.A.C.C.U.U.U.G.C.C | 14 |
| 4/4 (11897) | PS | mG.mG.mC.mA.A.A.G.G.U.G.G.A.A.A.U.G.A.A.G.A.A.mA.mG.mU.mA | 15 |
| | GS | U.A.C.U.U.U.C.U.U.C.A.U.U.U.C.C.A.C.C.U.U.U.G.C.C | 16 |
| FIG. 17B | | | |
| 0/0 (11893) | PS | G.C.A.A.A.G.G.U.G.G.A.A.A.U.G.A.A.G.A.A.A.G.U.A | 17 |
| | GS | U.A.C.U.U.U.C.U.U.C.A.U.U.U.C.C.A.C.C.U.U.U.G.C.C | 18 |
| 1/1 (11894) | PS | mG.G.C.A.A.A.G.G.U.G.G.A.A.A.U.G.A.A.G.A.A.A.G.U.mA | 19 |
| | GS | U.A.C.U.U.U.C.U.U.C.A.U.U.U.C.C.A.C.C.U.U.U.G.C.C | 20 |
| 2/2 (11895) | PS | mG.mG.C.A.A.A.G.G.U.G.G.A.A.A.U.G.A.A.G.A.A.A.G.mU.mA | 21 |
| | GS | U.A.C.U.U.U.C.U.U.C.A.U.U.U.C.C.A.C.C.U.U.U.G.C.C | 22 |
| 3/3 (11896) | PS | mG.mG.mC.A.A.A.G.G.U.G.G.A.A.A.U.G.A.A.G.A.A.A.mG.mU.mA | 23 |
| | GS | U.A.C.U.U.U.C.U.U.C.A.U.U.U.C.C.A.C.C.U.U.U.G.C.C | 24 |
| 4/4 (11897) | PS | mG.mG.mC.mA.A.A.G.G.U.G.G.A.A.A.U.G.A.A.G.A.A.mA.mG.mU.mA | 25 |
| | GS | U.A.C.U.U.U.C.U.U.C.A.U.U.U.C.C.A.C.C.U.U.U.G.C.C | 26 |
| FIG. 17D | | | |
| 4/4 PS | PS | mG.mG.mC.mA.A.A.G.G.U.G.G.A.A.A.U.G.A.A.G.A.A.mA.mG.mU.mA | 27 |

TABLE 3-continued

| Sequence Name | Polarity | Sequence (5'→3') | SEQ ID |
|---|---|---|---|
| (11897) | GS | U.A.C.U.U.U.C.U.U.C.A.U.U.U.C.C.A.C.C.U.U.U.G.C.C | 28 |
| 4/4 AS (11904) | PS | G.G.C.A.A.A.G.G.U.G.G.A.A.A.U.G.A.A.G.A.A.A.G.U.A | 29 |
|  | GS | mU.mA.mC.mU.U.U.C.U.U.C.A.U.U.U.C.C.A.C.C.U.U.mU.mG.mC.mC | 30 |
| 4/0-4/0 (11906) | PS | mG.mG.mC.mA.A.A.G.G.U.G.G.A.A.A.U.G.A.A.G.A.A.A.G.U.A | 31 |
|  | GS | mU.mA.mC.mU.U.U.C.U.U.C.A.U.U.U.C.C.A.C.C.U.U.U.G.C.C | 32 |
| 0/4-0/4 (11907) | PS | G.G.C.A.A.A.G.G.U.G.G.A.A.A.U.G.A.A.G.A.A.mA.mG.mU.mA | 33 |
|  | GS | U.A.C.U.U.U.C.U.U.C.A.U.U.U.C.C.A.C.C.U.U.mU.mG.mC.mC | 34 |

TABLE 4

| Sequence Name | Polarity | Sequence (5'→3') | SEQ ID |
|---|---|---|---|
| FIG. 6C | | | |
| 19-bp + 2 nt unmodified (10167) | PS | G.G.A.A.A.G.A.C.U.G.U.U.C.C.A.A.A.A.A.U.U | 35 |
|  | GS | U.U.U.U.U.G.G.A.A.C.A.G.U.C.U.U.U.C.C.U.U | 36 |
| 19-bp + 2 nt with 2'OMe (10459) | PS | mG.mG.mA.mA.A.G.A.C.U.G.U.U.C.C.A.A.A.mA.mA.mU.mU | 37 |
|  | GS | U.U.U.U.U.G.G.A.A.C.A.G.U.C.U.U.U.C.C.U.U | 38 |
| 25-mer with 2'OMe (10460) | PS | mC.mU.mC.mU.U.C.G.G.A.A.A.G.A.C.U.G.U.U.C.C.A.mA.mA.mA.mA | 39 |
|  | GS | U.U.U.U.U.G.G.A.A.C.A.G.U.C.U.U.U.C.C.G.A.A.G.A.G | 40 |
| 27-mer with 2'OMe (10462) | PS | mG.mU.mC.mU.C.U.U.C.G.G.A.A.A.G.A.C.U.G.U.U.C.C.A.mA.mA.mA.mA | 41 |
|  | GS | U.U.U.U.U.G.G.A.A.C.A.G.U.C.U.U.U.C.C.G.A.A.G.A.G.A.C | 42 |
| Example 7 | | | |
| 10036 | PS | C.G.A.U.G.U.G.U.C.U.A.U.U.G.A.A.G.A.U.U.C | 43 |
|  | GS | A.U.C.U.U.C.A.A.U.A.G.A.C.A.C.A.U.C.G.G.C | 44 |
| 10023 | PS | mG.mC.mC.mG.A.U.G.U.G.U.C.U.A.U.U.G.A.A.G.A.U.mU.mC.mU.mG | 45 |
|  | GS | C.A.G.A.A.U.C.U.U.C.A.A.U.A.G.A.C.A.C.A.U.C.G.G.C | 46 |
| 10174 | PS | mU.mG.mU.mG.G.C.C.G.A.U.G.U.G.U.C.U.A.U.U.G.A.mA.mG.mA.mU | 47 |
|  | GS | A.U.C.U.U.C.A.A.U.A.G.A.C.A.C.A.U.C.G.G.C.C.A.C.A | 48 |
| 10175 | PS | mG.mU.mG.mU.G.G.C.C.G.A.U.G.U.G.U.C.U.A.U.U.G.A.mA.mG.mA.mU | 49 |
|  | GS | A.U.C.U.U.C.A.A.U.A.G.A.C.A.C.A.U.C.G.G.C.C.A.C.A.C | 50 |
| FIG. 17E | | | |
| 19-bp + 2 nt siRNA (10036) | PS | C.G.A.U.G.U.G.U.C.U.A.U.U.G.A.A.G.A.U.U.C | 51 |
|  | GS | A.U.C.U.U.C.A.A.U.A.G.A.C.A.C.A.U.C.G.G.C | 52 |
| 25-bp 4/4 Sense Only (10023) | PS | mG.mC.mC.mG.A.U.G.U.G.U.C.U.A.U.U.G.A.A.G.A.U.mU.mC.mU.mG | 53 |
|  | GS | C.A.G.A.A.U.C.U.U.C.A.A.U.A.G.A.C.A.C.A.U.C.G.G.C | 54 |
| 25-bp 0/0 (10777) | PS | G.C.C.G.A.U.G.U.G.U.C.U.A.U.U.G.A.A.G.A.U.U.C.U.G | 55 |
|  | GS | C.A.G.A.A.U.C.U.U.C.A.A.U.A.G.A.C.A.C.A.U.C.G.G.C | 56 |

TABLE 5

| Sequence Name | Sequence (5'→3') | SEQ ID |
|---|---|---|
| Size Markers | | |
| 21 nt | AGAGCAGUGGCUGGUUGAGAU | 57 |
| 22 nt | AGAGCAGUGGCUGGUUGAGAUU | 58 |
| 23 nt | AGAGCAGUGGCUGGUUGAGAUUU | 59 |
| 24 nt | AGAGCAGUGGCUGGUUGAGAUUUA | 60 |
| 25 nt | AGAGCAGUGGCUGGUUGAGAUUUAA | 61 |

TABLE 5-continued

| Sequence Name | Sequence (5'→3') | SEQ ID |
|---|---|---|
| 26 nt Synthetic Substrates | AGAGCAGUGGCUGGUUGAGAUUUAAU | 62 |
| Synthetic Substrate FIG. 9A | ACUUGGGCAAAGGUGGAAAUGAAGAAA GUACAAAGACAGGAAACGCUGGA | 63 |
| Synthetic Substrate Example 8 | GAUGGUGUGGCCGAUGUGUCUAUUGAA GAUUCUGUGAUCUCACUCUCAGG | 64 |

REFERENCES

1. Chu, C. Y. & Rana, T. M. Small RNAs: regulators and guardians of the genome. J. Cell. Physiol. 213, 412-419 (2007).
2. Choung, S., Kim, Y. J., Kim, S., Park, H. O. & Choi, Y. C. Chemical modification of siRNAs to improve serum stability without loss of efficacy. Biochem. Biophys. Res. Commun. 342, 919-927 (2006).
3. Chiu, Y. L. & Rana, T. M. siRNA function in RNAi: a chemical modification analysis. RNA 9, 1034-1048 (2003).
4. Kubo, T., Zhelev, Z., Ohba, H. & Bakalova, R. Modified 27-nt dsRNAs with dramatically enhanced stability in serum and long-term RNAi activity. Oligonucleotides 17, 445-464 (2007).
5. Li, S., Crothers, J., Haqq, C. M. & Blackburn, E. H. Cellular and gene expression responses involved in the rapid growth inhibition of human cancer cells by RNA interference-mediated depletion of telomerase RNA. J. Biol. Chem. 280, 23709-23717 (2005).
6. Kim, D. H. et al. Synthetic dsRNA Dicer substrates enhance RNAi potency and efficacy. Nat. Biotechnol. 23, 222-226 (2005).
7. Hutvagner, G. & Simard, M. J. Argonaute proteins: key players in RNA silencing. Nat. Rev. Mol. Cell. Biol. 9, 22-32 (2008).
8. MacRae, I. J., Ma, E., Zhou, M., Robinson, C. V. & Doudna, J. A. In vitro reconstitution of the human RISC-loading complex. Proc. Natl. Acad. Sci. U.S.A. 105, 512-517 (2008).
9. Murchison, E. P., Partridge, J. F., Tam, O. H., Cheloufi, S. & Hannon, G. J. Characterization of Dicer-deficient murine embryonic stem cells. Proc. Natl. Acad. Sci. U.S.A. 102, 12135-12140 (2005).
10. Elbashir, S. M., Martinez, J., Patkaniowska, A., Lendeckel, W. & Tuschl, T. Functional anatomy of siRNAs for mediating efficient RNAi in Drosophila melanogaster embryo lysate. EMBO J. 20, 6877-6888 (2001).
11. Liu, J. et al. Argonaute2 is the catalytic engine of mammalian RNAi. Science 305, 1437-1441 (2004).
12. Kessler, C. & Manta, V. Specificity of restriction endonucleases and DNA modification methyltransferases a review (Edition 3). Gene 92, 1-248 (1990).
13. Yoshinari, K., Miyagishi, M. & Taira, K. Effects on RNAi of the tight structure, sequence and position of the targeted region. Nucleic Acids Res. 32, 691-699 (2004).
14. Robbins, M. et al. 2T-O-methyl-modified RNAs act as TLR7 antagonists. Mol. Ther. 15, 1663-1669 (2007).
15. Jackson, A. L. et al. Position-specific chemical modification of siRNAs reduces "off-target" transcript silencing. RNA 12, 1197-1205 (2006).
16. Judge, A. D., Bola, G., Lee, A. C. & MacLachlan, I. Design of noninflammatory synthetic siRNA mediating potent gene silencing in vivo. Mol. Ther. 13, 494-505 (2006).
17. Du, Z., Lee, J. K., Tjhen, R., Stroud, R. M. & James, T. L. Structural and biochemical insights into the dicing mechanism of mouse Dicer: a conserved lysine is critical for dsRNA cleavage. Proc. Natl. Acad. Sci. U.S.A. 105, 2391-2396 (2008).
18. Elbashir, S. M., Lendeckel, W. & Tuschl, T. RNA interference is mediated by 21- and 22-nucleotide RNAs. Genes Dev. 15, 188-200 (2001).
19. Caudy, A. A., Myers, M., Hannon, G. J. & Hammond, S. M. Fragile X-related protein and VIG associate with the RNA interference machinery. Genes Dev. 16, 2491-2496 (2002).
20. Schaniel, C. et al. Delivery of short hairpin RNAs—triggers of gene silencing—into mouse embryonic stem cells. Nat. Methods 3, 397-400 (2006).

EQUIVALENTS

Those skilled in the art will recognize, or be able to ascertain using no more than routine experimentation, many equivalents to the specific embodiments of the invention described herein. Such equivalents are intended to be encompassed by the following claims. The entire contents of all patents, published patent applications and other references cited herein are hereby expressly incorporated by reference in their entireties.

TABLE 1

Alternative RNAi Compound Sequences to SOD1 and PPIB

| Full Sequence Name | ID Number | Polarity | Sequence (5'→3') | SEQ ID |
|---|---|---|---|---|
| SOD1-125-25-10001 | 10001 | Sense | P.G.A.C.C.U.C.G.G.C.G.U.G.G.C.C.U.A.G.C.G.A.G.U.A | 65 |
| | | Antisense | U.A.A.C.U.C.G.C.U.A.G.G.C.C.A.C.G.C.C.G.A.G.G.U.C | 66 |
| SOD1-376-25-10002 | 10002 | Sense | P.G.G.A.U.G.A.A.G.A.G.A.G.G.C.A.U.G.U.U.G.G.A.G.A.C | 67 |
| | | Antisense | G.U.C.U.C.C.A.A.C.A.U.G.C.C.U.C.U.C.U.U.C.A.U.C.C | 68 |
| SOD1-371-25-10003 | 10003 | Sense | P.C.C.A.A.A.G.G.A.U.G.A.A.G.A.G.A.G.G.C.A.U.G.U.U.G | 69 |
| | | Antisense | C.A.A.C.A.U.G.C.C.U.C.U.C.U.U.C.A.U.C.C.U.U.U.G.G | 70 |
| SOD1-533-25-10004 | 10004 | Sense | P.A.A.A.G.G.U.G.G.A.A.A.U.G.A.A.G.A.A.A.G.U.A.C.A.A | 71 |
| | | Antisense | U.U.G.U.A.C.U.U.U.C.U.U.C.A.U.U.U.C.C.A.C.C.U.U.U | 72 |

TABLE 1-continued

Alternative RNAi Compound Sequences to SOD1 and PPIB

| Full Sequence Name | ID Number | Polarity | Sequence (5'→3') | SEQ ID |
|---|---|---|---|---|
| SOD1-062-25-10005 | 10005 | Sense | P.G.U.G.C.U.G.G.U.U.U.G.C.G.U.C.G.U.A.G.U.C.U.C.C.U | 73 |
| | | Antisense | A.G.G.A.G.A.C.U.A.C.G.A.C.G.C.A.A.A.C.C.A.G.C.A.C | 74 |
| SOD1-074-25-10006 | 10006 | Sense | P.G.U.C.G.U.A.G.U.C.U.C.C.U.G.C.A.G.C.G.U.C.U.G.G.G | 75 |
| | | Antisense | C.C.C.A.G.A.C.G.C.U.G.C.A.G.G.A.G.A.C.U.A.C.G.A.C | 76 |
| SOD1-202-25-10007 | 10007 | Sense | P.C.A.U.C.A.A.U.U.U.C.G.A.G.C.A.G.A.A.G.G.A.A.A.G.U | 77 |
| | | Antisense | A.C.U.U.U.C.C.U.U.C.U.G.C.U.C.G.A.A.A.U.U.G.A.U.G | 78 |
| SOD1-201-25-10008 | 10008 | Sense | P.U.C.A.U.C.A.A.U.U.U.C.G.A.G.C.A.G.A.A.G.G.A.A.A.G | 79 |
| | | Antisense | C.U.U.U.C.C.U.U.C.U.G.C.U.C.G.A.A.A.U.U.G.A.U.G.A | 80 |
| SOD1-320-25-10009 | 10009 | Sense | P.U.G.U.A.C.C.A.G.U.G.C.A.G.G.U.C.C.U.C.A.C.U.U.U.A | 81 |
| | | Antisense | U.A.A.A.G.U.G.A.G.G.A.C.C.U.G.C.A.C.U.G.G.U.A.C.A | 82 |
| SOD1-325-25-10010 | 10010 | Sense | P.C.A.G.U.G.C.A.G.G.U.C.C.U.C.A.C.U.U.U.A.A.U.C.C.U | 83 |
| | | Antisense | A.G.G.A.U.U.A.A.A.G.U.G.A.G.G.A.C.C.U.G.C.A.C.U.G | 84 |
| SOD1-396-25-10011 | 10011 | Sense | P.G.A.G.A.C.U.U.G.G.G.C.A.A.U.G.U.G.A.C.U.G.C.U.G.A | 85 |
| | | Antisense | U.C.A.G.C.A.G.U.C.A.C.A.U.U.G.C.C.C.A.A.G.U.C.U.C | 86 |
| SOD1-431-25-10012 | 10012 | Sense | P.G.U.G.G.C.C.G.A.U.G.U.G.U.C.U.A.U.U.G.A.A.G.A.U.U | 87 |
| | | Antisense | A.A.U.C.U.U.C.A.A.U.A.G.A.C.A.C.A.U.C.G.G.C.C.A.C | 88 |
| SOD1-440-25-10013 | 10013 | Sense | P.G.U.G.U.C.U.A.U.U.G.A.A.G.A.U.U.C.U.G.U.G.A.U.C.U | 89 |
| | | Antisense | A.G.A.U.C.A.C.A.G.A.A.U.C.U.U.C.A.A.U.A.G.A.C.A.C | 90 |
| SOD1-457-25-10014 | 10014 | Sense | P.U.G.U.G.A.U.C.U.C.A.C.U.C.U.C.A.G.G.A.G.A.C.C.A.U | 91 |
| | | Antisense | A.U.G.G.U.C.U.C.C.U.G.A.G.A.G.U.G.A.G.A.U.C.A.C.A | 92 |
| SOD1-530-25-10015 | 10015 | Sense | P.G.G.C.A.A.A.G.G.U.G.G.A.A.A.U.G.A.A.G.A.A.A.G.U.A | 93 |
| | | Antisense | U.A.C.U.U.U.C.U.U.C.A.U.U.U.C.C.A.C.C.U.U.U.G.C.C | 94 |
| SOD1-520-25-10016 | 10016 | Sense | P.A.G.A.U.G.A.C.U.U.G.G.G.C.A.A.A.G.G.U.G.G.A.A.A.U | 95 |
| | | Antisense | A.U.U.U.C.C.A.C.C.U.U.U.G.C.C.C.A.A.G.U.C.A.U.C.U | 96 |
| SOD1-568-25-10017 | 10017 | Sense | P.C.G.C.U.G.G.A.A.G.U.C.G.U.U.U.G.G.C.U.U.G.U.G.G.U | 97 |
| | | Antisense | A.C.C.A.C.A.A.G.C.C.A.A.A.C.G.A.C.U.U.C.C.A.G.C.G | 98 |
| SOD1-609-25-10018 | 10018 | Sense | P.A.A.U.A.A.A.C.A.U.U.C.C.C.U.U.G.G.A.U.G.U.A.G.U.C | 99 |
| | | Antisense | G.A.C.U.A.C.A.U.C.C.A.A.G.G.G.A.A.U.G.U.U.U.A.U.U | 100 |
| SOD1-662-25-10019 | 10019 | Sense | P.G.C.U.A.G.C.U.G.U.A.G.A.A.A.U.G.U.A.U.C.C.U.G.A.U | 101 |
| | | Antisense | A.U.C.A.G.G.A.U.A.C.A.U.U.U.C.U.A.C.A.G.C.U.A.G.C | 102 |
| SOD1-751-25-10020 | 10020 | Sense | P.C.C.U.G.U.A.G.U.G.A.G.A.A.A.C.U.G.A.U.U.U.A.U.G.A | 103 |
| | | Antisense | U.C.A.U.A.A.A.U.C.A.G.U.U.U.C.U.C.A.C.U.A.C.A.G.G | 104 |
| SOD1-844-25-10021 | 10021 | Sense | P.C.C.A.G.A.C.U.U.A.A.A.U.C.A.C.A.G.A.U.G.G.G.U.A.U | 105 |
| | | Antisense | A.U.A.C.C.C.A.U.C.U.G.U.G.A.U.U.U.A.A.G.U.C.U.G.G | 106 |
| SOD1-858-25-10022 | 10022 | Sense | P.C.A.G.A.U.G.G.G.U.A.U.U.A.A.A.C.U.U.G.U.C.A.G.A.A | 107 |
| | | Antisense | U.U.C.U.G.A.C.A.A.G.U.U.U.A.A.U.A.C.C.C.A.U.C.U.G | 108 |
| SOD1-434-25-10023 | 10023 | Sense | P.G.C.C.G.A.U.G.U.G.U.C.U.A.U.U.G.A.A.G.A.U.U.C.U.G | 109 |
| | | Antisense | C.A.G.A.A.U.C.U.U.C.A.A.U.A.G.A.C.A.C.A.U.C.G.G.C | 110 |
| SOD1-261-25-10024 | 10024 | Sense | P.G.A.C.U.G.A.C.U.G.A.A.G.G.C.C.U.G.C.A.U.G.G.A.U.U | 111 |
| | | Antisense | A.A.U.C.C.A.U.G.C.A.G.G.C.C.U.U.C.A.G.U.C.A.G.U.C | 112 |
| SOD1-434-25-10026 | 10026 | Sense | P.G.C.C.G.A.U.G.U.G.U.C.U.A.U.U.G.A.A.G.A.U.U.C.U.G | 113 |
| | | Antisense | C.A.G.A.A.U.C.U.U.C.A.A.U.A.G.A.C.A.C.A.U.C.G.G.C | 114 |
| SOD1-125-25-10027 | 10027 | Sense | P.G.A.C.C.U.C.G.G.C.G.U.G.G.C.C.U.A.G.C.G.A.G.U.U.A | 115 |
| | | Antisense | U.A.A.C.U.C.G.C.U.A.G.G.C.C.A.C.G.C.C.G.A.G.G.U.C | 116 |
| SOD1-751-25-10028 | 10028 | Sense | P.C.C.U.G.U.A.G.U.G.A.G.A.A.A.C.U.G.A.U.U.U.A.U.G.A | 117 |
| | | Antisense | U.C.A.U.A.A.A.U.C.A.G.U.U.U.C.U.C.A.C.U.A.C.A.G.G | 118 |
| SOD1-376-25-10029 | 10029 | Sense | P.G.G.A.U.G.A.A.G.A.G.A.G.G.C.A.U.G.U.U.G.G.A.G.A.C | 119 |
| | | Antisense | G.U.C.U.C.C.A.A.C.A.U.G.C.C.U.C.U.C.U.U.C.A.U.C.C | 120 |
| SOD1-533-25-10030 | 10030 | Sense | P.A.A.A.G.G.U.G.G.A.A.A.U.G.A.A.G.A.A.A.G.U.A.C.A.A | 121 |
| | | Antisense | U.U.G.U.A.C.U.U.U.C.U.U.C.A.U.U.U.C.C.A.C.C.U.U.U | 122 |

TABLE 1-continued

Alternative RNAi Compound Sequences to SOD1 and PPIB

| Full Sequence Name | ID Number | Polarity | Sequence (5'→3') | SEQ ID |
|---|---|---|---|---|
| SOD1-436-21-10033 (R1 var) | 10033 | Sense | P.C*G*A*fU.G.fU.G.U.C.U.A.U.U.G.A.A.G*A.fU*fU*C | 123 |
| | | Antisense | P.A.fU.fC.fU.U.C.A.A.U.A.G.A.C.A.fC.A*fU*fC*G*G*C | 124 |
| SOD1-395-21-10034 (R2) | 10034 | Sense | P.G*G*A*G.fC.fU.U.G.G.G.C.A.A.fU.G.fU*G*A*fU*U | 125 |
| | | Antisense | P.U.fC.A.fC.A.fU.fU.G.C.C.C.A.A.G.fU.fC.fU*fC*fC*U*U | 126 |
| SOD1-436-21-10036 (R1 unmod) | 10036 | Sense | P.C.G.A.U.G.U.G.U.C.U.A.U.U.G.A.A.G.A.U.U.C | 127 |
| | | Antisense | P.A.U.C.U.U.C.A.A.U.A.G.A.C.A.C.A.U.C.G.G.C | 128 |
| SOD1-395-21-10037 (R2 unmod) | 10037 | Sense | P.G.G.A.G.A.C.U.U.G.G.G.C.A.A.U.G.U.G.A.U.U | 129 |
| | | Antisense | P.U.C.A.C.A.U.U.G.C.C.C.A.A.G.U.C.U.C.C.U.U | 130 |
| SOD1-318-25-10078 | 10078 | Sense | P.G.C.U.G.U.A.C.C.A.G.U.G.C.A.G.G.U.C.C.U.C.A.C.U.U | 131 |
| | | Antisense | A.A.G.U.G.A.G.G.A.C.C.U.G.C.A.C.U.G.G.U.A.C.A.G.C. | 132 |
| SOD1-319-25-10079 | 10079 | Sense | P.C.U.G.U.A.C.C.A.G.U.G.C.A.G.G.U.C.C.U.C.A.C.U.U.U | 133 |
| | | Antisense | A.A.A.G.U.G.A.G.G.A.C.C.U.G.C.A.C.U.G.G.U.A.C.A.G | 134 |
| SOD1-321-25-10080 | 10080 | Sense | P.G.U.A.C.C.A.G.U.G.C.A.G.G.U.C.C.U.C.A.C.U.U.U.A.A | 135 |
| | | Antisense | U.U.A.A.A.G.U.G.A.G.G.A.C.C.U.G.C.A.C.U.G.G.U.A.C | 136 |
| SOD1-322-25-10081 | 10081 | Sense | P.U.A.C.C.A.G.U.G.C.A.G.G.U.C.C.U.C.A.C.U.U.U.A.A.U | 137 |
| | | Antisense | A.U.U.A.A.A.G.U.G.A.G.G.A.C.C.U.G.C.A.C.U.G.G.U.A | 138 |
| SOD1-432-25-10082 | 10082 | Sense | P.U.G.G.C.C.G.A.U.G.U.G.U.C.U.A.U.U.G.A.A.G.A.U.U.C | 139 |
| | | Antisense | G.A.A.U.C.U.U.C.A.A.U.A.G.A.C.A.C.A.U.C.G.G.C.C.A | 140 |
| SOD1-433-25-10083 | 10083 | Sense | P.G.G.C.C.G.A.U.G.U.G.U.C.U.A.U.U.G.A.A.G.A.U.U.C.U | 141 |
| | | Antisense | A.G.A.A.U.C.U.U.C.A.A.U.A.G.A.C.A.C.A.U.C.G.G.C.C | 142 |
| SOD1-435-25-10084 | 10084 | Sense | P.C.C.G.A.U.G.U.G.U.C.U.A.U.U.G.A.A.G.A.U.U.C.U.G.U | 143 |
| | | Antisense | A.C.A.G.A.A.U.C.U.U.C.A.A.u.A.G.A.C.A.c.A.U.C.G.G | 144 |
| SOD1-436-25-10085 | 10085 | Sense | P.C.G.A.U.G.U.G.U.C.U.A.U.U.G.A.A.G.A.U.U.C.U.G.U.G | 145 |
| | | Antisense | C.A.C.A.G.A.A.U.C.U.U.C.A.A.U.A.G.A.C.A.C.A.U.C.G | 146 |
| SCAD1-528-25-10086 | 10086 | Sense | P.U.G.G.G.C.A.A.A.G.G.U.G.G.A.A.A.U.G.A.A.G.A.A.A.G | 147 |
| | | Antisense | C.U.U.U.C.U.U.C.A.U.U.U.C.C.A.C.C.U.U.U.G.C.C.C.A | 148 |
| SOD1-529-25-10087 | 10087 | Sense | P.G.G.G.C.A.A.A.G.G.U.G.G.A.A.A.U.G.A.A.G.A.A.A.G.U | 149 |
| | | Antisense | A.C.U.U.U.C.U.U.C.A.U.U.U.C.C.A.C.C.U.U.U.G.C.C.C | 150 |
| SOD1-531-25-10088 | 10088 | Sense | P.G.C.A.A.A.G.G.U.G.G.A.A.A.U.G.A.A.G.A.A.A.G.U.A.C | 151 |
| | | Antisense | G.U.A.C.U.U.U.C.U.U.C.A.U.U.U.C.C.A.C.C.U.U.U.G.C | 152 |
| SOD1-532-25-10089 | 10089 | Sense | P.C.A.A.A.G.G.U.G.G.A.A.A.U.G.A.A.G.A.A.A.G.U.A.C.A | 153 |
| | | Antisense | U.G.U.A.C.U.U.U.C.U.U.C.A.U.U.U.C.C.A.C.C.U.U.U.G | 154 |
| SOD1-566-25-10090 | 10090 | Sense | P.A.A.C.G.C.U.G.G.A.A.G.U.C.G.U.U.U.G.G.C.U.U.G.U.G | 155 |
| | | Antisense | C.A.C.A.A.G.C.C.A.A.A.C.G.A.C.U.U.C.C.A.G.C.G.U.U | 156 |
| SOD1-567-25-10091 | 10091 | Sense | P.A.C.G.C.U.G.G.A.A.G.U.C.G.U.U.U.G.G.C.U.U.G.U.G.G | 157 |
| | | Antisense | C.C.A.C.A.A.G.C.C.A.A.A.C.G.A.C.U.U.C.C.A.G.C.G.U | 158 |
| SCAD1-569-25-10092 | 10092 | Sense | P.G.C.U.G.G.A.A.G.U.C.G.U.U.U.G.G.C.U.U.G.U.G.G.U.G | 159 |
| | | Antisense | C.A.C.C.A.C.A.A.G.C.C.A.A.A.C.G.A.C.U.U.C.C.A.G.C | 160 |
| SOD1-570-25-10093 | 10093 | Sense | P.C.U.G.G.A.A.G.U.C.G.U.U.U.G.G.C.U.U.G.U.G.G.U.G.U | 161 |
| | | Antisense | A.C.A.C.C.A.C.A.A.G.C.C.A.A.A.C.G.A.C.U.U.C.C.A.G | 162 |
| SOD1-369-25-10094 | 10094 | Sense | P.G.G.C.C.A.A.A.G.G.A.U.G.A.A.G.A.G.A.G.G.C.A.U.G.U | 163 |
| | | Antisense | A.C.A.U.G.C.C.U.C.U.C.U.U.C.A.U.C.C.U.U.U.G.G.C.C | 164 |
| SOD1-370-25-10095 | 10095 | Sense | P.G.C.C.A.A.A.G.G.A.U.G.A.A.G.A.G.A.G.G.C.A.U.G.U.U | 165 |
| | | Antisense | A.A.C.A.U.G.C.C.U.C.U.C.U.U.C.A.U.C.C.U.U.U.G.G.C | 166 |
| SOD1-372-25-10096 | 10096 | Sense | P.C.A.A.A.G.G.A.U.G.A.A.G.A.G.A.G.G.C.A.U.G.U.U.G.G | 167 |
| | | Antisense | C.C.A.A.C.A.U.G.C.C.U.C.U.C.U.U.C.A.U.C.C.U.U.U.G | 168 |
| SOD1-373-25-10097 | 10097 | Sense | P.A.A.A.G.G.A.U.G.A.A.G.A.G.A.G.G.C.A.U.G.U.U.G.G.A | 169 |
| | | Antisense | U.C.C.A.A.C.A.U.G.C.C.U.C.U.C.U.U.C.A.U.C.C.U.U.U | 170 |
| SOD1-436-21-10104 | 10104 | Sense | P.C*G*A*mU.G.mU.G.U.C.U.A.U.U.G.A.A.G*A.mU*mU*C | 171 |

TABLE 1-continued

Alternative RNAi Compound Sequences to SOD1 and PPIB

| Full Sequence Name | ID Number | Polarity | Sequence (5'→3') | SEQ ID |
|---|---|---|---|---|
| 10104 (R1 with 2'Ome) | | Anti-sense | P.A.mU.mC.mU.U.C.A.A.U.A.G.A.C.A.mC.A*mU*mC*G*G*C | 172 |
| SOD1-436-21-10105(R1) | 10105 | Sense | P.C*G*A*fU.G.fU.G.U.C.U.A.U.U.G.A.A.G*A*fU*fU*C | 173 |
| | | Anti-sense | P.A.fU.fC.fU.U.C.A.A.U.A.G.A.C.A.fC.A*fU*fC*G*G*C | 174 |
| SOD1-430-25-10174 | 10174 | Sense | 5'-P.U.G.U.G.G.C.C.G.A.U.G.U.G.U.C.U.A.U.U.G.A.A.G.A.U | 175 |
| | | Antisense | A.U.C.U.U.C.A.A.U.A.G.A.C.A.C.A.U.C.G.G.C.C.A.C.A | 176 |
| SOD1-429-26-10175 | 10175 | Sense | 5'-P.G.U.G.U.G.G.C.C.G.A.U.G.U.G.U.C.U.A.U.U.G.A.A.G.A.U | 177 |
| | | Antisense | A.U.C.U.U.C.A.A.U.A.G.A.C.A.C.A.U.C.G.G.C.C.A.C.A.C | 178 |
| PPIB-10167 | 10167 | Antisense | 5'-U.U.U.U.U.G.G.A.A.C.A.G.U.C.U.U.U.C.C | 179 |
| PPIB-10169 | 10169 | Antisense | 5'-mU.mU.mU.mU.U.G.G.A.A.C.A.G.U.C.U.U.mU.mU.mC.mC | 180 |

TABLE 2

Additional Alternative RNAi Compound Sequences to SOD1

| Additional Sequences Designed | | Polarity | Sequence | SEQ ID |
|---|---|---|---|---|
| 10255 | | Sense | P.A.U.G.A.A.G.A.A.A.G.U.A.C.A.A.A.G.A.C.A.G.G.A.A.A | 181 |
| | | Antisense | U.U.U.C.C.U.G.U.C.U.U.U.G.U.A.C.U.U.U.C.U.U.C.A.U | 182 |
| 10256 | | Sense | P.A.G.G.A.U.G.A.A.G.A.G.A.G.G.C.A.U.G.U.U.G.G.A.G.A | 183 |
| | | Antisense | U.C.U.C.C.A.A.C.A.U.G.C.C.U.C.U.C.U.U.C.A.U.C.C.U | 184 |
| 10257 | | Sense | P.C.U.G.A.C.A.A.A.G.A.U.G.G.U.G.U.G.G.C.C.G.A.U.G.U | 185 |
| | | Antisense | A.C.A.U.C.G.G.C.C.A.C.A.C.C.A.U.C.U.U.U.G.U.C.A.G | 186 |
| 10258 | | Sense | P.A.U.G.A.A.A.A.G.C.A.G.A.U.G.A.C.U.U.G.G.G.C.A.A | 187 |
| | | Antisense | U.U.G.C.C.C.A.A.G.U.C.A.U.C.U.G.C.U.U.U.U.U.C.A.U | 188 |
| 10259 | | Sense | P.C.U.G.C.U.G.A.C.A.A.A.G.A.U.G.G.U.G.U.G.G.C.C.G.A | 189 |
| | | Antisense | U.C.G.G.C.C.A.C.A.C.C.A.U.C.U.U.U.G.U.C.A.G.C.A.G | 190 |
| 10260 | | Sense | P.G.G.C.C.G.C.A.C.A.C.U.G.G.U.G.G.U.C.C.A.U.G.A.A.A | 191 |
| | | Antisense | U.U.U.C.A.U.G.G.A.C.C.A.C.C.A.G.U.G.U.G.C.G.G.C.C | 192 |
| 10261 | | Sense | P.A.C.U.C.U.C.A.G.G.A.G.A.C.C.A.U.U.G.C.A.U.C.A.U.U | 193 |
| | | Antisense | A.A.U.G.A.U.G.C.A.A.U.G.G.U.C.U.C.C.U.G.A.G.A.G.U | 194 |
| 10262 | | Sense | P.U.G.U.G.G.C.C.G.A.U.G.U.G.U.C.U.A.U.U.G.A.A.G.A.U | 195 |
| | | Antisense | A.U.C.U.U.C.A.A.U.A.G.A.C.A.C.A.U.C.G.G.C.C.A.C.A | 196 |
| 10263 | | Sense | P.A.G.A.G.G.C.A.U.G.U.U.G.G.A.G.A.C.U.U.G.G.G.C.A.A | 197 |
| | | Antisense | U.G.C.C.C.A.A.G.U.C.U.C.C.A.A.C.A.U.G.C.C.U.C.U | 198 |
| 10264 | | Sense | P.G.U.G.G.G.C.C.A.A.A.G.G.A.U.G.A.A.G.A.G.A.G.G.C.A | 199 |
| | | Antisense | U.G.C.C.U.C.U.C.U.U.C.A.U.C.C.U.U.U.G.G.C.C.C.A.C | 200 |
| 10265 | | Sense | P.C.U.U.G.G.G.C.A.A.U.G.U.G.A.C.U.G.C.U.G.A.C.A.A.A | 201 |
| | | Antisense | U.U.U.G.U.C.A.G.C.A.G.U.C.A.C.A.U.U.G.C.C.C.A.A.G | 202 |
| 10266 | | Sense | P.U.C.U.A.U.C.C.A.G.A.A.A.A.C.A.C.G.G.U.G.G.G.C.C.A | 203 |
| | | Antisense | U.G.G.C.C.C.A.C.C.G.U.G.U.U.U.U.C.U.G.G.A.U.A.G.A | 204 |
| 10267 | | Sense | P.A.A.A.A.A.G.C.A.G.A.U.G.A.C.U.U.G.G.G.C.A.A.A.G.G | 205 |
| | | Antisense | C.C.U.U.U.G.C.C.C.A.A.G.U.C.A.U.C.U.G.C.U.U.U.U.U | 206 |
| 10268 | | Sense | P.A.A.U.G.G.A.C.C.A.G.U.G.A.A.G.G.U.G.U.G.G.G.G.A.A | 207 |
| | | Antisense | U.U.C.C.C.C.A.C.A.C.C.U.U.C.A.C.U.G.G.U.C.C.A.U.U | 208 |
| 10269 | | Sense | P.U.G.U.U.A.U.C.C.U.G.C.U.A.G.C.U.G.U.A.G.A.A.A.U.G | 209 |
| | | Antisense | C.A.U.U.U.C.U.A.C.A.G.C.U.A.G.C.A.G.G.A.U.A.A.C.A | 210 |
| 10270 | | Sense | P.C.A.G.A.A.G.G.A.A.A.G.U.A.A.U.G.G.A.C.C.A.G.U.G.A | 211 |
| | | Antisense | U.C.A.C.U.G.G.U.C.C.A.U.U.A.C.U.U.U.C.C.U.U.C.U.G | 212 |

TABLE 2-continued

Additional Alternative RNAi Compound Sequences to SOD1

| Additional Sequences Designed | | | SEQ ID |
|---|---|---|---|
| 10271 | Sense | P.A.A.U.G.A.A.G.A.A.A.G.U.A.C.A.A.A.G.A.C.A.G.G.A.A | 213 |
| | Antisense | U.U.C.C.U.G.U.C.U.U.U.G.U.A.C.U.U.U.C.U.U.C.A.U.U | 214 |
| 10272 | Sense | P.C.G.A.G.C.A.G.A.A.G.G.A.A.A.G.U.A.A.U.G.G.A.C.C.A | 215 |
| | Antisense | U.G.G.U.C.C.A.U.U.A.C.U.U.U.C.C.U.U.C.U.G.C.U.C.G | 216 |
| 10273 | Sense | P.U.A.C.A.A.A.G.A.C.A.G.G.A.A.A.C.G.C.U.G.G.A.A.G.U | 217 |
| | Antisense | A.C.U.U.C.C.A.G.C.G.U.U.U.C.C.U.G.U.C.U.U.U.G.U.A | 218 |
| 10274 | Sense | P.A.A.U.U.U.C.G.A.G.C.A.G.A.A.G.G.A.A.A.G.U.A.A.U.G | 219 |
| | Antisense | C.A.U.U.A.C.U.U.U.C.C.U.U.C.U.G.C.U.C.G.A.A.A.U.U | 220 |
| 10275 | Sense | P.U.G.A.A.G.A.G.A.G.G.C.A.U.G.U.U.G.G.A.G.A.C.U.U.G | 221 |
| | Antisense | C.A.A.G.U.C.U.C.C.A.A.C.A.U.G.C.C.U.C.U.C.U.U.C.A | 222 |
| 10276 | Sense | P.A.C.U.U.G.G.G.C.A.A.A.G.G.U.G.G.A.A.A.U.G.A.A.G.A | 223 |
| | Antisense | U.C.U.U.C.A.U.U.U.C.C.A.C.C.U.U.U.G.C.C.C.A.A.G.U | 224 |
| 10277 | Sense | P.A.C.U.U.G.G.G.C.A.A.U.G.U.G.A.C.U.G.C.U.G.A.C.A.A | 225 |
| | Antisense | U.U.G.U.C.A.G.C.A.G.U.C.A.C.A.U.U.G.C.C.C.A.A

TABLE 2-continued

Additional Alternative RNAi Compound Sequences to SOD1

| Additional Sequences Designed | | | SEQ ID |
|---|---|---|---|
| 10296 | Sense | P.A.G.G.G.C.A.U.C.A.U.C.A.A.U.U.U.C.G.A.G.C.A.G.A.A | 263 |
| | Antisense | U.U.C.U.G.C.U.C.G.A.A.A.U.U.G.A.U.G.A.U.G.C.C.C.U | 264 |
| 10297 | Sense | P.C.C.A.U.G.U.U.C.A.U.G.A.G.U.U.U.G.G.A.G.A.U.A.A.U | 265 |
| | Antisense | A.U.U.A.U.C.U.C.C.A.A.A.C.U.C.A.U.G.A.A.C.A.U.G.G | 266 |
| 10298 | Sense | P.A.A.A.C.A.U.U.C.C.C.U.U.G.G.A.U.G.U.A.G.U.C.U.G.A | 267 |
| | Antisense | U.C.A.G.A.C.U.A.C.A.U.C.C.A.A.G.G.G.A.A.U.G.U.U.U | 268 |
| 10299 | Sense | P.U.C.A.A.U.U.U.C.G.A.G.C.A.G.A.A.G.G.A.A.A.G.U.A.A | 269 |
| | Antisense | U.U.A.C.U.U.U.C.C.U.U.C.U.G.C.U.C.G.A.A.A.U.U.G.A | 270 |
| 10300 | Sense | P.U.G.G.A.A.G.U.C.G.U.U.U.G.G.C.U.U.G.U.G.G.U.G.U.A | 271 |
| | Antisense | U.A.C.A.C.C.A.C.A.A.G.C.C.A.A.A.C.G.A.C.U.U.C.C TABLE 2-continued Additional Alternative RNAi Compound Sequences to SOD1

| Additional Sequences Designed | | | SEQ ID |
|---|---|---|---|
| | Antisense | A.U.G.A.A.C.A.U.G.G.A.A.U.C.C.A.U.G.C.A.G.G.C.C.U | 312 |
| 10321 | Sense | P.G.C.C.U.G.C.A.U.G.G.A.U.U.C.C.A.U.G.U.U.C.A.U.G.A | 313 |
| | Antisense | U.C.A.U.G.A.A.C.A.U.G.G.A.A.U.C.C.A.U.G.C.A.G.G.C | 314 |
| 10322 | Sense | P.C.C.U.G.C.A.U.G.G.A.U.U.C.C.A.U.G.U.U.C.A.U.G.A.G | 315 |
| | Antisense | C.U.C.A.U.G.A.A.C.A.U.G.G.A.A.U.C.C.A.U.G.C.A.G.G | 316 |
| 10323 | Sense | P.U.G.C.A.U.G.G.A.U.U.C.C.A.U.G.U.U.C.A.U.G.A.G.U.U | 317 |
| | Antisense | A.A.C.U.C.A.U.G.A.A.C.A.U.G.G.A.A.U.C.C.A.U.G.C.A | 318 |
| 10324 | Sense | P.C.A.U.G.G.A.U.U.C.C.A.U.G.U.U.C.A.U.G.A.G.U.U.U.G | 319 |
| | Antisense | C.A.A.A.C.U.C.A.U.G.A.A.C.A.U.G.G.A.A.U.C.C.A.U.G | 320 |
| 10325 | Sense | P.G.A.U.U.C.C.A.U.G.U.U.C.A.U.G.A.G.U.U.U.G.G.A.G.A | 321 |
| | Antisense | U.C.U.C.C.A.A.A.C.U.C.A.U.G.A.A.C.A.U.G.G.A.A.U.C | 322 |
| 10326 | Sense | P.U.C.A.U.G.A.G.U.U.U.G.G.A.G.A.U.A.A.U.A.C.A.G.C.A | 323 |
| | Antisense | U.G.C.U.G.U.A.U.U.A.U.C.U.C.C.A.A.A.C.U.C.A.U.G.A | 324 |
|

TABLE 2-continued

Additional Alternative RNAi Compound Sequences to SOD1

| Additional Sequences Designed | | | SEQ ID |
|---|---|---|---|
| 10345 | Sense | P.A.G.A.U.G.G.U.G.U.G.G.C.C.G.A.U.G.U.G.U.C.U.A.U.U | 361 |
| | Antisense | A.A.U.A.G.A.C.A.C.A.U.C.G.G.C.C.A.C.A.C.C.A.U.C.U | 362 |
| 10346 | Sense | P.G.A.U.G.G.U.G.U.G.G.C.C.G.A.U.G.U.G.U.C.U.A.U.U.G | 363 |
| | Antisense | C.A.A.U.A.G.A.C.A.C.A.U.C.G.G.C.C.A.C.A.C.C.A.U.C | 364 |
| 10347 | Sense | P.U.G.G.U.G.U.G.G.C.C.G.A.U.G.U.G.U.C.U.A.U.U.G.A.A | 365 |
| | Antisense | U.U.C.A.A.U.A.G.A.C.A.C.A.U.C.G.G.C.C.A.C.A.C.C.A | 366 |
| 10348 | Sense | P.G.A.U.G.U.G.U.C.U.A.U.U.G.A.A.G.A.U.U.C.U.G.U.G.A | 367 |
| | Antisense | U.C.A.C.A.G.A.A.U.C.U.U.C.A.A.U.A.G.A.C.A.C.A.U.C | 368 |
| 10349 | Sense | P.U.G.A.A.G.A.U.U.C.U.G.U.G.A.U.C.U.C.A.C.U.C.U.C.A | 369 |
| | Antisense | U.G.A.G.A.G.U.G.A.G.A.U.C.A.C.A.G.A.A.U.C.U.U.C.A | 370 |
| 10350 | Sense | P.G.A.A.G.A.U.U.C.U.G.U.G.A.U.C.U.C.A.C.U.C.U.C.A.G | 371 |
| | Antisense | C.U.G.A.G.A.G.U.G.A.G.A.U.C.A.C.A.G.A.A.U.C.U.U.C | 372 |
| 10351 | Sense | P.U.C.U.C.A.C.U.C.U.C.A.G.G.A.G.A.C.C.A.U.U.G.C.A.U | 373 |
| | Antisense | A.U.G.C.A.A.U.G.G.U.C.U.C.C.U.G.A.G.A.G.U.G.A.G.A | 374 |
| 10352 | Sense | P.C.A.C.U.C.U.C.A.G.G.A.G.A.C.C.A.U.U.G.C.A.U.C.A.U | 375 |
| | Antisense | A.U.G.A.U.G.C.A.A.U.G.G.U.C.U.C.C.U.G.A.G.A.G.U.G | 376 |
| 10353 | Sense | P.A.C.C.A.U.U.G.C.A.U.C.A.U.U.G.G.C.C.G.C.A.C.A.C.U | 377 |
| | Antisense | A.G.U.G.U.G.C.G.G.C.C.A.A.U.G.A.U.G.C.A.A.U.G.G.U | 378 |
| 10354 | Sense | P.G.C.A.G.A.U.G.A.C.U.U.G.G.G.C.A.A.A.G.G.U.G.G.A.A | 379 |
| | Antisense | U.U.C.C.A.C.C.U.U.U.G.C.C.C.A.A.G.U.C.A.U.C.U.G.C | 380 |
| 10355 | Sense | P.C.A.G.A.U.G.A.C.U.U.G.G.G.C.A.A.A.G.G.U.G.G.A.A.A | 381 |
| | Antisense | U.U.U.C.C.A.C.C.U.U.U.G.C.C.C.A.A.G.U.C.A.U.C.U.G | 382 |
| 10356 | Sense | P.G.A.C.U.U.G.G.G.C.A.A.A.G.G.U.G.G.A.A.A.U.G.A.A.G | 383 |
| | Antisense | C.U.U.C.A.U.U.U.C.C.A.C.C.U.U.U.G.C.C.C.A.A.G.U.C | 384 |
| 10357 | Sense | P.A.G.G.U.G.G.A.A.A.U.G.A.A.G.A.A.A.G.U.A.C.A.A.A.G | 385 |
| | Antisense | C.U.U.U.G.U.A.C.U.U.U.C.U.U.C.A.U.U.U.C.C.A.C.C.U | 386 |
| 10358 | Sense | P.G.G.U.G.G.A.A.A.U.G.A.A.G.A.A.A.G.U.A.C.A.A.A.G.A | 387 |
| | Antisense | U.C.U.U.U.G.U.A.C.U.U.U.C.U.U.C.A.U.U.U.C.C.A.C.C | 388 |
| 10359 | Sense | P.G.G.A.A.A.U.G.A.A.G.A.A.A.G.U.A.C.A.A.A.G.A.C.A.G | 389 |
| | Antisense | C.U.G.U.C.U.U.U.G.U.A.C.U.U.U.C.U.U.C.A.U.U.U.C.C | 390 |
| 10360 | Sense | P.A.G.A.A.A.G.U.A.C.A.A.A.G.A.C.A.G.G.A.A.A.C.G.C.U | 391 |
| | Antisense | A.G.C.G.U.U.U.C.C.U.G.U.C.U.U.U.G.U.A.C.U.U.U.C.U | 392 |
| 10361 | Sense | P.A.G.U.A.C.A.A.A.G.A.C.A.G.G.A.A.A.C.G.C.U.G.G.A.A | 393 |
| | Antisense | U.U.C.C.A.G.C.G.U.U.U.C.C.U.G.U.C.U.U.U.G.U.A.C.U | 394 |
| 10362 | Sense | P.A.A.G.A.C.A.G.G.A.A.A.C.G.C.U.G.G.A.A.G.U.C.G.U.U | 395 |
| | Antisense | A.A.C.G.A.C.U.U.C.C.A.G.C.G.U.U.U.C.C.U.G.U.C.U.U | 396 |
| 10363 | Sense | P.A.G.A.C.A.G.G.A.A.A.C.G.C.U.G.G.A.A.G.U.C.G.U.U.U | 397 |
| | Antisense | A.A.A.C.G.A.C.U.U.C.C.A.G.C.G.U.U.U.C.C.U.G.U.C.U | 398 |
| 10364 | Sense | P.A.G.G.A.A.A.C.G.C.U.G.G.A.A.G.U.C.G.U.U.U.G.G.C.U | 399 |
| | Antisense | A.G.C.C.A.A.A.C.G.A.C.U.U.C.C.A.G.C.G.U.U.U.C.C.U | 400 |
| 10365 | Sense | P.G.A.A.A.C.G.C.U.G.G.A.A.G.U.C.G.U.U.U.G.G.C.U.U | 401 |
| | Antisense | A.A.G.C.C.A.A.A.C.G.A.C.U.U.C.C.A.G.C.G.U.U.U.C.C | 402 |
| 10366 | Sense | P.G.A.A.A.C.G.C.U.G.G.A.A.G.U.C.G.U.U.U.G.G.C.U.U.G | 403 |
| | Antisense | C.A.A.G.C.C.A.A.A.C.G.A.C.U.U.C.C.A.G.C.G.U.U.U.C | 404 |
| 10367 | Sense | P.G.G.A.A.G.U.C.G.U.U.U.G.G.C.U.U.G.U.G.G.U.G.U.A.A | 405 |
| | Antisense | U.U.A.C.A.C.C.A.C.A.A.G.C.C.A.A.A.C.G.A.C.U.U.C.C | 406 |
| 10368 | Sense | P.G.A.A.G.U.C.G.U.U.U.G.G.C.U.U.G.U.G.G.U.G.U.A.A.U | 407 |
| | Antisense | A.U.U.A.C.A.C.C.A.C.A.A.G.C.C.A.A.A.C.G.A.C.U.U.C | 408 |
| 10369 | Sense | P.A.A.G.U.C.G.U.U.U.G.G.C.U.U.G.U.G.G.U.G.U.A.A.U.U | 409 |
| | Antisense | A.A.U.U.A.C.A.C.C.A.C.A.A.G.C.C.A.A.A.C.G.A.C.U.U | 410 |

TABLE 2-continued

| Additional Alternative RNAi Compound Sequences to SOD1 | | | |
|---|---|---|---|
| Additional Sequences Designed | | | SEQ ID |
| 10370 | Sense | P.U.G.U.G.G.U.G.U.A.A.U.U.G.G.G.A.U.C.G.C.C.C.A.A.U | 411 |
| | Antisense | A.U.U.G.G.G.C.G.A.U.C.C.C.A.A.U.U.A.C.A.C.C.A.C.A | 412 |
| 10371 | Sense | P.U.G.G.U.G.U.A.A.U.U.G.G.G.A.U.C.G.C.C.C.A.A.U.A.A | 413 |
| | Antisense | U.U.A.U.U.G.G.G.C.G.A.U.C.C.C.A.A.U.U.A.C.A.C.C.A | 414 |
| 10372 | Sense | P.C.U.G.G.C.C.U.A.U.A.A.A.G.U.A.G.U.C.G.C.G.G.A.G.A | 415 |
| | Antisense | U.C.U.C.C.G.C.G.A.C.U.A.C.U.U.U.A.U.A.G.G.C.C.A.G | 416 |
| 10373 | Sense | P.G.G.C.C.A.G.A.G.U.G.G.G.C.G.A.G.G.C.G.C.G.G.A.G.G | 417 |
| | Antisense | C.C.U.C.C.G.C.G.C.C.U.C.G.C.C.C.A.C.U.C.U.G.G.C.C | 418 |
| 10374 | Sense | P.C.C.A.G.A.G.U.G.G.G.C.G.A.G.G.C.G.C.G.G.A.G.G.U.C | 419 |
| | Antisense | G.A.C.C.U.C.C.G.C.G.C.C.U.C.G.C.C.C.A.C.U.C.U.G.G | 420 |
| 10375 | Sense | P.A.G.U.G.G.G.C.G.A.G.G.C.G.C.G.G.A.G.G.U.C.U.G.G.C | 421 |
| | Antisense | G.C.C.A.G.A.C.C.U.C.C.G.C.G.C.C.U.C.G.C.C.C.A.C.U | 422 |
| 10376 | Sense | P.G.G.C.G.A.G.G.C.G.C.G.G.A.G.G.U.C.U.G.G.C.C.U.A.U | 423 |
| | Antisense | A.U.A.G.G.C.C.A.G.A.C.C.U.C.C.G.C.G.C.C.U.C.G.C.C | 424 |
| 10377 | Sense | P.A.G.G.C.G.C.G.G.A.G.G.U.C.U.G.G.C.C.U.A.U.A.A.A.G | 425 |
| | Antisense | C.U.U.U.A.U.A.G.G.C.C.A.G.A.C.C.U.C.C.G.C.G.C.C.U | 426 |
| 10378 | Sense | P.G.C.G.G.A.G.G.U.C.U.G.G.C.C.U.A.U.A.A.A.G.U.A.G.U | 427 |
| | Antisense | A.C.U.A.C.U.U.U.A.U.A.G.G.C.C.A.G.A.C.C.U.C.C.G.C | 428 |
| 10379 | Sense | P.A.G.G.U.C.U.G.G.C.C.U.A.U.A.A.A.G.U.A.G.U.C.G.C.G | 429 |
| | Antisense | C.G.C.G.A.C.U.A.C.U.U.U.A.U.A.G.G.C.C.A.G.A.C.C.U | 430 |
| 10380 | Sense | P.G.C.C.U.A.U.A.A.A.G.U.A.G.U.C.G.C.G.G.A.G.A.C.G.G | 431 |
| | Antisense | C.C.G.U.C.U.C.C.G.C.G.A.C.U.A.C.U.U.U.A.U.A.G.G.C | 432 |
| 10381 | Sense | P.G.G.U.G.C.U.G.G.U.U.U.G.C.G.U.C.G.U.A.G.U.C.U.C.C | 433 |
| | Antisense | G.G.A.G.A.C.U.A.C.G.A.C.G.C.A.A.A.C.C.A.G.C.A.C.C | 434 |
| 10382 | Sense | P.C.U.G.G.U.U.U.G.C.G.U.C.G.U.A.G.U.C.U.C.C.U.G.C.A | 435 |
| | Antisense | U.G.C.A.G.G.A.G.A.C.U.A.C.G.A.C.G.C.A.A.A.C.C.A.G | 436 |
| 10383 | Sense | P.U.U.U.G.C.G.U.C.G.U.A.G.U.C.U.C.C.U.G.C.A.G.C.G.U | 437 |
| | Antisense | A.C.G.C.U.G.C.A.G.G.A.G.A.C.U.A.C.G.A.C.G.C.A.A.A | 438 |
| 10384 | Sense | P.C.G.U.C.G.U.A.G.U.C.U.C.C.U.G.C.A.G.C.G.U.C.U.G.G | 439 |
| | Antisense | C.C.A.G.A.C.G.C.U.G.C.A.G.G.A.G.A.C.U.A.C.G.A.C.G | 440 |
| 10385 | Sense | P.G.G.U.U.U.C.C.G.U.U.G.C.A.G.U.C.C.U.C.G.G.A.A.C.C | 441 |
| | Antisense | G.G.U.U.C.C.G.A.G.G.A.C.U.G.C.A.A.C.G.G.A.A.A.C.C | 442 |
| 10386 | Sense | P.U.C.C.G.U.U.G.C.A.G.U.C.C.U.C.G.G.A.A.C.C.A.G.G.A | 443 |
| | Antisense | U.C.C.U.G.G.U.U.C.C.G.A.G.G.A.C.U.G.C.A.A.C.G.G.A | 444 |
| 10387 | Sense | P.U.U.G.C.A.G.U.C.C.U.C.G.G.A.A.C.C.A.G.G.A.C.C.U.C | 445 |
| | Antisense | G.A.G.G.U.C.C.U.G.G.U.U.C.C.G.A.G.G.A.C.U.G.C.A.A | 446 |
| 10388 | Sense | P.A.G.U.C.C.U.C.G.G.A.A.C.C.A.G.G.A.C.C.U.C.G.G.C.G | 447 |
| | Antisense | C.G.C.C.G.A.G.G.U.C.C.U.G.G.U.U.C.C.G.A.G.G.A.C.U | 448 |
| 10389 | Sense | P.C.U.C.G.G.A.A.C.C.A.G.G.A.C.C.U.C.G.G.C.G.U.G.G.C | 449 |
| | Antisense | G.C.C.A.C.G.C.C.G.A.G.G.U.C.C.U.G.G.U.U.C.C.G.A.G | 450 |
| 10390 | Sense | P.G.A.A.C.C.A.G.G.A.C.C.U.C.G.G.C.G.U.G.G.C.C.U.A.G | 451 |
| | Antisense | C.U.A.G.G.C.C.A.C.G.C.C.G.A.G.G.U.C.C.U.G.G.U.U.C | 452 |
| 10391 | Sense | P.C.A.G.G.A.C.C.U.C.G.G.C.G.U.G.G.C.C.U.A.G.C.G.A.G | 453 |
| | Antisense | C.U.C.G.C.U.A.G.G.C.C.A.C.G.C.C.G.A.G.G.U.C.C.U.G | 454 |
| 10392 | Sense | P.A.C.C.U.C.G.G.C.G.U.G.G.C.C.U.A.G.C.G.A.G.U.U.A.U | 455 |
| | Antisense | A.U.A.A.C.U.C.G.C.U.A.G.G.C.C.A.C.G.C.C.G.A.G.G.U | 456 |
| 10393 | Sense | P.C.G.G.C.G.U.G.G.C.C.U.A.G.C.G.A.G.U.U.A.U.G.G.C.G | 457 |
| | Antisense | C.G.C.C.A.U.A.A.C.U.C.G.C.U.A.G.G.C.C.A.C.G.C.C.G | 458 |
| 10394 | Sense | P.G.U.G.G.C.C.U.A.G.C.G.A.G.U.U.A.U.G.G.C.G.A.C.G.A | 459 |

TABLE 2-continued

Additional Alternative RNAi Compound Sequences to SOD1

| Additional Sequences Designed | | | SEQ ID |
|---|---|---|---|
| | Antisense | U.C.G.U.C.G.C.C.A.U.A.A.C.U.C.G.C.U.A.G.G.C.C.A.C | 460 |
| 10395 | Sense | P.C.C.U.A.G.C.G.A.G.U.U.A.U.G.G.C.G.A.C.G.A.A.G.G.C | 461 |
| | Antisense | G.C.C.U.U.C.G.U.C.G.C.C.A.U.A.A.C.U.C.G.C.U.A.G.G | 462 |
| 10396 | Sense | P.G.C.G.A.G.U.U.A.U.G.G.C.G.A.C.G.A.A.G.G.C.C.G.U.G | 463 |
| | Antisense | C.A.C.G.G.C.C.U.U.C.G.U.C.G.C.C.A.U.A.A.C.U.C.G.C | 464 |
| 10397 | Sense | P.G.U.U.A.U.G.G.C.G.A.C.G.A.A.G.G.C.C.G.U.G.U.G.C.G | 465 |
| | Antisense | C.G.C.A.C.A.C.G.G.C.C.U.U.C.G.U.C.G.C.C.A.U.A.A.C | 466 |
| 10398 | Sense | P.U.G.G.C.G.A.C.G.A.A.G.G.C.C.G.U.G.U.G.C.G.U.G.C.U | 467 |
| | Antisense | A.G.C.A.C.G.C.A.C.A.C.G.G.C.C.U.U.C.G.U.C.G.C.C.A | 468 |
| 10399 | Sense | P.G.A.C.G.A.A.G.G.C.C.G.U.G.U.G.C.G.U.G.C.U.G.A.A.G | 469 |
| | Antisense | C.U.U.C.A.G.C.A.C.G.C.A.C.A.C.G.G.C.C.U.U.C.G.U.C | 470 |
| 10400 | Sense | P.A.C.G.A.A.G.G.C.C.G.U.G.U.G.C.G.U.G.C.U.G.A.A.G.G | 471 |
| | Antisense | C.C.U.U.C.A.G.C.A.C.G.C.A.C.A.C.G.G.C.C.U.U.C.G.U | 472 |
| 10401 | Sense | P.G.G.C.A.U.C.A.U.C.A.A.U.U.U.C.G.A.G.C.A.G.A.A.G.G | 473 |
| | Antisense | C.C.U.U.C.U.G.C.U.C.G.A.A.A.U.U.G.A.U.G.A.U.G.C.C | 474 |
| 10402 | Sense | P.A.U.C.A.A.U.U.U.C.G.A.G.C.A.G.A.A.G.G.A.A.A.G.U.A | 475 |
| | Antisense | U.A.C.U.U.U.C.C.U.U.C.U.G.C.U.C.G.A.A.A.U.U.G.A.U | 476 |
| 10403 | Sense | P.A.U.U.U.C.G.A.G.C.A.G.A.A.G.G.A.A.A.G.U.A.A.U.G.G | 477 |
| | Antisense | C.C.A.U.U.A.C.U.U.U.C.C.U.U.C.U.G.C.U.C.G.A.A.A.U | 478 |
| 10404 | Sense | P.U.C.G.A.G.C.A.G.A.A.G.G.A.A.A.G.U.A.A.U.G.G.A.C.C | 479 |
| | Antisense | G.G.U.C.C.A.U.U.A.C.U.U.U.C.C.U.U.C.U.G.C.U.C.G.A | 480 |
| 10405 | Sense | P.G.C.A.G.A.A.G.G.A.A.A.G.U.A.A.U.G.G.A.C.C.A.G.U.G | 481 |
| | Antisense | C.A.C.U.G.G.U.C.C.A.U.U.A.C.U.U.U.C.C.U.U.C.U.G.C | 482 |
| 10406 | Sense | P.A.A.G.G.A.A.A.G.U.A.A.U.G.G.A.C.C.A.G.U.G.A.A.G.G | 483 |
| | Antisense | C.C.U.U.C.A.C.U.G.G.U.C.C.A.U.U.A.C.U.U.U.C.C.U.U | 484 |
| 10407 | Sense | P.A.A.A.G.U.A.A.U.G.G.A.C.C.A.G.U.G.A.A.G.G.U.G.U.G | 485 |
| | Antisense | C.A.C.A.C.C.U.U.C.A.C.U.G.G.U.C.C.A.U.U.A.C.U.U.U | 486 |
| 10408 | Sense | P.U.A.A.U.G.G.A.C.C.A.G.U.G.A.A.G.G.U.G.U.G.G.G.G.A | 487 |
| | Antisense | U.C.C.C.C.A.C.A.C.C.U.U.C.A.C.U.G.G.U.C.C.A.U.U.A | 488 |
| 10409 | Sense | P.G.G.A.A.G.C.A.U.U.A.A.A.G.G.A.C.U.G.A.C.U.G.A.A.G | 489 |
| | Antisense | C.U.U.C.A.G.U.C.A.G.U.C.C.U.U.U.A.A.U.G.C.U.U.C.C | 490 |
| 10410 | Sense | P.G.C.A.U.U.A.A.A.G.G.A.C.U.G.A.C.U.G.A.A.G.G.C.C.U | 491 |
| | Antisense | A.G.G.C.C.U.U.C.A.G.U.C.A.G.U.C.C.U.U.U.A.A.U.G.C | 492 |
| 10411 | Sense | P.U.A.A.A.G.G.A.C.U.G.A.C.U.G.A.A.G.G.C.C.U.G.C.A.U | 493 |
| | Antisense | A.U.G.C.A.G.G.C.C.U.U.C.A.G.U.C.A.G.U.C.C.U.U.U.A | 494 |
| 10412 | Sense | P.G.G.A.C.U.G.A.C.U.G.A.A.G.G.C.C.U.G.C.A.U.G.G.A.U | 495 |
| | Antisense | A.U.C.C.A.U.G.C.A.G.G.C.C.U.U.C.A.G.U.C.A.G.U.C.C | 496 |
| 10413 | Sense | P.U.G.A.C.U.G.A.A.G.G.C.C.U.G.C.A.U.G.G.A.U.U.C.C.A | 497 |
| | Antisense | U.G.G.A.A.U.C.C.A.U.G.C.A.G.G.C.C.U.U.C.A.G.U.C.A | 498 |
| 10414 | Sense | P.C.U.G.A.A.G.G.C.C.U.G.C.A.U.G.G.A.U.U.C.C.A.U.G.U | 499 |
| | Antisense | A.C.A.U.G.G.A.A.U.C.C.A.U.G.C.A.G.G.C.C.U.U.C.A.G | 500 |
| 10415 | Sense | P.A.A.G.G.C.C.U.G.C.A.U.G.G.A.U.U.C.C.A.U.G.U.U.C.A | 501 |
| | Antisense | U.G.A.A.C.A.U.G.G.A.A.U.C.C.A.U.G.C.A.G.G.C.C.U.U | 502 |
| 10416 | Sense | P.G.G.C.C.U.G.C.A.U.G.G.A.U.U.C.C.A.U.G.U.U.C.A.U.G | 503 |
| | Antisense | C.A.U.G.A.A.C.A.U.G.G.A.A.U.C.C.A.U.G.C.A.G.G.C.C | 504 |
| 10417 | Sense | P.C.U.G.C.A.U.G.G.A.U.U.C.C.A.U.G.U.U.C.A.U.G.A.G.U | 505 |
| | Antisense | A.C.U.C.A.U.G.A.A.C.A.U.G.G.A.A.U.C.C.A.U.G.C.A.G | 506 |
| 10418 | Sense | P.A.U.G.G.A.U.U.C.C.A.U.G.U.U.C.A.U.G.A.G.U.U.U.G.G | 507 |
| | Antisense | C.C.A.A.A.C.U.C.A.U.G.A.A.C.A.U.G.G.A.A.U.C.C.A.U | 508 |

TABLE 2-continued

Additional Alternative RNAi Compound Sequences to SOD1

| Additional Sequences Designed | | | SEQ ID |
|---|---|---|---|
| 10419 | Sense | P.A.U.U.C.C.A.U.G.U.U.C.A.U.G.A.G.U.U.U.G.G.A.G.A.U | 509 |
| | Antisense | A.U.C.U.C.C.A.A.A.C.U.C.A.U.G.A.A.C.A.U.G.G.A.A.0 | 510 |
| 10420 | Sense | P.C.A.U.G.U.U.C.A.U.G.A.G.U.U.U.G.G.A.G.A.U.A.A.U.A | 511 |
| | Antisense | U.A.U.U.A.U.C.U.C.C.A.A.A.C.U.C.A.U.G.A.A.C.A.U.G | 512 |
| 10421 | Sense | P.U.U.C.A.U.G.A.G.U.U.U.G.G.A.G.A.U.A.A.U.A.C.A.G.C | 513 |
| | Antisense | G.C.U.G.U.A.U.U.A.U.C.U.C.C.A.A.A.C.U.C.A.U.G.A.A | 514 |
| 10422 | Sense | P.U.G.A.G.U.U.U.G.G.A.G.A.U.A.A.U.A.C.A.G.C.A.G.G.C | 515 |
| | Antisense | G.C.C.U.G.C.U.G.U.A.U.U.A.U.C.U.C.C.A.A.A.C.U.C.A | 516 |
| 10423 | Sense | P.U.U.U.G.G.A.G.A.U.A.A.U.A.C.A.G.C.A.G.G.C.U.G.U.A | 517 |
| | Antisense | U.A.C.A.G.C.C.U.G.C.U.G.U.A.U.U.A.U.C.U.C.C.A.A.A | 518 |
| 10424 | Sense | P.G.A.G.A.U.A.A.U.A.C.A.G.C.A.G.G.C.U.G.U.A.C.C.A.G | 519 |
| | Antisense | C.U.G.G.U.A.C.A.G.C.C.U.G.C.U.G.U.A.U.U.A.U.C.U.C | 520 |
| 10425 | Sense | P.U.A.A.U.A.C.A.G.C.A.G.G.C.U.G.U.A.C.C.A.G.U.G.C.A | 521 |
| | Antisense | U.G.C.A.C.U.G.G.U.A.C.A.G.C.C.U.G.C.U.G.U.A.U.U.A | 522 |
| 10426 | Sense | P.A.C.A.G.C.A.G.G.C.U.G.U.A.C.C.A.G.U.G.C.A.G.G.U.C | 523 |
| | Antisense | G.A.C.C.U.G.C.A.C.U.G.G.U.A.C.A.G.C.C.U.G.C.U.G.U | 524 |
| 10427 | Sense | P.C.A.G.G.C.U.G.U.A.C.C.A.G.U.G.C.A.G.G.U.C.C.U.C.A | 525 |
| | Antisense | U.G.A.G.G.A.C.C.U.G.C.A.C.U.G.G.U.A.C.A.G.C.C.U.G | 526 |
| 10428 | Sense | P.C.C.A.G.U.G.C.A.G.G.U.C.C.U.C.A.C.U.U.U.A.A.U.C.C | 527 |
| | Antisense | G.G.A.U.U.A.A.A.G.U.G.A.G.G.A.C.C.U.G.C.A.C.U.G.G | 528 |
| 10429 | Sense | P.G.U.G.C.A.G.G.U.C.C.U.C.A.C.U.U.U.A.A.U.C.C.U.C.U | 529 |
| | Antisense | A.G.A.G.G.A.U.U.A.A.A.G.U.G.A.G.G.A.C.C.U.G.C.A.C | 530 |
| 10430 | Sense | P.C.A.G.G.U.C.C.U.C.A.C.U.U.U.A.A.U.C.C.U.C.U.A.U.C | 531 |
| | Antisense | G.A.U.A.G.A.G.G.A.U.U.A.A.A.G.U.G.A.G.G.A.C.C.U.G | 532 |
| 10431 | Sense | P.G.U.C.C.U.C.A.C.U.U.U.A.A.U.C.C.U.C.U.A.U.C.C.A.G | 533 |
| | Antisense | C.U.G.G.A.U.A.G.A.G.G.A.U.U.A.A.A.G.U.G.A.G.G.A.C | 534 |
| 10432 | Sense | P.U.C.A.C.U.U.U.A.A.U.C.C.U.C.U.A.U.C.C.A.G.A.A.A.A | 535 |
| | Antisense | U.U.U.U.C.U.G.G.A.U.A.G.A.G.G.A.U.U.A.A.A.G.U.G.A | 536 |
| 10433 | Sense | P.U.U.U.A.A.U.C.C.U.C.U.A.U.C.C.A.G.A.A.A.A.C.A.C.G | 537 |
| | Antisense | C.G.U.G.U.U.U.U.C.U.G.G.A.U.A.G.A.G.G.A.U.U.A.A.A | 538 |
| 10434 | Sense | P.A.U.C.C.U.C.U.A.U.C.C.A.G.A.A.A.A.C.A.C.G.G.U.G.G | 539 |
| | Antisense | C.C.A.C.C.G.U.G.U.U.U.U.C.U.G.G.A.U.A.G.A.G.G.A.U | 540 |
| 10435 | Sense | P.A.A.G.G.A.U.G.A.A.G.A.G.A.G.G.C.A.U.G.U.U.G.G.A.G | 541 |
| | Antisense | C.U.C.C.A.A.C.A.U.G.C.C.U.C.U.C.U.U.C.A.U.C.C.U.U | 542 |
| 10436 | Sense | P.A.U.G.A.A.G.A.G.A.G.G.C.A.U.G.U.U.G.G.A.G.A.C.U.U | 543 |
| | Antisense | A.A.G.U.C.U.C.C.A.A.C.A.U.G.C.C.U.C.U.C.U.U.C.A.U | 544 |
| 10437 | Sense | P.G.A.A.G.A.G.A.G.G.C.A.U.G.U.U.G.G.A.G.A.C.U.U.G.G | 545 |
| | Antisense | C.C.A.A.G.U.C.U.C.C.A.A.C.A.U.G.C.C.U.C.U.C.U.U.C | 546 |
| 10438 | Sense | P.G.A.G.A.G.G.C.A.U.G.U.U.G.G.A.G.A.C.U.U.G.G.G.C.A | 547 |
| | Antisense | U.G.C.C.C.A.A.G.U.C.U.C.C.A.A.C.A.U.G.C.C.U.C.U.C | 548 |
| 10439 | Sense | P.A.U.G.U.U.G.G.A.G.A.C.U.U.G.G.G.C.A.A.U.G.U.G.A.C | 549 |
| | Antisense | G.U.C.A.C.A.U.U.G.C.C.C.A.A.G.U.C.U.C.C.A.A.C.A.U | 550 |
| 10440 | Sense | P.C.A.A.U.G.U.G.A.C.U.G.C.U.G.A.C.A.A.A.G.A.U.G.G.U | 551 |
| | Antisense | A.C.C.A.U.C.U.U.U.G.U.C.A.G.C.A.G.U.C.A.C.A.U.U.G | 552 |
| 10441 | Sense | P.G.U.G.A.C.U.G.C.U.G.A.C.A.A.A.G.A.U.G.G.U.G.U.G.G | 553 |
| | Antisense | C.C.A.C.A.C.C.A.U.C.U.U.U.G.U.C.A.G.C.A.G.U.C.A.C | 554 |
| 10442 | Sense | P.A.C.U.G.C.U.G.A.C.A.A.A.G.A.U.G.G.U.G.U.G.G.C.C.G | 555 |
| | Antisense | C.G.G.C.C.A.C.A.C.C.A.U.C.U.U.U.G.U.C.A.G.C.A.G.U | 556 |
| 10443 | Sense | P.G.C.U.G.A.C.A.A.A.G.A.U.G.G.U.G.U.G.G.C.C.G.A.U.G | 557 |
| | Antisense | C.A.U.C.G.G.C.C.A.C.A.C.C.A.U.C.U.U.U.U.G.U.C.A.G.C | 558 |

TABLE 2-continued

Additional Alternative RNAi Compound Sequences to SOD1

| Additional Sequences Designed | | | SEQ ID |
|---|---|---|---|
| 10444 | Sense | P.A.C.A.A.A.G.A.U.G.G.U.G.U.G.G.C.C.G.A.U.G.U.G.U.C | 559 |
| | Antisense | G.A.C.A.C.A.U.C.G.G.C.C.A.C.A.C.C.A.U.C.U.U.U.G.U | 560 |
| 10445 | Sense | P.A.A.A.G.A.U.G.G.U.G.U.G.G.C.C.G.A.U.G.U.G.U.C.U.A | 561 |
| | Antisense | U.A.G.A.C.A.C.A.U.C.G.G.C.C.A.C.A.C.C.A.U.C.U.U.U | 562 |
| 10446 | Sense | P.A.U.G.U.G.U.C.U.A.U.U.G.A.A.G.A.U.U.C.U.G.U.G.A.U | 563 |
| | Antisense | A.U.C.A.C.A.G.A.A.U.C.U.U.C.A.A.U.A.G.A.C.A.C.A.U | 564 |
| 10447 | Sense | P.U.G.U.C.U.A.U.U.G.A.A.G.A.U.U.C.U.G.U.G.A.U.C.U.C | 565 |
| | Antisense | G.A.G.A.U.C.A.C.A.G.A.A.U.C.U.U.C.A.A.U.A.G.A.C.A | 566 |
| 10448 | Sense | P.U.A.U.U.G.A.A.G.A.U.U.C.U.G.U.G.A.U.C.U.C.A.C.U.C | 567 |
| | Antisense | G.A.G.U.G.A.G.A.U.C.A.C.A.G.A.A.U.C.U.U.C.A.A.U.A | 568 |
| 10449 | Sense | P.U.U.G.A.A.G.A.U.U.C.U.G.U.G.A.U.C.U.C.A.C.U.C.U.C | 569 |
| | Antisense | G.A.G.A.G.U.G.A.G.A.U.C.A.C.A.G.A.A.U.C.U.U.C.A.A | 570 |
| 10450 | Sense | P.A.A.G.A.U.U.C.U.G.U.G.A.U.C.U.C.A.C.U.C.U.C.A.G.G | 571 |
| | Antisense | C.C.U.G.A.G.A.G.U.G.A.G.A.U.C.A.C.A.G.A.A.U.C.U.U | 572 |
| 10451 | Sense | P.U.U.C.U.G.U.G.A.U.C.U.C.A.C.U.C.U.C.A.G.G.A.G.A.C | 573 |
| | Antisense | G.U.C.U.C.C.U.G.A.G.A.G.U.G.A.G.A.U.C.A.C.A.G.A.A | 574 |
| 10452 | Sense | P.G.U.G.A.U.C.U.C.A.C.U.C.U.C.A.G.G.A.G.A.C.C.A.U.U | 575 |
| | Antisense | A.A.U.G.G.U.C.U.C.C.U.G.A.G.A.G.U.G.A.G.A.U.C.A.C | 576 |
| 10453 | Sense | P.A.U.C.U.C.A.C.U.C.U.C.A.G.G.A.G.A.C.C.A.U.U.G.C.A | 577 |
| | Antisense | U.G.C.A.A.U.G.G.U.C.U.C.C.U.G.A.G.A.G.U.G.A.G.A.U | 578 |
| 10454 | Sense | P.U.C.U.C.A.G.G.A.G.A.C.C.A.U.U.G.C.A.U.C.A.U.U.G.G | 579 |
| | Antisense | C.C.A.A.U.G.A.U.G.C.A.A.U.G.G.U.C.U.C.C.U.G.A.G.A | 580 |
| 10455 | Sense | P.A.G.G.A.G.A.C.C.A.U.U.G.C.A.U.C.A.U.U.G.G.C.C.G.C | 581 |
| | Antisense | G.C.G.G.C.C.A.A.U.G.A.U.G.C.A.A.U.G.G.U.C.U.C.C.U | 582 |
| 10456 | Sense | P.G.A.C.C.A.U.U.G.C.A.U.C.A.U.U.G.G.C.C.G.C.A.C.A.C | 583 |
| | Antisense | G.U.G.U.G.C.G.G.C.C.A.A.U.G.A.U.G.C.A.A.U.G.G.U.C | 584 |
| 10464 | Sense | P.A.A.A.G.A.A.U.C.C.A.A.A.U.U.C.A.A.A.C.U.A.A.A.A.A | 585 |
| | Antisense | U.U.U.U.U.A.G.U.U.U.G.A.A.U.U.U.G.G.A.U.U.C.U.U.U | 586 |
| 10465 | Sense | P.A.U.U.A.A.A.A.G.A.A.U.C.C.A.A.A.U.U.C.A.A.A.C.U.A | 587 |
| | Antisense | A.U.U.A.A.A.A.G.A.A.U.C.C.A.A.A.U.U.C.A.A.A.C.U.A | 588 |
| 10466 | Sense | P.G.G.C.U.A.U.U.A.A.A.A.G.A.A.U.C.C.A.A.A.U.U.C.A.A | 589 |
| | Antisense | U.U.G.A.A.U.U.U.G.G.A.U.U.C.U.U.U.U.A.A.U.A.G.C.C | 590 |
| 10467 | Sense | P.A.U.G.A.G.G.C.U.A.U.U.A.A.A.A.G.A.A.U.C.C.A.A.A.U | 591 |
| | Antisense | A.U.U.U.G.G.A.U.U.C.U.U.U.U.A.A.U.A.G.C.C.U.C.A.U | 592 |
| 10468 | Sense | P.U.A.U.U.A.U.G.A.G.G.C.U.A.U.U.A.A.A.A.G.A.A.U.C.C | 593 |
| | Antisense | G.G.A.U.U.C.U.U.U.U.A.A.U.A.G.C.C.U.C.A.U.A.A.U.A | 594 |
| 10469 | Sense | P.C.A.C.U.U.A.U.U.A.U.G.A.G.G.C.U.A.U.U.A.A.A.A.G.A | 595 |
| | Antisense | U.C.U.U.U.U.A.A.U.A.G.C.C.U.C.A.U.A.A.U.A.A.G.U.G | 596 |
| 10470 | Sense | P.A.U.G.G.C.A.C.U.U.A.U.U.A.U.G.A.G.G.C.U.A.U.U.A.A | 597 |
| | Antisense | U.U.A.A.U.A.G.C.C.U.C.A.U.A.A.U.A.A.G.U.G.C.C.A.U | 598 |
| 10471 | Sense | P.C.U.G.U.A.U.G.G.C.A.C.U.U.A.U.U.A.U.G.A.G.G.C.U.A | 599 |
| | Antisense | U.A.G.C.C.U.C.A.U.A.A.U.A.A.G.U.G.C.C.A.U.A.C.A.G | 600 |
| 10472 | Sense | P.U.C.A.U.U.C.A.A.G.C.C.U.G.U.G.A.A.U.A.A.A.A.A.C.C | 601 |
| | Antisense | G.G.U.U.U.U.U.A.U.U.C.A.C.A.G.G.C.U.U.G.A.A.U.G.A | 602 |
| 10473 | Sense | P.U.G.U.C.A.U.U.C.A.A.G.C.C.U.G.U.G.A.A.U.A.A.A.A.A | 603 |
| | Antisense | U.U.U.U.U.A.U.U.C.A.C.A.G.G.C.U.U.G.A.A.U.G.A.C.A | 604 |
| 10474 | Sense | P.U.U.U.G.U.C.A.U.U.C.A.A.G.C.C.U.G.U.G.A.A.U.A.A.A | 605 |
| | Antisense | U.U.U.A.U.U.C.A.C.A.G.G.C.U.U.G.A.A.U.G.A.C.A.A.A | 606 |
| 10475 | Sense | P.U.C.U.U.U.G.U.C.A.U.U.C.A.A.G.C.C.U.G.U.G.A.A.U.A | 607 |

TABLE 2-continued

Additional Alternative RNAi Compound Sequences to SOD1

| Additional Sequences Designed | | | SEQ ID |
|---|---|---|---|
| | Antisense | U.A.U.U.C.A.C.A.G.G.C.U.U.G.A.A.U.G.A.C.A.A.A.G.A | 608 |
| 10476 | Sense | P.U.U.U.C.U.U.U.G.U.C.A.U.U.C.A.A.G.C.C.U.G.U.G.A.A | 609 |
| | Antisense | U.U.C.A.C.A.G.G.C.U.U.G.A.A.U.G.A.C.A.A.A.G.A.A.A | 610 |
| 10477 | Sense | P.A.G.A.A.U.U.U.C.U.U.U.G.U.C.A.U.U.C.A.A.G.C.C.U.G | 611 |
| | Antisense | C.A.G.G.C.U.U.G.A.A.U.G.A.C.A.A.A.G.A.A.A.U.U.C.U | 612 |
| 10478 | Sense | P.U.G.U.C.A.G.A.A.U.U.U.C.U.U.U.G.U.C.A.U.U.C.A.A.G | 613 |
| | Antisense | C.U.U.G.A.A.U.G.A.C.A.A.A.G.A.A.A.U.U.C.U.G.A.C.A | 614 |
| 10479 | Sense | P.A.A.C.U.U.G.U.C.A.G.A.A.U.U.U.C.U.U.U.G.U.C.A.U.U | 615 |
| | Antisense | A.A.U.G.A.C.A.A.A.G.A.A.A.U.U.C.U.G.A.C.A.A.G.U.U | 616 |
| 10480 | Sense | P.A.U.U.A.A.A.C.U.U.G.U.C.A.G.A.A.U.U.U.C.U.U.U.G.U | 617 |
| | Antisense | A.C.A.A.A.G.A.A.A.U.U.C.U.G.A.C.A.A.G.U.U.U.A.A.U | 618 |
| 10481 | Sense | P.G.G.U.A.U.U.A.A.A.C.U.U.G.U.C.A.G.A.A.U.U.U.C.U.U | 619 |
| | Antisense | A.A.G.A.A.A.U.U.C.U.G.A.C.A.A.G.U.U.U.A.A.U.A.C.C | 620 |
| 10482 | Sense | P.U.U.U.G.C.C.A.G.A.C.U.U.A.A.A.U.C.A.C.A.G.A.U.G.G | 621 |
| | Antisense | C.C.A.U.C.U.G.U.G.A.U.U.U.A.A.G.U.C.U.G.G.C.A.A.A | 622 |
| 10483 | Sense | P.A.U.U.U.U.G.C.C.A.G.A.C.U.U.A.A.A.U.C.A.C.A.G.A.U | 623 |
| | Antisense | A.U.C.U.G.U.G.A.U.U.U.A.A.G.U.C.U.G.G.C.A.A.A.A.U | 624 |
| 10484 | Sense | P.G.U.A.U.U.U.U.G.C.C.A.G.A.C.U.U.A.A.A.U.C.A.C.A.G | 625 |
| | Antisense | C.U.G.U.G.A.U.U.U.A.A.G.U.C.U.G.G.C.A.A.A.A.U.A.C | 626 |
| 10485 | Sense | P.C.U.G.U.A.U.U.U.U.G.C.C.A.G.A.C.U.U.A.A.A.U.C.A.C | 627 |
| | Antisense | G.U.G.A.U.U.U.A.A.G.U.C.U.G.G.C.A.A.A.A.U.A.C.A.G | 628 |
| 10486 | Sense | P.A.C.C.U.G.U.A.U.U.U.U.G.C.C.A.G.A.C.U.U.A.A.A.U.C | 629 |
| | Antisense | G.A.U.U.U.A.A.G.U.C.U.G.G.C.A.A.A.A.U.A.C.A.G.G.U | 630 |
| 10487 | Sense | P.A.A.U.G.A.C.C.U.G.U.A.U.U.U.U.G.C.C.A.G.A.C.U.U.A | 631 |
| | Antisense | U.A.A.G.U.C.U.G.G.C.A.A.A.A.U.A.C.A.G.G.U.C.A.U.U | 632 |
| 10488 | Sense | P.U.U.U.C.A.A.U.G.A.C.C.U.G.U.A.U.U.U.U.G.C.C.A.G.A | 633 |
| | Antisense | U.C.U.G.G.C.A.A.A.A.U.A.C.A.G.G.U.C.A.U.U.G.A.A.A | 634 |
| 10489 | Sense | P.U.C.U.G.U.U.U.C.A.A.U.G.A.C.C.U.G.U.A.U.U.U.U.G.C | 635 |
| | Antisense | G.C.A.A.A.A.U.A.C.A.G.G.U.C.A.U.U.G.A.A.A.C.A.G.A | 636 |
| 10490 | Sense | P.A.A.U.G.U.C.U.G.U.U.U.C.A.A.U.G.A.C.C.U.G.U.A.U.U | 637 |
| | Antisense | A.A.U.A.C.A.G.G.U.C.A.U.U.G.A.A.A.C.A.G.A.C.A.U.U | 638 |
| 10491 | Sense | P.U.U.A.A.A.A.U.G.U.C.U.G.U.U.U.C.A.A.U.G.A.C.C.U.G | 639 |
| | Antisense | C.A.G.G.U.C.A.U.U.G.A.A.A.C.A.G.A.C.A.U.U.U.U.A.A | 640 |
| 10492 | Sense | P.U.C.A.G.U.U.A.A.A.A.U.G.U.C.U.G.U.U.U.C.A.A.U.G.A | 641 |
| | Antisense | U.C.A.U.U.G.A.A.A.C.A.G.A.C.A.U.U.U.U.A.A.C.U.G.A | 642 |
| 10493 | Sense | P.A.A.A.C.U.C.A.G.U.U.A.A.A.A.U.G.U.C.U.G.U.U.U.C.A | 643 |
| | Antisense | U.G.A.A.A.C.A.G.A.C.A.U.U.U.U.A.A.C.U.G.A.G.U.U.U | 644 |
| 10494 | Sense | P.U.A.U.A.A.A.A.C.U.C.A.G.U.U.A.A.A.A.U.G.U.C.U.G.U | 645 |
| | Antisense | A.C.A.G.A.C.A.U.U.U.U.A.A.C.U.G.A.G.U.U.U.U.A.U.A | 646 |
| 10495 | Sense | P.G.U.U.U.U.A.U.A.A.A.A.C.U.C.A.G.U.U.A.A.A.A.U.G.U | 647 |
| | Antisense | A.C.A.U.U.U.U.A.A.C.U.G.A.G.U.U.U.U.A.U.A.A.A.A.C | 648 |
| 10496 | Sense | P.U.A.U.A.G.U.U.U.U.A.U.A.A.A.A.C.U.C.A.G.U.U.A.A.A | 649 |
| | Antisense | U.U.U.A.A.C.U.G.A.G.U.U.U.U.A.U.A.A.A.A.C.U.A.U.A | 650 |
| 10497 | Sense | P.U.U.U.G.U.A.U.A.G.U.U.U.U.A.U.A.A.A.A.C.U.C.A.G.U | 651 |
| | Antisense | A.C.U.G.A.G.U.U.U.U.A.U.A.A.A.A.C.U.A.U.A.C.A.A.A | 652 |
| 10498 | Sense | P.A.A.G.A.U.U.U.G.U.A.U.A.G.U.U.U.U.A.U.A.A.A.A.C.U | 653 |
| | Antisense | A.G.U.U.U.U.A.U.A.A.A.A.C.U.A.U.A.C.A.A.A.U.C.U.U | 654 |
| 10499 | Sense | P.U.U.G.G.A.A.G.A.U.U.U.G.U.A.U.A.G.U.U.U.U.A.U.A.A | 655 |
| | Antisense | U.U.A.U.A.A.A.A.C.U.A.U.A.C.A.A.A.U.C.U.U.C.C.A.A | 656 |

TABLE 2-continued

Additional Alternative RNAi Compound Sequences to SOD1

| Additional Sequences Designed | | | SEQ ID |
|---|---|---|---|
| 10500 | Sense | P.U.C.A.C.U.U.G.G.A.A.G.A.U.U.U.G.U.A.U.A.G.U.U.U.U | 657 |
| | Antisense | A.A.A.A.C.U.A.U.A.C.A.A.A.U.C.U.U.C.C.A.A.G.U.G.A | 658 |
| 10501 | Sense | P.A.U.G.A.U.C.A.C.U.U.G.G.A.A.G.A.U.U.U.G.U.A.U.A.G | 659 |
| | Antisense | C.U.A.U.A.C.A.A.A.U.C.U.U.C.C.A.A.G.U.G.A.U.C.A.U | 660 |
| 10502 | Sense | P.A.U.U.U.A.U.G.A.U.C.A.C.U.U.G.G.A.A.G.A.U.U.U.G.U | 661 |
| | Antisense | A.C.A.A.A.U.C.U.U.C.C.A.A.G.U.G.A.U.C.A.U.A.A.A.U | 662 |
| 10503 | Sense | P.A.C.U.G.A.U.U.U.A.U.G.A.U.C.A.C.U.U.G.G.A.A.G.A.U | 663 |
| | Antisense | A.U.C.U.U.C.C.A.A.G.U.G.A.U.C.A.U.A.A.A.U.C.A.G.U | 664 |
| 10504 | Sense | P.A.G.A.A.A.C.U.G.A.U.U.U.A.U.G.A.U.C.A.C.U.U.G.G.A | 665 |
| | Antisense | U.C.C.A.A.G.U.G.A.U.C.A.U.A.A.A.U.C.A.G.U.U.U.C.U | 666 |
| 10505 | Sense | P.A.G.U.G.A.G.A.A.A.C.U.G.A.U.U.U.A.U.G.A.U.C.A.C.U | 667 |
| | Antisense | A.G.U.G.A.U.C.A.U.A.A.A.U.C.A.G.U.U.U.C.U.C.A.C.U | 668 |
| 10506 | Sense | P.C.U.G.U.A.G.U.G.A.G.A.A.A.C.U.G.A.U.U.U.A.U.G.A.U | 669 |
| | Antisense | A.U.C.A.U.A.A.A.U.C.A.G.U.U.U.C.U.C.A.C.U.A.C.A.G | 670 |
| 10507 | Sense | P.G.U.A.C.C.U.G.U.A.G.U.G.A.G.A.A.A.C.U.G.A.U.U.U.A | 671 |
| | Antisense | U.A.A.A.U.C.A.G.U.U.U.C.U.C.A.C.U.A.C.A.G.G.U.A.C | 672 |
| 10508 | Sense | P.U.A.A.A.G.U.A.C.C.U.G.U.A.G.U.G.A.G.A.A.A.C.U.G.A | 673 |
| | Antisense | U.C.A.G.U.U.U.C.U.C.A.C.U.A.C.A.G.G.U.A.C.U.U.U.A | 674 |
| 10509 | Sense | P.G.C.U.U.U.A.A.A.G.U.A.C.C.U.G.U.A.G.U.G.A.G.A.A.A | 675 |
| | Antisense | U.U.U.C.U.C.A.C.U.A.C.A.G.G.U.A.C.U.U.U.A.A.A.G.C | 676 |
| 10510 | Sense | P.A.G.U.U.G.C.U.U.U.A.A.A.G.U.A.C.C.U.G.U.A.G.U.G.A | 677 |
| | Antisense | U.C.A.C.U.A.C.A.G.G.U.A.C.U.U.U.A.A.A.G.C.A.A.C.U | 678 |
| 10511 | Sense | P.U.C.A.G.A.G.U.U.G.C.U.U.U.A.A.A.G.U.A.C.C.U.G.U.A | 679 |
| | Antisense | U.A.C.A.G.G.U.A.C.U.U.U.A.A.A.G.C.A.A.C.U.C.U.G.A | 680 |
| 10512 | Sense | P.U.U.U.U.U.C.A.G.A.G.U.U.G.C.U.U.U.A.A.A.G.U.A.C.C | 681 |
| | Antisense | G.G.U.A.C.U.U.U.A.A.A.G.C.A.A.C.U.C.U.G.A.A.A.A.A | 682 |
| 10513 | Sense | P.U.G.A.C.U.U.U.U.U.C.A.G.A.G.U.U.G.C.U.U.U.A.A.A.G | 683 |
| | Antisense | C.U.U.U.A.A.A.G.C.A.A.C.U.C.U.G.A.A.A.A.A.G.U.C.A | 684 |
| 10514 | Sense | P.U.G.U.G.U.G.A.C.U.U.U.U.U.C.A.G.A.G.U.U.G.C.U.U.U | 685 |
| | Antisense | A.A.A.G.C.A.A.C.U.C.U.G.A.A.A.A.A.G.U.C.A.C.A.C.A | 686 |
| 10515 | Sense | P.U.A.A.U.U.G.U.G.U.G.A.C.U.U.U.U.U.C.A.G.A.G.U.U.G | 687 |
| | Antisense | C.A.A.C.U.C.U.G.A.A.A.A.A.G.U.C.A.C.A.C.A.A.U.U.A | 688 |
| 10516 | Sense | P.A.G.U.G.U.A.A.U.U.G.U.G.U.G.A.C.U.U.U.U.U.C.A.G.A | 689 |
| | Antisense | U.C.U.G.A.A.A.A.A.G.U.C.A.C.A.C.A.A.U.U.A.C.A.C.U | 690 |
| 10517 | Sense | P.U.A.A.A.A.G.U.G.U.A.A.U.U.G.U.G.U.G.A.C.U.U.U.U.U | 691 |
| | Antisense | A.A.A.A.A.G.U.C.A.C.A.C.A.A.U.U.A.C.A.C.U.U.U.U.A | 692 |
| 10518 | Sense | P.A.U.C.U.U.A.A.A.A.G.U.G.U.A.A.U.U.G.U.G.U.G.A.C.U | 693 |
| | Antisense | A.G.U.C.A.C.A.C.A.A.U.U.A.C.A.C.U.U.U.U.A.A.G.A.U | 694 |
| 10519 | Sense | P.U.G.U.A.A.U.C.U.U.A.A.A.A.G.U.G.U.A.A.U.U.G.U.G.U | 695 |
| | Antisense | A.C.A.C.A.A.U.U.A.C.A.C.U.U.U.U.A.A.G.A.U.U.A.C.A | 696 |
| 10520 | Sense | P.A.C.A.C.U.G.U.A.A.U.C.U.U.A.A.A.A.G.U.G.U.A.A.U.U | 697 |
| | Antisense | A.A.U.U.A.C.A.C.U.U.U.U.A.A.G.A.U.U.A.C.A.G.U.G.U | 698 |
| 10521 | Sense | P.U.U.A.A.A.C.A.C.U.G.U.A.A.U.C.U.U.A.A.A.A.G.U.G.U | 699 |
| | Antisense | A.C.A.C.U.U.U.U.A.A.G.A.U.U.A.C.A.G.U.G.U.U.U.A.A | 700 |
| 10522 | Sense | P.A.A.C.A.U.U.A.A.A.C.A.C.U.G.U.A.A.U.C.U.U.A.A.A.A | 701 |
| | Antisense | U.U.U.U.A.A.G.A.U.U.A.C.A.G.U.G.U.U.U.A.A.U.G.U.U | 702 |
| 10523 | Sense | P.G.A.U.A.A.A.C.A.U.U.A.A.A.C.A.C.U.G.U.A.A.U.C.U.U | 703 |
| | Antisense | A.A.G.A.U.U.A.C.A.G.U.G.U.U.U.A.A.U.G.U.U.U.A.U.C | 704 |
| 10524 | Sense | P.U.C.C.U.G.A.U.A.A.A.C.A.U.U.A.A.A.C.A.C.U.G.U.A.A | 705 |
| | Antisense | U.U.A.C.A.G.U.G.U.U.U.A.A.U.G.U.U.U.A.U.C.A.G.G.A | 706 |

TABLE 2-continued

Additional Alternative RNAi Compound Sequences to SOD1

| Additional Sequences Designed | | | SEQ ID |
|---|---|---|---|
| 10525 | Sense | P.U.G.U.A.U.C.C.U.G.A.U.A.A.A.C.A.U.U.A.A.A.C.A.C.U | 707 |
| | Antisense | A.G.U.G.U.U.U.A.A.U.G.U.U.U.A.U.C.A.G.G.A.U.A.C.A | 708 |
| 10526 | Sense | P.G.A.A.A.U.G.U.A.U.C.C.U.G.A.U.A.A.A.C.A.U.U.A.A.A | 709 |
| | Antisense | U.U.U.A.A.U.G.U.U.U.A.U.C.A.G.G.A.U.A.C.A.U.U.U.C | 710 |
| 10527 | Sense | P.U.G.U.A.G.A.A.A.U.G.U.A.U.C.C.U.G.A.U.A.A.A.C.A.U | 711 |
| | Antisense | A.U.G.U.U.U.A.U.C.A.G.G.A.U.A.C.A.U.U.U.C.U.A.C.A | 712 |
| 10528 | Sense | P.U.A.G.C.U.G.U.A.G.A.A.A.U.G.U.A.U.C.C.U.G.A.U.A.A | 713 |
| | Antisense | U.U.A.U.C.A.G.G.A.U.A.C.A.U.U.U.C.U.A.C.A.G.C.U.A | 714 |
| 10529 | Sense | P.C.U.G.C.U.A.G.C.U.G.U.A.G.A.A.A.U.G.U.A.U.C.C.U.G | 715 |
| | Antisense | C.A.G.G.A.U.A.C.A.U.U.U.C.U.A.C.A.G.C.U.A.G.C.A.G | 716 |
| 10530 | Sense | P.U.A.U.C.C.U.G.C.U.A.G.C.U.G.U.A.G.A.A.A.U.G.U.A.U | 717 |
| | Antisense | A.U.A.C.A.U.U.U.C.U.A.C.A.G.C.U.A.G.C.A.G.G.A.U.A | 718 |
| 10531 | Sense | P.C.U.G.U.U.A.U.C.C.U.G.C.U.A.G.C.U.G.U.A.G.A.A.A.U | 719 |
| | Antisense | A.U.U.U.C.U.A.C.A.G.C.U.A.G.C.A.G.G.A.U.A.A.C.A.G | 720 |
| 10532 | Sense | P.U.C.A.U.C.U.G.U.U.A.U.C.C.U.G.C.U.A.G.C.U.G.U.A.G | 721 |
| | Antisense | C.U.A.C.A.G.C.U.A.G.C.A.G.G.A.U.A.A.C.A.G.A.U.G.A | 722 |
| 10533 | Sense | P.U.A.A.C.U.C.A.U.C.U.G.U.U.A.U.C.C.U.G.C.U.A.G.C.U | 723 |
| | Antisense | A.G.C.U.A.G.C.A.G.G.A.U.A.A.C.A.G.A.U.G.A.G.U.U.A | 724 |
| 10534 | Sense | P.C.C.U.U.A.A.C.U.C.A.U.C.U.G.U.U.A.U.C.C.U.G.C.U.A | 725 |
| | Antisense | U.A.G.C.A.G.G.A.U.A.A.C.A.G.A.U.G.A.G.U.U.A.A.G.G | 726 |
| 10535 | Sense | P.G.U.C.G.U.U.U.G.G.C.U.U.G.U.G.G.U.G.U.A.A.U.U.G.G | 727 |
| | Antisense | C.C.A.A.U.U.A.C.A.C.C.A.C.A.A.G.C.C.A.A.A.C.G.A.C | 728 |
| 10536 | Sense | P.C.U.G.G.A.A.G.U.C.G.U.U.U.G.G.C.U.U.G.U.G.G.U.G.U | 729 |
| | Antisense | A.C.A.C.C.A.C.A.A.G.C.C.A.A.A.C.G.A.C.U.U.C.C.A.G | 730 |
| 10537 | Sense | P.A.A.A.C.G.C.U.G.G.A.A.G.U.C.G.U.U.U.G.G.C.U.U.G.U | 731 |
| | Antisense | A.C.A.A.G.C.C.A.A.A.C.G.A.C.U.U.C.C.A.G.C.G.U.U.U | 732 |
| 10538 | Sense | P.C.A.G.G.A.A.A.C.G.C.U.G.G.A.A.G.U.C.G.U.U.U.G.G.C | 733 |
| | Antisense | G.C.C.A.A.A.C.G.A.C.U.U.C.C.A.G.C.G.U.U.U.C.C.U.G | 734 |
| 10539 | Sense | P.G.A.C.A.G.G.A.A.A.C.G.C.U.G.G.A.A.G.U.C.G.U.U.U.G | 735 |
| | Antisense | C.A.A.A.C.G.A.C.U.U.C.C.A.G.C.G.U.U.U.C.C.U.G.U.C | 736 |
| 10540 | Sense | P.A.A.A.G.A.C.A.G.G.A.A.A.C.G.C.U.G.G.A.A.G.U.C.G.U | 737 |
| | Antisense | A.C.G.A.C.U.U.C.C.A.G.C.G.U.U.U.C.C.U.G.U.C.U.U.U | 738 |
| 10541 | Sense | P.A.C.A.A.A.G.A.C.A.G.G.A.A.A.C.G.C.U.G.G.A.A.G.U.C | 739 |
| | Antisense | G.A.C.U.U.C.C.A.G.C.G.U.U.U.C.C.U.G.U.C.U.U.U.G.U | 740 |
| 10542 | Sense | P.G.U.A.C.A.A.A.G.A.C.A.G.G.A.A.A.C.G.C.U.G.G.A.A.G | 741 |
| | Antisense | C.U.U.C.C.A.G.C.G.U.U.U.C.C.U.G.U.C.U.U.U.G.U.A.C | 742 |
| 10543 | Sense | P.A.A.G.U.A.C.A.A.A.G.A.C.A.G.G.A.A.A.C.G.C.U.G.G.A | 743 |
| | Antisense | U.C.C.A.G.C.G.U.U.U.C.C.U.G.U.C.U.U.U.U.G.U.A.C.U.U | 744 |
| 10544 | Sense | P.A.A.A.G.U.A.C.A.A.A.G.A.C.A.G.G.A.A.A.C.G.C.U.G.G | 745 |
| | Antisense | C.C.A.G.C.G.U.U.U.C.C.U.G.U.C.U.U.U.U.G.U.A.C.U.U.U | 746 |
| 10545 | Sense | P.G.A.A.A.G.U.A.C.A.A.A.G.A.C.A.G.G.A.A.A.C.G.C.U.G | 747 |
| | Antisense | C.A.G.C.G.U.U.U.C.C.U.G.U.C.U.U.U.U.G.U.A.C.U.U.U.C | 748 |
| 10546 | Sense | P.U.G.A.A.G.A.A.A.G.U.A.C.A.A.A.G.A.C.A.G.G.A.A.A.C | 749 |
| | Antisense | G.U.U.U.C.C.U.G.U.C.U.U.U.U.G.U.A.C.U.U.U.C.U.U.C.A | 750 |
| 10547 | Sense | P.G.A.A.A.U.G.A.A.G.A.A.A.G.U.A.C.A.A.A.G.A.C.A.G.G | 751 |
| | Antisense | C.C.U.G.U.C.U.U.U.U.G.U.A.C.U.U.U.C.U.U.C.A.U.U.U.C | 752 |
| 10548 | Sense | P.A.A.G.G.U.G.G.A.A.A.U.G.A.A.G.A.A.A.G.U.A.C.A.A.A | 753 |
| | Antisense | U.U.U.G.U.A.C.U.U.U.C.U.U.C.A.U.U.U.C.C.A.C.C.U.U | 754 |
| 10549 | Sense | P.U.U.G.G.G.C.A.A.A.G.G.U.G.G.A.A.A.U.G.A.A.G.A.A.A | 755 |

TABLE 2-continued

Additional Alternative RNAi Compound Sequences to SOD1

| Additional Sequences Designed | | | SEQ ID |
|---|---|---|---|
| | Antisense | U.U.U.C.U.U.C.A.U.U.U.C.C.A.C.C.U.U.U.G.C.C.C.A.A | 756 |
| 10550 | Sense | P.A.U.G.A.C.U.U.G.G.G.C.A.A.A.G.G.U.G.G.A.A.A.U.G.A | 757 |
| | Antisense | U.C.A.U.U.U.C.C.A.C.C.U.U.U.G.C.C.C.A.A.G.U.C.A.U | 758 |
| 10551 | Sense | P.G.U.C.C.A.U.G.A.A.A.A.G.C.A.G.A.U.G.A.C.U.U.G.G | 759 |
| | Antisense | C.C.A.A.G.U.C.A.U.C.U.G.C.U.U.U.U.U.C.A.U.G.G.A.C | 760 |
| 10552 | Sense | P.G.G.U.G.G.U.C.C.A.U.G.A.A.A.A.G.C.A.G.A.U.G.A.C | 761 |
| | Antisense | G.U.C.A.U.C.U.G.C.U.U.U.U.U.C.A.U.G.G.A.C.C.A.C.C | 762 |
| 10553 | Sense | P.C.A.C.U.G.G.U.G.G.U.C.C.A.U.G.A.A.A.A.A.G.C.A.G.A | 763 |
| | Antisense | U.C.U.G.C.U.U.U.U.U.C.A.U.G.G.A.C.C.A.C.C.A.G.U.G | 764 |
| 10554 | Sense | P.G.C.A.C.A.C.U.G.G.U.G.G.U.C.C.A.U.G.A.A.A.A.G.C | 765 |
| | Antisense | G.C.U.U.U.U.U.C.A.U.G.G.A.C.C.A.C.C.A.G.U.G.U.G.C | 766 |
| 10555 | Sense | P.U.G.G.C.C.G.C.A.C.A.C.U.G.G.U.G.G.U.C.C.A.U.G.A.A | 767 |
| | Antisense | U.U.C.A.U.G.G.A.C.C.A.C.C.A.G.U.G.U.G.C.G.G.C.C.A | 768 |

We claim:

1. A blunt-ended double-stranded RNA (dsRNA) construct, for inhibiting expression of a target gene, comprising a sense strand of 25, 26, 27, 28, 29, or 30 nucleotides in length, having a 5'-end and a 3'-end, wherein the sense strand consists of 2'-modified ribose sugars except for nucleotides 11, 12, and 13 relative to the 3'-end of the sense strand, which prevents processing of the double-stranded RNA construct by Dicer, and an antisense strand of 25, 26, 27, 28, 29, or 30 nucleotides in length having a 5'-end and a 3'-end, wherein the antisense strand is unmodified, wherein the antisense strand hybridizes to the sense strand and to mRNA of the target gene, wherein the dsRNA inhibits expression of the target gene in a sequence-dependent manner, and wherein the dsRNA does not form a hairpin.

2. The dsRNA of claim 1, wherein the target gene is SOD1, PPIB, RIP140, PCSK9, TNFα, AP2 (adipocyte lipid-binding protein), or MAP4K4.

3. The dsRNA of claim 1, wherein nucleotides 11, 12, and 13 relative to the 3'-end of the sense strand are purine nucleotides, optionally having phosphorothioate linkages.

4. A composition comprising the dsRNA of claim 1, and a pharmaceutically acceptable carrier or diluent.

5. The dsRNA of claim 1, wherein the 2'-modified ribose sugars are 2'-O-alkyl nucleotides, 2'-deoxy-2'-fluoro nucleotides, 2'-deoxy nucleotides, 2'-H (deoxyribonucleotides), or a combination thereof.

6. The dsRNA of claim 5, wherein the 2'-O-alkyl nucleotides are 2'-O-methyl nucleotides.

7. The dsRNA of claim 1, wherein, compared to a dsRNA of a nucleotide sequence of the dsRNA of claim 1 but wherein the sense strand does not include 2'-modifications, the dsRNA exhibits:

(i) enhanced target specificity;

(ii) reduced off-target silencing;

(iii) improved stability in serum and/or cerebral spinal fluid; and/or (iv) reduced induction of interferon response in primary cells.

8. A blunt-ended double-stranded RNA (dsRNA) construct comprising a sense strand having a 5'-end and a 3'-end, wherein the sense strand is 25, 26 or 27 nucleotides in length, and an antisense strand having a 5'-end and a 3'-end, wherein the antisense strand is 25, 26 or 27 nucleotides in length, for inhibiting expression of a target gene, wherein the sense strand consists of 2'-modified ribose sugars except for nucleotides 11, 12 and 13 relative to the 3' end of the sense strand, which prevents processing of the double-stranded RNA construct by Dicer, and wherein the dsRNA does not form a hairpin.

* * * * *

SEQUENCE LISTING

<160> NUMBER OF SEQ ID NOS: 827

<210> SEQ ID NO 1
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 1
gguggaaaug aagaaaguau u                                    21

<210> SEQ ID NO 2
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 2
uacuuucuuc auuccaccu u                                     21

<210> SEQ ID NO 3
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 3
ggcaaaggug gaaaugaaga aagua                                25

<210> SEQ ID NO 4
<211> LENGTH: 25
<212> TYPE: RNA
<213> ORGANISM: Artificial Sequence
<220> FEATURE:
<223> OTHER INFORMATION: Synthetic oligonucleotide

```
<400> SEQUENCE: 4
uacuuucuuc auuccaccu uugcc                                          25

<210> SEQ ID NO 5
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 5
ggcaaaggug gaaaugaaga aagua                                         25

<210> SEQ ID NO 6
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 6
uacuuucuuc auuccaccu uugcc                                          25

<210> SEQ ID NO 7
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 7
agguggaaau gaagaaagua caaag                                         25

<210> SEQ ID NO 8
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 8
cuuuguacuu ucuucauuuc caccu                                         25

<210> SEQ ID NO 9
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 9
gcacucugau ugacaaauac gauuu                                         25

<210> SEQ ID NO 10
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 10
aaaucguauu ugucaaucag agugc                                         25

<210> SEQ ID NO 11
<211> LENGTH: 21
```

```
<212> TYPE: RNA
<213> ORGANISM: Artificial Sequence
<220> FEATURE:
<223> OTHER INFORMATION: Synthetic oligonucleotide

<400> SEQUENCE: 11
gguggaaaug aagaaaguau u                                             21

<210> SEQ ID NO 12
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 12
uacuuucuuc auuccaccu u                                              21

<210> SEQ ID NO 13
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 13
ggcaaaggug gaaugaaga aagua                                          25

<210> SEQ ID NO 14
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 14
uacuuucuuc auuccaccu uugcc                                          25

<210> SEQ ID NO 15
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 15
ggcaaaggug gaaugaaga aagua                                          25

<210> SEQ ID NO 16
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 16
uacuuucuuc auuccaccu uugcc                                          25

<210> SEQ ID NO 17
<211> LENGTH: 25
<212> TYPE: RNA
<213> ORGANISM: Artificial Sequence
<220> FEATURE:
<223> OTHER INFORMATION: Synthetic oligonucleotide
```

```
<400> SEQUENCE: 17
ggcaaaggug gaaaugaaga aagua                                              25

<210> SEQ ID NO 18
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 18
uacuuucuuc auuuccaccu uugcc                                              25

<210> SEQ ID NO 19
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 19
ggcaaaggug gaaaugaaga aagua                                              25

<210> SEQ ID NO 20
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 20
uacuuucuuc auuuccaccu uugcc                                              25

<210> SEQ ID NO 21
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 21
ggcaaaggug gaaaugaaga aagua                                              25

<210> SEQ ID NO 22
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 22
uacuuucuuc auuuccaccu uugcc                                              25

<210> SEQ ID NO 23
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 23
ggcaaaggug gaaaugaaga aagua                                              25

<210> SEQ ID NO 24
<211> LENGTH: 25
```

```
<212> TYPE: RNA
<213> ORGANISM: Artificial Sequence
<220> FEATURE:
<223> OTHER INFORMATION: Synthetic oligonucleotide

<400> SEQUENCE: 24
uacuuucuuc auuccaccu uugcc                                          25

<210> SEQ ID NO 25
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 25
ggcaaaggug gaaaugaaga aagua                                         25

<210> SEQ ID NO 26
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 26
uacuuucuuc auuccaccu uugcc                                          25

<210> SEQ ID NO 27
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 27
ggcaaaggug gaaaugaaga aagua                                         25

<210> SEQ ID NO 28
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 28
uacuuucuuc auuccaccu uugcc                                          25

<210> SEQ ID NO 29
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 29
ggcaaaggug gaaaugaaga aagua                                         25

<210> SEQ ID NO 30
<211> LENGTH: 25
<212> TYPE: RNA
<213> ORGANISM: Artificial Sequence
<220> FEATURE:
<223> OTHER INFORMATION: Synthetic oligonucleotide
```

```
<400> SEQUENCE: 30
uacuuucuuc auuuccaccu uugcc                                          25

<210> SEQ ID NO 31
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 31
ggcaaaggug gaaaugaaga agua                                           25

<210> SEQ ID NO 32
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 32
uacuuucuuc auuuccaccu uugcc                                          25

<210> SEQ ID NO 33
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 33
ggcaaaggug gaaaugaaga agua                                           25

<210> SEQ ID NO 34
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 34
uacuuucuuc auuuccaccu uugcc                                          25

<210> SEQ ID NO 35
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 35
ggaaagacug uuccaaaaau u                                              21

<210> SEQ ID NO 36
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 36
uuuuuggaac agucuuuccu u                                              21

<210> SEQ ID NO 37
```

<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 37
ggaaagacug uuccaaaaau u                                              21

<210> SEQ ID NO 38
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 38
uuuuuggaac agucuuuccu u                                              21

<210> SEQ ID NO 39
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 39
cucuucggaa agacuguucc aaaaa                                          25

<210> SEQ ID NO 40
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 40
uuuuuggaac agucuuuccg aagag                                          25

<210> SEQ ID NO 41
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 41
gucucuucgg aaagacuguu ccaaaaa                                        27

<210> SEQ ID NO 42
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 42
uuuuuggaac agucuuuccg aagagac                                        27

<210> SEQ ID NO 43
<211> LENGTH: 21
<212> TYPE: RNA
<213> ORGANISM: Artificial Sequence
<220> FEATURE:
<223> OTHER INFORMATION: Synthetic oligonucleotide

```
<400> SEQUENCE: 43
cgaugugucu auugaagauu c                                              21

<210> SEQ ID NO 44
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 44
aucuucaaua gacacaucgg c                                              21

<210> SEQ ID NO 45
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 45
gccgaugugu cuauugaaga uucug                                          25

<210> SEQ ID NO 46
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 46
cagaaucuuc aauagacaca ucggc                                          25

<210> SEQ ID NO 47
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 47
uguggccgau gugucuauug aagau                                          25

<210> SEQ ID NO 48
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 48
aucuucaaua gacacaucgg ccaca                                          25

<210> SEQ ID NO 49
<211> LENGTH: 26
<212> TYPE: RNA
<213> ORGANISM: Artificial Sequence
<220> FEATURE:
<223> OTHER INFORMATION: Synthetic oligonucleotide

<400> SEQUENCE: 49
guguggccga ugugucuauu gaagau                                         26

<210> SEQ ID NO 50
```

```
<211> LENGTH: 26
<212> TYPE: RNA
<213> ORGANISM: Artificial Sequence
<220> FEATURE:
<223> OTHER INFORMATION: Synthetic oligonucleotide

<400> SEQUENCE: 50
aucuucaaua gacacaucgg ccacac                                          26

<210> SEQ ID NO 51
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 51
cgaugugucu auugaagauu c                                               21

<210> SEQ ID NO 52
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 52
aucuucaaua gacacaucgg c                                               21

<210> SEQ ID NO 53
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 53
gccgaugugu cuauugaaga uucug                                           25

<210> SEQ ID NO 54
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 54
cagaaucuuc aauagacaca ucggc                                           25

<210> SEQ ID NO 55
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 55
gccgaugugu cuauugaaga uucug                                           25

<210> SEQ ID NO 56
<211> LENGTH: 25
<212> TYPE: RNA
<213> ORGANISM: Artificial Sequence
<220> FEATURE:
<223> OTHER INFORMATION: Synthetic oligonucleotide
```

<400> SEQUENCE: 56
cagaaucuuc aauagacaca ucggc                                              25

<210> SEQ ID NO 57
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 57
agagcagugg cugguugaga u                                                  21

<210> SEQ ID NO 58
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 58
agagcagugg cugguugaga uu                                                 22

<210> SEQ ID NO 59
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 59
agagcagugg cugguugaga uuu                                                23

<210> SEQ ID NO 60
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 60
agagcagugg cugguugaga uuua                                               24

<210> SEQ ID NO 61
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 61
agagcagugg cugguugaga uuuaa                                              25

<210> SEQ ID NO 62
<211> LENGTH: 26
<212> TYPE: RNA
<213> ORGANISM: Artificial Sequence
<220> FEATURE:
<223> OTHER INFORMATION: Synthetic oligonucleotide

<400> SEQUENCE: 62
agagcagugg cugguugaga uuuaau                                             26

<210> SEQ ID NO 63

<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 63 acugggcaa agguggaaau gaagaaagua caaagacagg aaacgcugga            50

<210> SEQ ID NO 64
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 64
gauggugugg ccgauguguc uauugaagau ucugugaucu cacucucagg            50

<210> SEQ ID NO 65
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 65
gaccucggcg uggccuagcg aguua                                      25

<210> SEQ ID NO 66
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 66
uaacucgcua ggccacgccg agguc                                      25

<210> SEQ ID NO 67
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 67
ggaugaagag aggcauguug gagac                                      25

<210> SEQ ID NO 68
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 68
gucuccaaca ugccucucuu caucc                                      25

<210> SEQ ID NO 69
<211> LENGTH: 25
<212> TYPE: RNA
<213> ORGANISM: Artificial Sequence
<220> FEATURE:
<223> OTHER INFORMATION: Synthetic oligonucleotide -continued

```
<400> SEQUENCE: 69
ccaaaggaug aagagaggca uguug                                          25

<210> SEQ ID NO 70
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 70
caacaugccu cucuucaucc uuugg                                          25

<210> SEQ ID NO 71
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 71
aaagguggaa augaagaaag uacaa                                          25

<210> SEQ ID NO 72
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 72
uuguacuuuc uucauuucca ccuuu                                          25

<210> SEQ ID NO 73
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 73
gugcugguuu gcgucguagu cuccu                                          25

<210> SEQ ID NO 74
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 74
aggagacuac gacgcaaacc agcac                                          25

<210> SEQ ID NO 75
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 75
gucguagucu ccugcagcgu cuggg                                          25

<210> SEQ ID NO 76
```

```
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 76
cccagacgcu gcaggagacu acgac                                              25

<210> SEQ ID NO 77
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 77
caucaauuuc gagcagaagg aaagu                                              25

<210> SEQ ID NO 78
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 78 acuuccuuc ugcucgaaau ugaug                                               25

<210> SEQ ID NO 79
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 79
ucaucaauuu cgagcagaag gaaag                                              25

<210> SEQ ID NO 80
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 80 cuuccuucu gcucgaaauu gauga                                               25

<210> SEQ ID NO 81
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 81
uguaccagug cagguccuca cuuua                                              25

<210> SEQ ID NO 82
<211> LENGTH: 25
<212> TYPE: RNA
<213> ORGANISM: Artificial Sequence
<220> FEATURE:
<223> OTHER INFORMATION: Synthetic oligonucleotide
```

```
<400> SEQUENCE: 82
uaaagugagg accugcacug guaca                                          25

<210> SEQ ID NO 83
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 83
cagugcaggu ccucacuuua auccu                                          25

<210> SEQ ID NO 84
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 84
aggauuaaag ugaggaccug cacug                                          25

<210> SEQ ID NO 85
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 85
gagacuuggg caaugugacu gcuga                                          25

<210> SEQ ID NO 86
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 86
ucagcaguca cauugcccaa gucuc                                          25

<210> SEQ ID NO 87
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 87
guggccgaug ugucuauuga agauu                                          25

<210> SEQ ID NO 88
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 88
aaucuucaau agacacaucg gccac                                          25

<210> SEQ ID NO 89
```

```
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 89
gugucuauug aagauucugu gaucu                                          25

<210> SEQ ID NO 90
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 90
agaucacaga aucuucaaua gacac                                          25

<210> SEQ ID NO 91
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 91
ugugaucuca cucucaggag accau                                          25

<210> SEQ ID NO 92
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 92
auggucuccu gagagugaga ucaca                                          25

<210> SEQ ID NO 93
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 93
ggcaaaggug gaaaugaaga aagua                                          25

<210> SEQ ID NO 94
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 94
uacuuucuuc auuccaccu uugcc                                           25

<210> SEQ ID NO 95
<211> LENGTH: 25
<212> TYPE: RNA
<213> ORGANISM: Artificial Sequence
<220> FEATURE:
<223> OTHER INFORMATION: Synthetic oligonucleotide
```

```
<400> SEQUENCE: 95
agaugacuug ggcaaaggug gaaau                                              25

<210> SEQ ID NO 96
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 96
auuuccaccu uugcccaagu caucu                                              25

<210> SEQ ID NO 97
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 97
cgcuggaagu cguuggcuu guggu                                               25

<210> SEQ ID NO 98
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 98
accacaagcc aaacgacuuc cagcg                                              25

<210> SEQ ID NO 99
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 99
aauaaacauu cccuuggaug uaguc                                              25

<210> SEQ ID NO 100
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 100
gacuacaucc aagggaaugu uuauu                                              25

<210> SEQ ID NO 101
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 101
gcuagcugua gaauguauc cugau                                               25

<210> SEQ ID NO 102
```

```
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 102
aucaggauac auuucuacag cuagc                                        25

<210> SEQ ID NO 103
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 103
ccuguaguga gaaacugauu uauga                                        25

<210> SEQ ID NO 104
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 104
ucauaaauca guuucucacu acagg                                        25

<210> SEQ ID NO 105
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 105
ccagacuuaa aucacagaug gguau                                        25

<210> SEQ ID NO 106
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 106
auacccaucu gugauuuaag ucugg                                        25

<210> SEQ ID NO 107
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 107
cagaugggua uuaaacuugu cagaa                                        25

<210> SEQ ID NO 108
<211> LENGTH: 25
<212> TYPE: RNA
<213> ORGANISM: Artificial Sequence
<220> FEATURE:
<223> OTHER INFORMATION: Synthetic oligonucleotide
```

<400> SEQUENCE: 108
uucugacaag uuuaauaccc aucug                                              25

<210> SEQ ID NO 109
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 109
gccgaugugu cuauugaaga uucug                                              25

<210> SEQ ID NO 110
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 110
cagaaucuuc aauagacaca ucggc                                              25

<210> SEQ ID NO 111
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 111
gacugacuga aggccugcau ggauu                                              25

<210> SEQ ID NO 112
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 112
aauccaugca ggccuucagu caguc                                              25

<210> SEQ ID NO 113
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 113
gccgaugugu cuauugaaga uucug                                              25

<210> SEQ ID NO 114
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 114
cagaaucuuc aauagacaca ucggc                                              25

<210> SEQ ID NO 115

```
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 115
gaccucggcg uggccuagcg aguua                                              25

<210> SEQ ID NO 116
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 116
uaacucgcua ggccacgccg agguc                                              25

<210> SEQ ID NO 117
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 117
ccuguaguga gaaacugauu uauga                                              25

<210> SEQ ID NO 118
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 118
ucauaaauca guuucucacu acagg                                              25

<210> SEQ ID NO 119
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 119
ggaugaagag aggcauguug gagac                                              25

<210> SEQ ID NO 120
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 120
gucuccaaca ugccucucuu caucc                                              25

<210> SEQ ID NO 121
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 121
```

-continued aaagguggaa augaagaaag uacaa 25

<210> SEQ ID NO 122
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 122
uuguacuuuc uucauuccca ccuuu 25

<210> SEQ ID NO 123
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 123
cgaugugucu auugaagauu c 21

<210> SEQ ID NO 124
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 124
aucuucaaua gacacaucgg c 21

<210> SEQ ID NO 125
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 125
ggagacuugg gcaaugugau u 21

<210> SEQ ID NO 126
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 126
ucacauugcc caagucuccu u 21

<210> SEQ ID NO 127
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 127
cgaugugucu auugaagauu c 21

<210> SEQ ID NO 128
<211> LENGTH: 21
<212> TYPE: RNA

```
<213> ORGANISM: Artificial Sequence
<220> FEATURE:
<223> OTHER INFORMATION: Synthetic oligonucleotide"

<400> SEQUENCE: 128
aucuucaaua gacacaucgg c                                              21

<210> SEQ ID NO 129
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 129
ggagacuugg gcaaugugau u                                              21

<210> SEQ ID NO 130
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 130
ucacauugcc caagucuccu u                                              21

<210> SEQ ID NO 131
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 131
gcuguaccag ugcagguccu cacuu                                          25

<210> SEQ ID NO 132
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 132
aagugaggac cugcacuggu acagc                                          25

<210> SEQ ID NO 133
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 133
cuguaccagu gcagguccuc acuuu                                          25

<210> SEQ ID NO 134
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 134
aaagugagga ccugcacugg uacag                                          25
```

```
<210> SEQ ID NO 135
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 135
guaccagugc agguccucac uuuaa                                              25

<210> SEQ ID NO 136
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 136
uuaaagugag gaccugcacu gguac                                              25

<210> SEQ ID NO 137
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 137
uaccagugca gguccucacu uuaau                                              25

<210> SEQ ID NO 138
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 138
auuaaaguga ggaccugcac uggua                                              25

<210> SEQ ID NO 139
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 139
uggccgaugu gucuauugaa gauuc                                              25

<210> SEQ ID NO 140
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 140
gaaucuucaa uagacacauc ggcca                                              25

<210> SEQ ID NO 141
<211> LENGTH: 25
<212> TYPE: RNA
<213> ORGANISM: Artificial Sequence
<220> FEATURE:
```

<223> OTHER INFORMATION: Synthetic oligonucleotide

<400> SEQUENCE: 141
ggccgaugug ucuauugaag auucu                               25

<210> SEQ ID NO 142
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 142
agaaucuuca auagacacau cggcc                               25

<210> SEQ ID NO 143
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 143
ccgauguguc uauugaagau ucugu                               25

<210> SEQ ID NO 144
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 144
acagaaucuu caauagacac aucgg                               25

<210> SEQ ID NO 145
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 145
cgaugugucu auugaagauu cugug                               25

<210> SEQ ID NO 146
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 146
cacagaaucu ucaauagaca caucg                               25

<210> SEQ ID NO 147
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 147
ugggcaaagg uggaaaugaa gaaag                               25

```
<210> SEQ ID NO 148
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 148
cuuucuucau uuccaccuuu gccca                                              25

<210> SEQ ID NO 149
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 149
gggcaaaggu ggaaaugaag aaagu                                              25

<210> SEQ ID NO 150
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 150
acuuucuuca uuuccaccuu ugccc                                              25

<210> SEQ ID NO 151
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 151
gcaaaggugg aaugaagaa aguac                                               25

<210> SEQ ID NO 152
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 152
guacuuucuu cauuuccacc uuugc                                              25

<210> SEQ ID NO 153
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 153
caaaggugga augaagaaa guaca                                               25

<210> SEQ ID NO 154
<211> LENGTH: 25
<212> TYPE: RNA
<213> ORGANISM: Artificial Sequence
<220> FEATURE:
<223> OTHER INFORMATION: Synthetic oligonucleotide
```

```
<400> SEQUENCE: 154
uguacuuucu ucauuccac cuuug                                          25

<210> SEQ ID NO 155
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 155
aacgcuggaa gucguuggc uugug                                          25

<210> SEQ ID NO 156
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 156
cacaagccaa acgacuucca gcguu                                         25

<210> SEQ ID NO 157
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 157
acgcuggaag ucguuggcu ugugg                                          25

<210> SEQ ID NO 158
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 158
ccacaagcca aacgacuucc agcgu                                         25

<210> SEQ ID NO 159
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 159
gcuggaaguc guuggcuug uggug                                          25

<210> SEQ ID NO 160
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 160
caccacaagc caaacgacuu ccagc                                         25

<210> SEQ ID NO 161
<211> LENGTH: 25
```

<212> TYPE: RNA
<213> ORGANISM: Artificial Sequence
<220> FEATURE:
<223> OTHER INFORMATION: Synthetic oligonucleotide

<400> SEQUENCE: 161
cuggaagucg uuuggcuugu ggugu                                         25

<210> SEQ ID NO 162
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 162
acaccacaag ccaaacgacu uccag                                         25

<210> SEQ ID NO 163
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 163
ggccaaagga ugaagagagg caugu                                         25

<210> SEQ ID NO 164
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 164
acaugccucu cuucauccuu uggcc                                         25

<210> SEQ ID NO 165
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 165
gccaaaggau gaagagaggc auguu                                         25

<210> SEQ ID NO 166
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 166
aacaugccuc ucuucauccu uuggc                                         25

<210> SEQ ID NO 167
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 167
caaaggauga agagaggcau guugg                                    25

<210> SEQ ID NO 168
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 168
ccaacaugcc ucucuucauc cuuug                                    25

<210> SEQ ID NO 169
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 169
aaaggaugaa gagaggcaug uugga                                    25

<210> SEQ ID NO 170
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 170
uccaacaugc cucucuucau ccuuu                                    25

<210> SEQ ID NO 171
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 171
cgaugugucu auugaagauu c                                        21

<210> SEQ ID NO 172
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 172
aucuucaaua gacacaucgg c                                        21

<210> SEQ ID NO 173
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 173
cgaugugucu auugaagauu c                                        21

<210> SEQ ID NO 174
<211> LENGTH: 21
<212> TYPE: RNA
<213> ORGANISM: Artificial Sequence

```
<220> FEATURE:
<223> OTHER INFORMATION: Synthetic oligonucleotide

<400> SEQUENCE: 174
aucuucaaua gacacaucgg c                                              21

<210> SEQ ID NO 175
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 175
uguggccgau gugucuauug aagau                                          25

<210> SEQ ID NO 176
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 176
aucuucaaua gacacaucgg ccaca                                          25

<210> SEQ ID NO 177
<211> LENGTH: 26
<212> TYPE: RNA
<213> ORGANISM: Artificial Sequence
<220> FEATURE:
<223> OTHER INFORMATION: Synthetic oligonucleotide

<400> SEQUENCE: 177
guguggccga ugugucuauu gaagau                                         26

<210> SEQ ID NO 178
<211> LENGTH: 26
<212> TYPE: RNA
<213> ORGANISM: Artificial Sequence
<220> FEATURE:
<223> OTHER INFORMATION: Synthetic oligonucleotide

<400> SEQUENCE: 178
aucuucaaua gacacaucgg ccacac                                         26

<210> SEQ ID NO 179
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 179
uuuuuggaac agucuuucc                                                 19

<210> SEQ ID NO 180
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 180
uuuuuggaac agucuuucc                                                 19
```

<210> SEQ ID NO 181
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 181
augaagaaag uacaaagaca ggaaa                                          25

<210> SEQ ID NO 182
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 182
uuuccugucu uuguacuuuc uucau                                          25

<210> SEQ ID NO 183
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 183
aggaugaaga gaggcauguu ggaga                                          25

<210> SEQ ID NO 184
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 184
ucuccaacau gccucucuuc auccu                                          25

<210> SEQ ID NO 185
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 185
cugacaaaga ugguguggcc gaugu                                          25

<210> SEQ ID NO 186
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 186
acaucggcca caccaucuuu gucag                                          25

<210> SEQ ID NO 187
<211> LENGTH: 25
<212> TYPE: RNA
<213> ORGANISM: Artificial Sequence
<220> FEATURE:
<223> OTHER INFORMATION: Synthetic oligonucleotide

```
<400> SEQUENCE: 187
augaaaaagc agaugacuug ggcaa                                          25

<210> SEQ ID NO 188
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 188
uugcccaagu caucugcuuu uucau                                          25

<210> SEQ ID NO 189
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 189
cugcugacaa agauggugug gccga                                          25

<210> SEQ ID NO 190
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 190
ucggccacac caucuuuguc agcag                                          25

<210> SEQ ID NO 191
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 191
ggccgcacac uggguggucca ugaaa                                         25

<210> SEQ ID NO 192
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 192
uuucauggac caccagugug cggcc                                          25

<210> SEQ ID NO 193
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 193
acucucagga gaccauugca ucauu                                          25

<210> SEQ ID NO 194
```

```
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 194
aaugaugcaa uggucuccug agagu                                    25

<210> SEQ ID NO 195
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 195
uguggccgau gugcuauug aagau                                     25

<210> SEQ ID NO 196
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 196
aucuucaaua gacacaucgg ccaca                                    25

<210> SEQ ID NO 197
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 197
agaggcaugu uggagacuug ggcaa                                    25

<210> SEQ ID NO 198
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 198
uugcccaagu cuccaacaug ccucu                                    25

<210> SEQ ID NO 199
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 199
gugggccaaa ggaugaagag aggca                                    25

<210> SEQ ID NO 200
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 200
```
ugccucucuu cauccuuugg cccac            25

<210> SEQ ID NO 201
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 201
cuugggcaau gugacugcug acaaa            25

<210> SEQ ID NO 202
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 202
uuugucagca gucacauugc ccaag            25

<210> SEQ ID NO 203
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 203
ucuauccaga aaacacggug ggcca            25

<210> SEQ ID NO 204
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 204
uggcccaccg uguuuucugg auaga            25

<210> SEQ ID NO 205
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 205
aaaaagcaga ugacuugggc aaagg            25

<210> SEQ ID NO 206
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 206
ccuuugccca agucaucugc uuuuu            25

<210> SEQ ID NO 207
<211> LENGTH: 25
<212> TYPE: RNA

```
<213> ORGANISM: Artificial Sequence
<220> FEATURE:
<223> OTHER INFORMATION: Synthetic oligonucleotide

<400> SEQUENCE: 207
aauggaccag ugaaggugug gggaa                                            25

<210> SEQ ID NO 208
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 208
uuccccacac cuucacuggu ccauu                                            25

<210> SEQ ID NO 209
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 209
uguuauccug cuagcuguag aaaug                                            25

<210> SEQ ID NO 210
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 210
cauuucuaca gcuagcagga uaaca                                            25

<210> SEQ ID NO 211
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 211
cagaaggaaa guaauggacc aguga                                            25

<210> SEQ ID NO 212
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 212
ucacuggucc auuacuuucc uucug                                            25

<210> SEQ ID NO 213
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 213
aaugaagaaa guacaaagac aggaa                                            25
```

<210> SEQ ID NO 214
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 214
uuccugucuu uguacuuucu ucauu                                          25

<210> SEQ ID NO 215
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 215
cgagcagaag gaaaguaaug gacca                                          25

<210> SEQ ID NO 216
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 216
ugguccauua cuuccuucu gcucg                                           25

<210> SEQ ID NO 217
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 217
uacaaagaca ggaaacgcug gaagu                                          25

<210> SEQ ID NO 218
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 218
acuuccagcg uuuccugucu uugua                                          25

<210> SEQ ID NO 219
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 219
aauuucgagc agaaggaaag uaaug                                          25

<210> SEQ ID NO 220
<211> LENGTH: 25
<212> TYPE: RNA
<213> ORGANISM: Artificial Sequence
<220> FEATURE:

<223> OTHER INFORMATION: Synthetic oligonucleotide

<400> SEQUENCE: 220
cauuacuuuc cuucugcucg aaauu                                          25

<210> SEQ ID NO 221
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 221
ugaagagagg cauguuggag acuug                                          25

<210> SEQ ID NO 222
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 222
caagucucca acaugccucu cuuca                                          25

<210> SEQ ID NO 223
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 223
acuugggcaa agguggaaau gaaga                                          25

<210> SEQ ID NO 224
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 224
ucuucauuuc caccuuugcc caagu                                          25

<210> SEQ ID NO 225
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 225
acuugggcaa ugugacugcu gacaa                                          25

<210> SEQ ID NO 226
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 226
uugucagcag ucacauugcc caagu                                          25

<210> SEQ ID NO 227
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 227
uuggccgcac acuggugguc cauga 25

<210> SEQ ID NO 228
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 228
ucauggacca ccagugugcg gccaa 25

<210> SEQ ID NO 229
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 229
uuucgagcag aaggaaagua augga 25

<210> SEQ ID NO 230
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 230
uccauuacuu uccuucugcu cgaaa 25

<210> SEQ ID NO 231
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 231
gaaaaagcag augacuuggg caaag 25

<210> SEQ ID NO 232
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 232
cuuugcccaa gucaucugcu uuuuc 25

<210> SEQ ID NO 233
<211> LENGTH: 25
<212> TYPE: RNA
<213> ORGANISM: Artificial Sequence
<220> FEATURE:
<223> OTHER INFORMATION: Synthetic oligonucleotide -continued

<400> SEQUENCE: 233
cccagugcag ggcaucauca auuuc                                                25

<210> SEQ ID NO 234
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 234
gaaauugaug augcccugca cuggg                                                25

<210> SEQ ID NO 235
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 235
accagugcag guccucacuu uaauc                                                25

<210> SEQ ID NO 236
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 236
gauuaaagug aggaccugca cuggu                                                25

<210> SEQ ID NO 237
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 237
ggggaagcau uaaaggacug acuga                                                25

<210> SEQ ID NO 238
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 238
ucagucaguc cuuuaaugcu ucccc                                                25

<210> SEQ ID NO 239
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 239
gguguggccg augugucuau ugaag                                                25

<210> SEQ ID NO 240
<211> LENGTH: 25

```
<212> TYPE: RNA
<213> ORGANISM: Artificial Sequence
<220> FEATURE:
<223> OTHER INFORMATION: Synthetic oligonucleotide

<400> SEQUENCE: 240
cuucaauaga cacaucggcc acacc                                              25

<210> SEQ ID NO 241
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 241 gugugggaa gcauuaaagg acuga                                               25

<210> SEQ ID NO 242
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 242
ucaguccuuu aaugcuuccc cacac                                              25

<210> SEQ ID NO 243
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 243
cucucaggag accauugcau cauug                                              25

<210> SEQ ID NO 244
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 244
caaugaugca auggucuccu gagag                                              25

<210> SEQ ID NO 245
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 245
cauguuggag acuugggcaa uguga                                              25

<210> SEQ ID NO 246
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 246
```
ucacauugcc caagucucca acaug                                              25

<210> SEQ ID NO 247
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 247
ugacuugggc aaagguggaa augaa                                              25

<210> SEQ ID NO 248
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 248
uucauuucca ccuuugccca aguca                                              25

<210> SEQ ID NO 249
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 249
aggaaaguaa uggaccagug aaggu                                              25

<210> SEQ ID NO 250
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 250
accuucacug guccauuacu uuccu                                              25

<210> SEQ ID NO 251
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 251
ggcccagugc agggcaucau caauu                                              25

<210> SEQ ID NO 252
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 252
aauugaugau gcccugcacu gggcc                                              25

<210> SEQ ID NO 253
<211> LENGTH: 25
<212> TYPE: RNA
<213> ORGANISM: Artificial Sequence

```
<220> FEATURE:
<223> OTHER INFORMATION: Synthetic oligonucleotide

<400> SEQUENCE: 253
uuccauguuc augaguuugg agaua                                          25

<210> SEQ ID NO 254
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 254
uaucuccaaa cucaugaaca uggaa                                          25

<210> SEQ ID NO 255
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 255
aggcauguug gagacuuggg caaug                                          25

<210> SEQ ID NO 256
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 256
cauugcccaa gucuccaaca ugccu                                          25

<210> SEQ ID NO 257
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 257 ugugcuauu gaagauucug ugauc                                           25

<210> SEQ ID NO 258
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 258
gaucacagaa ucuucaauag acaca                                          25

<210> SEQ ID NO 259
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 259
agguccucac uuuaauccuc uaucc                                          25
```

```
<210> SEQ ID NO 260
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 260
ggauagagga uuaaagugag gaccu                                              25

<210> SEQ ID NO 261
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 261
ucacucucag gagaccauug cauca                                              25

<210> SEQ ID NO 262
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 262
ugaugcaaug gucuccugag aguga                                              25

<210> SEQ ID NO 263
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 263
agggcaucau caauuucgag cagaa                                              25

<210> SEQ ID NO 264
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 264
uucugcucga aauugaugau gcccu                                              25

<210> SEQ ID NO 265
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 265
ccauguucau gaguuuggag auaau                                              25

<210> SEQ ID NO 266
<211> LENGTH: 25
<212> TYPE: RNA
<213> ORGANISM: Artificial Sequence
<220> FEATURE:
<223> OTHER INFORMATION: Synthetic oligonucleotide
```

```
<400> SEQUENCE: 266
auuaucucca aacucaugaa caugg                                              25

<210> SEQ ID NO 267
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 267
aaacauuccc uuggauguag ucuga                                              25

<210> SEQ ID NO 268
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 268
ucagacuaca uccaagggaa uguuu                                              25

<210> SEQ ID NO 269
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 269
ucaauuucga gcagaaggaa aguaa                                              25

<210> SEQ ID NO 270
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 270
uuacuuuccu ucugcucgaa auuga                                              25

<210> SEQ ID NO 271
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 271
uggaagucgu uuggcuugug gugua                                              25

<210> SEQ ID NO 272
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 272
uacaccacaa gccaaacgac uucca                                              25

<210> SEQ ID NO 273
```

```
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 273
uggaaaugaa gaaaguacaa agaca                                            25

<210> SEQ ID NO 274
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 274
ugucuuugua cuuucuucau uucca                                            25

<210> SEQ ID NO 275
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 275
gcccagugca gggcaucauc aauuu                                            25

<210> SEQ ID NO 276
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 276
aaauugauga ugcccugcac ugggc                                            25

<210> SEQ ID NO 277
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 277
augguguggc cgaugugucu auuga                                            25

<210> SEQ ID NO 278
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 278
ucaauagaca caucggccac accau                                            25

<210> SEQ ID NO 279
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 279
```
gggcaaugug acugcugaca aagau                                              25

<210> SEQ ID NO 280
<211> LENGTH: 25
<212> TYPE: RNA
<213> ORGANISM: Artificial Sequence
<220> FEATURE:
<223> OTHER INFORMATION: Synthetic oligonucleotide"

<400> SEQUENCE: 280
aucuuuguca gcagucacau ugccc                                              25

<210> SEQ ID NO 281
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 281
cucacuuuaa uccucuaucc agaaa                                              25

<210> SEQ ID NO 282
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 282
uuucuggaua gaggauuaaa gugag                                              25

<210> SEQ ID NO 283
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 283
uccauguuca ugaguuugga gauaa                                              25

<210> SEQ ID NO 284
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 284
uuaucuccaa acucaugaac augga                                              25

<210> SEQ ID NO 285
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 285
gggaagcauu aaaggacuga cugaa                                              25

<210> SEQ ID NO 286
<211> LENGTH: 25
<212> TYPE: RNA

```
<213> ORGANISM: Artificial Sequence
<220> FEATURE:
<223> OTHER INFORMATION: Synthetic oligonucleotide

<400> SEQUENCE: 286
uucagucagu ccuuuaaugc uuccc                                           25

<210> SEQ ID NO 287
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 287
ccagugcagg gcaucaucaa uuucg                                           25

<210> SEQ ID NO 288
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 288
cgaaauugau gaugcccugc acugg                                           25

<210> SEQ ID NO 289
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 289
gcaucaucaa uuucgagcag aagga                                           25

<210> SEQ ID NO 290
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 290
uccuucugcu cgaaauugau gaugc                                           25

<210> SEQ ID NO 291
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 291
caucaucaau uucgagcaga aggaa                                           25

<210> SEQ ID NO 292
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 292
uuccuucugc ucgaaauuga ugaug                                           25
```

```
<210> SEQ ID NO 293
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 293
caauuucgag cagaaggaaa guaau                                      25

<210> SEQ ID NO 294
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 294
auuacuuucc uucugcucga aauug                                      25

<210> SEQ ID NO 295
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 295
agaaggaaag uaauggacca gugaa                                      25

<210> SEQ ID NO 296
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 296
uucacugguc cauuacuuuc cuucu                                      25

<210> SEQ ID NO 297
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 297
gaaggaaagu aauggaccag ugaag                                      25

<210> SEQ ID NO 298
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 298
cuucacuggu ccauuacuuu ccuuc                                      25

<210> SEQ ID NO 299
<211> LENGTH: 25
<212> TYPE: RNA
<213> ORGANISM: Artificial Sequence
<220> FEATURE:
```

<223> OTHER INFORMATION: Synthetic oligonucleotide

<400> SEQUENCE: 299
gaaaguaaug gaccagugaa ggugu                                              25

<210> SEQ ID NO 300
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 300
acaccuucac gguccauua cuuuc                                               25

<210> SEQ ID NO 301
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 301
cauuaaagga cugacugaag gccug                                              25

<210> SEQ ID NO 302
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 302
caggccuuca gucaguccuu uaaug                                              25

<210> SEQ ID NO 303
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 303
gacugaaggc cugcauggau uccau                                              25

<210> SEQ ID NO 304
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 304
auggaaucca ugcaggccuu caguc                                              25

<210> SEQ ID NO 305
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 305
acugaaggcc ugcauggauu ccaug                                              25

<210> SEQ ID NO 306
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 306
cauggaaucc augcaggccu ucagu                                              25

<210> SEQ ID NO 307
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 307
ugaaggccug cauggauucc auguu                                              25

<210> SEQ ID NO 308
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 308
aacauggaau ccaugcaggc cuuca                                              25

<210> SEQ ID NO 309
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 309
gaaggccugc auggauucca uguuc                                              25

<210> SEQ ID NO 310
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 310
gaacauggaa uccaugcagg ccuuc                                              25

<210> SEQ ID NO 311
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 311
aggccugcau ggauuccaug uucau                                              25

<210> SEQ ID NO 312
<211> LENGTH: 25
<212> TYPE: RNA
<213> ORGANISM: Artificial Sequence
<220> FEATURE:
<223> OTHER INFORMATION: Synthetic oligonucleotide

```
<400> SEQUENCE: 312
augaacaugg aauccaugca ggccu                                   25

<210> SEQ ID NO 313
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 313
gccugcaugg auuccauguu cauga                                   25

<210> SEQ ID NO 314
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 314
ucaugaacau ggaauccaug caggc                                   25

<210> SEQ ID NO 315
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 315
ccugcaugga uuccauguuc augag                                   25

<210> SEQ ID NO 316
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 316
cucaugaaca uggaauccau gcagg                                   25

<210> SEQ ID NO 317
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 317
ugcauggauu ccauguucau gaguu                                   25

<210> SEQ ID NO 318
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 318
aacucaugaa cauggaaucc augca                                   25

<210> SEQ ID NO 319
<211> LENGTH: 25
```

```
<212> TYPE: RNA
<213> ORGANISM: Artificial Sequence
<220> FEATURE:
<223> OTHER INFORMATION: Synthetic oligonucleotide

<400> SEQUENCE: 319
cauggauucc auguucauga guuug                                           25

<210> SEQ ID NO 320
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 320
caaacucaug aacauggaau ccaug                                           25

<210> SEQ ID NO 321
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 321
gauuccaugu ucaugaguuu ggaga                                           25

<210> SEQ ID NO 322
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 322
ucuccaaacu caugaacaug gaauc                                           25

<210> SEQ ID NO 323
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 323
ucaugaguuu ggagauaaua cagca                                           25

<210> SEQ ID NO 324
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 324
ugcuguauua ucuccaaacu cauga                                           25

<210> SEQ ID NO 325
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 325
```
ggagauaaua cagcaggcug uacca                                              25

<210> SEQ ID NO 326
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 326
ugguacagcc ugcuguauua ucucc                                              25

<210> SEQ ID NO 327
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 327
gauaauacag caggcuguac cagug                                              25

<210> SEQ ID NO 328
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 328
cacugguaca gccugcugua uuauc                                              25

<210> SEQ ID NO 329
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 329
ugcagguccu cacuuuaauc cucua                                              25

<210> SEQ ID NO 330
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 330
uagaggauua aagugaggac cugca                                              25

<210> SEQ ID NO 331
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 331
gguccucacu uuaauccucu aucca                                              25

<210> SEQ ID NO 332
<211> LENGTH: 25
<212> TYPE: RNA
<213> ORGANISM: Artificial Sequence

```
<220> FEATURE:
<223> OTHER INFORMATION: Synthetic oligonucleotide"

<400> SEQUENCE: 332
uggauagagg auuaaaguga ggacc                                              25

<210> SEQ ID NO 333
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 333
uccucacuuu aauccucuau ccaga                                              25

<210> SEQ ID NO 334
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 334
ucuggauaga ggauuaaagu gagga                                              25

<210> SEQ ID NO 335
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 335
ccucacuuua auccucuauc cagaa                                              25

<210> SEQ ID NO 336
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 336
uucuggauag aggauuaaag ugagg                                              25

<210> SEQ ID NO 337
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 337
ugggccaaag gaugaagaga ggcau                                              25

<210> SEQ ID NO 338
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 338
augccucucu ucauccuuug gccca                                              25
```

```
<210> SEQ ID NO 339
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 339
gaggcauguu ggagacuugg gcaau                                               25

<210> SEQ ID NO 340
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 340
auugcccaag ucuccaacau gccuc                                               25

<210> SEQ ID NO 341
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 341
ggcauguugg agacuugggc aaugu                                               25

<210> SEQ ID NO 342
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 342
acauugccca agucuccaac augcc                                               25

<210> SEQ ID NO 343
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 343
gcauguugga gacuugggca augug                                               25

<210> SEQ ID NO 344
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 344
cacauugccc aagucuccaa caugc                                               25

<210> SEQ ID NO 345
<211> LENGTH: 25
<212> TYPE: RNA
<213> ORGANISM: Artificial Sequence
<220> FEATURE:
<223> OTHER INFORMATION: Synthetic oligonucleotide
```

<400> SEQUENCE: 345
uggagacuug ggcaauguga cugcu                                          25

<210> SEQ ID NO 346
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 346
agcagucaca uugcccaagu cucca                                          25

<210> SEQ ID NO 347
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 347
ggcaauguga cugcugacaa agaug                                          25

<210> SEQ ID NO 348
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 348
caucuuuguc agcagucaca uugcc                                          25

<210> SEQ ID NO 349
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 349
gcaaugugac ugcugacaaa gaugg                                          25

<210> SEQ ID NO 350
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 350
ccaucuuugu cagcagucac auugc                                          25

<210> SEQ ID NO 351
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 351
ugacaaagau gguguggccg augug                                          25

<210> SEQ ID NO 352

```
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 352
cacaucggcc acaccaucuu uguca                                    25

<210> SEQ ID NO 353
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 353
gcauggauuc cauguucaug aguuu                                    25

<210> SEQ ID NO 354
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 354
aaacucauga acauggaauc caugc                                    25

<210> SEQ ID NO 355
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 355
gacaaagaug guguggccga ugugu                                    25

<210> SEQ ID NO 356
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 356
acacaucggc cacaccaucu uuguc                                    25

<210> SEQ ID NO 357
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 357
caaagauggu guggccgaug ugucu                                    25

<210> SEQ ID NO 358
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 358
```
agacacaucg gccacaccau cuuug                                              25

<210> SEQ ID NO 359
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 359
aagauggugu ggccgaugug ucuau                                              25

<210> SEQ ID NO 360
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 360
auagacacau cggccacacc aucuu                                              25

<210> SEQ ID NO 361
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 361
agauggugug gccgaugugu cuauu                                              25

<210> SEQ ID NO 362
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 362
aauagacaca ucggccacac caucu                                              25

<210> SEQ ID NO 363
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 363
gauggugugg ccgauguguc uauug                                              25

<210> SEQ ID NO 364
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 364
caauagacac aucggccaca ccauc                                              25

<210> SEQ ID NO 365
<211> LENGTH: 25
<212> TYPE: RNA

<213> ORGANISM: Artificial Sequence
<220> FEATURE:
<223> OTHER INFORMATION: Synthetic oligonucleotide

<400> SEQUENCE: 365
ugguguggcc gaugugucua uugaa                                         25

<210> SEQ ID NO 366
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 366
uucaauagac acaucggcca cacca                                         25

<210> SEQ ID NO 367
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 367
gaugugucua uugaagauuc uguga                                         25

<210> SEQ ID NO 368
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 368
ucacagaauc uucaauagac acauc                                         25

<210> SEQ ID NO 369
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 369
ugaagauucu gugaucucac ucuca                                         25

<210> SEQ ID NO 370
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 370
ugagagugag aucacagaau cuuca                                         25

<210> SEQ ID NO 371
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 371
gaagauucug ugaucucacu cucag                                         25

<210> SEQ ID NO 372
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 372
cugagaguga gaucacagaa ucuuc                                          25

<210> SEQ ID NO 373
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 373
ucucacucuc aggagaccau ugcau                                          25

<210> SEQ ID NO 374
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 374
augcaauggu cuccugagag ugaga                                          25

<210> SEQ ID NO 375
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 375
cacucucagg agaccauugc aucau                                          25

<210> SEQ ID NO 376
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 376
augaugcaau ggucuccuga gagug                                          25

<210> SEQ ID NO 377
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 377
accauugcau cauuggccgc acacu                                          25

<210> SEQ ID NO 378
<211> LENGTH: 25
<212> TYPE: RNA
<213> ORGANISM: Artificial Sequence
<220> FEATURE:

<223> OTHER INFORMATION: Synthetic oligonucleotide

<400> SEQUENCE: 378
agugugcggc caaugaugca auggu                               25

<210> SEQ ID NO 379
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 379
gcagaugacu ugggcaaagg uggaa                               25

<210> SEQ ID NO 380
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 380
uuccaccuuu gcccaaguca ucugc                               25

<210> SEQ ID NO 381
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 381
cagaugacuu gggcaaaggu ggaaa                               25

<210> SEQ ID NO 382
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 382
uuuccaccuu ugcccaaguc aucug                               25

<210> SEQ ID NO 383
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 383
gacuugggca agguggaaa ugaag                                25

<210> SEQ ID NO 384
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 384
cuucauuucc accuuugccc aaguc                               25

```
<210> SEQ ID NO 385
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 385
agguggaaau gaagaaagua caaag                                              25

<210> SEQ ID NO 386
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 386
cuuuguacuu ucuucauuuc caccu                                              25

<210> SEQ ID NO 387
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 387
gguggaaaug aagaaaguac aaaga                                              25

<210> SEQ ID NO 388
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 388
ucuuuguacu uucuucauuu ccacc                                              25

<210> SEQ ID NO 389
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 389
ggaaaugaag aaaguacaaa gacag                                              25

<210> SEQ ID NO 390
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 390
cugucuuugu acuuucuuca uuucc                                              25

<210> SEQ ID NO 391
<211> LENGTH: 25
<212> TYPE: RNA
<213> ORGANISM: Artificial Sequence
<220> FEATURE:
<223> OTHER INFORMATION: Synthetic oligonucleotide
```

<400> SEQUENCE: 391
agaaaguaca aagacaggaa acgcu                                          25

<210> SEQ ID NO 392
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 392
agcguuuccu gucuuuguac uuucu                                          25

<210> SEQ ID NO 393
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 393
aguacaaaga caggaaacgc uggaa                                          25

<210> SEQ ID NO 394
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 394
uuccagcguu uccugucuuu guacu                                          25

<210> SEQ ID NO 395
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 395
aagacaggaa acgcuggaag ucguu                                          25

<210> SEQ ID NO 396
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 396
aacgacuucc agcguuuccu gucuu                                          25

<210> SEQ ID NO 397
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 397
agacaggaaa cgcuggaagu cguuu                                          25

<210> SEQ ID NO 398
<211> LENGTH: 25

```
<212> TYPE: RNA
<213> ORGANISM: Artificial Sequence
<220> FEATURE:
<223> OTHER INFORMATION: Synthetic oligonucleotide

<400> SEQUENCE: 398
aaacgacuuc cagcguuucc ugucu                                              25

<210> SEQ ID NO 399
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 399
aggaaacgcu ggaagucguu uggcu                                              25

<210> SEQ ID NO 400
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 400
agccaaacga cuuccagcgu uuccu                                              25

<210> SEQ ID NO 401
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 401
ggaaacgcug gaagucguuu ggcuu                                              25

<210> SEQ ID NO 402
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 402
aagccaaacg acuuccagcg uuucc                                              25

<210> SEQ ID NO 403
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 403
gaaacgcugg aagucguuug gcuug                                              25

<210> SEQ ID NO 404
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 404
```
caagccaaac gacuuccagc guuuc                                          25

<210> SEQ ID NO 405
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 405
ggaagucguu uggcuugugg uguaa                                          25

<210> SEQ ID NO 406
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 406
uuacaccaca agccaaacga cuucc                                          25

<210> SEQ ID NO 407
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 407
gaagucguuu ggcuuguggu guaau                                          25

<210> SEQ ID NO 408
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 408
auuacaccac aagccaaacg acuuc                                          25

<210> SEQ ID NO 409
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 409
aagucguuug gcuugguggug uaauu                                         25

<210> SEQ ID NO 410
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 410
aauuacacca caagccaaac gacuu                                          25

<210> SEQ ID NO 411
<211> LENGTH: 25
<212> TYPE: RNA
<213> ORGANISM: Artificial Sequence -continued
<220> FEATURE:
<223> OTHER INFORMATION: Synthetic oligonucleotide

<400> SEQUENCE: 411
ugugguguaa uugggaucgc ccaau                                           25

<210> SEQ ID NO 412
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 412
auugggcgau cccaauuaca ccaca                                           25

<210> SEQ ID NO 413
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 413
ugguguaauu gggaucgccc aauaa                                           25

<210> SEQ ID NO 414
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 414 uuaugggcg aucccaauua cacca                                            25

<210> SEQ ID NO 415
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 415
cuggccuaua aaguagucgc ggaga                                           25

<210> SEQ ID NO 416
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 416
ucuccgcgac uacuuuauag gccag                                           25

<210> SEQ ID NO 417
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 417
ggccagagug ggcgaggcgc ggagg                                           25

<210> SEQ ID NO 418
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 418
ccuccgcgcc ucgcccacuc uggcc                                              25

<210> SEQ ID NO 419
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 419
ccagaguggg cgaggcgcgg agguc                                              25

<210> SEQ ID NO 420
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 420
gaccuccgcg ccucgcccac ucugg                                              25

<210> SEQ ID NO 421
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 421
agugggcgag gcgcggaggu cuggc                                              25

<210> SEQ ID NO 422
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 422
gccagaccuc cgcgccucgc ccacu                                              25

<210> SEQ ID NO 423
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 423
ggcgaggcgc ggaggucugg ccuau                                              25

<210> SEQ ID NO 424
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 424
auaggccaga ccuccgcgcc ucgcc                                       25

<210> SEQ ID NO 425
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 425
aggcgcggag gucuggccua uaaag                                       25

<210> SEQ ID NO 426
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 426
cuuuauaggc cagaccuccg cgccu                                       25

<210> SEQ ID NO 427
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 427
gcggaggucu ggccuauaaa guagu                                       25

<210> SEQ ID NO 428
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 428
acuacuuuau aggccagacc uccgc                                       25

<210> SEQ ID NO 429
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 429
aggucuggcc uauaaaguag ucgcg                                       25

<210> SEQ ID NO 430
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 430
cgcgacuacu uuauaggcca gaccu                                       25

<210> SEQ ID NO 431

```
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 431
gccuauaaag uagucgcgga gacgg                                  25

<210> SEQ ID NO 432
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 432
ccgucuccgc gacuacuuua uaggc                                  25

<210> SEQ ID NO 433
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 433
ggugcugguu ugcgucguag ucucc                                  25

<210> SEQ ID NO 434
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 434
ggagacuacg acgcaaacca gcacc                                  25

<210> SEQ ID NO 435
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 435
cugguuugcg ucguagucuc cugca                                  25

<210> SEQ ID NO 436
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 436
ugcaggagac uacgacgcaa accag                                  25

<210> SEQ ID NO 437
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 437
```
uuugcgucgu agucccugc agcgu 25

<210> SEQ ID NO 438
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 438
acgcugcagg agacuacgac gcaaa 25

<210> SEQ ID NO 439
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 439
cgucguaguc uccugcagcg ucugg 25

<210> SEQ ID NO 440
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 440
ccagacgcug caggagacua cgacg 25

<210> SEQ ID NO 441
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 441
gguuuccguu gcaguccucg gaacc 25

<210> SEQ ID NO 442
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 442
gguuccgagg acugcaacgg aaacc 25

<210> SEQ ID NO 443
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 443
uccguugcag uccucggaac cagga 25

<210> SEQ ID NO 444
<211> LENGTH: 25
<212> TYPE: RNA

```
<213> ORGANISM: Artificial Sequence
<220> FEATURE:
<223> OTHER INFORMATION: Synthetic oligonucleotide

<400> SEQUENCE: 444
uccugguucc gaggacugca acgga                                          25

<210> SEQ ID NO 445
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 445
uugcagbccu cggaaccagg accuc                                          25

<210> SEQ ID NO 446
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 446
gagguccugg uuccgaggac ugcaa                                          25

<210> SEQ ID NO 447
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 447
aguccucgga accaggaccu cggcg                                          25

<210> SEQ ID NO 448
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 448
cgccgagguc cugguuccga ggacu                                          25

<210> SEQ ID NO 449
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 449
cucggaacca ggaccucggc guggc                                          25

<210> SEQ ID NO 450
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 450
gccacgccga gguccugguu ccgag                                          25
```

<210> SEQ ID NO 451
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 451
gaaccaggac cucggcgugg ccuag                                         25

<210> SEQ ID NO 452
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 452
cuaggccacg ccgagguccu gguuc                                         25

<210> SEQ ID NO 453
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 453
caggaccucg gcguggccua gcgag                                         25

<210> SEQ ID NO 454
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 454
cucgcuaggc cacgccgagg uccug                                         25

<210> SEQ ID NO 455
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 455
accucggcgu ggccuagcga guuau                                         25

<210> SEQ ID NO 456
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 456
auaacucgcu aggccacgcc gaggu                                         25

<210> SEQ ID NO 457
<211> LENGTH: 25
<212> TYPE: RNA
<213> ORGANISM: Artificial Sequence
<220> FEATURE:

<223> OTHER INFORMATION: Synthetic oligonucleotide

<400> SEQUENCE: 457
cggcguggcc uagcgaguua uggcg                                              25

<210> SEQ ID NO 458
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 458
cgccauaacu cgcuaggcca cgccg                                              25

<210> SEQ ID NO 459
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 459
guggccuagc gaguuauggc gacga                                              25

<210> SEQ ID NO 460
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 460
ucgucgccau aacucgcuag gccac                                              25

<210> SEQ ID NO 461
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 461
ccuagcgagu uauggcgacg aaggc                                              25

<210> SEQ ID NO 462
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 462
gccuucgucg ccauaacucg cuagg                                              25

<210> SEQ ID NO 463
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 463
gcgaguuaug cgcgacgaagg ccgug                                             25

```
<210> SEQ ID NO 464
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 464
cacggccuuc gucgccauaa cucgc                                  25

<210> SEQ ID NO 465
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 465
guuauggcga cgaaggccgu gugcg                                  25

<210> SEQ ID NO 466
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 466
cgcacacggc cuucgucgcc auaac                                  25

<210> SEQ ID NO 467
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 467
uggcgacgaa ggccgugugc gugcu                                  25

<210> SEQ ID NO 468
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 468
agcacgcaca cggccuucgu cgcca                                  25

<210> SEQ ID NO 469
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 469
gacgaaggcc gugugcgugc ugaag                                  25

<210> SEQ ID NO 470
<211> LENGTH: 25
<212> TYPE: RNA
<213> ORGANISM: Artificial Sequence
<220> FEATURE:
<223> OTHER INFORMATION: Synthetic oligonucleotide
```

-continued

<400> SEQUENCE: 470
cuucagcacg cacacggccu ucguc                                          25

<210> SEQ ID NO 471
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 471
acgaaggccg ugugcgugcu gaagg                                          25

<210> SEQ ID NO 472
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 472
ccuucagcac gcacacggcc uucgu                                          25

<210> SEQ ID NO 473
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 473
ggcaucauca auuucgagca gaagg                                          25

<210> SEQ ID NO 474
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 474
ccuucugcuc gaaauugaug augcc                                          25

<210> SEQ ID NO 475
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 475
aucaauuucg agcagaagga aagua                                          25

<210> SEQ ID NO 476
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 476
uacuuuccuu cugcucgaaa uugau                                          25

<210> SEQ ID NO 477
<211> LENGTH: 25

```
<212> TYPE: RNA
<213> ORGANISM: Artificial Sequence
<220> FEATURE:
<223> OTHER INFORMATION: Synthetic oligonucleotide

<400> SEQUENCE: 477
auuucgagca gaaggaaagu aaugg                                      25

<210> SEQ ID NO 478
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 478
ccauuacuuu ccuucugcuc gaaau                                      25

<210> SEQ ID NO 479
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 479
ucgagcagaa ggaaaguaau ggacc                                      25

<210> SEQ ID NO 480
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 480
gguccauuac uuccuucug cucga                                       25

<210> SEQ ID NO 481
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 481
gcagaaggaa aguaauggac cagug                                      25

<210> SEQ ID NO 482
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 482
cacuggucca uuacuuuccu ucugc                                      25

<210> SEQ ID NO 483
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 483
```
aaggaaagua auggaccagu gaagg                                          25

<210> SEQ ID NO 484
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 484
ccuucacugg uccauuacuu uccuu                                          25

<210> SEQ ID NO 485
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 485
aaaguaaugg accagugaag gugug                                          25

<210> SEQ ID NO 486
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 486
cacaccuuca cugguccauu acuuu                                          25

<210> SEQ ID NO 487
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 487
uaauggacca gugaaggugu gggga                                          25

<210> SEQ ID NO 488
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 488
uccccacacc uucacugguc cauua                                          25

<210> SEQ ID NO 489
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 489
ggaagcauua aaggacugac ugaag                                          25

<210> SEQ ID NO 490
<211> LENGTH: 25
<212> TYPE: RNA
<213> ORGANISM: Artificial Sequence

```
<220> FEATURE:
<223> OTHER INFORMATION: Synthetic oligonucleotide

<400> SEQUENCE: 490
cuucagucag uccuuuaaug cuucc                                          25

<210> SEQ ID NO 491
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 491
gcauuaaagg acugacugaa ggccu                                          25

<210> SEQ ID NO 492
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 492
aggccuucag ucagccuuu aaugc                                           25

<210> SEQ ID NO 493
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 493
uaaaggacug acugaaggcc ugcau                                          25

<210> SEQ ID NO 494
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 494
augcaggccu ucagucaguc cuuua                                          25

<210> SEQ ID NO 495
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 495
ggacugacug aaggccugca uggau                                          25

<210> SEQ ID NO 496
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 496
auccaugcag gccuucaguc agucc                                          25
```

-continued

```
<210> SEQ ID NO 497
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 497
ugacugaagg ccugcaugga uucca                                          25

<210> SEQ ID NO 498
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 498
uggaauccau gcaggccuuc aguca                                          25

<210> SEQ ID NO 499
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 499
cugaaggccu gcauggauuc caugu                                          25

<210> SEQ ID NO 500
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 500
acauggaauc caugcaggcc uucag                                          25

<210> SEQ ID NO 501
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 501
aaggccugca uggauuccau guuca                                          25

<210> SEQ ID NO 502
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 502
ugaacaugga auccaugcag gccuu                                          25

<210> SEQ ID NO 503
<211> LENGTH: 25
<212> TYPE: RNA
<213> ORGANISM: Artificial Sequence
<220> FEATURE:
<223> OTHER INFORMATION: Synthetic oligonucleotide
```

<400> SEQUENCE: 503
ggccugcaug gauuccaugu ucaug                                   25

<210> SEQ ID NO 504
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 504
caugaacaug gaauccaugc aggcc                                   25

<210> SEQ ID NO 505
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 505
cugcauggau uccauguuca ugagu                                   25

<210> SEQ ID NO 506
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 506
acucaugaac auggaaucca ugcag                                   25

<210> SEQ ID NO 507
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 507
auggauucca uguucaugag uuugg                                   25

<210> SEQ ID NO 508
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 508
ccaaacucau gaacauggaa uccau                                   25

<210> SEQ ID NO 509
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 509
auuccauguu caugaguuug gagau                                   25

<210> SEQ ID NO 510

```
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 510
aucuccaaac ucaugaacau ggaau                                         25

<210> SEQ ID NO 511
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 511
cauguucaug aguuuggaga uaaua                                         25

<210> SEQ ID NO 512
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 512
uauuaucucc aaacucauga acaug                                         25

<210> SEQ ID NO 513
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 513
uucaugaguu uggagauaau acagc                                         25

<210> SEQ ID NO 514
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 514
gcuguauuau cuccaaacuc augaa                                         25

<210> SEQ ID NO 515
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 515
ugaguuugga gauaauacag caggc                                         25

<210> SEQ ID NO 516
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 516
```

```
gccugcugua uuaucuccaa acuca                                              25

<210> SEQ ID NO 517
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 517
uuuggagaua auacagcagg cugua                                              25

<210> SEQ ID NO 518
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 518
uacagccugc uguauuaucu ccaaa                                              25

<210> SEQ ID NO 519
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 519
gagauaauac agcaggcugu accag                                              25

<210> SEQ ID NO 520
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 520
cugguacagc cugcuguauu aucuc                                              25

<210> SEQ ID NO 521
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 521
uaauacagca ggcuguacca gugca                                              25

<210> SEQ ID NO 522
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 522
ugcacuggua cagccugcug uauua                                              25

<210> SEQ ID NO 523
<211> LENGTH: 25
<212> TYPE: RNA
```

```
<213> ORGANISM: Artificial Sequence
<220> FEATURE:
<223> OTHER INFORMATION: Synthetic oligonucleotide

<400> SEQUENCE: 523
acagcaggcu guaccagugc agguc                                              25

<210> SEQ ID NO 524
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 524
gaccugcacu gguacagccu gcugu                                              25

<210> SEQ ID NO 525
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 525
caggcuguac cagugcaggu ccuca                                              25

<210> SEQ ID NO 526
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 526
ugaggaccug cacugguaca gccug                                              25

<210> SEQ ID NO 527
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 527
ccagugcagg uccucacuuu aaucc                                              25

<210> SEQ ID NO 528
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 528
ggauuaaagu gaggaccugc acugg                                              25

<210> SEQ ID NO 529
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 529
gugcaggucc ucacuuuaau ccucu                                              25
```

<210> SEQ ID NO 530
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 530
agaggauuaa agugaggacc ugcac                                    25

<210> SEQ ID NO 531
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 531
cagguccuca cuuuaauccu cuauc                                    25

<210> SEQ ID NO 532
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 532
gauagaggau uaaagugagg accug                                    25

<210> SEQ ID NO 533
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 533
guccucacuu uaauccucua uccag                                    25

<210> SEQ ID NO 534
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 534
cuggauagag gauuaaagug aggac                                    25

<210> SEQ ID NO 535
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 535
ucacuuuaau ccucuaucca gaaaa                                    25

<210> SEQ ID NO 536
<211> LENGTH: 25
<212> TYPE: RNA
<213> ORGANISM: Artificial Sequence
<220> FEATURE:

<223> OTHER INFORMATION: Synthetic oligonucleotide

<400> SEQUENCE: 536
uuuucuggau agaggauuaa aguga                                              25

<210> SEQ ID NO 537
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 537
uuuaauccuc uauccagaaa acacg                                              25

<210> SEQ ID NO 538
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 538
cguguuuucu ggauagagga uuaaa                                              25

<210> SEQ ID NO 539
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 539
auccucuauc cagaaaacac ggugg                                              25

<210> SEQ ID NO 540
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 540
ccaccguguu uucuggauag aggau                                              25

<210> SEQ ID NO 541
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 541
aaggaugaag agaggcaugu uggag                                              25

<210> SEQ ID NO 542
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 542
cuccaacaug ccucucuuca uccuu                                              25

<210> SEQ ID NO 543
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 543
augaagagag gcauguugga gacuu                                          25

<210> SEQ ID NO 544
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 544
aagucuccaa caugccucuc uucau                                          25

<210> SEQ ID NO 545
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 545
gaagagaggc auguggaga cuugg                                           25

<210> SEQ ID NO 546
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 546
ccaagucucc aacaugccuc ucuuc                                          25

<210> SEQ ID NO 547
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 547
gagaggcaug uuggagacuu gggca                                          25

<210> SEQ ID NO 548
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 548
ugcccaaguc uccaacaugc cucuc                                          25

<210> SEQ ID NO 549
<211> LENGTH: 25
<212> TYPE: RNA
<213> ORGANISM: Artificial Sequence
<220> FEATURE:
<223> OTHER INFORMATION: Synthetic oligonucleotide

```
<400> SEQUENCE: 549
auguuggaga cuugggcaau gugac                                              25

<210> SEQ ID NO 550
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 550
gucacauugc ccaagucucc aacau                                              25

<210> SEQ ID NO 551
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 551
caaugugacu gcugacaaag auggu                                              25

<210> SEQ ID NO 552
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 552
accaucuuug ucagcaguca cauug                                              25

<210> SEQ ID NO 553
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 553
gugacugcug acaaagaugg ugugg                                              25

<210> SEQ ID NO 554
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 554
ccacaccauc uuugucagca gucac                                              25

<210> SEQ ID NO 555
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 555
acugcugaca aagauggugu ggccg                                              25

<210> SEQ ID NO 556
<211> LENGTH: 25
```

```
<212> TYPE: RNA
<213> ORGANISM: Artificial Sequence
<220> FEATURE:
<223> OTHER INFORMATION: Synthetic oligonucleotide

<400> SEQUENCE: 556
cggccacacc aucuuuguca gcagu                                               25

<210> SEQ ID NO 557
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 557
gcugacaaag auguguggc cgaug                                                25

<210> SEQ ID NO 558
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 558
caucggccac accaucuuug ucagc                                               25

<210> SEQ ID NO 559
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 559
acaaagaugg uguggccgau guguc                                               25

<210> SEQ ID NO 560
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 560
gacacaucgg ccacaccauc uuugu                                               25

<210> SEQ ID NO 561
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 561
aaagauggug uggccgaugu gucua                                               25

<210> SEQ ID NO 562
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 562
```
uagacacauc ggccacacca ucuuu                                     25

<210> SEQ ID NO 563
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 563
augugucuau ugaagauucu gugau                                     25

<210> SEQ ID NO 564
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 564
aucacagaau cuucaauaga cacau                                     25

<210> SEQ ID NO 565
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 565
ugucuauuga agauucgug aucuc                                      25

<210> SEQ ID NO 566
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 566
gagaucacag aaucuucaau agaca                                     25

<210> SEQ ID NO 567
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 567
uauugaagau ucugugaucu cacuc                                     25

<210> SEQ ID NO 568
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 568
gagugagauc acagaaucuu caaua                                     25

<210> SEQ ID NO 569
<211> LENGTH: 25
<212> TYPE: RNA
<213> ORGANISM: Artificial Sequence

```
<220> FEATURE:
<223> OTHER INFORMATION: Synthetic oligonucleotide

<400> SEQUENCE: 569
uugaagauuc ugugaucuca cucuc                                              25

<210> SEQ ID NO 570
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 570
gagagugaga ucacagaauc uucaa                                              25

<210> SEQ ID NO 571
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 571
aagauucugu gaucucacuc ucagg                                              25

<210> SEQ ID NO 572
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 572
ccugagagug agaucacaga aucuu                                              25

<210> SEQ ID NO 573
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 573
uucugugauc ucacucucag gagac                                              25

<210> SEQ ID NO 574
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 574
gucuccugag agugagauca cagaa                                              25

<210> SEQ ID NO 575
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 575
gugaucucac ucucaggaga ccauu                                              25
```

<210> SEQ ID NO 576
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 576
aauggucucc ugagagugag aucac                                          25

<210> SEQ ID NO 577
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 577
aucucacucu caggagacca uugca                                          25

<210> SEQ ID NO 578
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 578
ugcaaugguc uccugagagu gagau                                          25

<210> SEQ ID NO 579
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 579
ucucaggaga ccauugcauc auugg                                          25

<210> SEQ ID NO 580
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 580
ccaaugaugc aauggucucc ugaga                                          25

<210> SEQ ID NO 581
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 581
aggagaccau ugcaucauug gccgc                                          25

<210> SEQ ID NO 582
<211> LENGTH: 25
<212> TYPE: RNA
<213> ORGANISM: Artificial Sequence
<220> FEATURE:
<223> OTHER INFORMATION: Synthetic oligonucleotide

```
<400> SEQUENCE: 582
gcggccaaug augcaauggu cuccu                                              25

<210> SEQ ID NO 583
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 583
gaccauugca ucauuggccg cacac                                              25

<210> SEQ ID NO 584
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 584
gugugcggcc aaugaugcaa ugguc                                              25

<210> SEQ ID NO 585
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 585
aaagaaucca aauucaaacu aaaaa                                              25

<210> SEQ ID NO 586
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 586
uuuuuaguuu gaauuuggau ucuuu                                              25

<210> SEQ ID NO 587
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 587
auuaaaagaa uccaaauuca aacua                                              25

<210> SEQ ID NO 588
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 588
auuaaaagaa uccaaauuca aacua                                              25

<210> SEQ ID NO 589
```

```
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 589
ggcuauuaaa agaauccaaa uucaa                                           25

<210> SEQ ID NO 590
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 590
uugaauuugg auucuuuuaa uagcc                                           25

<210> SEQ ID NO 591
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 591
augaggcuau uaaaagaauc caaau                                           25

<210> SEQ ID NO 592
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 592
auuuggauuc uuuuaauagc cucau                                           25

<210> SEQ ID NO 593
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 593
uauuaugagg cuauuaaaag aaucc                                           25

<210> SEQ ID NO 594
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 594
ggauucuuuu aauagccuca uaaua                                           25

<210> SEQ ID NO 595
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 595
```

-continued cacuuauuau gaggcuauua aaaga                                          25

<210> SEQ ID NO 596
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 596
ucuuuuaaua gccucauaau aagug                                          25

<210> SEQ ID NO 597
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 597
auggcacuua uuaugaggcu auuaa                                          25

<210> SEQ ID NO 598
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 598
uuaauagccu cauaauaagu gccau                                          25

<210> SEQ ID NO 599
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 599
cuguauggca cuuauuauga ggcua                                          25

<210> SEQ ID NO 600
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 600 uagcccauaua auaagugcca uacag                                         25

<210> SEQ ID NO 601
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 601
ucauucaagc cugugaauaa aaacc                                          25

<210> SEQ ID NO 602
<211> LENGTH: 25
<212> TYPE: RNA

```
<213> ORGANISM: Artificial Sequence
<220> FEATURE:
<223> OTHER INFORMATION: Synthetic oligonucleotide

<400> SEQUENCE: 602
gguuuuuauu cacaggcuug aauga                                              25

<210> SEQ ID NO 603
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 603
ugucauucaa gccugugaau aaaaa                                              25

<210> SEQ ID NO 604
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 604
uuuuuauuca caggcuugaa ugaca                                              25

<210> SEQ ID NO 605
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 605 uuugcauuc aagccuguga auaaa                                               25

<210> SEQ ID NO 606
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 606
uuuauucaca ggcuugaaug acaaa                                              25

<210> SEQ ID NO 607
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 607
ucuuugucau ucaagccugu gaaua                                              25

<210> SEQ ID NO 608
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 608
uauucacagg cuugaaugac aaaga                                              25
```

<210> SEQ ID NO 609
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 609 uuucuuguc auucaagccu gugaa                                              25

<210> SEQ ID NO 610
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 610
uucacaggcu ugaaugacaa agaaa                                             25

<210> SEQ ID NO 611
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 611
agaauuucuu ugucauucaa gccug                                             25

<210> SEQ ID NO 612
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 612
caggcuugaa ugacaaagaa auucu                                             25

<210> SEQ ID NO 613
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 613
ugucagaauu ucuuugucau ucaag                                             25

<210> SEQ ID NO 614
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 614
cuugaaugac aaagaaauuc ugaca                                             25

<210> SEQ ID NO 615
<211> LENGTH: 25
<212> TYPE: RNA
<213> ORGANISM: Artificial Sequence
<220> FEATURE:

<223> OTHER INFORMATION: Synthetic oligonucleotide

<400> SEQUENCE: 615
aacuugucag aauuucuuug ucauu                                              25

<210> SEQ ID NO 616
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 616
aaugacaaag aaauucugac aaguu                                              25

<210> SEQ ID NO 617
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 617
auuaaacuug ucagaauuuc uuugu                                              25

<210> SEQ ID NO 618
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 618
acaaagaaau ucugacaagu uuaau                                              25

<210> SEQ ID NO 619
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 619
gguauuaaac uugucagaau uucuu                                              25

<210> SEQ ID NO 620
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 620
aagaaauucu gacaaguuua auacc                                              25

<210> SEQ ID NO 621
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 621
uuugccagac uuaaaucaca gaugg                                              25

```
<210> SEQ ID NO 622
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 622
ccaucuguga uuuaagucug gcaaa                                              25

<210> SEQ ID NO 623
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 623
auuuugccag acuuaaauca cagau                                              25

<210> SEQ ID NO 624
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 624
aucugugauu uaagucuggc aaaau                                              25

<210> SEQ ID NO 625
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 625
guauuuugcc agacuuaaau cacag                                              25

<210> SEQ ID NO 626
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 626
cugugauuua agucuggcaa aauac                                              25

<210> SEQ ID NO 627
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 627
cuguauuuug ccagacuuaa aucac                                              25

<210> SEQ ID NO 628
<211> LENGTH: 25
<212> TYPE: RNA
<213> ORGANISM: Artificial Sequence
<220> FEATURE:
<223> OTHER INFORMATION: Synthetic oligonucleotide
```

```
<400> SEQUENCE: 628
gugauuuaag ucuggcaaaa uacag                                          25

<210> SEQ ID NO 629
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 629
accuguauuu ugccagacuu aaauc                                          25

<210> SEQ ID NO 630
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 630
gauuuaaguc uggcaaaaua caggu                                          25

<210> SEQ ID NO 631
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 631
aaugaccugu auuuugccag acuua                                          25

<210> SEQ ID NO 632
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 632
uaagucuggc aaaauacagg ucauu                                          25

<210> SEQ ID NO 633
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 633
uuucaaugac cuguauuuug ccaga                                          25

<210> SEQ ID NO 634
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 634
ucuggcaaaa uacaggucau ugaaa                                          25

<210> SEQ ID NO 635
<211> LENGTH: 25
```

```
<212> TYPE: RNA
<213> ORGANISM: Artificial Sequence
<220> FEATURE:
<223> OTHER INFORMATION: Synthetic oligonucleotide

<400> SEQUENCE: 635
ucuguuucaa ugaccuguau uuugc                                          25

<210> SEQ ID NO 636
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 636
gcaaaauaca ggucauugaa acaga                                          25

<210> SEQ ID NO 637
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 637
aaugucuguu ucaaugaccu guauu                                          25

<210> SEQ ID NO 638
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 638
aauacagguc auugaaacag acauu                                          25

<210> SEQ ID NO 639
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 639
uuaaaauguc uguuucaaug accug                                          25

<210> SEQ ID NO 640
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 640
caggucauug aaacagacau uuuaa                                          25

<210> SEQ ID NO 641
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 641
```
ucaguuaaaa ugucuguuuc aauga                                            25

<210> SEQ ID NO 642
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 642
ucauugaaac agacauuuua acuga                                            25

<210> SEQ ID NO 643
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 643
aaacucaguu aaaugucug uuuca                                             25

<210> SEQ ID NO 644
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 644
ugaaacagac auuuuaacug aguuu                                            25

<210> SEQ ID NO 645
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 645
uauaaaacuc aguuaaaaug ucugu                                            25

<210> SEQ ID NO 646
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 646
acagacauuu uaacugaguu uuaua                                            25

<210> SEQ ID NO 647
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 647
guuuuauaaa acucaguuaa aaugu                                            25

<210> SEQ ID NO 648
<211> LENGTH: 25
<212> TYPE: RNA
<213> ORGANISM: Artificial Sequence

```
<220> FEATURE:
<223> OTHER INFORMATION: Synthetic oligonucleotide

<400> SEQUENCE: 648
acauuuuaac ugaguuuuau aaaac                                         25

<210> SEQ ID NO 649
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 649
uauaguuuua uaaaacucag uuaaa                                         25

<210> SEQ ID NO 650
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 650
uuuaacugag uuuuauaaaa cuaua                                         25

<210> SEQ ID NO 651
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 651
uuuguauagu uuuauaaaac ucagu                                         25

<210> SEQ ID NO 652
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 652
acugaguuuu auaaaacuau acaaa                                         25

<210> SEQ ID NO 653
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 653
aagauuugua uaguuuuaua aaacu                                         25

<210> SEQ ID NO 654
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 654
aguuuuauaa aacuauacaa aucuu                                         25
```

```
<210> SEQ ID NO 655
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 655
uuggaagauu uguauaguuu uauaa                                   25

<210> SEQ ID NO 656
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 656
uuauaaaacu auacaaaucu uccaa                                   25

<210> SEQ ID NO 657
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 657
ucacuuggaa gauuguaua guuuu                                    25

<210> SEQ ID NO 658
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 658
aaaacuauac aaaucuucca aguga                                   25

<210> SEQ ID NO 659
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 659
augaucacuu ggaagauuug uauag                                   25

<210> SEQ ID NO 660
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 660
cuauacaaau cuuccaagug aucau                                   25

<210> SEQ ID NO 661
<211> LENGTH: 25
<212> TYPE: RNA
<213> ORGANISM: Artificial Sequence
<220> FEATURE:
<223> OTHER INFORMATION: Synthetic oligonucleotide
```

```
<400> SEQUENCE: 661
auuuaugauc acuggaaga uuugu                                          25

<210> SEQ ID NO 662
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 662
acaaaucuuc caagugauca uaaau                                         25

<210> SEQ ID NO 663
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 663
acugauuuau gaucacuugg aagau                                         25

<210> SEQ ID NO 664
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 664
aucuuccaag ugaucauaaa ucagu                                         25

<210> SEQ ID NO 665
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 665
agaaacugau uuaugaucac uugga                                         25

<210> SEQ ID NO 666
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 666
uccaagugau cauaaaucag uuucu                                         25

<210> SEQ ID NO 667
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 667
agugagaaac ugauuuauga ucacu                                         25

<210> SEQ ID NO 668
```

```
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 668
agugaucaua aaucaguuuc ucacu                                     25

<210> SEQ ID NO 669
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 669
cuguagugag aaacugauuu augau                                     25

<210> SEQ ID NO 670
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 670
aucauaaauc aguuucucac uacag                                     25

<210> SEQ ID NO 671
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 671
guaccuguag ugagaaacug auuua                                     25

<210> SEQ ID NO 672
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 672
uaaaucaguu ucucacuaca gguac                                     25

<210> SEQ ID NO 673
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 673
uaaaguaccu guagugagaa acuga                                     25

<210> SEQ ID NO 674
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 674
```
ucaguuucuc acuacaggua cuuua                                         25

<210> SEQ ID NO 675
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 675
gcuuuaaagu accuguagug agaaa                                         25

<210> SEQ ID NO 676
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 676
uuucucacua cagguacuuu aaagc                                         25

<210> SEQ ID NO 677
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 677
aguugcuuua aaguaccugu aguga                                         25

<210> SEQ ID NO 678
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 678
ucacuacagg uacuuuaaag caacu                                         25

<210> SEQ ID NO 679
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 679
ucagaguugc uuuaaaguac cugua                                         25

<210> SEQ ID NO 680
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 680
uacagguacu uuaaagcaac ucuga                                         25

<210> SEQ ID NO 681
<211> LENGTH: 25
<212> TYPE: RNA

```
<213> ORGANISM: Artificial Sequence
<220> FEATURE:
<223> OTHER INFORMATION: Synthetic oligonucleotide

<400> SEQUENCE: 681
uuuuucagag uugcuuuaaa guacc                                              25

<210> SEQ ID NO 682
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 682
gguacuuuaa agcaacucug aaaaa                                              25

<210> SEQ ID NO 683
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 683
ugacuuuuuc agaguugcuu uaaag                                              25

<210> SEQ ID NO 684
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 684
cuuuaaagca acucugaaaa aguca                                              25

<210> SEQ ID NO 685
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 685
ugugugacuu uuucagaguu gcuuu                                              25

<210> SEQ ID NO 686
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 686
aaagcaacuc ugaaaaaguc acaca                                              25

<210> SEQ ID NO 687
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 687
uaauugugug acuuuuucag aguug                                              25
```

-continued

```
<210> SEQ ID NO 688
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 688
caacucugaa aaagucacac aauua                                              25

<210> SEQ ID NO 689
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 689
aguguaauug ugugacuuuu ucaga                                              25

<210> SEQ ID NO 690
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 690
ucugaaaaag ucacacaauu acacu                                              25

<210> SEQ ID NO 691
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 691
uaaaagugua auugugugac uuuuu                                              25

<210> SEQ ID NO 692
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 692
aaaaagucac acaauuacac uuuua                                              25

<210> SEQ ID NO 693
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 693
aucuuaaaag uguaauugug ugacu                                              25

<210> SEQ ID NO 694
<211> LENGTH: 25
<212> TYPE: RNA
<213> ORGANISM: Artificial Sequence
<220> FEATURE:
```

<223> OTHER INFORMATION: Synthetic oligonucleotide

<400> SEQUENCE: 694
agucacacaa uuacacuuuu aagau                                  25

<210> SEQ ID NO 695
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 695
uguaaucuua aaguguaau ugugu                                   25

<210> SEQ ID NO 696
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 696
acacaauuac acuuuuaaga uuaca                                  25

<210> SEQ ID NO 697
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 697
acacuguaau cuuaaaagug uaauu                                  25

<210> SEQ ID NO 698
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 698
aauuacacuu uuaagauuac agugu                                  25

<210> SEQ ID NO 699
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 699
uuaaacacug uaaucuuaaa agugu                                  25

<210> SEQ ID NO 700
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 700
acacuuuuaa gauuacagug uuuaa                                  25

```
<210> SEQ ID NO 701
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 701
aacauuaaac acuguaaucu uaaaa                                      25

<210> SEQ ID NO 702
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 702
uuuuaagauu acaguguuua auguu                                      25

<210> SEQ ID NO 703
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 703
gauaaacauu aaacacugua aucuu                                      25

<210> SEQ ID NO 704
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 704
aagauuacag uguuuaaugu uuauc                                      25

<210> SEQ ID NO 705
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 705
uccugauaaa cauuaaacac uguaa                                      25

<210> SEQ ID NO 706
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 706
uuacaguguu uaauguuuau cagga                                      25

<210> SEQ ID NO 707
<211> LENGTH: 25
<212> TYPE: RNA
<213> ORGANISM: Artificial Sequence
<220> FEATURE:
<223> OTHER INFORMATION: Synthetic oligonucleotide
```

<400> SEQUENCE: 707
uguauccuga uaaacauuaa acacu					25

<210> SEQ ID NO 708
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 708
aguguuuaau guuuaucagg auaca					25

<210> SEQ ID NO 709
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 709
gaaauguauc cugauaaaca uuaaa					25

<210> SEQ ID NO 710
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 710
uuuaauguuu aucaggauac auuuc					25

<210> SEQ ID NO 711
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 711
uguagaaaug uauccugaua aacau					25

<210> SEQ ID NO 712
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 712
auguuuauca ggauacauuu cuaca					25

<210> SEQ ID NO 713
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 713
uagcuguaga aauguauccu gauaa					25

<210> SEQ ID NO 714
<211> LENGTH: 25

```
<212> TYPE: RNA
<213> ORGANISM: Artificial Sequence
<220> FEATURE:
<223> OTHER INFORMATION: Synthetic oligonucleotide

<400> SEQUENCE: 714
uuaucaggau acauuucuac agcua                                              25

<210> SEQ ID NO 715
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 715
cugcuagcug uagaaaugua uccug                                              25

<210> SEQ ID NO 716
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 716
caggauacau uucuacagcu agcag                                              25

<210> SEQ ID NO 717
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 717
uauccugcua gcuguagaaa uguau                                              25

<210> SEQ ID NO 718
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 718
auacauuucu acagcuagca ggaua                                              25

<210> SEQ ID NO 719
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 719
cuguuauccu gcuagcugua gaaau                                              25

<210> SEQ ID NO 720
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 720
```
auuucuacag cuagcaggau aacag    25

<210> SEQ ID NO 721
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 721
ucaucuguua uccugcuagc uguag    25

<210> SEQ ID NO 722
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 722
cuacagcuag caggauaaca gauga    25

<210> SEQ ID NO 723
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 723
uaacucaucu guuaccugc uagcu    25

<210> SEQ ID NO 724
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 724
agcuagcagg auaacagaug aguua    25

<210> SEQ ID NO 725
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 725
ccuuaacuca ucuguuaucc ugcua    25

<210> SEQ ID NO 726
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 726
uagcaggaua acagaugagu uaagg    25

<210> SEQ ID NO 727
<211> LENGTH: 25
<212> TYPE: RNA
<213> ORGANISM: Artificial Sequence

```
<220> FEATURE:
<223> OTHER INFORMATION: Synthetic oligonucleotide

<400> SEQUENCE: 727
gucguuuggc uuguggugua auugg                                              25

<210> SEQ ID NO 728
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 728
ccaauuacac cacaagccaa acgac                                              25

<210> SEQ ID NO 729
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 729
cuggaagucg uuuggcuugu ggugu                                              25

<210> SEQ ID NO 730
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 730
acaccacaag ccaaacgacu uccag                                              25

<210> SEQ ID NO 731
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 731
aaacgcugga agucguuugg cuugu                                              25

<210> SEQ ID NO 732
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 732
acaagccaaa cgacuuccag cguuu                                              25

<210> SEQ ID NO 733
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 733
caggaaacgc uggaagucgu uuggc                                              25
```

```
<210> SEQ ID NO 734
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 734
gccaaacgac uuccagcguu uccug                                              25

<210> SEQ ID NO 735
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 735
gacaggaaac gcuggaaguc guuug                                              25

<210> SEQ ID NO 736
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 736
caaacgacuu ccagcguuuc cuguc                                              25

<210> SEQ ID NO 737
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 737
aaagacagga aacgcuggaa gucgu                                              25

<210> SEQ ID NO 738
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 738
acgacuucca gcguuuccug ucuuu                                              25

<210> SEQ ID NO 739
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 739
acaaagacag gaaacgcugg aaguc                                              25

<210> SEQ ID NO 740
<211> LENGTH: 25
<212> TYPE: RNA
<213> ORGANISM: Artificial Sequence
<220> FEATURE:
<223> OTHER INFORMATION: Synthetic oligonucleotide
```

-continued

<400> SEQUENCE: 740
gacuuccagc guuccuguc uuugu                                                 25

<210> SEQ ID NO 741
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 741
guacaaagac aggaaacgcu ggaag                                                25

<210> SEQ ID NO 742
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 742
cuuccagcgu uccugucuu uguac                                                 25

<210> SEQ ID NO 743
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 743
aaguacaaag acaggaaacg cugga                                                25

<210> SEQ ID NO 744
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 744
uccagcguuu ccugucuuug uacuu                                                25

<210> SEQ ID NO 745
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 745
aaaguacaaa gacaggaaac gcugg                                                25

<210> SEQ ID NO 746
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 746
ccagcguuuc cugucuuugu acuuu                                                25

<210> SEQ ID NO 747

```
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 747
gaaaguacaa agacaggaaa cgcug                                    25

<210> SEQ ID NO 748
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 748
cagcguuucc ugucuuugua cuuuc                                    25

<210> SEQ ID NO 749
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 749
ugaagaaagu acaagacag gaaac                                     25

<210> SEQ ID NO 750
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 750
guuuccuguc uuuguacuuu cuuca                                    25

<210> SEQ ID NO 751
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 751
gaaaugaaga aaguacaaag acagg                                    25

<210> SEQ ID NO 752
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 752
ccugucuuug uacuuucuuc auuuc                                    25

<210> SEQ ID NO 753
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 753
```
aagguggaaa ugaagaaagu acaaa                                    25

<210> SEQ ID NO 754
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 754
uuuguacuuu cuucauuucc accuu                                    25

<210> SEQ ID NO 755
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 755
uugggcaaag guggaaauga agaaa                                    25

<210> SEQ ID NO 756
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 756
uuucuucauu uccaccuuug cccaa                                    25

<210> SEQ ID NO 757
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 757
augacuuggg caaaggugga aauga                                    25

<210> SEQ ID NO 758
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 758 ucauuccac cuuugcccaa gucau                                     25

<210> SEQ ID NO 759
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 759
guccaugaaa aagcagauga cuugg                                    25

<210> SEQ ID NO 760
<211> LENGTH: 25
<212> TYPE: RNA

<213> ORGANISM: Artificial Sequence
<220> FEATURE:
<223> OTHER INFORMATION: Synthetic oligonucleotide

<400> SEQUENCE: 760
ccaagucauc ugcuuuuca uggac                                              25

<210> SEQ ID NO 761
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 761
ggugguccau gaaaaagcag augac                                             25

<210> SEQ ID NO 762
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 762
gucaucugcu uuucaugga ccacc                                              25

<210> SEQ ID NO 763
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 763
cacugguggu ccaugaaaaa gcaga                                             25

<210> SEQ ID NO 764
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 764
ucugcuuuuu cauggaccac cagug                                             25

<210> SEQ ID NO 765
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 765
gcacacuggu gguccaugaa aaagc                                             25

<210> SEQ ID NO 766
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 766
gcuuuuucau ggaccaccag ugugc                                             25

<210> SEQ ID NO 767
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 767
uggccgcaca cuggugucc augaa                                              25

<210> SEQ ID NO 768
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 768
uucauggacc accagugugc ggcca                                             25

<210> SEQ ID NO 769
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 769
cgaugugucu auugaagauu c                                                 21

<210> SEQ ID NO 770
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 770
aucuucaaua gacacaucgg c                                                 21

<210> SEQ ID NO 771
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 771
ggagacuugg gcaaugugau u                                                 21

<210> SEQ ID NO 772
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 772
ucacauugcc caagucuccu u                                                 21

<210> SEQ ID NO 773
<211> LENGTH: 21
<212> TYPE: RNA
<213> ORGANISM: Artificial Sequence
<220> FEATURE:

<223> OTHER INFORMATION: Synthetic oligonucleotide

<400> SEQUENCE: 773
cgaugugucu auugaagauu c                                              21

<210> SEQ ID NO 774
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 774
aucuucaaua gacacaucgg c                                              21

<210> SEQ ID NO 775
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 775
ggagacuugg gcaaugugau u                                              21

<210> SEQ ID NO 776
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 776
ucacauugcc caagucuccu u                                              21

<210> SEQ ID NO 777
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 777
cgaugugucu auugaagauu c                                              21

<210> SEQ ID NO 778
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 778
aucuucaaua gacacaucgg c                                              21

<210> SEQ ID NO 779
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 779
cgaugugucu auugaagauu c                                              21

```
<210> SEQ ID NO 780
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 780
aucuucaaua gacacaucgg c                                              21

<210> SEQ ID NO 781
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 781
cgaugugucu auugaagau                                                 19

<210> SEQ ID NO 782
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 782
aucuucaaua gacacaucg                                                 19

<210> SEQ ID NO 783
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 783
cgaugugucu auugaagau                                                 19

<210> SEQ ID NO 784
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 784
aucuucaaua gacacaucg                                                 19

<210> SEQ ID NO 785
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 785
cgaugugucu auugaagauu c                                              21

<210> SEQ ID NO 786
<211> LENGTH: 21
<212> TYPE: RNA
<213> ORGANISM: Artificial Sequence
<220> FEATURE:
<223> OTHER INFORMATION: Synthetic oligonucleotide
```

-continued

<400> SEQUENCE: 786
aucuucaaua gacacaucgg c					21

<210> SEQ ID NO 787
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 787
cgaugugucu auugaagauu c					21

<210> SEQ ID NO 788
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 788
aucuucaaua gacacaucgg c					21

<210> SEQ ID NO 789
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 789
cgaugugucu auugaagau					19

<210> SEQ ID NO 790
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 790
aucuucaaua gacacaucg					19

<210> SEQ ID NO 791
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 791
cgaugugucu auugaagau					19

<210> SEQ ID NO 792
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 792
aucuucaaua gacacaucg					19

<210> SEQ ID NO 793
<211> LENGTH: 19

```
<212> TYPE: RNA
<213> ORGANISM: Artificial Sequence
<220> FEATURE:
<223> OTHER INFORMATION: Synthetic oligonucleotide

<400> SEQUENCE: 793
cgaugugucu auugaagau                                                19

<210> SEQ ID NO 794
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 794
aucuucaaua gacacaucg                                                19

<210> SEQ ID NO 795
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 795
cgaugugucu auugaaggu                                                19

<210> SEQ ID NO 796
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 796
aucuucaaua gacacaucg                                                19

<210> SEQ ID NO 797
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 797
cgaugugucu auugaaggu                                                19

<210> SEQ ID NO 798
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 798
aucuucaaua gacacaucg                                                19

<210> SEQ ID NO 799
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 799
```

```
cgaugugucu auugaagau                                              19

<210> SEQ ID NO 800
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 800
aucuucaaua gacacaucg                                              19

<210> SEQ ID NO 801
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 801
cgaugugucu auugaagau                                              19

<210> SEQ ID NO 802
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 802
aucuucaaua gacacaucg                                              19

<210> SEQ ID NO 803
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 803
uguggccgau gugucuauug aagau                                       25

<210> SEQ ID NO 804
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 804
aucuucaaua gacacaucgg ccaca                                       25

<210> SEQ ID NO 805
<211> LENGTH: 26
<212> TYPE: RNA
<213> ORGANISM: Artificial Sequence
<220> FEATURE:
<223> OTHER INFORMATION: Synthetic oligonucleotide

<400> SEQUENCE: 805
guguggccga ugugucuauu gaagau                                      26

<210> SEQ ID NO 806
<211> LENGTH: 26
<212> TYPE: RNA
<213> ORGANISM: Artificial Sequence
```

```
<220> FEATURE:
<223> OTHER INFORMATION: Synthetic oligonucleotide

<400> SEQUENCE: 806
aucuucaaua gacacaucgg ccacac                                          26

<210> SEQ ID NO 807
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 807 ggguguggccg augugucuau ugaagau                                        27

<210> SEQ ID NO 808
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 808
aucuucaaua gacacaucgg ccacacc                                         27

<210> SEQ ID NO 809
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 809
ggcaaaggug gaaugaaga aagua                                            25

<210> SEQ ID NO 810
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 810
uacuuucuuc auuccaccu uugcc                                            25

<210> SEQ ID NO 811
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 811
gccgaugugu cuauugaaga uucug                                           25

<210> SEQ ID NO 812
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 812
cagaaucuuc aauagacaca ucggc                                           25
```

<210> SEQ ID NO 813
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 813
gccgaugugu cuauugaaga uucug					25

<210> SEQ ID NO 814
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 814
uacuuucuuc auuccaccu u					21

<210> SEQ ID NO 815
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 815
gguggaaaug aagaaaguau u					21

<210> SEQ ID NO 816
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 816
ggcaaaggug gaaaugaaga aagua					25

<210> SEQ ID NO 817
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 817
uacuuucuuc auuccaccu uugcc					25

<210> SEQ ID NO 818
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 818
ggcaaaggug gaaaugaaga aagua					25

<210> SEQ ID NO 819
<211> LENGTH: 25
<212> TYPE: RNA
<213> ORGANISM: Artificial Sequence
<220> FEATURE:
<223> OTHER INFORMATION: Synthetic oligonucleotide -continued

<400> SEQUENCE: 819
uacuuucuuc auuccaccu uugcc                                          25

<210> SEQ ID NO 820
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 820
ggaaagacug uuccaaaaau u                                             21

<210> SEQ ID NO 821
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 821
uuuuuggaac agucuuuccu u                                             21

<210> SEQ ID NO 822
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 822
cucuucggaa agacuguucc aaaaa                                         25

<210> SEQ ID NO 823
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 823
uuuuuggaac agucuuuccg aagag                                         25

<210> SEQ ID NO 824
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 824
cucuucggaa agacuguucc aaaaa                                         25

<210> SEQ ID NO 825
<211> LENGTH: 25
<212> TYPE: RNA
<213> ORGANISM: Artificial Sequence
<220> FEATURE:
<223> OTHER INFORMATION: Synthetic oligonucleotide

<400> SEQUENCE: 825
uuuuuggaac agucuuuccg aagag                                         25

<210> SEQ ID NO 826

```
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 826
gucucuucgg aaagacuguu ccaaaaa                                            27

<210> SEQ ID NO 827
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 827
uuuuuggaac agucuuuccg aagagac                                            27
```